(12) United States Patent
Donovan et al.

(10) Patent No.: US 10,913,939 B2
(45) Date of Patent: Feb. 9, 2021

(54) COMPOSITIONS AND METHODS FOR EXPRESSION OF NITROGENASE IN PLANT CELLS

(71) Applicant: Monsanto Technology LLC, St. Louis, MO (US)

(72) Inventors: William P. Donovan, St. Louis, MO (US); Natalia Ivleva, St. Louis, MO (US); Jeffrey M. Staub, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 554 days.

(21) Appl. No.: 15/080,571

(22) Filed: Mar. 24, 2016

(65) Prior Publication Data
US 2016/0304842 A1 Oct. 20, 2016

Related U.S. Application Data

(60) Provisional application No. 62/141,733, filed on Apr. 1, 2015, provisional application No. 62/236,340, filed on Oct. 2, 2015.

(51) Int. Cl.
*C12N 15/82* (2006.01)
*C12N 9/02* (2006.01)

(52) U.S. Cl.
CPC ....... *C12N 9/0095* (2013.01); *C12N 15/8243* (2013.01); *C12Y 118/06001* (2013.01)

(58) Field of Classification Search
None
See application file for complete search history.

(56) References Cited

U.S. PATENT DOCUMENTS

| 5,877,402 | A | 3/1999 | Maliga et al. | |
|---|---|---|---|---|
| 6,492,578 | B1 * | 12/2002 | Staub | C12N 9/1092 435/418 |
| 2014/0196178 | A1 * | 7/2014 | Zaltsman | C12N 15/8243 800/306 |

OTHER PUBLICATIONS

Dixon (Microbiology 130.11 (1984): 2745-2755). (Year: 1984).*
Kucho et al. (Microbes and environments 32.4 (2017): 344-351). (Year: 2017).*
Guo et al (2004, Proc. Natl. Acad. Sci. USA 101: 9205-9210). (Year: 2004).*
Ladha et al. (Plant and Soil 252: 151-167, 2003). (Year: 2003).*
Prasad et al. (Plant Molecular Biology 18: 873-885, 1992). (Year: 1992).*
Logan et al. (Journal of Experimental Botany 51.346 (2000): 865-871). (Year: 2000).*
Oldroyd, et al. (Current opinion in biotechnology 26 (2013):19-24). (Year: 2013).*
UniProt Accession P00459, integrated into UniProt on Jul. 21, 1986. (Year: 1986).*
Jacobson et al. (Journal of Bacteriology, Feb. 1989, p. 1017-1027). (Year: 1989).*
UniProt Accession C1DH25 integrated into UniProt on May 26, 2009. (Year: 2009).*
GenBank Accession No. AAA22140, dated Apr. 26, 1993.
GenBank Accession No. AAA22142, dated Apr. 26, 1993.
GenBank Accession No. AAA64709, dated Apr. 4, 1995.
GenBank Accession No. AAA64732, dated Apr. 4, 1995.
GenBank Accession No. ACO76403, dated Jan. 31, 2014.
GenBank Accession No. ACO76432, dated Jan. 31, 2014.
GenBank Accession No. AGK13780, dated Dec. 11, 2013.
GenBank Accession No. AGK13783, dated Dec. 11, 2013.
GenBank Accession No. AGK18381, dated Dec. 11, 2013.
GenBank Accession No. AGK18385, dated Dec. 11, 2013.
GenBank Accession No. AJE19640, dated Jul. 2, 2015.
Cheng et al., "The *Klebsiella pneumoniae* nitrogenase Fe protein gene (nifH) functionally substitutes for the chlL gene in *Chlamydomonas reinhardtii*," *Biochem Biophys Res Commun*, 329:966-975. 2005.
Colon-Lopez et al., "Analysis of the nifHDK operon and structure of the NifH protein from the unicellular, diazotrophic cyanobacterium, *Cyanothece* strain sp. ATCC 51142(1)," *Biochim Biophys Acta*, 1473:363-375, 1999.
Coruzzi et al., "Tissue-specific and light-regulated expression of a pea nuclear gene encoding the small subunit of ribulose-1,5-bisphosphate carboxylase," *EMBO J*, 3:1671-1679, 1984.
Finn et al., "Pfam: the protein families database," *Nucl Acids Res*, 42:D222-D230, 2014.
Gavini et al., "Peptidyl-prolyl cis/trans isomerase-independent functional NifH mutant of *Azotobacter vinelandii*," *J Bacteriol*, 188:6020-6025, 2006.
Holland et al., "Nitrogenase MoFe protein subunits from *Klebsiella pneumoniae* expressed in foreign hosts: characteristics and interations," *J Biol Chem*, 262:8814-8820, 1987.
Howard et al., "*Klebsiella pneumoniae* nifM gene product is required for stabilization and activation of nitrogenase iron protein in *Escherichia coli*," *J Biol Chem*, 261:772-778, 1986.
Jang et al., "Subcellular targeting of green fluorescent protein to plastids in transgenic rice plants provides a high-level expression system," *Mol Breed*, 5:453-461, 1999.
Logan et al., "Mitochondria-targeted GFP highlights the heterogeneity of mitochondrial shape, size and movement within living plant cells," *J Exp Bot*, 51:865-871, 2000.
Seefeldt et al., "Mapping the site(s) of MgATP and MgADP interaction with the nitrogenase of *Azotobacter vinelandii* Lysine 15 of the iron protein plays a major role in MgATP interaction," *J Biol Chem*, 267:6680-6688, 1992.

(Continued)

Primary Examiner — Charles Logsdon
(74) Attorney, Agent, or Firm — Dentons US LLP

(57) ABSTRACT

The disclosure provides nucleic acid constructs encoding novel chimeric peptides that are useful for nuclear and chloroplast expression of active nitrogenase components including dinitrogenase reductase and dinitrogenase, in plant cells. The disclosure thus provides nucleic acid constructs encoding the chimeric proteins, as well as plant expression constructs comprising the same for expression and/or targeting to the nucleus, plastids, or mitochondria of plant cells. The disclosure also provides methods of use for the novel chimeric peptides that function to provide active dinitrogenase reductase, dinitrogenase, and thus nitrogenase, expressed in plant cells, and plants comprising such nucleic acid constructs.

30 Claims, 12 Drawing Sheets

Specification includes a Sequence Listing.

(56) References Cited

OTHER PUBLICATIONS

Staub et al., "Accumulation of D1 polypeptide in tobacco plastids is regulated via the untranslated region of the psbA mRNA," *EMBO J*, 12:601-606, 1993.

Staub et al., "Translation of psbA mRNA is regulated by light via the 5'-untranslated region in tobacco plastids," *Plant J*, 6:547-553, 1994.

Staub et al., "High-yield production of a human therapeutic protein in tobacco chloroplasts," *Nature Biotechnol*, 18:333-338, 2000.

Wang et al., "A Minimal Nitrogen Fixation Gene Cluster from *Paenibacillus* sp. WLY78 Enables Expression of Active Nitrogenase in *Escherichia coli*," *Plos Genet*, 9:1003865, 2013.

Buren, S., et al., "State of the art in eukaryotic nitrogenase engineering," FEMS Microbiol Lett., Feb. 1, 2018, 365(2).

Buren et al., "Extreme bioengineering to meet the nitrogen challenge," PNAS 115(36):8849-8851, 2018.

Ivleva et al., "Expression of Active Subunit of Nitrogenase via Integration into Plant Organelle Genome," PLoS One 11(8):e0160951, 2016.

Liu et al., "Engineering Nitrogen Fixation Activity in an Oxygenic Phototroph," mBio 9:e01029-18, 2018.

Rosenblueth et al., "Nitrogen Fixation in Cereals," Front. Microbiol. 9:1794, 2018.

Temme et al., "Refactoring the nitrogen fixation gene cluster from Klebsiella oxytoca," PNAS 109(18):7085-7090, 2012.

Yang et al., "Polyprotein strategy for stoichiometric assembly of nitrogen fixation components for synthetic biology," PNAS 115(36):E8509-E8517, 2018.

Boyd et al., "Evolution of Molybdenum Nitrogenase during the Transition from Anaerobic to Aerobic Metabolism," Journal of Bacteriology 197(9):1690-1699, 2015.

Curatti et al., "Challenges to develop nitrogen-fixing cereals by direct nif-gene transfer," Plant Science 225:130-137, 2014.

Dixon et al., "Nif gene transfer and expression in chloroplasts: Prospects and problems," Plant and Soil 194:193-203, 1997.

Hardy et al., "Nitrogen Fixation Research: A Key to World Food?," Science 188:633-643, 1975.

* cited by examiner

SEQ ID NO:36 = *Cyanthoece* nifH
SEQ ID NO:24 = *Azotobacter vinelandii* nifH
SEQ ID NO:32 = *Klebsiella pneumonia* nifH

SEQUENCE LISTING

```
<160> NUMBER OF SEQ ID NOS: 141

<210> SEQ ID NO 1
<211> LENGTH: 31
<212> TYPE: PRT
<213> ORGANISM: Arabidopsis thaliana

<400> SEQUENCE: 1

Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr
            20                  25                  30
```

```
<210> SEQ ID NO 2
<211> LENGTH: 33
<212> TYPE: PRT
<213> ORGANISM: Arabidopsis thaliana

<400> SEQUENCE: 2

Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
            20                  25                  30

Ala

<210> SEQ ID NO 3
<211> LENGTH: 35
<212> TYPE: PRT
<213> ORGANISM: Arabidopsis thaliana

<400> SEQUENCE: 3

Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
            20                  25                  30

Ala Lys Glu
        35

<210> SEQ ID NO 4
<211> LENGTH: 45
<212> TYPE: PRT
<213> ORGANISM: Arabidopsis thaliana

<400> SEQUENCE: 4

Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
            20                  25                  30

Ala Lys Glu Ile Lys Phe Gly Val Glu Ala Arg Ala Leu
        35                  40                  45

<210> SEQ ID NO 5
<211> LENGTH: 60
<212> TYPE: PRT
<213> ORGANISM: Arabidopsis thaliana

<400> SEQUENCE: 5

Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
            20                  25                  30

Ala Lys Glu Ile Lys Phe Gly Val Glu Ala Arg Ala Leu Met Leu Lys
        35                  40                  45

Gly Val Glu Asp Leu Ala Asp Ala Val Lys Val Thr
    50                  55                  60

<210> SEQ ID NO 6
<211> LENGTH: 76
<212> TYPE: PRT
<213> ORGANISM: Arabidopsis thaliana

<400> SEQUENCE: 6

Met Tyr Arg Phe Ala Ser Asn Leu Ala Ser Lys Ala Arg Ile Ala Gln
1               5                   10                  15
```

-continued

Asn Ala Arg Gln Val Ser Ser Arg Met Ser Trp Ser Arg Asn Tyr Ala
            20                  25                  30

Ala Lys Glu Ile Lys Phe Gly Val Glu Ala Arg Ala Leu Met Leu Lys
        35                  40                  45

Gly Val Glu Asp Leu Ala Asp Ala Val Lys Val Thr Met Gly Pro Lys
50                  55                  60

Gly Arg Asn Val Val Ile Glu Gln Ser Trp Gly Ala
65                  70                  75

<210> SEQ ID NO 7
<211> LENGTH: 63
<212> TYPE: PRT
<213> ORGANISM: Typhonium venosum

<400> SEQUENCE: 7

Met Met Ser Ser Arg Leu Val Gly Thr Ala Leu Cys Arg Gln Leu Ser
1               5                   10                  15

His Val Pro Val Pro Gln Tyr Leu Pro Ala Leu Arg Pro Thr Ala Asp
            20                  25                  30

Thr Ala Ser Ser Leu Leu His Gly Cys Ser Ala Ala Pro Ala Gln
        35                  40                  45

Arg Ala Gly Leu Trp Pro Pro Ser Trp Phe Ser Pro Pro Arg His
    50                  55                  60

<210> SEQ ID NO 8
<211> LENGTH: 65
<212> TYPE: PRT
<213> ORGANISM: Typhonium venosum

<400> SEQUENCE: 8

Met Met Ser Ser Arg Leu Val Gly Thr Ala Leu Cys Arg Gln Leu Ser
1               5                   10                  15

His Val Pro Val Pro Gln Tyr Leu Pro Ala Leu Arg Pro Thr Ala Asp
            20                  25                  30

Thr Ala Ser Ser Leu Leu His Gly Cys Ser Ala Ala Pro Ala Gln
        35                  40                  45

Arg Ala Gly Leu Trp Pro Pro Ser Trp Phe Ser Pro Pro Arg His Ala
    50                  55                  60

Ser
65

<210> SEQ ID NO 9
<211> LENGTH: 66
<212> TYPE: PRT
<213> ORGANISM: Neurospora crassa

<400> SEQUENCE: 9

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala
65

<210> SEQ ID NO 10
<211> LENGTH: 68
<212> TYPE: PRT
<213> ORGANISM: Neurospora crassa

<400> SEQUENCE: 10

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Tyr Ser
65

<210> SEQ ID NO 11
<211> LENGTH: 70
<212> TYPE: PRT
<213> ORGANISM: Neurospora crassa

<400> SEQUENCE: 11

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Tyr Ser Ser Glu
65              70

<210> SEQ ID NO 12
<211> LENGTH: 31
<212> TYPE: PRT
<213> ORGANISM: Pisum sativum

<400> SEQUENCE: 12

Met Ala Met Ala Asn Leu Ala Arg Arg Lys Gly Tyr Ser Leu Leu Ser
1               5                   10                  15

Ser Glu Thr Leu Arg Tyr Ser Phe Ser Leu Arg Ser Arg Ala Phe
            20                  25                  30

<210> SEQ ID NO 13
<211> LENGTH: 66
<212> TYPE: PRT
<213> ORGANISM: Flaveria pringlei

<400> SEQUENCE: 13

Met Asp Arg Ala Arg Arg Leu Ala Asn Lys Ala Ile Leu Gly Arg Leu
1               5                   10                  15

Val Ser Gln Thr Lys His Asn Pro Ser Ile Ser Ser Pro Ala Leu Cys
            20                  25                  30

Ser Pro Ser Arg Tyr Val Ser Ser Leu Ser Pro Tyr Val Cys Ser Gly
        35                  40                  45

Thr Asn Val Arg Ser Asp Arg Asn Leu Asn Gly Phe Gly Ser Gln Val
    50                  55                  60

Arg Thr
65

<210> SEQ ID NO 14
<211> LENGTH: 68
<212> TYPE: PRT
<213> ORGANISM: Flaveria pringlei

<400> SEQUENCE: 14

Met Asp Arg Ala Arg Arg Leu Ala Asn Lys Ala Ile Leu Gly Arg Leu
1               5                   10                  15

Val Ser Gln Thr Lys His Asn Pro Ser Ile Ser Ser Pro Ala Leu Cys
            20                  25                  30

Ser Pro Ser Arg Tyr Val Ser Ser Leu Ser Pro Tyr Val Cys Ser Gly
        35                  40                  45

Thr Asn Val Arg Ser Asp Arg Asn Leu Asn Gly Phe Gly Ser Gln Val
    50                  55                  60

Arg Thr Ile Ser
65

<210> SEQ ID NO 15
<211> LENGTH: 74
<212> TYPE: PRT
<213> ORGANISM: Flaveria pringlei

<400> SEQUENCE: 15

Met Asp Arg Ala Arg Arg Leu Ala Asn Lys Ala Ile Leu Gly Arg Leu
1               5                   10                  15

Val Ser Gln Thr Lys His Asn Pro Ser Ile Ser Ser Pro Ala Leu Cys
            20                  25                  30

Ser Pro Ser Arg Tyr Val Ser Ser Leu Ser Pro Tyr Val Cys Ser Gly
        35                  40                  45

Thr Asn Val Arg Ser Asp Arg Asn Leu Asn Gly Phe Gly Ser Gln Val
    50                  55                  60

Arg Thr Ile Ser Val Glu Ala Leu Lys Pro
65                  70

<210> SEQ ID NO 16
<211> LENGTH: 86
<212> TYPE: PRT
<213> ORGANISM: Pisum sativum

<400> SEQUENCE: 16

Met Glu Arg Ala Arg Arg Leu Ala Asn Arg Ala Thr Leu Lys Arg Leu
1               5                   10                  15

Leu Ser Glu Ala Lys Gln Asn Arg Lys Thr Glu Ser Thr Ser Thr Thr
            20                  25                  30

Thr Thr Thr Pro Leu Pro Phe Ser Leu Ser Gly Ser Ser Ser Arg Tyr
        35                  40                  45

Val Ser Ser Val Ser Asn Ser Ile Leu Arg Gly Arg Gly Ser Lys Pro
    50                  55                  60

Asp Asn Asn Val Ser Arg Arg Val Gly Gly Phe Leu Gly Val Gly Tyr
65                  70                  75                  80

Pro Ser Gln Ser Arg Ser
                85

<210> SEQ ID NO 17
<211> LENGTH: 88

```
<212> TYPE: PRT
<213> ORGANISM: Pisum sativum

<400> SEQUENCE: 17

Met Glu Arg Ala Arg Arg Leu Ala Asn Arg Ala Thr Leu Lys Arg Leu
1               5                   10                  15

Leu Ser Glu Ala Lys Gln Asn Arg Lys Thr Glu Ser Thr Ser Thr Thr
                20                  25                  30

Thr Thr Thr Pro Leu Pro Phe Ser Leu Ser Gly Ser Ser Ser Arg Tyr
            35                  40                  45

Val Ser Ser Val Ser Asn Ser Ile Leu Arg Gly Arg Gly Ser Lys Pro
        50                  55                  60

Asp Asn Asn Val Ser Arg Arg Val Gly Gly Phe Leu Gly Val Gly Tyr
65                  70                  75                  80

Pro Ser Gln Ser Arg Ser Ile Ser
                85

<210> SEQ ID NO 18
<211> LENGTH: 52
<212> TYPE: PRT
<213> ORGANISM: Phaseolus vulgaris

<400> SEQUENCE: 18

Met Ala Ala Val Leu Arg Ser Leu Arg Arg Asp Val Ala Ser Ala
1               5                   10                  15

Thr Phe Ser Ala Tyr Arg Ser Leu Thr Gly Ser Thr Lys Pro Ala Tyr
                20                  25                  30

Val Ala Gln Lys Trp Ser Cys Leu Ala Arg Pro Phe Ser Ser Arg Pro
            35                  40                  45

Ala Gly Asn Asp
            50

<210> SEQ ID NO 19
<211> LENGTH: 54
<212> TYPE: PRT
<213> ORGANISM: Phaseolus vulgaris

<400> SEQUENCE: 19

Met Ala Ala Val Leu Arg Ser Leu Arg Arg Asp Val Ala Ser Ala
1               5                   10                  15

Thr Phe Ser Ala Tyr Arg Ser Leu Thr Gly Ser Thr Lys Pro Ala Tyr
                20                  25                  30

Val Ala Gln Lys Trp Ser Cys Leu Ala Arg Pro Phe Ser Ser Arg Pro
            35                  40                  45

Ala Gly Asn Asp Val Ile
            50

<210> SEQ ID NO 20
<211> LENGTH: 65
<212> TYPE: PRT
<213> ORGANISM: Arabidopsis thaliana

<400> SEQUENCE: 20

Met Ile Ala Gly Val Leu Pro Arg Ser Ser Leu Pro Ser Arg Gln Thr
1               5                   10                  15

Leu Ser Ala Ala Leu Ala Ser Phe Asn Ser Cys Ile Ser His Asn Leu
                20                  25                  30

Thr Pro Ala Thr Thr Gly Ala Ser Val Ser Ser Arg Phe Thr Leu Ala
            35                  40                  45
```

Ser Ser Pro Asn Ser Phe Gly Ile Arg Ala Arg Asn Ile His Ile Arg
            50                  55                  60

Ser
65

<210> SEQ ID NO 21
<211> LENGTH: 66
<212> TYPE: PRT
<213> ORGANISM: Arabidopsis thaliana

<400> SEQUENCE: 21

Met Ile Ala Gly Val Leu Pro Arg Ser Ser Leu Pro Ser Arg Gln Thr
1               5                   10                  15

Leu Ser Ala Ala Leu Ala Ser Phe Asn Ser Cys Ile Ser His Asn Leu
            20                  25                  30

Thr Pro Ala Thr Thr Gly Ala Ser Val Ser Ser Arg Phe Thr Leu Ala
        35                  40                  45

Ser Ser Pro Asn Ser Phe Gly Ile Arg Ala Arg Asn Ile His Ile Arg
            50                  55                  60

Ser Glu
65

<210> SEQ ID NO 22
<211> LENGTH: 68
<212> TYPE: PRT
<213> ORGANISM: Arabidopsis thaliana

<400> SEQUENCE: 22

Met Ile Ala Gly Val Leu Pro Arg Ser Ser Leu Pro Ser Arg Gln Thr
1               5                   10                  15

Leu Ser Ala Ala Leu Ala Ser Phe Asn Ser Cys Ile Ser His Asn Leu
            20                  25                  30

Thr Pro Ala Thr Thr Gly Ala Ser Val Ser Ser Arg Phe Thr Leu Ala
        35                  40                  45

Ser Ser Pro Asn Ser Phe Gly Ile Arg Ala Arg Asn Ile His Ile Arg
            50                  55                  60

Ser Glu Pro Ser
65

<210> SEQ ID NO 23
<211> LENGTH: 47
<212> TYPE: PRT
<213> ORGANISM: Oryza sativa

<400> SEQUENCE: 23

Met Ala Pro Ser Val Met Ala Ser Ser Ala Thr Thr Val Ala Pro Phe
1               5                   10                  15

Gln Gly Leu Lys Ser Thr Ala Gly Met Pro Val Ala Arg Arg Ser Gly
            20                  25                  30

Asn Ser Ser Phe Gly Asn Val Ser Asn Gly Gly Arg Ile Arg Cys
        35                  40                  45

<210> SEQ ID NO 24
<211> LENGTH: 290
<212> TYPE: PRT
<213> ORGANISM: Azotobacter vinelandii

<400> SEQUENCE: 24

Met Ala Met Arg Gln Cys Ala Ile Tyr Gly Lys Gly Gly Ile Gly Lys

```
                1               5                  10                 15
           Ser Thr Thr Thr Gln Asn Leu Val Ala Ala Leu Ala Glu Met Gly Lys
                            20                  25                  30

Lys Val Met Ile Val Gly Cys Asp Pro Lys Ala Asp Ser Thr Arg Leu
                            35                  40                  45

Ile Leu His Ser Lys Ala Gln Asn Thr Ile Met Glu Met Ala Ala Glu
                            50                  55                  60

Ala Gly Thr Val Glu Asp Leu Glu Leu Glu Asp Val Leu Lys Ala Gly
            65                  70                  75                  80

Tyr Gly Gly Val Lys Cys Val Glu Ser Gly Gly Pro Glu Pro Gly Val
                            85                  90                  95

Gly Cys Ala Gly Arg Gly Val Ile Thr Ala Ile Asn Phe Leu Glu Glu
                           100                 105                 110

Glu Gly Ala Tyr Glu Asp Asp Leu Asp Phe Val Phe Tyr Asp Val Leu
                           115                 120                 125

Gly Asp Val Val Cys Gly Gly Phe Ala Met Pro Ile Arg Glu Asn Lys
                           130                 135                 140

Ala Gln Glu Ile Tyr Ile Val Cys Ser Gly Glu Met Met Ala Met Tyr
           145                 150                 155                 160

Ala Ala Asn Asn Ile Ser Lys Gly Ile Val Lys Tyr Ala Asn Ser Gly
                           165                 170                 175

Ser Val Arg Leu Gly Gly Leu Ile Cys Asn Ser Arg Asn Thr Asp Arg
                           180                 185                 190

Glu Asp Glu Leu Ile Ile Ala Leu Ala Asn Lys Leu Gly Thr Gln Met
                           195                 200                 205

Ile His Phe Val Pro Arg Asp Asn Val Val Gln Arg Ala Glu Ile Arg
                           210                 215                 220

Arg Met Thr Val Ile Glu Tyr Asp Pro Lys Ala Lys Gln Ala Asp Glu
           225                 230                 235                 240

Tyr Arg Ala Leu Ala Arg Lys Val Val Asp Asn Lys Leu Leu Val Ile
                           245                 250                 255

Pro Asn Pro Ile Thr Met Asp Glu Leu Glu Glu Leu Leu Met Glu Phe
                           260                 265                 270

Gly Ile Met Glu Val Glu Asp Glu Ser Ile Val Gly Lys Thr Ala Glu
                           275                 280                 285

Glu Val
               290

<210> SEQ ID NO 25
<211> LENGTH: 873
<212> TYPE: DNA
<213> ORGANISM: Azotobacter vinelandii

<400> SEQUENCE: 25
atggctatgc gtcaatgcgc catctacggc aaaggtggta tcggtaagtc caccactact      60
cagaacctgg tggcagccct ggctgagatg ggcaagaagg tcatgatcgt tggttgtgac     120
ccgaaagctg actccacccg cctgatcctg cactccaagg cccagaacac catcatggaa     180
atggctgccg aagccggtac cgtggaagat ctggagctgg aagacgtgct gaaggctggc     240
tacggcggcg tcaagtgcgt tgagtccggt ggtccggagc cgggcgttgg ctgcgccggc     300
cgtggtgtta tcaccgccat caacttcctg gaagaggaag cgcctacga agacgatctg     360 gacttcgtat tctacgacgt gctgggcgac gtggtgtgtg gcggcttcgc catgccgatc     420
cgcgagaaca aggcccagga aatctacatc gtctgctccg gtgagatgat ggccatgtac     480
```

```
gccgccaaca acatctccaa gggcatcgtg aagtatgcca actccggcag cgtgcgtctg    540
ggcggcctga tctgcaacag ccgtaacacc gaccgcgaag acgagctgat catcgctctg    600
gccaacaagc tgggcaccca gatgatccac ttcgtgccgc gtgacaacgt cgtgcagcgc    660
gccgaaatcc gccgcatgac cgtgatcgaa tacgatccga agccaagca agccgacgaa     720 taccgcgctc tggcccgcaa ggtcgtcgac aacaaactgc tggtcatccc gaacccgatc    780
accatggacg agctcgaaga gctgctgatg gaattcggca tcatggaagt cgaagacgaa    840
tccatcgtcg gcaaaaccgc cgaagaagtc tga                                 873
```

<210> SEQ ID NO 26
<211> LENGTH: 293
<212> TYPE: PRT
<213> ORGANISM: Azotobacter vinelandii

<400> SEQUENCE: 26

```
Met Ala Ser Glu Arg Leu Ala Asp Gly Asp Ser Arg Tyr Tyr Leu Leu
1               5                   10                  15

Lys Val Ala His Glu Gln Phe Gly Cys Ala Pro Gly Glu Leu Ser Glu
            20                  25                  30

Glu Gln Leu Gln Gln Ala Asp Arg Ile Ile Gly Arg Gln Arg His Ile
        35                  40                  45

Glu Asp Ala Val Leu Arg Ser Pro Asp Ala Ile Gly Val Val Ile Pro
    50                  55                  60

Pro Ser Gln Leu Glu Glu Ala Trp Ala His Ile Ala Ser Arg Tyr Glu
65                  70                  75                  80

Ser Pro Glu Ala Leu Gln Gln Ala Leu Asp Ala Gln Ala Leu Asp Ala
                85                  90                  95

Ala Gly Met Arg Ala Met Leu Ala Arg Glu Leu Arg Val Glu Ala Val
            100                 105                 110

Leu Asp Cys Val Cys Ala Gly Leu Pro Glu Ile Ser Asp Thr Asp Val
        115                 120                 125

Ser Leu Tyr Tyr Phe Asn His Ala Glu Gln Phe Lys Val Pro Ala Gln
    130                 135                 140

His Lys Ala Arg His Ile Leu Val Thr Ile Asn Glu Asp Phe Pro Glu
145                 150                 155                 160

Asn Thr Arg Glu Ala Ala Arg Thr Arg Ile Glu Thr Ile Leu Lys Arg
                165                 170                 175

Leu Arg Gly Lys Pro Glu Arg Phe Ala Glu Gln Ala Met Lys His Ser
            180                 185                 190

Glu Cys Pro Thr Ala Met Gln Gly Gly Leu Leu Gly Glu Val Val Pro
        195                 200                 205

Gly Thr Leu Tyr Pro Glu Leu Asp Ala Cys Leu Phe Gln Met Ala Arg
    210                 215                 220

Gly Glu Leu Ser Pro Val Leu Glu Ser Pro Ile Gly Phe His Val Leu
225                 230                 235                 240

Tyr Cys Glu Ser Val Ser Pro Ala Arg Gln Leu Thr Leu Glu Glu Ile
                245                 250                 255

Leu Pro Arg Leu Arg Asp Arg Leu Gln Leu Arg Gln Arg Lys Ala Tyr
            260                 265                 270

Gln Arg Lys Trp Leu Glu Ser Leu Leu Gln Gln Asn Ala Thr Leu Glu
        275                 280                 285

Asn Leu Ala His Gly
    290
```

<210> SEQ ID NO 27
<211> LENGTH: 882
<212> TYPE: DNA
<213> ORGANISM: Azotobacter vinelandii

<400> SEQUENCE: 27

```
atggcatctg agcgtctcgc cgacggcgac agccgctatt acttgctgaa ggtcgcccac      60
gagcagttcg gctgcgcgcc cggcgagctc agcgaggagc agctccagca ggccgaccgc     120
atcatcggcc ggcagaggca tatcgaggac gccgtgttgc gcagccccga tgcgatcggt     180
gtggtgatcc cgccctccca gctcgaagag gcctgggcac acatcgccag ccgctacgag     240
agtcccgagg cgctacagca ggccctcgac gcgcaggcgc tggatgctgc cggcatgcgc     300
gccatgctgg cccgggagct cagggtcgag gccgttctcg actgcgtctg cgccggcctg     360
ccggagatca gcgacaccga tgtgagcctc tactacttca accacgccga gcaattcaag     420
gtgcccgccc agcacaaggc ccggcacatc ctggtcacca tcaacgagga ttttccggaa     480
aacacccgcg aagccgcccg gacgcgcatc gagaccatcc tcaagcggct cgcggcaag     540
ccggagcgct tcgccgagca ggcgatgaag cactccgaat gtcccaccgc gatgcagggc     600
ggattgctcg gcgaggtggt cccgggaacg ctttatcccg aactggacgc ctgcctgttc     660
cagatggcgc ggggagaact gagtccggta ctggaatcgc cgatcggttt tcacgtgctg     720
tactgcgaaa gcgtgagccc cgcccggcag ctcacccctcg aggagatcct gccgcgtctg     780
cgcgacaggc tgcagctccg gcagcgcaag gcgtatcagc gcaaatggct ggaaagcctg     840
ctccaacaaa acgctacttt ggagaacctc gcccatggat aa                        882
```

<210> SEQ ID NO 28
<211> LENGTH: 402
<212> TYPE: PRT
<213> ORGANISM: Azotobacter vinelandii

<400> SEQUENCE: 28

```
Met Ala Asp Val Tyr Leu Asp Asn Asn Ala Thr Thr Arg Val Asp Asp
1               5                   10                  15

Glu Ile Val Gln Ala Met Leu Pro Phe Phe Thr Glu Gln Phe Gly Asn
            20                  25                  30

Pro Ser Ser Leu His Ser Phe Gly Asn Gln Val Gly Met Ala Leu Lys
        35                  40                  45

Lys Ala Arg Gln Ser Val Gln Lys Leu Leu Gly Ala Glu His Asp Ser
    50                  55                  60

Glu Ile Leu Phe Thr Ser Cys Gly Thr Glu Ser Asp Ser Thr Ala Ile
65                  70                  75                  80

Leu Ser Ala Leu Lys Ala Gln Pro Glu Arg Lys Thr Val Ile Thr Thr
                85                  90                  95

Val Val Glu His Pro Ala Val Leu Ser Leu Cys Asp Tyr Leu Ala Ser
            100                 105                 110

Glu Gly Tyr Thr Val His Lys Leu Pro Val Asp Lys Lys Gly Arg Leu
        115                 120                 125

Asp Leu Glu His Tyr Ala Ser Leu Leu Thr Asp Val Ala Val Val
    130                 135                 140

Ser Val Met Trp Ala Asn Asn Glu Thr Gly Thr Leu Phe Pro Ile Glu
145                 150                 155                 160

Glu Met Ala Arg Leu Ala Asp Asp Ala Gly Ile Met Phe His Thr Asp
                165                 170                 175
```

Ala Val Gln Ala Val Gly Lys Val Pro Ile Asp Leu Lys Asn Ser Ser
                180                 185                 190

Ile His Met Leu Ser Leu Cys Gly His Lys Leu His Ala Pro Lys Gly
            195                 200                 205

Val Gly Val Leu Tyr Leu Arg Arg Gly Thr Arg Phe Arg Pro Leu Leu
210                 215                 220

Arg Gly Gly His Gln Glu Arg Gly Arg Arg Ala Gly Thr Glu Asn Ala
225                 230                 235                 240

Ala Ser Ile Ile Gly Leu Gly Val Ala Ala Glu Arg Ala Leu Gln Phe
                245                 250                 255

Met Glu His Glu Asn Thr Glu Val Asn Ala Leu Arg Asp Lys Leu Glu
            260                 265                 270

Ala Gly Ile Leu Ala Val Val Pro His Ala Phe Val Thr Gly Asp Pro
        275                 280                 285

Asp Asn Arg Leu Pro Asn Thr Ala Asn Ile Ala Phe Glu Tyr Ile Glu
290                 295                 300

Gly Glu Ala Ile Leu Leu Leu Asn Lys Val Gly Ile Ala Ala Ser
305                 310                 315                 320

Ser Gly Ser Ala Cys Thr Ser Gly Ser Leu Glu Pro Ser His Val Met
                325                 330                 335

Arg Ala Met Asp Ile Pro Tyr Thr Ala Ala His Gly Thr Val Arg Phe
            340                 345                 350

Ser Leu Ser Arg Tyr Thr Thr Glu Glu Ile Asp Arg Val Ile Arg
        355                 360                 365

Glu Val Pro Pro Ile Val Ala Gln Leu Arg Asn Val Ser Pro Tyr Trp
        370                 375                 380

Ser Gly Asn Gly Pro Val Glu Asp Pro Gly Lys Ala Phe Ala Pro Val
385                 390                 395                 400

Tyr Gly

<210> SEQ ID NO 29
<211> LENGTH: 1209
<212> TYPE: DNA
<213> ORGANISM: Azotobacter vinelandii

<400> SEQUENCE: 29

```
atggctgacg tctatctcga taacaacgcc accacccggg tggacgacga aatcgtccag    60
gccatgctgc cgttcttcac cgaacagttc ggcaacccct cgtcgctgca cagcttcggc   120
aaccaggtcg gcatggcgct gaagaaggcc cgccagagcg tgcagaaact gctcggtgcc   180
gaacacgatt cggaaatcgt cttcacctcc tgcggcaccg agtcggactc caccgcgatc   240
ctctcggcgc tcaaggccca gcccgaacgc aagaccgtca tcaccaccgt ggtcgaacac   300
ccggccgtcc tcagcctgtg cgattacctc gccagtgagg gctacaccgt gcacaagctg   360
ccggtggaca gaaaggccg tctggatctg gagcattacg ccagcctgct gaccgacgat   420
gtcgccgtgg tgtcggtgat gtgggccaac aacgagaccg gtaccctgtt cccgatcgaa   480
gagatggcgc gcctggccga cgacgccggc atcatgtttc acaccgatgc cgtgcaggcc   540
gtgggcaagg taccgatcga cctgaagaat cgtcgatcc acatgctttc gctgtcgggc   600
cacaagctgc acgcgcccaa aggtgtcggc gtgctctatc tgcgccgcgg cacccgcttc   660
cgtccgctgc tgcgcggtgg tcaccaggag cgcggccgtc gtgccggcac cgagaacgcc   720
gcctccatca tcggcctggg tgtcgccgcc gaacgcgcgc tgcagttcat ggagcacgag   780
```

```
aacaccgagg tcaagcgcct gcgcgacaag ctggaggccg gtatcctcgc cgtcgtgccc    840
catgccttcg tcaccggcga tccggacaac cgcttgccca acaccgccaa catcgcgttc    900
gagtacatcg agggcgaggc catcctgctg ctgctgaaca aggtcggcat cgccgcctcc    960
agcggttcgg cctgcaccct cggctccttg gagccctccc acgtgatgcg cgccatggac   1020
attccctata ctgccgccca cggcaccgtg cgcttctccc tgtcgcgcta caccaccgag   1080
gaggagatcg accgggtgat ccgcgaggtt ccgccgatcg tggcccagtt gcgcaagctg   1140
tcgccctact ggagcggcaa cggtccggtg aggacccgg gcaaggcctt cgctccggtc    1200
tacggctga                                                           1209
```

<210> SEQ ID NO 30
<211> LENGTH: 312
<212> TYPE: PRT
<213> ORGANISM: Azotobacter vinelandii

<400> SEQUENCE: 30

Met Trp Asp Tyr Ser Glu Lys Val Lys Glu His Phe Tyr Asn Pro Lys
1               5                   10                  15

Asn Ala Gly Ala Val Glu Gly Ala Asn Ala Ile Gly Asp Val Gly Ser
            20                  25                  30

Leu Ser Cys Gly Asp Ala Leu Arg Leu Thr Leu Lys Val Asp Pro Glu
        35                  40                  45

Thr Asp Val Ile Leu Asp Ala Gly Phe Gln Thr Phe Gly Cys Gly Ser
    50                  55                  60

Ala Ile Ala Ser Ser Ser Ala Leu Thr Glu Met Val Lys Gly Leu Thr
65                  70                  75                  80

Leu Asp Glu Ala Leu Lys Ile Ser Asn Gln Asp Ile Ala Asp Tyr Leu
                85                  90                  95

Asp Gly Leu Pro Pro Glu Lys Met His Cys Ser Val Met Gly Arg Glu
            100                 105                 110

Ala Leu Gln Ala Ala Val Ala Asn Tyr Arg Gly Glu Thr Ile Glu Asp
        115                 120                 125

Asp His Glu Glu Gly Ala Leu Ile Cys Lys Cys Phe Ala Val Asp Glu
    130                 135                 140

Val Met Val Arg Asp Thr Ile Arg Ala Asn Lys Leu Ser Thr Val Glu
145                 150                 155                 160

Asp Val Thr Asn Tyr Thr Lys Ala Gly Gly Gly Cys Ser Ala Cys His
                165                 170                 175

Glu Ala Ile Glu Arg Val Leu Thr Glu Glu Leu Ala Ala Arg Gly Glu
            180                 185                 190

Val Phe Val Ala Ala Pro Ile Lys Ala Lys Lys Val Lys Val Leu
        195                 200                 205

Ala Pro Glu Pro Ala Pro Ala Pro Val Ala Glu Ala Pro Ala Ala
    210                 215                 220

Pro Lys Leu Ser Asn Leu Gln Arg Ile Arg Ile Glu Thr Val Leu
225                 230                 235                 240

Ala Ala Ile Arg Pro Thr Leu Gln Arg Asp Lys Gly Asp Val Glu Leu
                245                 250                 255

Ile Asp Val Asp Gly Lys Asn Val Tyr Val Lys Leu Thr Gly Ala Cys
            260                 265                 270

Thr Gly Cys Gln Met Ala Ser Met Thr Leu Gly Gly Ile Gln Gln Arg
        275                 280                 285

Leu Ile Glu Glu Leu Gly Glu Phe Val Lys Val Ile Pro Val Ser Ala

Ala Ala His Ala Gln Met Glu Val
305              310

<210> SEQ ID NO 31
<211> LENGTH: 939
<212> TYPE: DNA
<213> ORGANISM: Azotobacter vinelandii

<400> SEQUENCE: 31

```
atgtgggatt attcggaaaa agtcaaagag cacttctaca accccaagaa tgctggagcc   60
gtggaaggcg ccaacgccat cggcgacgtc ggatcgctga gttgcggtga tgcgctgcgc  120
ctgaccctga aggtggaccc ggaaaccgac gtgattctgg atgccggctt ccagaccttc  180
ggctgtggtt ccgccatcgc ttcctcctcg gcgctgaccg agatggtcaa gggcctgacc  240
ctggacgagg cgctgaagat cagtaaccag gacatcgccg actacctcga tggcctgccg  300
ccggagaaga tgcactgctc ggtgatgggc gcgaagccc tgcaggccgc ggtggccaac  360
taccgtggcg agacgatcga ggacgaccac gaagagggcg cgctgatctg caagtgcttc  420
gccgtcgacg aggtgatggt ccgcgatacc atccgtgcca acaagctgtc taccgttgag  480
gacgtgacca attacaccaa ggccggcggt ggctgctccg cctgccacga ggctatcgag  540
cgcgtgctga ccgaagagct ggccgctcgc ggtgaagtct tcgtcgcggc ccgataaag  600
gccaagaaga aggtcaaggt gctcgccccc gagccggctc ccgccccggt ggccgaagcc  660
ccggcggctg ccccgaagct gagcaacctg cagcgcatcc gtcgcatcga accgtgctg  720
gcggcgatcc gtccgacctt gcagcgcgac aagggcgacg tcgaactgat cgatgtcgac  780
ggcaagaacg tttatgtcaa gctcaccggc gcctgcaccg gctgccagat ggccagcatg  840
accctcggcg gcatccagca gcgcctgatc gaggagctcg gcgagttcgt caaggtgatt  900
ccggtcagcg ctgcggctca cgcgcagatg gaggtctga                         939
```

<210> SEQ ID NO 32
<211> LENGTH: 293
<212> TYPE: PRT
<213> ORGANISM: Klebsiella pneumonia

<400> SEQUENCE: 32

Met Thr Met Arg Gln Cys Ala Ile Tyr Gly Lys Gly Gly Ile Gly Lys
1               5                   10                  15

Ser Thr Thr Thr Gln Asn Leu Val Ala Ala Leu Ala Glu Met Gly Lys
            20                  25                  30

Lys Val Met Ile Val Gly Cys Asp Pro Lys Ala Asp Ser Thr Arg Leu
        35                  40                  45

Ile Leu His Ala Lys Ala Gln Asn Thr Ile Met Glu Met Ala Ala Glu
    50                  55                  60

Val Gly Ser Val Glu Asp Leu Glu Leu Glu Asp Val Leu Gln Ile Gly
65                  70                  75                  80

Tyr Gly Asp Val Arg Cys Ala Glu Ser Gly Gly Pro Glu Pro Gly Val
                85                  90                  95

Gly Cys Ala Gly Arg Gly Val Ile Thr Ala Ile Asn Phe Leu Glu Glu
            100                 105                 110

Glu Gly Ala Tyr Glu Asp Asp Leu Asp Phe Val Phe Tyr Asp Val Leu
        115                 120                 125

Gly Asp Val Val Cys Gly Gly Phe Ala Met Pro Ile Arg Glu Asn Lys
    130                 135                 140

```
Ala Gln Glu Ile Tyr Ile Val Cys Ser Gly Glu Met Met Ala Met Tyr
145                 150                 155                 160

Ala Ala Asn Asn Ile Ser Lys Gly Ile Val Lys Tyr Ala Lys Ser Gly
            165                 170                 175

Lys Val Arg Leu Gly Gly Leu Ile Cys Asn Ser Arg Gln Thr Asp Arg
        180                 185                 190

Glu Asp Glu Leu Ile Ile Ala Leu Ala Glu Lys Leu Gly Thr Gln Met
    195                 200                 205

Ile His Phe Val Pro Arg Asp Asn Ile Val Gln Arg Ala Glu Ile Arg
210                 215                 220

Arg Met Thr Val Ile Glu Tyr Asp Pro Ala Cys Lys Gln Ala Asn Glu
225                 230                 235                 240

Tyr Arg Thr Leu Ala Gln Lys Ile Val Asn Asn Thr Met Lys Val Val
                245                 250                 255

Pro Thr Pro Cys Thr Met Asp Glu Leu Glu Ser Leu Leu Met Glu Phe
            260                 265                 270

Gly Ile Met Glu Glu Asp Thr Ser Ile Ile Gly Lys Thr Ala Ala
        275                 280                 285

Glu Glu Asn Ala Ala
    290

<210> SEQ ID NO 33
<211> LENGTH: 882
<212> TYPE: DNA
<213> ORGANISM: Klebsiella pneumonia

<400> SEQUENCE: 33
atgaccatgc gtcaatgcgc tatttacggt aaaggcggta tcggtaaatc caccaccacg      60
cagaacctcg tcgccgcgct ggcggagatg ggtaagaaag tgatgatcgt cggctgcgat     120
ccgaaggcgg actccacccg tctgattctg cacgccaaag cacagaacac cattatggag     180
atggccgcgg aagtcggctc ggtcgaggac ctcgaactcg aagacgtgct gcaaattggc     240
tacggcgatg tgcgctgcgc ggaatccggc ggcccggagc caggcgtcgg ctgcgcggga     300
cgcggcgtga tcacggcgat caactttctt gaagaagaag gcgcctacga ggacgatctc     360
gatttcgtgt tctatgacgt gctcggcgac gtggtctgcg gcggcttcgc catgccgatc     420
cgcgaaaaca aagcccagga gatctacatc gtctgctccg gcgaaatgat ggcgatgtac     480
gcggccaaca atatctccaa agggatcgtt aaatacgcca aatccggcaa ggtgcgcctc     540
ggcggcctga tctgtaactc acgtcagacc gaccgtgaag acgaactgat tattgccctg     600
gcggaaaagc tcggtaccca gatgatccac tttgtgcccc gcgacaacat cgtgcagcgc     660
gcggagatcc gccgcatgac ggttatcgag tacgaccccg cctgtaaaca ggccaacgaa     720
taccgcaccc tggcgcagaa gatcgtcaac aacaccatga agtggtgcc gacgccctgc     780 accatggatg agctggaatc gctgctgatg gagttcggca tcatggaaga ggaagacacc     840
agcatcattg gcaaaaccgc cgccgaagaa aacgcggcct ga                         882

<210> SEQ ID NO 34
<211> LENGTH: 266
<212> TYPE: PRT
<213> ORGANISM: Klebsiella pneumonia

<400> SEQUENCE: 34

Met Glu Pro Trp Gln Arg Phe Gly Arg Gln Arg Leu Ala Gln Ser Arg
1               5                   10                  15
```

Trp Asn Cys Glu Pro Ala Ala Ile Ala Ala Val Asp Arg Gln Ala Phe
             20                  25                  30

Glu Ala Ala Trp Gln Arg Gln Ala Gln Met Glu Gln Val Ile Val Ala
         35                  40                  45

Gln Ile Ala Pro Glu Ala Ile Pro Ala Ala Leu Gln Glu Gly Leu Ala
     50                  55                  60

Thr Ser Leu Gly Ala Trp Leu Asp Glu Gly Gly Phe Thr Pro Ala Glu
65                  70                  75                  80

Arg Ala Ala Ile Val Leu His His Ala Arg Leu Glu Thr Ala Phe Ala
                 85                  90                  95

Gly Ile Ala Ser Gln Ala Pro Arg Pro Asp Pro Ala Thr Val Gln Ala
            100                 105                 110

Trp Tyr Leu Arg His Gln Ala Gln Phe Met Arg Pro Glu Gln Arg Leu
        115                 120                 125

Thr Arg His Leu Leu Leu Thr Val Asp Gly Asp Asp Gln Thr Val Tyr
    130                 135                 140

Ser Arg Ile Arg Glu Leu His Gly Gln Ile Glu Ala Ser Arg Glu Ala
145                 150                 155                 160

Phe Ala Pro Leu Ala Gln Arg His Ser His Cys Pro Ser Ala Leu Asp
                165                 170                 175

Gly Gly Leu Leu Gly Trp Ile Gly Arg Gly Leu Leu Tyr Pro Gln Leu
            180                 185                 190

Glu Glu Ala Leu Phe Ala Leu Ala Glu Asn Ala Leu Ser Ala Pro Val
        195                 200                 205

Ala Ser Glu Leu Gly Trp His Leu Val Trp Cys Glu Ala Ile Arg Pro
    210                 215                 220

Ala Ala Pro Met Thr Pro Glu Gln Ala Leu Glu Ser Ala Arg Asp Tyr
225                 230                 235                 240

Leu Ser Gln Gln Ser Gln Arg Arg His Gln Arg Gln Trp Leu Ala Glu
                245                 250                 255

Met Leu Ala Arg Gln Pro Gly Leu Cys Gly
            260                 265

<210> SEQ ID NO 35
<211> LENGTH: 801
<212> TYPE: DNA
<213> ORGANISM: Klebsiella pneumonia

<400> SEQUENCE: 35
atggagccct ggcaacgatt tggccggcag cggctggcgc agagccgctg gaactgcgag      60
ccggcggcca tcgccgcggt cgaccggcag gccttcgagg cggcctggca gcgccaggcc     120
cagatggagc aggttattgt cgcccagatt gcgccgaggg cgatccccgc cgcgctgcag     180
gagggcctcg ccacttcgct gggcgcctgg ctggatgagg aggatttac gccagcggag     240 cggcggcgca tcgtcctgca ccacgcccgg ctggaaaccg ccttcgcggg gattgccagc     300
caggcgccgc ggccggatcc cgccacggtg caggcctggt atctgcggca tcaggcgcag     360
tttatgcgcc cggaacagcg cctgacccgc catctgctgc tcaccgtcga tggcgacgac     420
cagacggttt actcgcgcat acgggagctt catgggcaaa tcgaagcctc cgcgaggcg      480 tttgcgccgc tggcccagcg acactcccac tgcccgagcg cgctggacgg cggactgctg     540
ggctggatcg gccgggggct gctctatccg cagctggagg aggcgctgtt tgcgctggcg     600
gaaaatgcgc tgagcgcgcc ggtggccagc gagctcggct ggcatctggt ctggtgtgag     660

```
gccattcgcc ctgccgcgcc gatgacgcct gagcaggcgc tggaaagcgc ccgcgattac    720
ctcagtcaac agagccagcg ccgccaccag cgccagtggc tggccgagat gctagcgcgc    780
cagccggggc tgtgcggata a                                              801
```

<210> SEQ ID NO 36
<211> LENGTH: 327
<212> TYPE: PRT
<213> ORGANISM: Cyanothece spp ATCC51142

<400> SEQUENCE: 36

```
Met Gly Arg Asn Ser Gln Gly Phe Leu Thr Thr Ile Arg Ile Ile Val
1               5                   10                  15

Thr Ser Ala Thr Asp Gln Pro Ser Asn Phe Ile His Ser Leu Ser Asn
            20                  25                  30

Lys Arg Glu Ser Thr Met Arg Gln Ile Ala Phe Tyr Gly Lys Gly Gly
        35                  40                  45

Ile Gly Lys Ser Thr Thr Ser Gln Asn Thr Ile Ala Ala Leu Ala Glu
    50                  55                  60

Thr Asn Arg Ile Met Ile Val Gly Cys Asp Pro Lys Ala Asp Ser Thr
65                  70                  75                  80

Arg Leu Met Leu His Thr Lys Ala Gln Thr Thr Ile Leu His Leu Ala
                85                  90                  95

Ala Glu Arg Gly Thr Val Glu Asp Ile Glu Leu Glu Glu Val Leu Leu
            100                 105                 110

Glu Gly Tyr Gln Gly Val Lys Cys Val Glu Ser Gly Gly Pro Glu Pro
        115                 120                 125

Gly Val Gly Cys Ala Gly Arg Gly Ile Ile Thr Ala Ile Asn Phe Leu
    130                 135                 140

Glu Glu Glu Gly Ala Tyr Glu Asp Leu Asp Phe Val Ser Tyr Asp Val
145                 150                 155                 160

Leu Gly Asp Val Val Cys Gly Gly Phe Ala Met Pro Ile Arg Glu Gly
                165                 170                 175

Lys Ala Gln Glu Ile Tyr Ile Val Thr Ser Gly Glu Met Met Ala Met
            180                 185                 190

Tyr Ala Ala Asn Asn Ile Ala Arg Gly Ile Leu Lys Tyr Ala His Thr
        195                 200                 205

Gly Gly Val Arg Leu Gly Gly Leu Ile Cys Asn Ser Arg Asn Val Asn
    210                 215                 220

Cys Glu Ala Glu Leu Ile Glu Glu Leu Ala Arg Arg Leu Gly Thr Gln
225                 230                 235                 240

Met Ile His Phe Val Pro Arg Ser Lys Gln Val Gln Glu Ala Glu Leu
                245                 250                 255

Arg Arg Met Thr Val Ile Glu Tyr Ser Pro Asp His Pro Gln Ala Gln
            260                 265                 270

Glu Tyr Arg Glu Leu Ser Arg Lys Ile Glu Asn Asn Thr Asn Leu Val
        275                 280                 285

Ile Pro Thr Pro Ile Thr Met Glu Glu Leu Glu Glu Leu Leu Val Asp
    290                 295                 300

Phe Gly Ile Leu Gly Gly Glu Asp Glu Tyr Glu Lys Ala Leu Gln Ala
305                 310                 315                 320

Asp Lys Ala Ala Thr Lys Ala
                325
```

<210> SEQ ID NO 37

<211> LENGTH: 984
<212> TYPE: DNA
<213> ORGANISM: Cyanothece spp ATCC51142

<400> SEQUENCE: 37

```
atgggacgca actcccaagg tttcctaacc acaatacgaa tcatcgttac gtcagcaacg    60
gatcaacctt ccaactttat acactcactg tctaacaagc gagaatcaac tatgcgtcag   120
attgcatttt acggaaaagg cggtatcggt aagtctacca cttctcagaa taccattgct   180
gcgttagctg aaaccaaccg catcatgatt gttggttgtg accctaaagc tgattctacc   240
cgcttaatgc ttcacaccaa agcacaaacc accattctgc acttagcagc agaacgggga   300
accgttgaag acatcgaact cgaagaagta ttactcgaag ataccaagg agtcaagtgt    360
gttgagtccg gtggtcctga gcctggagtt ggatgtgcgg tcgtggtat tatcaccgcc    420
attaacttct tagaagaaga aggtgcttac gaagacctag acttcgtatc ctacgacgta   480
ttaggagacg ttgtatgtgg tggtttcgct atgcctatcc gtgaaggaaa agcacaagaa   540
atctacatcg taacctccgg ggaaatgatg gcgatgtacc tgcaaacaa cattgctcgt    600
ggtatttaa atacgctca cactggtggt gttcgtttag gtggtttaat ttgtaacagc    660
cgtaacgtta actgtgaagc tgagttaatc gaagaattag ctcgtcgtct cggaacccaa   720
atgattcact tcgtaccccg ttctaagcag gtacaagaag ctgaattacg tcgtatgact   780
gttatcgaat attctcctga tcaccctcag gctcaggaat accgtgagtt atctcgcaaa   840
atcgagaata acaccaacct cgttattcct actcctatca ccatggaaga actcgaagaa   900
ctcttagttg acttcggtat tctcggtggt gaagacgagt atgagaaagc tcttcaagct   960
gataaagctg ctaccaaagc ttag                                           984
```

<210> SEQ ID NO 38
<211> LENGTH: 185
<212> TYPE: PRT
<213> ORGANISM: Artificial Sequence
<220> FEATURE:
<223> OTHER INFORMATION: Recombinant

<400> SEQUENCE: 38

```
Met Lys Phe Phe Leu Lys Asp Gly Glu Thr Ser Arg Ala Leu Ser Arg
1               5                   10                  15

Ser Glu Ser Leu Leu Arg Arg Val Lys Glu Leu Gly Thr Asn Ser Gln
            20                  25                  30

Gln Ser Glu Ile Ser Glu Cys Val Asp Glu Phe Asn Glu Leu Ala Ser
        35                  40                  45

Phe Asn His Leu Leu Val Thr Val Glu His Arg Glu Trp Met Glu Gln
    50                  55                  60

His Pro Asn Gln Ser Ser Lys Leu Arg Val Pro Ser Arg Ile Gly Glu
65                  70                  75                  80

Met Leu Lys Glu Ile Arg Ala Phe Leu Lys Val Arg Val Val Thr Pro
                85                  90                  95

Met His Lys Glu Thr Ala Ser Asp Thr Leu Asn Ala Phe Leu Glu Glu
            100                 105                 110

Tyr Cys Arg Ile Thr Gly Leu Ala Arg Glu Asp Ala Leu Arg Glu Lys
        115                 120                 125

Met Arg Lys Val Lys Ser Val Val Leu Phe His His Ser Glu Leu Leu
    130                 135                 140

Lys Phe Glu Val Thr Glu Asn Met Phe Ser Tyr Thr Glu Leu Leu Lys
145                 150                 155                 160
```

Leu Asn Leu Ser Leu Arg Val Ile Ser Ser Gln Ile Leu Gly Met Ala
            165                 170                 175

Ile Asp Tyr Lys Asp Asp Asp Lys
            180             185

<210> SEQ ID NO 39
<211> LENGTH: 558
<212> TYPE: DNA
<213> ORGANISM: Artificial Sequence
<220> FEATURE:
<223> OTHER INFORMATION: Recombinant

<400> SEQUENCE: 39
atgaagtttt tccttaagga tggtgaaact tctagagctc tttcaagatc tgagagtttg      60
cttaggagag ttaaggaatt aggtactaat tctcaacagt cagaaatttc tgagtgtgtt     120
gatgaattta atgaacttgc ttcattcaac catcttttgg tgacagtgga gcatagagaa     180
tggatggagc aacaccctaa tcaatcttca aagcttaggg ttccttcaag aattggagaa     240
atgcttaaag aaataagagc attttttgaag gttagggtgg ttactcctat gcataaggag     300
actgcttctg atactcttaa tgcttttctt gaagaatatt gtagaattac aggtcttgct     360
agagaagacg cattgagaga aagatgagg aaagttaagt ctgttgtgct ttttcatcac     420
tcagaacttt tgaagttcga agttactgag aacatgtttt cttatactga acttcttaag     480
cttaatttgt ctcttagagt tatttcatct cagatacttg gtatggctat tgattataag     540
gatgatgacg ataaatga                                                   558

<210> SEQ ID NO 40
<211> LENGTH: 320
<212> TYPE: PRT
<213> ORGANISM: Artificial Sequence
<220> FEATURE:
<223> OTHER INFORMATION: Recombinant

<400> SEQUENCE: 40

Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
            20                  25                  30

Met Arg Gln Cys Ala Ile Tyr Gly Lys Gly Ile Gly Lys Ser Thr
            35                  40                  45

Thr Thr Gln Asn Leu Val Ala Ala Leu Ala Glu Met Gly Lys Lys Val
        50                  55                  60

Met Ile Val Gly Cys Asp Pro Lys Ala Asp Ser Thr Arg Leu Ile Leu
65                  70                  75                  80

His Ser Lys Ala Gln Asn Thr Ile Met Glu Met Ala Ala Glu Ala Gly
                85                  90                  95

Thr Val Glu Asp Leu Glu Leu Glu Asp Val Leu Lys Ala Gly Tyr Gly
            100                 105                 110

Gly Val Lys Cys Val Glu Ser Gly Gly Pro Glu Pro Gly Val Gly Cys
        115                 120                 125

Ala Gly Arg Gly Val Ile Thr Ala Ile Asn Phe Leu Glu Glu Glu Gly
    130                 135                 140

Ala Tyr Glu Asp Asp Leu Asp Phe Val Phe Tyr Asp Val Leu Gly Asp
145                 150                 155                 160

Val Val Cys Gly Gly Phe Ala Met Pro Ile Arg Glu Asn Lys Ala Gln
                165                 170                 175

```
Glu Ile Tyr Ile Val Cys Ser Gly Glu Met Met Ala Met Tyr Ala Ala
            180                 185                 190

Asn Asn Ile Ser Lys Gly Ile Val Lys Tyr Ala Asn Ser Gly Ser Val
            195                 200                 205

Arg Leu Gly Gly Leu Ile Cys Asn Ser Arg Asn Thr Asp Arg Glu Asp
210                 215                 220

Glu Leu Ile Ile Ala Leu Ala Asn Lys Leu Gly Thr Gln Met Ile His
225                 230                 235                 240

Phe Val Pro Arg Asp Asn Val Val Gln Arg Ala Glu Ile Arg Met
                245                 250                 255

Thr Val Ile Glu Tyr Asp Pro Lys Ala Lys Gln Ala Asp Glu Tyr Arg
            260                 265                 270

Ala Leu Ala Arg Lys Val Val Asp Asn Lys Leu Leu Val Ile Pro Asn
            275                 280                 285

Pro Ile Thr Met Asp Glu Leu Glu Glu Leu Leu Met Glu Phe Gly Ile
            290                 295                 300

Met Glu Val Glu Asp Glu Ser Ile Val Gly Lys Thr Ala Glu Glu Val
305                 310                 315                 320
```

<210> SEQ ID NO 41
<211> LENGTH: 963
<212> TYPE: DNA
<213> ORGANISM: Artificial Sequence
<220> FEATURE:
<223> OTHER INFORMATION: Recombinant

<400> SEQUENCE: 41

```
atgtatagat tcgcttctaa tcttgcatca aaggctagaa ttgctcagaa tgcaaggcag    60
gtttcttcaa gaatgtcatg gtctaggaat tatgctatgc gtcaatgcgc catctacggc   120
aaaggtggta tcggtaagtc caccactact cagaacctgg tggcagccct ggctgagatg   180
ggcaagaagg tcatgatcgt tggttgtgac ccgaaagctg actccacccg cctgatcctg   240
cactccaagg cccagaacac catcatggaa atggctgccg aagccggtac cgtggaagat   300
ctggagctgg aagacgtgct gaaggctggc tacggcggcg tcaagtgcgt tgagtccggt   360
ggtccggagc cgggcgttgg ctgcgccggc cgtggtgtta tcaccgccat caacttcctg   420
gaagaggaag cgcctacga agacgatctg gacttcgtat ctacgacgt gctgggcgac   480
gtggtgtgtg gcggcttcgc catgccgatc cgcgagaaca aggcccagga aatctacatc   540
gtctgctccg gtgagatgat ggccatgtac gccgccaaca catctccaa gggcatcgtg   600
aagtatgcca actccggcag cgtgcgtctg ggcggcctga tctgcaacag ccgtaacacc   660
gaccgcgaag acgagctgat catcgctctg gccaacaagc tgggcaccca gatgatccac   720
ttcgtgccgc gtgacaacgt cgtgcagcgc gccgaaatcc gccgcatgac cgtgatcgaa   780
tacgatccga agccaagca agccgacgaa taccgcgctc tggcccgcaa ggtcgtcgac   840
aacaaactgc tggtcatccc gaacccgatc accatggacg agctcgaaga gctgctgatg   900
gaattcggca tcatggaagt cgaagacgaa tccatcgtcg gcaaaaccgc gaagaagtc    960
tga                                                                  963
```

<210> SEQ ID NO 42
<211> LENGTH: 323
<212> TYPE: PRT
<213> ORGANISM: Artificial Sequence
<220> FEATURE:
<223> OTHER INFORMATION: Recombinant

<400> SEQUENCE: 42

Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
            20                  25                  30

Ser Glu Arg Leu Ala Asp Gly Asp Ser Arg Tyr Tyr Leu Leu Lys Val
        35                  40                  45

Ala His Glu Gln Phe Gly Cys Ala Pro Gly Glu Leu Ser Glu Glu Gln
    50                  55                  60

Leu Gln Gln Ala Asp Arg Ile Ile Gly Arg Gln Arg His Ile Glu Asp
65                  70                  75                  80

Ala Val Leu Arg Ser Pro Asp Ala Ile Gly Val Val Ile Pro Pro Ser
                85                  90                  95

Gln Leu Glu Glu Ala Trp Ala His Ile Ala Ser Arg Tyr Glu Ser Pro
            100                 105                 110

Glu Ala Leu Gln Gln Ala Leu Asp Ala Gln Ala Leu Asp Ala Ala Gly
        115                 120                 125

Met Arg Ala Met Leu Ala Arg Glu Leu Arg Val Glu Ala Val Leu Asp
130                 135                 140

Cys Val Cys Ala Gly Leu Pro Glu Ile Ser Asp Thr Asp Val Ser Leu
145                 150                 155                 160

Tyr Tyr Phe Asn His Ala Glu Gln Phe Lys Val Pro Ala Gln His Lys
                165                 170                 175

Ala Arg His Ile Leu Val Thr Ile Asn Glu Asp Phe Pro Glu Asn Thr
            180                 185                 190

Arg Glu Ala Ala Arg Thr Arg Ile Glu Thr Ile Leu Lys Arg Leu Arg
        195                 200                 205

Gly Lys Pro Glu Arg Phe Ala Glu Gln Ala Met Lys His Ser Glu Cys
210                 215                 220

Pro Thr Ala Met Gln Gly Gly Leu Leu Gly Val Val Pro Gly Thr
225                 230                 235                 240

Leu Tyr Pro Glu Leu Asp Ala Cys Leu Phe Gln Met Ala Arg Gly Glu
                245                 250                 255

Leu Ser Pro Val Leu Glu Ser Pro Ile Gly Phe His Val Leu Tyr Cys
            260                 265                 270

Glu Ser Val Ser Pro Ala Arg Gln Leu Thr Leu Glu Glu Ile Leu Pro
        275                 280                 285

Arg Leu Arg Asp Arg Leu Gln Leu Arg Gln Arg Lys Ala Tyr Gln Arg
290                 295                 300

Lys Trp Leu Glu Ser Leu Leu Gln Gln Asn Ala Thr Leu Glu Asn Leu
305                 310                 315                 320

Ala His Gly

<210> SEQ ID NO 43
<211> LENGTH: 972
<212> TYPE: DNA
<213> ORGANISM: Artificial Sequence
<220> FEATURE:
<223> OTHER INFORMATION: Recombinant

<400> SEQUENCE: 43
atgtatagat tcgcttctaa tcttgcatca aaggctagaa ttgctcagaa tgcaaggcag    60
gtttcttcaa gaatgtcatg gtctaggaat tatgcatctg agcgtctcgc cgacggcgac   120

```
agccgctatt acttgctgaa ggtcgcccac gagcagttcg gctgcgcgcc cggcgagctc    180
agcgaggagc agctccagca ggccgaccgc atcatcggcc ggcagaggca tatcgaggac    240
gccgtgttgc gcagccccga tgcgatcggt gtggtgatcc cgccctccca gctcgaagag    300
gcctgggcac acatcgccag ccgctacgag agtcccgagg cgctacagca ggccctcgac    360
gcgcaggcgc tggatgctgc cggcatgcgc gccatgctgg cccgggagct cagggtcgag    420
gccgttctcg actgcgtctg cgccggcctg ccggagatca cgacaccga tgtgagcctc     480 tactacttca accacgccga gcaattcaag gtgcccgccc agcacaaggc ccggcacatc    540
ctggtcacca tcaacgagga ttttccggaa acacccgcg aagccgcccg gacgcgcatc     600
gagaccatcc tcaagcggct gcgcggcaag ccggagcgct cgccgagca ggcgatgaag     660 cactccgaat gtcccaccgc gatgcagggc ggattgctcg gcgaggtggt cccgggaacg    720
ctttatcccg aactggacgc ctgcctgttc cagatggcgc ggggagaact gagtccggta    780
ctggaatcgc cgatcggttt tcacgtgctg tactgcgaaa gcgtgagccc cgccggcag     840 ctcaccctcg aggagatcct gccgcgtctg cgcgacaggc tgcagctccg gcagcgcaag    900
gcgtatcagc gcaaatggct ggaaagcctg ctccaacaaa acgctacttt ggagaaccctc   960 gcccatggat aa                                                        972

<210> SEQ ID NO 44
<211> LENGTH: 432
<212> TYPE: PRT
<213> ORGANISM: Artificial Sequence
<220> FEATURE:
<223> OTHER INFORMATION: Recombinant

<400> SEQUENCE: 44

Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
            20                  25                  30

Asp Val Tyr Leu Asp Asn Asn Ala Thr Thr Arg Val Asp Asp Glu Ile
        35                  40                  45

Val Gln Ala Met Leu Pro Phe Phe Thr Glu Gln Phe Gly Asn Pro Ser
    50                  55                  60

Ser Leu His Ser Phe Gly Asn Gln Val Gly Met Ala Leu Lys Lys Ala
65                  70                  75                  80

Arg Gln Ser Val Gln Lys Leu Leu Gly Ala Glu His Asp Ser Glu Ile
                85                  90                  95

Val Phe Thr Ser Cys Gly Thr Glu Ser Asp Ser Thr Ala Ile Leu Ser
            100                 105                 110

Ala Leu Lys Ala Gln Pro Glu Arg Lys Thr Val Ile Thr Thr Val Val
        115                 120                 125

Glu His Pro Ala Val Leu Ser Leu Cys Asp Tyr Leu Ala Ser Glu Gly
    130                 135                 140

Tyr Thr Val His Lys Leu Pro Val Asp Lys Gly Arg Leu Asp Leu
145                 150                 155                 160

Glu His Tyr Ala Ser Leu Leu Thr Asp Asp Val Ala Val Ser Val
                165                 170                 175

Met Trp Ala Asn Asn Glu Thr Gly Thr Leu Phe Pro Ile Glu Glu Met
            180                 185                 190

Ala Arg Leu Ala Asp Asp Ala Gly Ile Met Phe His Thr Asp Ala Val
        195                 200                 205
```

```
Gln Ala Val Gly Lys Val Pro Ile Asp Leu Lys Asn Ser Ser Ile His
        210                 215                 220
Met Leu Ser Leu Ser Gly His Lys Leu His Ala Pro Lys Gly Val Gly
225                 230                 235                 240
Val Leu Tyr Leu Arg Arg Gly Thr Arg Phe Arg Pro Leu Leu Arg Gly
                245                 250                 255
Gly His Gln Glu Arg Gly Arg Arg Ala Gly Thr Glu Asn Ala Ala Ser
            260                 265                 270
Ile Ile Gly Leu Gly Val Ala Ala Glu Arg Ala Leu Gln Phe Met Glu
        275                 280                 285
His Glu Asn Thr Glu Val Lys Arg Leu Arg Asp Lys Leu Glu Ala Gly
290                 295                 300
Ile Leu Ala Val Val Pro His Ala Phe Val Thr Gly Asp Pro Asp Asn
305                 310                 315                 320
Arg Leu Pro Asn Thr Ala Asn Ile Ala Phe Glu Tyr Ile Glu Gly Glu
                325                 330                 335
Ala Ile Leu Leu Leu Leu Asn Lys Val Gly Ile Ala Ala Ser Ser Gly
            340                 345                 350
Ser Ala Cys Thr Ser Gly Ser Leu Glu Pro Ser His Val Met Arg Ala
        355                 360                 365
Met Asp Ile Pro Tyr Thr Ala Ala His Gly Thr Val Arg Phe Ser Leu
370                 375                 380
Ser Arg Tyr Thr Thr Glu Glu Glu Ile Asp Arg Val Ile Arg Glu Val
385                 390                 395                 400
Pro Pro Ile Val Ala Gln Leu Arg Lys Leu Ser Pro Tyr Trp Ser Gly
                405                 410                 415
Asn Gly Pro Val Glu Asp Pro Gly Lys Ala Phe Ala Pro Val Tyr Gly
            420                 425                 430

<210> SEQ ID NO 45
<211> LENGTH: 1299
<212> TYPE: DNA
<213> ORGANISM: Artificial Sequence
<220> FEATURE:
<223> OTHER INFORMATION: Recombinant

<400> SEQUENCE: 45
atgtatagat tcgcttctaa tcttgcatca aaggctagaa ttgctcagaa tgcaaggcag    60
gtttcttcaa gaatgtcatg gtctaggaat tatgctgacg tctatctcga taacaacgcc   120
accacccggg tggacgacga aatcgtccag gccatgctgc cgttcttcac cgaacagttc   180
ggcaacccct cgtcgctgca cagcttcggc aaccaggtcg gcatggcgct gaagaaggcc   240
cgccagagcg tgcagaaact gctcggtgcc gaacacgatt cggaaatcgt cttcacctcc   300
tgcggcaccg agtcggactc caccgcgatc ctctcggcgc tcaaggccca gcccgaacgc   360
aagaccgtca tcaccaccgt ggtcgaacac ccggccgtcc tcagcctgtg cgattacctc   420
gccagtgagg gctacaccgt gcacaagctg ccggtggaca agaaaggccg tctggatctg   480
gagcattacg ccagcctgct gaccgacgat gtcgccgtgg tgtcggtgat gtgggccaac   540
aacgagaccg gtaccctgtt cccgatcgaa gagatggcgc gcctggccga cgacgccggc   600
atcatgtttc acaccgatgc cgtgcaggcc gtgggcaagg taccgatcga cctgaagaat   660
tcgtcgatcc acatgctttc gctgtcgggc cacaagctgc acgcgcccaa aggtgtcggc   720
gtgctctatc tgcgccgcgg cacccgcttc cgtccgctgc tgcgcggtgg tcaccaggag   780
cgcggccgtc gtgccggcac cgagaacgcc gcctccatca tcggcctggg tgtcgccgcc   840
```

```
gaacgcgcgc tgcagttcat ggagcacgag aacaccgagg tcaagcgcct gcgcgacaag      900
ctggaggccg gtatcctcgc cgtcgtgccc catgccttcg tcaccggcga tccggacaac      960
cgcttgccca acaccgccaa catcgcgttc gagtacatcg agggcgaggc catcctgctg     1020
ctgctgaaca aggtcggcat cgccgcctcc agcggttcgg cctgcacctc cggctccttg     1080
gagccctccc acgtgatgcg cgccatggac attccctata ctgccgccca cggcaccgtg     1140
cgcttctccc tgtcgcgcta caccaccgag gaggagatcg accgggtgat ccgcgaggtt     1200
ccgccgatcg tggcccagtt gcgcaagctg tcgccctact ggagcggcaa cggtccggtg     1260
gaggacccgg gcaaggcctt cgctccggtc tacggctga                            1299
```

<210> SEQ ID NO 46
<211> LENGTH: 343
<212> TYPE: PRT
<213> ORGANISM: Artificial Sequence
<220> FEATURE:
<223> OTHER INFORMATION: Recombinant

<400> SEQUENCE: 46

```
Met Tyr Arg Phe Ala Ser Asn Leu Ala Ser Lys Ala Arg Ile Ala Gln
 1               5                  10                  15

Asn Ala Arg Gln Val Ser Ser Arg Met Ser Trp Ser Arg Asn Tyr Ala
            20                  25                  30

Trp Asp Tyr Ser Glu Lys Val Lys Glu His Phe Tyr Asn Pro Lys Asn
        35                  40                  45

Ala Gly Ala Val Glu Gly Ala Asn Ala Ile Gly Asp Val Gly Ser Leu
    50                  55                  60

Ser Cys Gly Asp Ala Leu Arg Leu Thr Leu Lys Val Asp Pro Glu Thr
65                  70                  75                  80

Asp Val Ile Leu Asp Ala Gly Phe Gln Thr Phe Gly Cys Gly Ser Ala
                85                  90                  95

Ile Ala Ser Ser Ser Ala Leu Thr Glu Met Val Lys Gly Leu Thr Leu
            100                 105                 110

Asp Glu Ala Leu Lys Ile Ser Asn Gln Asp Ile Ala Asp Tyr Leu Asp
        115                 120                 125

Gly Leu Pro Pro Glu Lys Met His Cys Ser Val Met Gly Arg Glu Ala
    130                 135                 140

Leu Gln Ala Ala Val Ala Asn Tyr Arg Gly Glu Thr Ile Glu Asp Asp
145                 150                 155                 160

His Glu Glu Gly Ala Leu Ile Cys Lys Cys Phe Ala Val Asp Glu Val
                165                 170                 175

Met Val Arg Asp Thr Ile Arg Ala Asn Lys Leu Ser Thr Val Glu Asp
            180                 185                 190

Val Thr Asn Tyr Thr Lys Ala Gly Gly Gly Cys Ser Ala Cys His Glu
        195                 200                 205

Ala Ile Glu Arg Val Leu Thr Glu Glu Leu Ala Ala Arg Gly Glu Val
    210                 215                 220

Phe Val Ala Ala Pro Ile Lys Ala Lys Lys Val Lys Val Leu Ala
225                 230                 235                 240

Pro Glu Pro Ala Pro Ala Pro Val Ala Glu Ala Pro Ala Ala Pro
                245                 250                 255

Lys Leu Ser Asn Leu Gln Arg Ile Arg Arg Ile Glu Thr Val Leu Ala
            260                 265                 270

Ala Ile Arg Pro Thr Leu Gln Arg Asp Lys Gly Asp Val Glu Leu Ile
```

-continued

```
                275                 280                 285
Asp Val Asp Gly Lys Asn Val Tyr Val Lys Leu Thr Gly Ala Cys Thr
            290                 295                 300
Gly Cys Gln Met Ala Ser Met Thr Leu Gly Gly Ile Gln Gln Arg Leu
305                 310                 315                 320
Ile Glu Glu Leu Gly Glu Phe Val Lys Val Ile Pro Val Ser Ala Ala
                325                 330                 335
Ala His Ala Gln Met Glu Val
            340
```

<210> SEQ ID NO 47
<211> LENGTH: 1032
<212> TYPE: DNA
<213> ORGANISM: Artificial Sequence
<220> FEATURE:
<223> OTHER INFORMATION: Recombinant

<400> SEQUENCE: 47

```
atgtatagat tcgcttctaa tcttgcatca aaggctagaa ttgctcagaa tgcaaggcag    60
gtttcttcaa gaatgtcatg gtctaggaat tatgcatggg attattcgga aaaagtcaaa   120
gagcacttct acaaccccaa gaatgctgga gccgtgaagg cgccaacgc catcggcgac    180
gtcggatcgc tgagttgcgg tgatgcgctg cgcctgaccc tgaaggtgga cccggaaacc   240
gacgtgattc tggatgccgg cttccagacc ttcggctgtg gttccgccat cgcttcctcc   300
tcggcgctga ccgagatggt caagggcctg accctggacg aggcgctgaa gatcagtaac   360
caggacatcg ccgactacct cgatggcctg ccgccggaga gatgcactg ctcggtgatg    420
ggccgcgaag ccctgcaggc gcggtggcc aactaccgtg gcgagacgat cgaggacgac    480
cacgaagagg gcgcgctgat ctgcaagtgc ttcgcgtcg acgaggtgat ggtccgcgat    540
accatccgtg ccaacaagct gtctaccgtt gaggacgtga ccaattacac caaggccggc   600
ggtggctgct ccgcctgcca cgaggctatc gagcgcgtgc tgaccgaaga gctggccgct   660
cgcggtgaag tcttcgtcgc ggccccgata aaggccaaga agaaggtcaa ggtgctcgcc   720
cccgagccgg ctcccgcccc ggtggccgaa gccccggcgg ctgccccgaa gctgagcaac   780
ctgcagcgca tccgtcgcat cgagaccgtg ctggcggcga tccgtccgac cttgcagcgc   840
gacaagggcg acgtcgaact gatcgatgtc gacggcaaga acgtttatgt caagctcacc   900
ggcgcctgca ccggctgcca gatggccagc atgaccctcg gcggcatcca gcagcgcctg   960
atcgaggagc tcggcgagtt cgtcaaggtg attccggtca gcgctgcggc tcacgcgcag  1020
atggaggtct aa                                                     1032
```

<210> SEQ ID NO 48
<211> LENGTH: 322
<212> TYPE: PRT
<213> ORGANISM: Artificial Sequence
<220> FEATURE:
<223> OTHER INFORMATION: Recombinant

<400> SEQUENCE: 48

```
Met Tyr Arg Phe Ala Ser Asn Leu Ala Ser Lys Ala Arg Ile Ala Gln
1               5                   10                  15
Asn Ala Arg Gln Val Ser Ser Arg Met Ser Trp Ser Arg Asn Tyr Ala
            20                  25                  30
Ala Ala Met Arg Gln Cys Ala Ile Tyr Gly Lys Gly Gly Ile Gly Lys
        35                  40                  45
```

Ser Thr Thr Gln Asn Leu Val Ala Ala Leu Ala Glu Met Gly Lys
    50                  55                  60

Lys Val Met Ile Val Gly Cys Asp Pro Lys Ala Asp Ser Thr Arg Leu
65                  70                  75                  80

Ile Leu His Ser Lys Ala Gln Asn Thr Ile Met Glu Met Ala Ala Glu
                85                  90                  95

Ala Gly Thr Val Glu Asp Leu Glu Leu Glu Asp Val Leu Lys Ala Gly
            100                 105                 110

Tyr Gly Gly Val Lys Cys Val Ser Gly Gly Pro Glu Pro Gly Val
            115                 120                 125

Gly Cys Ala Gly Arg Gly Val Ile Thr Ala Ile Asn Phe Leu Glu Glu
    130                 135                 140

Glu Gly Ala Tyr Glu Asp Asp Leu Asp Phe Val Phe Tyr Asp Val Leu
145                 150                 155                 160

Gly Asp Val Val Cys Gly Gly Phe Ala Met Pro Ile Arg Glu Asn Lys
                165                 170                 175

Ala Gln Glu Ile Tyr Ile Val Cys Ser Gly Glu Met Met Ala Met Tyr
            180                 185                 190

Ala Ala Asn Asn Ile Ser Lys Gly Ile Val Lys Tyr Ala Asn Ser Gly
            195                 200                 205

Ser Val Arg Leu Gly Gly Leu Ile Cys Asn Ser Arg Asn Thr Asp Arg
    210                 215                 220

Glu Asp Glu Leu Ile Ile Ala Leu Ala Asn Lys Leu Gly Thr Gln Met
225                 230                 235                 240

Ile His Phe Val Pro Arg Asp Asn Val Val Gln Arg Ala Glu Ile Arg
                245                 250                 255

Arg Met Thr Val Ile Glu Tyr Asp Pro Lys Ala Lys Gln Ala Asp Glu
            260                 265                 270

Tyr Arg Ala Leu Ala Arg Lys Val Val Asp Asn Lys Leu Leu Val Ile
            275                 280                 285

Pro Asn Pro Ile Thr Met Asp Glu Leu Glu Glu Leu Leu Met Glu Phe
    290                 295                 300

Gly Ile Met Glu Val Glu Asp Glu Ser Ile Val Gly Lys Thr Ala Glu
305                 310                 315                 320

Glu Val

<210> SEQ ID NO 49
<211> LENGTH: 969
<212> TYPE: DNA
<213> ORGANISM: Artificial Sequence
<220> FEATURE:
<223> OTHER INFORMATION: Recombinant

<400> SEQUENCE: 49
atgtatagat tgcttctaa tcttgcatca aggctagaa ttgctcagaa tgcaaggcag      60
gtttcttcaa gaatgtcatg gtcccgaaat tacgcagccg ctatgcgtca atgcgccatc    120
tacggcaaag gtggtatcgg taagtccacc actactcaga acctggtggc agccctggct   180
gagatgggca agaaggtcat gatcgttggt tgtgacccga agctgactc cacccgcctg    240 atcctgcact ccaaggccca gaacaccatc atggaaatgg ctgccgaagc cggtaccgtg   300
gaagatctgg agctggaaga cgtgctgaag gctggctacg gcggcgtcaa gtgcgttgag   360
tccggtggtc cggagccggg cgttggctgc gccggccgtg gtgttatcac cgccatcaac   420
ttcctggaag aggaaggcgc ctacgaagac gatctggact cgtattcta cgacgtgctg   480

-continued

```
ggcgacgtgg tgtgtggcgg cttcgccatg ccgatccgcg agaacaaggc ccaggaaatc    540
tacatcgtct gctccggtga gatgatggcc atgtacgccg ccaacaacat ctccaagggc    600
atcgtgaagt atgccaactc cggcagcgtg cgtctgggcg gcctgatctg caacagccgt    660
aacaccgacc gcgaagacga gctgatcatc gctctggcca acaagctggg cacccagatg    720
atccacttcg tgccgcgtga caacgtcgtg cagcgcgccg aaatccgccg catgaccgtg    780
atcgaatacg atccgaaagc caagcaagcc gacgaatacc gcgctctggc ccgcaaggtc    840
gtcgacaaca aactgctggt catcccgaac ccgatcacca tggacgagct cgaagagctg    900
ctgatggaat cggcatcat ggaagtcgaa gacgaatcca tcgtcggcaa aaccgccgaa    960
gaagtctga                                                            969
```

<210> SEQ ID NO 50
<211> LENGTH: 324
<212> TYPE: PRT
<213> ORGANISM: Artificial Sequence
<220> FEATURE:
<223> OTHER INFORMATION: Recombinant

<400> SEQUENCE: 50

```
Met Tyr Arg Phe Ala Ser Asn Leu Ala Ser Lys Ala Arg Ile Ala Gln
 1               5                  10                  15

Asn Ala Arg Gln Val Ser Ser Arg Met Ser Trp Ser Arg Asn Tyr Ala
             20                  25                  30

Ala Lys Glu Ala Met Arg Gln Cys Ala Ile Tyr Gly Lys Gly Gly Ile
         35                  40                  45

Gly Lys Ser Thr Thr Thr Gln Asn Leu Val Ala Ala Leu Ala Glu Met
     50                  55                  60

Gly Lys Lys Val Met Ile Val Gly Cys Asp Pro Lys Ala Asp Ser Thr
 65                  70                  75                  80

Arg Leu Ile Leu His Ser Lys Ala Gln Asn Thr Ile Met Glu Met Ala
                 85                  90                  95

Ala Glu Ala Gly Thr Val Glu Asp Leu Glu Leu Glu Asp Val Leu Lys
            100                 105                 110

Ala Gly Tyr Gly Gly Val Lys Cys Val Glu Ser Gly Gly Pro Glu Pro
        115                 120                 125

Gly Val Gly Cys Ala Gly Arg Gly Val Ile Thr Ala Ile Asn Phe Leu
    130                 135                 140

Glu Glu Glu Gly Ala Tyr Glu Asp Asp Leu Asp Phe Val Phe Tyr Asp
145                 150                 155                 160

Val Leu Gly Asp Val Val Cys Gly Gly Phe Ala Met Pro Ile Arg Glu
                165                 170                 175

Asn Lys Ala Gln Glu Ile Tyr Ile Val Cys Ser Gly Glu Met Met Ala
            180                 185                 190

Met Tyr Ala Ala Asn Asn Ile Ser Lys Gly Ile Val Lys Tyr Ala Asn
        195                 200                 205

Ser Gly Ser Val Arg Leu Gly Gly Leu Ile Cys Asn Ser Arg Asn Thr
    210                 215                 220

Asp Arg Glu Asp Glu Leu Ile Ile Ala Leu Ala Asn Lys Leu Gly Thr
225                 230                 235                 240

Gln Met Ile His Phe Val Pro Arg Asp Asn Val Val Gln Arg Ala Glu
                245                 250                 255

Ile Arg Arg Met Thr Val Ile Glu Tyr Asp Pro Lys Ala Lys Gln Ala
            260                 265                 270
```

Asp Glu Tyr Arg Ala Leu Ala Arg Lys Val Val Asp Asn Lys Leu Leu
            275                 280                 285

Val Ile Pro Asn Pro Ile Thr Met Asp Glu Leu Glu Glu Leu Leu Met
    290                 295                 300

Glu Phe Gly Ile Met Glu Val Glu Asp Glu Ser Ile Val Gly Lys Thr
305                 310                 315                 320

Ala Glu Glu Val

<210> SEQ ID NO 51
<211> LENGTH: 975
<212> TYPE: DNA
<213> ORGANISM: Artificial Sequence
<220> FEATURE:
<223> OTHER INFORMATION: Recombinant

<400> SEQUENCE: 51

```
atgtatagat tgcttctaa tcttgcatca aaggctagaa ttgctcagaa tgcaaggcag      60
gtttcttcaa gaatgtcatg gtcccgaaat tacgcagcca aggaagctat gcgtcaatgc    120
gccatctacg gcaaaggtgg tatcggtaag tccaccacta ctcagaacct ggtggcagcc    180
ctggctgaga tgggcaagaa ggtcatgatc gttggttgtg acccgaaagc tgactccacc    240
cgcctgatcc tgcactccaa ggcccagaac accatcatgg aaatggctgc cgaagccggt    300
accgtggaag atctggagct ggaagacgtg ctgaaggctg gctacggcgg cgtcaagtgc    360
gttgagtccg gtggtccgga gccgggcgtt ggctgcgccg ccgtggtgt tatcaccgcc     420
atcaacttcc tggaagagga aggcgcctac gaagacgatc tggacttcgt attctacgac    480
gtgctgggcg acgtggtgtg tggcggcttc gccatgccga tccgcgagaa caaggcccag    540
gaaatctaca tcgtctgctc cggtgagatg atggccatgt acgccgccaa caacatctcc    600
aagggcatcg tgaagtatgc caactccggc agcgtgcgtc tgggcggcct gatctgcaac    660
agccgtaaca ccgaccgcga agacgagctg atcatcgctc tggccaacaa gctgggcacc    720
cagatgatcc acttcgtgcc gcgtgacaac gtcgtgcagc gcgccgaaat ccgccgcatg    780
accgtgatcg aatacgatcc gaaagccaag caagccgacg aataccgcgc tctggccgc    840
aaggtcgtcg acaacaaact gctggtcatc ccgaacccga tcaccatgga cgagctcgaa    900
gagctgctga tggaattcgg catcatggaa gtcgaagacg aatccatcgt cggcaaaacc    960
gccgaagaag tctga                                                    975
```

<210> SEQ ID NO 52
<211> LENGTH: 335
<212> TYPE: PRT
<213> ORGANISM: Artificial Sequence
<220> FEATURE:
<223> OTHER INFORMATION: Recombinant

<400> SEQUENCE: 52

Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
            20                  25                  30

Ala Lys Glu Ile Lys Phe Gly Val Glu Ala Arg Ala Leu Met Ala Met
        35                  40                  45

Arg Gln Cys Ala Ile Tyr Gly Lys Gly Gly Ile Gly Lys Ser Thr Thr
    50                  55                  60

Thr Gln Asn Leu Val Ala Ala Leu Ala Glu Met Gly Lys Lys Val Met
65                  70                  75                  80

Ile Val Gly Cys Asp Pro Lys Ala Asp Ser Thr Arg Leu Ile Leu His
                    85                  90                  95

Ser Lys Ala Gln Asn Thr Ile Met Glu Met Ala Ala Glu Ala Gly Thr
            100                 105                 110

Val Glu Asp Leu Glu Leu Glu Asp Val Leu Lys Ala Gly Tyr Gly Gly
        115                 120                 125

Val Lys Cys Val Glu Ser Gly Gly Pro Glu Pro Gly Val Gly Cys Ala
    130                 135                 140

Gly Arg Gly Val Ile Thr Ala Ile Asn Phe Leu Glu Glu Glu Gly Ala
145                 150                 155                 160

Tyr Glu Asp Asp Leu Asp Phe Val Phe Tyr Asp Val Leu Gly Asp Val
                165                 170                 175

Val Cys Gly Gly Phe Ala Met Pro Ile Arg Glu Asn Lys Ala Gln Glu
            180                 185                 190

Ile Tyr Ile Val Cys Ser Gly Glu Met Met Ala Met Tyr Ala Ala Asn
        195                 200                 205

Asn Ile Ser Lys Gly Ile Val Lys Tyr Ala Asn Ser Gly Ser Val Arg
    210                 215                 220

Leu Gly Gly Leu Ile Cys Asn Ser Arg Asn Thr Asp Arg Glu Asp Glu
225                 230                 235                 240

Leu Ile Ile Ala Leu Ala Asn Lys Leu Gly Thr Gln Met Ile His Phe
                245                 250                 255

Val Pro Arg Asp Asn Val Val Gln Arg Ala Glu Ile Arg Arg Met Thr
            260                 265                 270

Val Ile Glu Tyr Asp Pro Lys Ala Lys Gln Ala Asp Glu Tyr Arg Ala
        275                 280                 285

Leu Ala Arg Lys Val Val Asp Asn Lys Leu Leu Val Ile Pro Asn Pro
    290                 295                 300

Ile Thr Met Asp Glu Leu Glu Glu Leu Leu Met Glu Phe Gly Ile Met
305                 310                 315                 320

Glu Val Glu Asp Glu Ser Ile Val Gly Lys Thr Ala Glu Glu Val
                325                 330                 335

<210> SEQ ID NO 53
<211> LENGTH: 1008
<212> TYPE: DNA
<213> ORGANISM: Artificial Sequence
<220> FEATURE:
<223> OTHER INFORMATION: Recombinant

<400> SEQUENCE: 53
atgtatagat tgcttctaa tcttgcatct aaggctagga ttgcacaaaa tgccaggcag     60
gtttcttcac gtatgagttg gtcccgaaat tacgcagcca aggaaatcaa attcggtgtg    120
gaggcacggg ctttgatggc tatgcgtcaa tgcgccatct acggcaaagg tggtatcggt    180
aagtccacca ctactcagaa cctggtggca gccctggctg agatgggcaa gaaggtcatg    240
atcgttggtt gtgacccgaa agctgactcc acccgcctga tcctgcactc caaggcccag    300
aacaccatca tggaaatggc tgccgaagcc ggtaccgtgg aagatctgga gctggaagac    360
gtgctgaagg ctggctacgg cggcgtcaag tgcgttgagt ccggtggtcc ggagccgggc    420
gttggctgcg ccggccgtgg tgttatcacc gccatcaact tcctggaaga ggaaggcgcc    480
tacgaagacg atctggactt cgtattctac gacgtgctgg gcgacgtggt gtgtggcggc    540
ttcgccatgc cgatccgcga gaacaaggcc caggaaatct acatcgtctg ctccggtgag    600

```
atgatggcca tgtacgccgc caacaacatc tccaagggca tcgtgaagta tgccaactcc    660
ggcagcgtgc gtctgggcgg cctgatctgc aacagccgta acaccgaccg cgaagacgag    720
ctgatcatcg ctctggccaa caagctgggc acccagatga tccacttcgt gccgcgtgac    780
aacgtcgtgc agcgcgccga atccgccgc atgaccgtga tcgaatacga tccgaaagcc    840
aagcaagccg acgaataccg cgctctggcc cgcaaggtcg tcgacaacaa actgctggtc    900
atcccgaacc cgatcaccat ggacgagctc gaagagctgc tgatggaatt cggcatcatg    960
gaagtcgaag acgaatccat cgtcggcaaa accgccgaag aagtctga             1008
```

<210> SEQ ID NO 54
<211> LENGTH: 350
<212> TYPE: PRT
<213> ORGANISM: Artificial Sequence
<220> FEATURE:
<223> OTHER INFORMATION: Recombinant

<400> SEQUENCE: 54

```
Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
            20                  25                  30

Ala Lys Glu Ile Lys Phe Gly Val Glu Ala Arg Ala Leu Met Leu Lys
        35                  40                  45

Gly Val Glu Asp Leu Ala Asp Ala Val Lys Val Thr Met Ala Met Arg
    50                  55                  60

Gln Cys Ala Ile Tyr Gly Lys Gly Ile Gly Lys Ser Thr Thr Thr
65                  70                  75                  80

Gln Asn Leu Val Ala Ala Leu Ala Glu Met Gly Lys Lys Val Met Ile
                85                  90                  95

Val Gly Cys Asp Pro Lys Ala Asp Ser Thr Arg Leu Ile Leu His Ser
            100                 105                 110

Lys Ala Gln Asn Thr Ile Met Glu Met Ala Ala Glu Ala Gly Thr Val
        115                 120                 125

Glu Asp Leu Glu Leu Glu Asp Val Leu Lys Ala Gly Tyr Gly Gly Val
    130                 135                 140

Lys Cys Val Glu Ser Gly Gly Pro Glu Pro Gly Val Gly Cys Ala Gly
145                 150                 155                 160

Arg Gly Val Ile Thr Ala Ile Asn Phe Leu Glu Glu Gly Ala Tyr
                165                 170                 175

Glu Asp Asp Leu Asp Phe Val Phe Tyr Asp Val Leu Gly Asp Val Val
            180                 185                 190

Cys Gly Gly Phe Ala Met Pro Ile Arg Glu Asn Lys Ala Gln Glu Ile
        195                 200                 205

Tyr Ile Val Cys Ser Gly Glu Met Met Ala Met Tyr Ala Ala Asn Asn
    210                 215                 220

Ile Ser Lys Gly Ile Val Lys Tyr Ala Asn Ser Gly Ser Val Arg Leu
225                 230                 235                 240

Gly Gly Leu Ile Cys Asn Ser Arg Asn Thr Asp Arg Glu Asp Glu Leu
                245                 250                 255

Ile Ile Ala Leu Ala Asn Lys Leu Gly Thr Gln Met Ile His Phe Val
            260                 265                 270

Pro Arg Asp Asn Val Val Gln Arg Ala Glu Ile Arg Arg Met Thr Val
        275                 280                 285

Ile Glu Tyr Asp Pro Lys Ala Lys Gln Ala Asp Glu Tyr Arg Ala Leu
```

```
                290                 295                 300

Ala Arg Lys Val Val Asp Asn Lys Leu Leu Val Ile Pro Asn Pro Ile
305                 310                 315                 320

Thr Met Asp Glu Leu Glu Glu Leu Leu Met Glu Phe Gly Ile Met Glu
                325                 330                 335

Val Glu Asp Glu Ser Ile Val Gly Lys Thr Ala Glu Glu Val
                340                 345                 350

<210> SEQ ID NO 55
<211> LENGTH: 1053
<212> TYPE: DNA
<213> ORGANISM: Artificial Sequence
<220> FEATURE:
<223> OTHER INFORMATION: Recombinant

<400> SEQUENCE: 55
atgtatagat tgcttctaa tcttgcatct aaggctagga ttgcacaaaa tgccaggcag      60
gtttcttcac gtatgagttg gtcccgaaat tacgcagcca aggaaatcaa attcggtgtg    120
gaggcacggg ctttgatgtt aaaaggagtt gaggatctcg cagacgccgt gaaagtaact    180
atggctatgc gtcaatgcgc catctacggc aaaggtggta tcggtaagtc caccactact    240
cagaacctgg tggcagccct ggctgagatg ggcaagaagg tcatgatcgt tggttgtgac    300
ccgaaagctg actccacccg cctgatcctg cactccaagg cccagaacac catcatggaa    360
atggctgccg aagccggtac cgtggaagat ctggagctgg aagacgtgct gaaggctggc    420
tacggcggcg tcaagtgcgt tgagtccggt ggtccggagc cgggcgttgg ctgcgccggc    480
cgtggtgtta tcaccgccat caacttcctg gaagaggaag gcgcctacga agacgatctg    540
gacttcgtat tctacgacgt gctgggcgac gtggtgtgtg gcggcttcgc catgccgatc    600
cgcgagaaca aggcccagga atctacatc gtctgctccg gtgagatgat ggccatgtac    660
gccgccaaca acatctccaa gggcatcgtg aagtatgcca actccggcag cgtgcgtctg    720
ggcggcctga tctgcaacag ccgtaacacc gaccgcgaag acgagctgat catcgctctg    780
gccaacaagc tgggcacccc gatgatccac ttcgtgccgc gtgacaacgt cgtgcagcgc    840
gccgaaatcc gccgcatgac cgtgatcgaa tacgatccga agccaagca agccgacgaa    900 taccgcgctc tggcccgcaa ggtcgtcgac aacaaactgc tggtcatccc gaacccgatc    960
accatggacg agctcgaaga gctgctgatg gaattcggca tcatggaagt cgaagacgaa   1020
tccatcgtcg gcaaaaccgc cgaagaagtc tga                                1053

<210> SEQ ID NO 56
<211> LENGTH: 366
<212> TYPE: PRT
<213> ORGANISM: Artificial Sequence
<220> FEATURE:
<223> OTHER INFORMATION: Recombinant

<400> SEQUENCE: 56

Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
                20                  25                  30

Ala Lys Glu Ile Lys Phe Gly Val Glu Ala Arg Ala Leu Met Leu Lys
            35                  40                  45

Gly Val Glu Asp Leu Ala Asp Ala Val Lys Val Thr Met Gly Pro Lys
        50                  55                  60
```

```
Gly Arg Asn Val Val Ile Glu Gln Ser Trp Gly Ala Met Ala Met Arg
 65                  70                  75                  80

Gln Cys Ala Ile Tyr Gly Lys Gly Ile Gly Lys Ser Thr Thr Thr
                 85                  90                  95

Gln Asn Leu Val Ala Ala Leu Ala Glu Met Gly Lys Lys Val Met Ile
            100                 105                 110

Val Gly Cys Asp Pro Lys Ala Asp Ser Thr Arg Leu Ile Leu His Ser
        115                 120                 125

Lys Ala Gln Asn Thr Ile Met Glu Met Ala Ala Glu Ala Gly Thr Val
    130                 135                 140

Glu Asp Leu Glu Leu Glu Asp Val Leu Lys Ala Gly Tyr Gly Gly Val
145                 150                 155                 160

Lys Cys Val Glu Ser Gly Gly Pro Glu Pro Gly Val Gly Cys Ala Gly
                165                 170                 175

Arg Gly Val Ile Thr Ala Ile Asn Phe Leu Glu Glu Glu Gly Ala Tyr
            180                 185                 190

Glu Asp Asp Leu Asp Phe Val Phe Tyr Asp Val Leu Gly Asp Val Val
        195                 200                 205

Cys Gly Gly Phe Ala Met Pro Ile Arg Glu Asn Lys Ala Gln Glu Ile
    210                 215                 220

Tyr Ile Val Cys Ser Gly Glu Met Met Ala Met Tyr Ala Ala Asn Asn
225                 230                 235                 240

Ile Ser Lys Gly Ile Val Lys Tyr Ala Asn Ser Gly Ser Val Arg Leu
                245                 250                 255

Gly Gly Leu Ile Cys Asn Ser Arg Asn Thr Asp Arg Glu Asp Glu Leu
            260                 265                 270

Ile Ile Ala Leu Ala Asn Lys Leu Gly Thr Gln Met Ile His Phe Val
        275                 280                 285

Pro Arg Asp Asn Val Val Gln Arg Ala Glu Ile Arg Arg Met Thr Val
    290                 295                 300

Ile Glu Tyr Asp Pro Lys Ala Lys Gln Ala Asp Glu Tyr Arg Ala Leu
305                 310                 315                 320

Ala Arg Lys Val Val Asp Asn Lys Leu Leu Val Ile Pro Asn Pro Ile
                325                 330                 335

Thr Met Asp Glu Leu Glu Glu Leu Leu Met Glu Phe Gly Ile Met Glu
            340                 345                 350

Val Glu Asp Glu Ser Ile Val Gly Lys Thr Ala Glu Glu Val
        355                 360                 365

<210> SEQ ID NO 57
<211> LENGTH: 1101
<212> TYPE: DNA
<213> ORGANISM: Artificial Sequence
<220> FEATURE:
<223> OTHER INFORMATION: Recombinant

<400> SEQUENCE: 57
atgtatagat tgcttctaa tcttgcatct aaggctagga ttgcacaaaa tgccaggcag      60
gtttcttcac gtatgagttg gtcccgaaat tacgcagcca aggaaatcaa attcggtgtg     120
gaggcacggg ctttgatgtt aaaaggagtt gaggatctcg cagacgccgt gaaagtaact     180
atgggaccta agggcaggaa cgtcgtaata gaacagagct gggggcgat ggctatgcgt      240 caatgcgcca tctacggcaa agtggggtatc ggtaagtcca ccactactca gaacctggtg    300
gcagccctgg ctgagatggg caagaaggtc atgatcgttg gttgtgaccc gaaagctgac     360
```

-continued

| | |
|---|---|
| tccacccgcc tgatcctgca ctccaaggcc cagaacacca tcatggaaat ggctgccgaa | 420 |
| gccggtaccg tggaagatct ggagctggaa gacgtgctga aggctggcta cggcggcgtc | 480 |
| aagtgcgttg agtccggtgg tccggagccg ggcgttggct gcgccggccg tggtgttatc | 540 |
| accgccatca acttcctgga agaggaaggc gcctacgaag acgatctgga cttcgtattc | 600 |
| tacgacgtgc tgggcgacgt ggtgtgtggc ggcttcgcca tgccgatccg cgagaacaag | 660 |
| gcccaggaaa tctacatcgt ctgctccggt gagatgatgg ccatgtacgc cgccaacaac | 720 |
| atctccaagg gcatcgtgaa gtatgccaac tccggcagcg tgcgtctggg cggcctgatc | 780 |
| tgcaacagcc gtaacaccga ccgcgaagac gagctgatca tcgctctggc caacaagctg | 840 |
| ggcacccaga tgatccactt cgtgccgcgt gacaacgtcg tgcagcgcgc cgaaatccgc | 900 |
| cgcatgaccg tgatcgaata cgatccgaaa gccaagcaag ccgacgaata ccgcgctctg | 960 |
| gcccgcaagg tcgtcgacaa caaactgctg gtcatcccga cccgatcac catggacgag | 1020 |
| ctcgaagagc tgctgatgga attcggcatc atggaagtcg aagacgaatc catcgtcggc | 1080 |
| aaaaccgccg aagaagtctg a | 1101 |

<210> SEQ ID NO 58
<211> LENGTH: 352
<212> TYPE: PRT
<213> ORGANISM: Artificial Sequence
<220> FEATURE:
<223> OTHER INFORMATION: Recombinant

<400> SEQUENCE: 58

Met Met Ser Ser Arg Leu Val Gly Thr Ala Leu Cys Arg Gln Leu Ser
1               5                   10                  15

His Val Pro Val Pro Gln Tyr Leu Pro Ala Leu Arg Pro Thr Ala Asp
            20                  25                  30

Thr Ala Ser Ser Leu Leu His Gly Cys Ser Ala Ala Pro Ala Gln
        35                  40                  45

Arg Ala Gly Leu Trp Pro Pro Ser Trp Phe Ser Pro Pro Arg His Ala
    50                  55                  60

Met Arg Gln Cys Ala Ile Tyr Gly Lys Gly Gly Ile Gly Lys Ser Thr
65                  70                  75                  80

Thr Thr Gln Asn Leu Val Ala Ala Leu Ala Glu Met Gly Lys Lys Val
                85                  90                  95

Met Ile Val Gly Cys Asp Pro Lys Ala Asp Ser Thr Arg Leu Ile Leu
            100                 105                 110

His Ser Lys Ala Gln Asn Thr Ile Met Glu Met Ala Ala Glu Ala Gly
        115                 120                 125

Thr Val Glu Asp Leu Glu Leu Glu Asp Val Leu Lys Ala Gly Tyr Gly
    130                 135                 140

Gly Val Lys Cys Val Glu Ser Gly Gly Pro Glu Pro Gly Val Gly Cys
145                 150                 155                 160

Ala Gly Arg Gly Val Ile Thr Ala Ile Asn Phe Leu Glu Glu Glu
                165                 170                 175

Ala Tyr Glu Asp Asp Leu Asp Phe Val Phe Tyr Asp Val Leu Gly Asp
            180                 185                 190

Val Val Cys Gly Gly Phe Ala Met Pro Ile Arg Glu Asn Lys Ala Gln
        195                 200                 205

Glu Ile Tyr Ile Val Cys Ser Gly Glu Met Met Ala Met Tyr Ala Ala
    210                 215                 220

Asn Asn Ile Ser Lys Gly Ile Val Lys Tyr Ala Asn Ser Gly Ser Val

```
                225                 230                 235                 240
Arg Leu Gly Gly Leu Ile Cys Asn Ser Arg Asn Thr Asp Arg Glu Asp
                        245                 250                 255

Glu Leu Ile Ile Ala Leu Ala Asn Lys Leu Gly Thr Gln Met Ile His
                260                 265                 270

Phe Val Pro Arg Asp Asn Val Val Gln Arg Ala Glu Ile Arg Arg Met
            275                 280                 285

Thr Val Ile Glu Tyr Asp Pro Lys Ala Lys Gln Ala Asp Glu Tyr Arg
        290                 295                 300

Ala Leu Ala Arg Lys Val Val Asp Asn Lys Leu Leu Val Ile Pro Asn
305                 310                 315                 320

Pro Ile Thr Met Asp Glu Leu Glu Glu Leu Leu Met Glu Phe Gly Ile
                325                 330                 335

Met Glu Val Glu Asp Glu Ser Ile Val Gly Lys Thr Ala Glu Glu Val
                340                 345                 350

<210> SEQ ID NO 59
<211> LENGTH: 1059
<212> TYPE: DNA
<213> ORGANISM: Artificial Sequence
<220> FEATURE:
<223> OTHER INFORMATION: Recombinant

<400> SEQUENCE: 59
atgatgtctt caagacttgt tggtactgct ctttgtaggc aattgtctca gtgtcctgtc      60
cctcaatatt tgcctgcttt acgtcctaca gctgataccg catcaagtct cctgcatggt     120
tgctccgcag ccgcaccagc ccagcgagcg ggactatggc accgagctg gttttcgccc      180 ccacggcacg ctatgcgtca atgcgccatc tacggcaaag gtggtatcgg taagtccacc     240
actactcaga acctggtggc agccctggct gagatgggca agaaggtcat gatcgttggt     300
tgtgacccga agctgactc caccgcctg atcctgcact ccaaggccca gaacaccatc       360
atggaaatgg ctgccgaagc cggtaccgtg aagatctgg agctggaaga cgtgctgaag      420
gctggctacg gcggcgtcaa gtgcgttgag tccggtggtc ggagccgggc gttggctgc      480 gccggccgtg gtgttatcac cgccatcaac ttcctggaag aggaaggcgc ctacgaagac     540
gatctggact cgtattcta cgacgtgctg ggcgacgtgg tgtgtggcgg cttcgccatg      600
ccgatccgcg agaacaaggc ccaggaaatc tacatcgtct gctccggtga gatgatggcc     660
atgtacgccg ccaacaacat ctccaagggc atcgtgaagt atgccaactc cggcagcgtg     720
cgtctgggcg gcctgatctg caacagccgt aacaccgacc gcgaagacga gctgatcatc     780
gctctggcca acaagctggg cacccagatg atccacttcg tgccgcgtga caacgtcgtg     840
cagcgcgccg aaatccgccg catgaccgtg atcgaatacg atccgaaagc caagcaagcc     900
gacgaatacc gcgctctggc ccgcaaggtc gtcgacaaca aactgctggt catcccgaac     960
ccgatcacca tggacgagct cgaagagctg ctgatggaat cggcatcat ggaagtcgaa     1020 gacgaatcca tcgtcggcaa aaccgccgaa gaagtctga                            1059

<210> SEQ ID NO 60
<211> LENGTH: 355
<212> TYPE: PRT
<213> ORGANISM: Artificial Sequence
<220> FEATURE:
<223> OTHER INFORMATION: Recombinant

<400> SEQUENCE: 60
```

Met Met Ser Ser Arg Leu Val Gly Thr Ala Leu Cys Arg Gln Leu Ser
1               5                   10                  15

His Val Pro Val Pro Gln Tyr Leu Pro Ala Leu Arg Pro Thr Ala Asp
            20                  25                  30

Thr Ala Ser Ser Leu Leu His Gly Cys Ser Ala Ala Pro Ala Gln
        35                  40                  45

Arg Ala Gly Leu Trp Pro Pro Ser Trp Phe Ser Pro Pro Arg His Ala
    50                  55                  60

Ser Thr Ala Met Arg Gln Cys Ala Ile Tyr Gly Lys Gly Ile Gly
65                  70                  75                  80

Lys Ser Thr Thr Thr Gln Asn Leu Val Ala Ala Leu Ala Glu Met Gly
                85                  90                  95

Lys Lys Val Met Ile Val Gly Cys Asp Pro Lys Ala Asp Ser Thr Arg
            100                 105                 110

Leu Ile Leu His Ser Lys Ala Gln Asn Thr Ile Met Glu Met Ala Ala
            115                 120                 125

Glu Ala Gly Thr Val Glu Asp Leu Glu Leu Gly Asp Val Leu Lys Ala
    130                 135                 140

Gly Tyr Gly Gly Val Lys Cys Val Glu Ser Gly Gly Pro Glu Pro Gly
145                 150                 155                 160

Val Gly Cys Ala Gly Arg Gly Val Ile Thr Ala Ile Asn Phe Leu Glu
                165                 170                 175

Glu Glu Gly Ala Tyr Glu Asp Asp Leu Asp Phe Val Phe Tyr Asp Val
            180                 185                 190

Leu Gly Asp Val Val Cys Gly Gly Phe Ala Met Pro Ile Arg Glu Asn
            195                 200                 205

Lys Ala Gln Glu Ile Tyr Ile Val Cys Ser Gly Glu Met Met Ala Met
    210                 215                 220

Tyr Ala Ala Asn Asn Ile Ser Lys Gly Ile Val Lys Tyr Ala Asn Ser
225                 230                 235                 240

Gly Ser Val Arg Leu Gly Gly Leu Ile Cys Asn Ser Arg Asn Thr Asp
                245                 250                 255

Arg Glu Asp Glu Leu Ile Ile Ala Leu Ala Asn Lys Leu Gly Thr Gln
            260                 265                 270

Met Ile His Phe Val Pro Arg Asp Asn Val Val Gln Arg Ala Glu Ile
        275                 280                 285

Arg Arg Met Thr Val Ile Glu Tyr Asp Pro Lys Ala Lys Gln Ala Asp
    290                 295                 300

Glu Tyr Arg Ala Leu Ala Arg Lys Val Val Asp Asn Lys Leu Leu Val
305                 310                 315                 320

Ile Pro Asn Pro Ile Thr Met Asp Glu Leu Glu Glu Leu Leu Met Glu
                325                 330                 335

Phe Gly Ile Met Glu Val Glu Asp Glu Ser Ile Val Gly Lys Thr Ala
            340                 345                 350

Glu Glu Val
        355

<210> SEQ ID NO 61
<211> LENGTH: 1068
<212> TYPE: DNA
<213> ORGANISM: Artificial Sequence
<220> FEATURE:
<223> OTHER INFORMATION: Recombinant

<400> SEQUENCE: 61

```
atgatgtctt caagacttgt tggtactgct ctttgtaggc aattgtctca tgtgcctgtc      60
cctcaatatt tgcctgcttt acgtcctaca gctgataccg catcaagtct cctgcatggt     120
tgctccgcag ccgcaccagc ccagcgagcg ggactatggc caccgagctg gttttcgccc     180
ccacggcacg ccagcacagc tatgcgtcaa tgcgccatct acggcaaagg tggtatcggt     240
aagtccacca ctactcagaa cctggtggca gccctggctg agatgggcaa gaaggtcatg     300
atcgttggtt gtgacccgaa agctgactcc acccgcctga tcctgcactc caaggcccag     360
aacaccatca tggaaatggc tgccgaagcc ggtaccgtgg aagatctgga gctggaagac     420
gtgctgaagg ctggctacgg cggcgtcaag tgcgttgagt ccggtggtcc ggagccgggc     480
gttggctgcg ccggccgtgg tgttatcacc gccatcaact tcctggaaga ggaaggcgcc     540
tacgaagacg atctggactt cgtattctac gacgtgctgg gcgacgtggt gtgtggcggc     600
ttcgccatgc cgatccgcga gaacaaggcc caggaaatct acatcgtctg ctccggtgag     660
atgatggcca tgtacgccgc caacaacatc tccaagggca tcgtgaagta tgccaactcc     720
ggcagcgtgc gtctgggcgg cctgatctgc aacagccgta acaccgaccg cgaagacgag     780
ctgatcatcg ctctggccaa caagctgggc acccagatga tccacttcgt gccgcgtgac     840
aacgtcgtgc agcgcgccga aatccgccgc atgaccgtga tcgaatacga tccgaaagcc     900
aagcaagccg acgaataccg cgctctggcc cgcaaggtcg tcgacaacaa actgctggtc     960
atcccgaacc cgatcaccat ggacgagctc aagagctgc tgatggaatt cggcatcatg    1020
gaagtcgaag acgaatccat cgtcggcaaa accgccgaag aagtctga                1068
```

<210> SEQ ID NO 62
<211> LENGTH: 355
<212> TYPE: PRT
<213> ORGANISM: Artificial Sequence
<220> FEATURE:
<223> OTHER INFORMATION: Recombinant

<400> SEQUENCE: 62

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Ala Met Arg Gln Cys Ala Ile Tyr Gly Lys Gly Gly Ile Gly
65                  70                  75                  80

Lys Ser Thr Thr Thr Gln Asn Leu Val Ala Ala Leu Ala Glu Met Gly
                85                  90                  95

Lys Lys Val Met Ile Val Gly Cys Asp Pro Lys Ala Asp Ser Thr Arg
            100                 105                 110

Leu Ile Leu His Ser Lys Ala Gln Asn Thr Ile Met Glu Met Ala Ala
        115                 120                 125

Glu Ala Gly Thr Val Glu Asp Leu Glu Leu Glu Asp Val Leu Lys Ala
    130                 135                 140

Gly Tyr Gly Gly Val Lys Cys Val Glu Ser Gly Gly Pro Glu Pro Gly
145                 150                 155                 160

Val Gly Cys Ala Gly Arg Gly Val Ile Thr Ala Ile Asn Phe Leu Glu
                165                 170                 175

```
Glu Glu Gly Ala Tyr Glu Asp Asp Leu Asp Phe Val Phe Tyr Asp Val
            180                 185                 190
Leu Gly Asp Val Val Cys Gly Phe Ala Met Pro Ile Arg Glu Asn
            195                 200                 205
Lys Ala Gln Glu Ile Tyr Ile Val Cys Ser Gly Glu Met Met Ala Met
210                 215                 220
Tyr Ala Ala Asn Asn Ile Ser Lys Gly Ile Val Lys Tyr Ala Asn Ser
225                 230                 235                 240
Gly Ser Val Arg Leu Gly Gly Leu Ile Cys Asn Ser Arg Asn Thr Asp
                245                 250                 255
Arg Glu Asp Glu Leu Ile Ile Ala Leu Ala Asn Lys Leu Gly Thr Gln
            260                 265                 270
Met Ile His Phe Val Pro Arg Asp Asn Val Val Gln Arg Ala Glu Ile
            275                 280                 285
Arg Arg Met Thr Val Ile Glu Tyr Asp Pro Lys Ala Lys Gln Ala Asp
            290                 295                 300
Glu Tyr Arg Ala Leu Ala Arg Lys Val Val Asp Asn Lys Leu Leu Val
305                 310                 315                 320
Ile Pro Asn Pro Ile Thr Met Asp Glu Leu Glu Glu Leu Leu Met Glu
                325                 330                 335
Phe Gly Ile Met Glu Val Glu Asp Glu Ser Ile Val Gly Lys Thr Ala
            340                 345                 350
Glu Glu Val
        355

<210> SEQ ID NO 63
<211> LENGTH: 1068
<212> TYPE: DNA
<213> ORGANISM: Artificial Sequence
<220> FEATURE:
<223> OTHER INFORMATION: Recombinant

<400> SEQUENCE: 63
atggcttcta ctagagttct tgcttctaga ttggcttcac aaatggctgc atcagctaag      60
gttgcaaggc ctgcagtgag gtggcacaa gtcagtaagc gtactattca acaggtagt     120
ccattacaaa cactcaaacg aacacagatg acctccatcg taaatgccac gacccggcag    180
gcgtttcaga aacgcgccgc tatgcgtcaa tgcgccatct acggcaaagg tggtatcggt    240
aagtccacca ctactcagaa cctggtggca gccctggctg agatgggcaa gaaggtcatg    300
atcgttggtt gtgaccccga agctgactcc acccgcctga tcctgcactc caaggcccag    360
aacaccatca tggaaatggc tgccgaagcc ggtaccgtgg aagatctgga gctggaagac    420
gtgctgaagg ctggctacgg cggcgtcaag tgcgttgagt ccggtggtcc ggagccgggc    480
gttggctgcg ccggccgtgg tgttatcacc gccatcaact tcctggaaga ggaaggcgcc    540
tacgaagacg atctggactt cgtattctac gacgtgctgg gcgacgtggt gtgtggcggc    600
ttcgccatgc cgatccgcga gaacaaggcc caggaaatct acatcgtctg ctccggtgag    660
atgatggcca tgtacgccgc caacaacatc tccaagggca tcgtgaagta tgccaactcc    720
ggcagcgtgc gtctgggcgg cctgatctgc aacagccgta acaccgaccg cgaagacgag    780
ctgatcatcg ctctggccaa caagctgggc acccagatga tccacttcgt gccgcgtgac    840
aacgtcgtgc agcgcgccga aatccgccgc atgaccgtga tcgaatacga tccgaaagcc    900
aagcaagccg acgaataccg cgctctggcc cgcaaggtcg tcgacaacaa actgctggtc    960
atcccgaacc cgatcaccat ggacgagctc gaagagctgc tgatggaatt cggcatcatg   1020
```
gaagtcgaag acgaatccat cgtcggcaaa accgccgaag aagtctga                    1068

<210> SEQ ID NO 64
<211> LENGTH: 357
<212> TYPE: PRT
<213> ORGANISM: Artificial Sequence
<220> FEATURE:
<223> OTHER INFORMATION: Recombinant

<400> SEQUENCE: 64

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Tyr Ser Ala Met Arg Gln Cys Ala Ile Tyr Gly Lys Gly Gly
65                  70                  75                  80

Ile Gly Lys Ser Thr Thr Thr Gln Asn Leu Val Ala Ala Leu Ala Glu
                85                  90                  95

Met Gly Lys Lys Val Met Ile Val Gly Cys Asp Pro Lys Ala Asp Ser
            100                 105                 110

Thr Arg Leu Ile Leu His Ser Lys Ala Gln Asn Thr Ile Met Glu Met
        115                 120                 125

Ala Ala Glu Ala Gly Thr Val Glu Asp Leu Glu Leu Asp Val Leu
    130                 135                 140

Lys Ala Gly Tyr Gly Gly Val Lys Cys Val Glu Ser Gly Gly Pro Glu
145                 150                 155                 160

Pro Gly Val Gly Cys Ala Gly Arg Gly Val Ile Thr Ala Ile Asn Phe
                165                 170                 175

Leu Glu Glu Glu Gly Ala Tyr Glu Asp Asp Leu Asp Phe Val Phe Tyr
            180                 185                 190

Asp Val Leu Gly Asp Val Val Cys Gly Gly Phe Ala Met Pro Ile Arg
        195                 200                 205

Glu Asn Lys Ala Gln Glu Ile Tyr Ile Val Cys Ser Gly Glu Met Met
    210                 215                 220

Ala Met Tyr Ala Ala Asn Asn Ile Ser Lys Gly Ile Val Lys Tyr Ala
225                 230                 235                 240

Asn Ser Gly Ser Val Arg Leu Gly Gly Leu Ile Cys Asn Ser Arg Asn
                245                 250                 255

Thr Asp Arg Glu Asp Glu Leu Ile Ile Ala Leu Ala Asn Lys Leu Gly
            260                 265                 270

Thr Gln Met Ile His Phe Val Pro Arg Asp Asn Val Val Gln Arg Ala
        275                 280                 285

Glu Ile Arg Arg Met Thr Val Ile Glu Tyr Asp Pro Lys Ala Lys Gln
    290                 295                 300

Ala Asp Glu Tyr Arg Ala Leu Ala Arg Lys Val Val Asp Asn Lys Leu
305                 310                 315                 320

Leu Val Ile Pro Asn Pro Ile Thr Met Asp Glu Leu Glu Glu Leu Leu
                325                 330                 335

Met Glu Phe Gly Ile Met Glu Val Glu Asp Glu Ser Ile Val Gly Lys
            340                 345                 350

Thr Ala Glu Glu Val
        355

<210> SEQ ID NO 65
<211> LENGTH: 1074
<212> TYPE: DNA
<213> ORGANISM: Artificial Sequence
<220> FEATURE:
<223> OTHER INFORMATION: Recombinant

<400> SEQUENCE: 65

| | | |
|---|---|---|
| atggcttcta ctagagttct tgcttctaga ttggcttcac aaatggctgc atcagctaag | 60 |
| gttgcaaggc ctgcagtgag ggtggcacaa gtcagtaagc gtactattca aacaggtagt | 120 |
| ccattacaaa cactcaaacg aacacagatg acctccatcg taaatgccac gacccggcag | 180 |
| gcgtttcaga aacgcgccta ttcggctatg cgtcaatgcg ccatctacgg caaaggtggt | 240 |
| atcggtaagt ccaccactac tcagaacctg gtggcagccc tggctgagat gggcaagaag | 300 |
| gtcatgatcg ttggttgtga cccgaaagct gactccaccc gcctgatcct gcactccaag | 360 |
| gcccagaaca ccatcatgga aatggctgcc gaagccggta ccgtggaaga tctggagctg | 420 |
| gaagacgtgc tgaaggctgg ctacggcggc gtcaagtgcg ttgagtccgg tggtccggag | 480 |
| ccgggcgttg gctgcgccgg ccgtggtgtt atcaccgcca tcaacttcct ggaagaggaa | 540 |
| ggcgcctacg aagacgatct ggacttcgta ttctacgacg tgctgggcga cgtggtgtgt | 600 |
| ggcggcttcg ccatgccgat ccgcgagaac aaggcccagg aaatctacat cgtctgctcc | 660 |
| ggtgagatga tggccatgta cgccgccaac aacatctcca agggcatcgt gaagtatgcc | 720 |
| aactccggca gcgtgcgtct gggcggcctg atctgcaaca gccgtaacac cgaccgcgaa | 780 |
| gacgagctga tcatcgctct ggccaacaag ctgggcaccc agatgatcca cttcgtgccg | 840 |
| cgtgacaacg tcgtgcagcg cgccgaaatc cgccgcatga ccgtgatcga atacgatccg | 900 |
| aaagccaagc aagccgacga ataccgcgct ctggcccgca aggtcgtcga caacaaactg | 960 |
| ctggtcatcc cgaacccgat caccatggac gagctcgaag agctgctgat ggaattcggc | 1020 |
| atcatggaag tcgaagacga atccatcgtc ggcaaaaccg ccgaagaagt ctga | 1074 |

<210> SEQ ID NO 66
<211> LENGTH: 359
<212> TYPE: PRT
<213> ORGANISM: Artificial Sequence
<220> FEATURE:
<223> OTHER INFORMATION: Recombinant

<400> SEQUENCE: 66

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Tyr Ser Ser Glu Ala Met Arg Gln Cys Ala Ile Tyr Gly Lys
65                  70                  75                  80

Gly Gly Ile Gly Lys Ser Thr Thr Thr Gln Asn Leu Val Ala Ala Leu
                85                  90                  95

Ala Glu Met Gly Lys Lys Val Met Ile Val Gly Cys Asp Pro Lys Ala
            100                 105                 110

Asp Ser Thr Arg Leu Ile Leu His Ser Lys Ala Gln Asn Thr Ile Met
            115                 120                 125

Glu Met Ala Ala Glu Ala Gly Thr Val Glu Asp Leu Glu Leu Glu Asp
    130                 135                 140

Val Leu Lys Ala Gly Tyr Gly Val Lys Cys Val Glu Ser Gly Gly
145                 150                 155                 160

Pro Glu Pro Gly Val Gly Cys Ala Gly Arg Gly Val Ile Thr Ala Ile
                165                 170                 175

Asn Phe Leu Glu Glu Glu Gly Ala Tyr Glu Asp Leu Asp Phe Val
            180                 185                 190

Phe Tyr Asp Val Leu Gly Asp Val Val Cys Gly Gly Phe Ala Met Pro
            195                 200                 205

Ile Arg Glu Asn Lys Ala Gln Glu Ile Tyr Ile Val Cys Ser Gly Glu
            210                 215                 220

Met Met Ala Met Tyr Ala Ala Asn Asn Ile Ser Lys Gly Ile Val Lys
225                 230                 235                 240

Tyr Ala Asn Ser Gly Ser Val Arg Leu Gly Gly Leu Ile Cys Asn Ser
                245                 250                 255

Arg Asn Thr Asp Arg Glu Asp Glu Leu Ile Ile Ala Leu Ala Asn Lys
            260                 265                 270

Leu Gly Thr Gln Met Ile His Phe Val Pro Arg Asp Asn Val Val Gln
            275                 280                 285

Arg Ala Glu Ile Arg Arg Met Thr Val Ile Glu Tyr Asp Pro Lys Ala
            290                 295                 300

Lys Gln Ala Asp Glu Tyr Arg Ala Leu Ala Arg Lys Val Val Asp Asn
305                 310                 315                 320

Lys Leu Leu Val Ile Pro Asn Pro Ile Thr Met Asp Glu Leu Glu Glu
                325                 330                 335

Leu Leu Met Glu Phe Gly Ile Met Glu Val Glu Asp Glu Ser Ile Val
            340                 345                 350

Gly Lys Thr Ala Glu Glu Val
            355

<210> SEQ ID NO 67
<211> LENGTH: 1080
<212> TYPE: DNA
<213> ORGANISM: Artificial Sequence
<220> FEATURE:
<223> OTHER INFORMATION: Recombinant

<400> SEQUENCE: 67
atggcttcta ctagagttct tgcttctaga ttggcttcac aaatggctgc atcagctaag      60
gttgcaaggc ctgcagtgag ggtggcacaa gtcagtaagc gtactattca acaggtagt     120
ccattacaaa cactcaaacg aacacagatg acctccatcg taaatgccac gacccggcag    180
gcgtttcaga aacgcgccta ttcgagcgaa gctatgcgtc aatgcgccat ctacggcaaa    240
ggtggtatcg gtaagtccac cactactcag aacctggtgg cagccctggc tgagatgggc    300
aagaaggtca tgatcgttgg ttgtgacccg aaagctgact ccacccgcct gatcctgcac    360
tccaaggccc agaacaccat catggaaatg gctgccgaag ccggtaccgt ggaagatctg    420
gagctggaag acgtgctgaa ggctggctac ggcggcgtca agtgcgttga gtccggtggt    480
ccggagccgg gcgttggctg cgccggccgt ggtgttatca ccgccatcaa cttcctggaa    540
gaggaaggcg cctacgaaga cgatctggac ttcgtattct acgacgtgct gggcgacgtg    600

```
gtgtgtggcg gcttcgccat gccgatccgc gagaacaagg cccaggaaat ctacatcgtc    660
tgctccggtg agatgatggc catgtacgcc gccaacaaca tctccaaggg catcgtgaag    720
tatgccaact ccggcagcgt gcgtctgggc ggcctgatct gcaacagccg taacaccgac    780
cgcgaagacg agctgatcat cgctctggcc aacaagctgg gcacccagat gatccacttc    840
gtgccgcgtg acaacgtcgt gcagcgcgcc gaaatccgcc gcatgaccgt gatcgaatac    900
gatccgaaag ccaagcaagc cgacgaatac cgcgctctgg cccgcaaggt cgtcgacaac    960
aaactgctgg tcatcccgaa cccgatcacc atggacgagc tcgaagagct gctgatggaa   1020
ttcggcatca tggaagtcga agacgaatcc atcgtcggca aaaccgccga agaagtctga   1080
```

<210> SEQ ID NO 68
<211> LENGTH: 320
<212> TYPE: PRT
<213> ORGANISM: Artificial Sequence
<220> FEATURE:
<223> OTHER INFORMATION: Recombinant

<400> SEQUENCE: 68

```
Met Ala Met Ala Asn Leu Ala Arg Arg Lys Gly Tyr Ser Leu Leu Ser
1               5                   10                  15

Ser Glu Thr Leu Arg Tyr Ser Phe Ser Leu Arg Ser Arg Ala Phe Ala
            20                  25                  30

Met Arg Gln Cys Ala Ile Tyr Gly Lys Gly Ile Gly Lys Ser Thr
        35                  40                  45

Thr Thr Gln Asn Leu Val Ala Ala Leu Ala Glu Met Gly Lys Lys Val
    50                  55                  60

Met Ile Val Gly Cys Asp Pro Lys Ala Asp Ser Thr Arg Leu Ile Leu
65                  70                  75                  80

His Ser Lys Ala Gln Asn Thr Ile Met Glu Met Ala Ala Glu Ala Gly
                85                  90                  95

Thr Val Glu Asp Leu Glu Leu Glu Asp Val Leu Lys Ala Gly Tyr Gly
            100                 105                 110

Gly Val Lys Cys Val Glu Ser Gly Gly Pro Glu Pro Gly Val Gly Cys
        115                 120                 125

Ala Gly Arg Gly Val Ile Thr Ala Ile Asn Phe Leu Glu Glu Glu Gly
    130                 135                 140

Ala Tyr Glu Asp Asp Leu Asp Phe Val Phe Tyr Asp Val Leu Gly Asp
145                 150                 155                 160

Val Val Cys Gly Gly Phe Ala Met Pro Ile Arg Glu Asn Lys Ala Gln
                165                 170                 175

Glu Ile Tyr Ile Val Cys Ser Gly Glu Met Met Ala Met Tyr Ala Ala
            180                 185                 190

Asn Asn Ile Ser Lys Gly Ile Val Lys Tyr Ala Asn Ser Gly Ser Val
        195                 200                 205

Arg Leu Gly Gly Leu Ile Cys Asn Ser Arg Asn Thr Asp Arg Glu Asp
    210                 215                 220

Glu Leu Ile Ile Ala Leu Ala Asn Lys Leu Gly Thr Gln Met Ile His
225                 230                 235                 240

Phe Val Pro Arg Asp Asn Val Val Gln Arg Ala Glu Ile Arg Arg Met
                245                 250                 255

Thr Val Ile Glu Tyr Asp Pro Lys Ala Lys Gln Ala Asp Glu Tyr Arg
            260                 265                 270

Ala Leu Ala Arg Lys Val Val Asp Asn Lys Leu Leu Val Ile Pro Asn
        275                 280                 285
```

Pro Ile Thr Met Asp Glu Leu Glu Glu Leu Leu Met Glu Phe Gly Ile
    290                 295                 300

Met Glu Val Glu Asp Glu Ser Ile Val Gly Lys Thr Ala Glu Glu Val
305                 310                 315                 320

<210> SEQ ID NO 69
<211> LENGTH: 963
<212> TYPE: DNA
<213> ORGANISM: Artificial Sequence
<220> FEATURE:
<223> OTHER INFORMATION: Recombinant

<400> SEQUENCE: 69
atggctatgg caaatcttgc tagaaggaag ggttattcac ttttgtcatc tgaaactctt      60
aggtactcat tttctcttag atcaagagct ttcgctatgc gtcaatgcgc catctacggc     120
aaaggtggta tcggtaagtc caccactact cagaacctgg tggcagccct ggctgagatg     180
ggcaagaagg tcatgatcgt tggttgtgac ccgaaagctg actccacccg cctgatcctg     240
cactccaagg cccagaacac catcatggaa atggctgccg aagccggtac cgtggaagat     300
ctggagctgg aagacgtgct gaaggctggc tacggcggcg tcaagtgcgt tgagtccggt     360
ggtccggagc cgggcgttgg ctgcgccggc cgtggtgtta tcaccgccat caacttcctg     420
gaagaggaag cgcctacga agacgatctg gacttcgtat tctacgacgt gctgggcgac     480
gtggtgtgtg cggcttcgc catgccgatc cgcgagaaca aggcccagga aatctacatc     540
gtctgctccg gtgagatgat ggccatgtac gccgccaaca acatctccaa gggcatcgtg     600
aagtatgcca actccggcag cgtgcgtctg gcggcctga tctgcaacag ccgtaacacc     660
gaccgcgaag acgagctgat catcgctctg gccaacaagc tgggcaccca gatgatccac     720
ttcgtgccgc gtgacaacgt cgtgcagcgc gccgaaatcc gccgcatgac cgtgatcgaa     780
tacgatccga agccaagca agccgacgaa taccgcgctc tggcccgcaa ggtcgtcgac     840
aacaaactgc tggtcatccc gaacccgatc accatggacg agctcgaaga gctgctgatg     900
gaattcggca tcatggaagt cgaagacgaa tccatcgtcg gcaaaaccgc cgaagaagtc     960
tga                                                                  963

<210> SEQ ID NO 70
<211> LENGTH: 353
<212> TYPE: PRT
<213> ORGANISM: Artificial Sequence
<220> FEATURE:
<223> OTHER INFORMATION: Recombinant

<400> SEQUENCE: 70

Met Asp Arg Ala Arg Arg Leu Ala Asn Lys Ala Ile Leu Gly Arg Leu
1               5                   10                  15

Val Ser Gln Thr Lys His Asn Pro Ser Ile Ser Ser Pro Ala Leu Cys
                20                  25                  30

Ser Pro Ser Arg Tyr Val Ser Ser Leu Ser Pro Tyr Val Cys Ser Gly
            35                  40                  45

Thr Asn Val Arg Ser Asp Arg Asn Leu Asn Gly Phe Gly Ser Gln Val
        50                  55                  60

Arg Thr Arg Gln Cys Ala Ile Tyr Gly Lys Gly Ile Gly Lys Ser
65                  70                  75                  80

Thr Thr Thr Gln Asn Leu Val Ala Ala Leu Ala Glu Met Gly Lys Lys
                85                  90                  95

Val Met Ile Val Gly Cys Asp Pro Lys Ala Asp Ser Thr Arg Leu Ile
                100                 105                 110

Leu His Ser Lys Ala Gln Asn Thr Ile Met Glu Met Ala Ala Glu Ala
            115                 120                 125

Gly Thr Val Glu Asp Leu Glu Leu Glu Asp Val Leu Lys Ala Gly Tyr
        130                 135                 140

Gly Gly Val Lys Cys Val Ser Gly Gly Pro Glu Pro Gly Val Gly
145                 150                 155                 160

Cys Ala Gly Arg Gly Val Ile Thr Ala Ile Asn Phe Leu Glu Glu
                165                 170                 175

Gly Ala Tyr Glu Asp Asp Leu Asp Phe Val Phe Tyr Asp Val Leu Gly
            180                 185                 190

Asp Val Val Cys Gly Gly Phe Ala Met Pro Ile Arg Glu Asn Lys Ala
        195                 200                 205

Gln Glu Ile Tyr Ile Val Cys Ser Gly Glu Met Met Ala Met Tyr Ala
    210                 215                 220

Ala Asn Asn Ile Ser Lys Gly Ile Val Lys Tyr Ala Asn Ser Gly Ser
225                 230                 235                 240

Val Arg Leu Gly Gly Leu Ile Cys Asn Ser Arg Asn Thr Asp Arg Glu
                245                 250                 255

Asp Glu Leu Ile Ile Ala Leu Ala Asn Lys Leu Gly Thr Gln Met Ile
            260                 265                 270

His Phe Val Pro Arg Asp Asn Val Gln Arg Ala Glu Ile Arg Arg
        275                 280                 285

Met Thr Val Ile Glu Tyr Asp Pro Lys Ala Lys Gln Ala Asp Glu Tyr
    290                 295                 300

Arg Ala Leu Ala Arg Lys Val Val Asp Asn Lys Leu Leu Val Ile Pro
305                 310                 315                 320

Asn Pro Ile Thr Met Asp Glu Leu Glu Glu Leu Leu Met Glu Phe Gly
                325                 330                 335

Ile Met Glu Val Glu Asp Glu Ser Ile Val Gly Lys Thr Ala Glu Glu
            340                 345                 350

Val

<210> SEQ ID NO 71
<211> LENGTH: 1062
<212> TYPE: DNA
<213> ORGANISM: Artificial Sequence
<220> FEATURE:
<223> OTHER INFORMATION: Recombinant

<400> SEQUENCE: 71
atggatagag ctaggagact tgctaataag gcaattttgg gtaggcttgt ttctcaaact    60
aaacataatc cttcaatttc ttcaccagct ttgtgttcac cttctagata tgtttcatct   120
ctttcaccat acgtgtgctc tggaacaaac gttaggtcag atagaaattt gaacggtttt   180
ggatctcagg tgaggactcg tcaatgcgcc atctacggca aggtggtat cggtaagtcc   240 accactactc agaacctggt ggcagccctg gctgagatgg caagaaggt catgatcgtt   300 ggttgtgacc cgaaagctga ctccacccgc ctgatcctgc actccaaggc ccagaacacc   360
atcatggaaa tggctgccga agccggtacc gtggaagatc tggagctgga agacgtgctg   420
aaggctggct acggcggcgt caagtgcgtt gagtccggtg gtccggagcc gggcgttggc   480
tgcgccggcc gtggtgttat caccgccatc aacttcctgg aagaggaagg cgcctacgaa   540
gacgatctgg acttcgtatt ctacgacgtg ctgggcgacg tggtgtgtgg cggcttcgcc   600

```
atgccgatcc gcgagaacaa ggcccaggaa atctacatcg tctgctccgg tgagatgatg    660
gccatgtacg ccgccaacaa catctccaag ggcatcgtga agtatgccaa ctccggcagc    720
gtgcgtctgg gcggcctgat ctgcaacagc cgtaacaccg accgcgaaga cgagctgatc    780
atcgctctgg ccaacaagct gggcacccag atgatccact cgtgccgcg tgacaacgtc     840 gtgcagcgcg ccgaaatccg ccgcatgacc gtgatcgaat cgatccgaa agccaagcaa     900 gccgacgaat accgcgctct ggcccgcaag gtcgtcgaca caaaactgct ggtcatcccg    960
aacccgatca ccatggacga gctcgaagag ctgctgatgg aattcggcat catggaagtc   1020
gaagacgaat ccatcgtcgg caaaaccgcc gaagaagtct ga                      1062
```

<210> SEQ ID NO 72
<211> LENGTH: 357
<212> TYPE: PRT
<213> ORGANISM: Artificial Sequence
<220> FEATURE:
<223> OTHER INFORMATION: Recombinant

<400> SEQUENCE: 72

```
Met Asp Arg Ala Arg Arg Leu Ala Asn Lys Ala Ile Leu Gly Arg Leu
1               5                   10                  15

Val Ser Gln Thr Lys His Asn Pro Ser Ile Ser Pro Ala Leu Cys
            20                  25                  30

Ser Pro Ser Arg Tyr Val Ser Leu Ser Pro Tyr Val Cys Ser Gly
        35                  40                  45

Thr Asn Val Arg Ser Asp Arg Asn Leu Asn Gly Phe Gly Ser Gln Val
50                  55                  60

Arg Thr Ile Ser Ala Met Arg Gln Cys Ala Ile Tyr Gly Lys Gly Gly
65                  70                  75                  80

Ile Gly Lys Ser Thr Thr Thr Gln Asn Leu Val Ala Ala Leu Ala Glu
                85                  90                  95

Met Gly Lys Lys Val Met Ile Val Gly Cys Asp Pro Lys Ala Asp Ser
            100                 105                 110

Thr Arg Leu Ile Leu His Ser Lys Ala Gln Asn Thr Ile Met Glu Met
        115                 120                 125

Ala Ala Glu Ala Gly Thr Val Glu Asp Leu Glu Leu Glu Asp Val Leu
130                 135                 140

Lys Ala Gly Tyr Gly Gly Val Lys Cys Val Glu Ser Gly Gly Pro Glu
145                 150                 155                 160

Pro Gly Val Gly Cys Ala Gly Arg Gly Val Ile Thr Ala Ile Asn Phe
                165                 170                 175

Leu Glu Glu Glu Gly Ala Tyr Glu Asp Asp Leu Asp Phe Val Phe Tyr
            180                 185                 190

Asp Val Leu Gly Asp Val Val Cys Gly Gly Phe Ala Met Pro Ile Arg
        195                 200                 205

Glu Asn Lys Ala Gln Glu Ile Tyr Ile Val Cys Ser Gly Glu Met Met
210                 215                 220

Ala Met Tyr Ala Ala Asn Asn Ile Ser Lys Gly Ile Val Lys Tyr Ala
225                 230                 235                 240

Asn Ser Gly Ser Val Arg Leu Gly Gly Leu Ile Cys Asn Ser Arg Asn
                245                 250                 255

Thr Asp Arg Glu Asp Glu Leu Ile Ile Ala Leu Ala Asn Lys Leu Gly
            260                 265                 270

Thr Gln Met Ile His Phe Val Pro Arg Asp Asn Val Val Gln Arg Ala
```

```
                275                 280                 285
Glu Ile Arg Arg Met Thr Val Ile Glu Tyr Asp Pro Lys Ala Lys Gln
        290                 295                 300

Ala Asp Glu Tyr Arg Ala Leu Ala Arg Lys Val Val Asp Asn Lys Leu
305                 310                 315                 320

Leu Val Ile Pro Asn Pro Ile Thr Met Asp Glu Leu Glu Leu Leu
                325                 330                 335

Met Glu Phe Gly Ile Met Glu Val Glu Asp Glu Ser Ile Val Gly Lys
            340                 345                 350

Thr Ala Glu Glu Val
            355

<210> SEQ ID NO 73
<211> LENGTH: 1074
<212> TYPE: DNA
<213> ORGANISM: Artificial Sequence
<220> FEATURE:
<223> OTHER INFORMATION: Recombinant

<400> SEQUENCE: 73
atggatagag ctagaaggct tgctaataag gcaattttgg gtaggttggt ttctcaaact      60
aagcataatc cttctatctc ttcaccagca ttatgttcac catcacgtta tgttagttcc     120
ctcagtccct acgtgtgctc cggaacaaat gtgcgcagcg accggaacct aaacggcttt     180
gggagccagg tccgaaccat atcggctatg cgtcaatgcg ccatctacgg caaaggtggt     240
atcggtaagt ccaccactac tcagaacctg gtggcagccc tggctgagat gggcaagaag     300
gtcatgatcg ttggttgtga cccgaaagct gactccaccc gcctgatcct gcactccaag     360
gcccagaaca ccatcatgga aatggctgcc gaagccggta ccgtggaaga tctggagctg     420
gaagacgtgc tgaaggctgg ctacggcggc gtcaagtgcg ttgagtccgg tggtccggag     480
ccgggcgttg gctgcgccgg ccgtggtgtt atcaccgcca tcaacttcct ggaagaggaa     540
ggcgcctacg aagacgatct ggacttcgta ttctacgacg tgctgggcga cgtggtgtgt     600
ggcggcttcg ccatgccgat ccgcgagaac aaggcccagg aaatctacat cgtctgctcc     660
ggtgagatga tggccatgta cgccgccaac aacatctcca agggcatcgt gaagtatgcc     720
aactccggca gcgtgcgtct gggcggcctg atctgcaaca gccgtaacac cgaccgcgaa     780
gacgagctga tcatcgctct ggccaacaag ctgggcaccc cagatgatcc cttcgtgccg     840
cgtgacaacg tcgtgcagcg cgccgaaatc cgccgcatga ccgtgatcga atacgatccg     900
aaagccaagc aagccgacga ataccgcgct ctggcccgca aggtcgtcga caacaaactg     960
ctggtcatcc cgaacccgat caccatggac gagctcgaag agctgctgat ggaattcggc    1020
atcatggaag tcgaagacga atccatcgtc ggcaaaaccg ccgaagaagt ctga          1074

<210> SEQ ID NO 74
<211> LENGTH: 363
<212> TYPE: PRT
<213> ORGANISM: Artificial Sequence
<220> FEATURE:
<223> OTHER INFORMATION: Recombinant

<400> SEQUENCE: 74

Met Asp Arg Ala Arg Arg Leu Ala Asn Lys Ala Ile Leu Gly Arg Leu
1               5                   10                  15

Val Ser Gln Thr Lys His Asn Pro Ser Ile Ser Ser Pro Ala Leu Cys
            20                  25                  30
```

| | | | | | | | | | | | |
|---|---|---|---|---|---|---|---|---|---|---|---|
|Ser|Pro|Ser|Arg|Tyr|Val|Ser|Ser|Leu|Ser|Pro|Tyr|Val|Cys|Ser|Gly|
| | |35| | | |40| | | |45| |

Ser Pro Ser Arg Tyr Val Ser Ser Leu Ser Pro Tyr Val Cys Ser Gly
            35                  40                  45

Thr Asn Val Arg Ser Asp Arg Asn Leu Asn Gly Phe Gly Ser Gln Val
 50                  55                  60

Arg Thr Ile Ser Val Glu Ala Leu Lys Pro Ala Met Arg Gln Cys Ala
 65                  70                  75                  80

Ile Tyr Gly Lys Gly Gly Ile Gly Lys Ser Thr Thr Gln Asn Leu
                85                  90                  95

Val Ala Ala Leu Ala Glu Met Gly Lys Lys Val Met Ile Val Gly Cys
                100                 105                 110

Asp Pro Lys Ala Asp Ser Thr Arg Leu Ile Leu His Ser Lys Ala Gln
                115                 120                 125

Asn Thr Ile Met Glu Met Ala Ala Glu Ala Gly Thr Val Glu Asp Leu
130                 135                 140

Glu Leu Glu Asp Val Leu Lys Ala Gly Tyr Gly Gly Val Lys Cys Val
145                 150                 155                 160

Glu Ser Gly Gly Pro Glu Pro Gly Val Gly Cys Ala Gly Arg Gly Val
                165                 170                 175

Ile Thr Ala Ile Asn Phe Leu Glu Glu Glu Gly Ala Tyr Glu Asp Asp
                180                 185                 190

Leu Asp Phe Val Phe Tyr Asp Val Leu Gly Asp Val Val Cys Gly Gly
                195                 200                 205

Phe Ala Met Pro Ile Arg Glu Asn Lys Ala Gln Glu Ile Tyr Ile Val
210                 215                 220

Cys Ser Gly Glu Met Met Ala Met Tyr Ala Ala Asn Asn Ile Ser Lys
225                 230                 235                 240

Gly Ile Val Lys Tyr Ala Asn Ser Gly Ser Val Arg Leu Gly Gly Leu
                245                 250                 255

Ile Cys Asn Ser Arg Asn Thr Asp Arg Glu Asp Glu Leu Ile Ile Ala
                260                 265                 270

Leu Ala Asn Lys Leu Gly Thr Gln Met Ile His Phe Val Pro Arg Asp
                275                 280                 285

Asn Val Val Gln Arg Ala Glu Ile Arg Arg Met Thr Val Ile Glu Tyr
290                 295                 300

Asp Pro Lys Ala Lys Gln Ala Asp Glu Tyr Arg Ala Leu Ala Arg Lys
305                 310                 315                 320

Val Val Asp Asn Lys Leu Leu Val Ile Pro Asn Pro Ile Thr Met Asp
                325                 330                 335

Glu Leu Glu Glu Leu Leu Met Glu Phe Gly Ile Met Glu Val Glu Asp
                340                 345                 350

Glu Ser Ile Val Gly Lys Thr Ala Glu Glu Val
                355                 360

<210> SEQ ID NO 75
<211> LENGTH: 1092
<212> TYPE: DNA
<213> ORGANISM: Artificial Sequence
<220> FEATURE:
<223> OTHER INFORMATION: Recombinant

<400> SEQUENCE: 75
atggatagag ctagaaggct tgctaataag gcaattttgg gtaggttggt ttctcaaact    60
aagcataatc cttctatctc ttccaccagca ttatgttcac catcacgtta tgttagttcc   120
ctcagtccct acgtgtgctc cggaacaaat gtgcgcagcg accggaacct aaacggcttt   180

```
gggagccagg tccgaaccat atcggtagaa gccctgaaac cggctatgcg tcaatgcgcc    240
atctacggca aggtggtat cggtaagtcc accactactc agaacctggt ggcagccctg     300
gctgagatgg gcaagaaggt catgatcgtt ggttgtgacc cgaaagctga ctccacccgc    360
ctgatcctgc actccaaggc ccagaacacc atcatggaaa tggctgccga agccggtacc    420
gtggaagatc tggagctgga agacgtgctg aaggctggct acggcggcgt caagtgcgtt    480
gagtccggtg gtccggagcc gggcgttggc tgcgccggcc gtggtgttat caccgccatc    540
aacttcctgg aagaggaagg cgcctacgaa gacgatctgg acttcgtatt ctacgacgtg    600
ctgggcgacg tggtgtgtgg cggcttcgcc atgccgatcc gcgagaacaa ggcccaggaa    660
atctacatcg tctgctccgg tgagatgatg gccatgtacg ccgccaacaa catctccaag    720
ggcatcgtga agtatgccaa ctccggcagc gtgcgtctgg cggcctgat ctgcaacagc     780
cgtaacaccg accgcgaaga cgagctgatc atcgctctgg ccaacaagct gggcacccag    840
atgatccact tcgtgccgcg tgacaacgtc gtgcagcgcg ccgaaatccg ccgcatgacc    900
gtgatcgaat acgatccgaa agccaagcaa gccgacgaat accgcgctct ggcccgcaag    960
gtcgtcgaca acaaactgct ggtcatcccg aacccgatca ccatggacga gctcgaagag    1020
ctgctgatgg aattcggcat catggaagtc gaagacgaat ccatcgtcgg caaaaccgcc    1080
gaagaagtct ga                                                        1092
```

<210> SEQ ID NO 76
<211> LENGTH: 375
<212> TYPE: PRT
<213> ORGANISM: Artificial Sequence
<220> FEATURE:
<223> OTHER INFORMATION: Recombinant

<400> SEQUENCE: 76

```
Met Glu Arg Ala Arg Arg Leu Ala Asn Arg Ala Thr Leu Lys Arg Leu
1               5                   10                  15

Leu Ser Glu Ala Lys Gln Asn Arg Lys Thr Glu Ser Thr Ser Thr Thr
            20                  25                  30

Thr Thr Thr Pro Leu Pro Phe Ser Leu Ser Gly Ser Ser Ser Arg Tyr
        35                  40                  45

Val Ser Val Ser Asn Ser Ile Leu Arg Gly Arg Gly Ser Lys Pro
    50                  55                  60

Asp Asn Asn Val Ser Arg Arg Val Gly Gly Phe Leu Gly Val Gly Tyr
65                  70                  75                  80

Pro Ser Gln Ser Arg Ser Ala Met Arg Gln Cys Ala Ile Tyr Gly Lys
                85                  90                  95

Gly Gly Ile Gly Lys Ser Thr Thr Thr Gln Asn Leu Val Ala Ala Leu
            100                 105                 110

Ala Glu Met Gly Lys Lys Val Met Ile Val Gly Cys Asp Pro Lys Ala
        115                 120                 125

Asp Ser Thr Arg Leu Ile Leu His Ser Lys Ala Gln Asn Thr Ile Met
    130                 135                 140

Glu Met Ala Ala Glu Ala Gly Thr Val Glu Asp Leu Glu Leu Glu Asp
145                 150                 155                 160

Val Leu Lys Ala Gly Tyr Gly Gly Val Lys Cys Val Glu Ser Gly Gly
                165                 170                 175

Pro Glu Pro Gly Val Gly Cys Ala Gly Arg Gly Val Ile Thr Ala Ile
            180                 185                 190

Asn Phe Leu Glu Glu Glu Gly Ala Tyr Glu Asp Asp Leu Asp Phe Val
```

```
                195                 200                 205
Phe Tyr Asp Val Leu Gly Asp Val Val Cys Gly Gly Phe Ala Met Pro
    210                 215                 220
Ile Arg Glu Asn Lys Ala Gln Glu Ile Tyr Ile Val Cys Ser Gly Glu
225                 230                 235                 240
Met Met Ala Met Tyr Ala Ala Asn Asn Ile Ser Lys Gly Ile Val Lys
                245                 250                 255
Tyr Ala Asn Ser Gly Ser Val Arg Leu Gly Gly Leu Ile Cys Asn Ser
                260                 265                 270
Arg Asn Thr Asp Arg Glu Asp Glu Leu Ile Ile Ala Leu Ala Asn Lys
            275                 280                 285
Leu Gly Thr Gln Met Ile His Phe Val Pro Arg Asp Asn Val Val Gln
        290                 295                 300
Arg Ala Glu Ile Arg Arg Met Thr Val Ile Glu Tyr Asp Pro Lys Ala
305                 310                 315                 320
Lys Gln Ala Asp Glu Tyr Arg Ala Leu Ala Arg Lys Val Val Asp Asn
                325                 330                 335
Lys Leu Leu Val Ile Pro Asn Pro Ile Thr Met Asp Glu Leu Glu Glu
            340                 345                 350
Leu Leu Met Glu Phe Gly Ile Met Glu Val Glu Asp Glu Ser Ile Val
        355                 360                 365
Gly Lys Thr Ala Glu Glu Val
    370                 375

<210> SEQ ID NO 77
<211> LENGTH: 1128
<212> TYPE: DNA
<213> ORGANISM: Artificial Sequence
<220> FEATURE:
<223> OTHER INFORMATION: Recombinant

<400> SEQUENCE: 77
atggaaagag ctagaaggct tgctaataga gcaactctta agagattgct ttctgaggcc      60
aagcaaaata ggaaaactga gtctacatct acaaccacaa ccacgccttt gccattttca     120
ctctctggtt caagttcaag gtatgttcct agtgtttcaa atagtattct gcgtggtaga     180
ggatccaaac ccgataacaa cgtgtccagg cgtgtcggag gcttcttggg agttgggtac     240
ccgtctcaga gccgttcagc tatgcgtcaa tgcgccatct acggcaaagg tggtatcggt     300
aagtccacca ctactcagaa cctggtggca gccctggctg agatgggcaa gaaggtcatg     360
atcgttggtt gtgacccgaa agctgactcc acccgcctga tcctgcactc caaggcccag     420
aacaccatca tggaaatggc tgccgaagcc ggtaccgtgg aagatctgga gctggaagac     480
gtgctgaagg ctggctacgg cggcgtcaag tgcgttgagt ccgtggtgcc ggagccgggc     540
gttggctgcg ccggccgtgg tgttatcacc gccatcaact tcctggaaga ggaaggcgcc     600
tacgaagacg atctggactt cgtattctac gacgtgctgg cgacgtggt gtgtggcggc      660 ttcgccatgc cgatccgcga gaacaaggcc caggaaatct acatcgtctg ctccggtgag     720
atgatggcca tgtacgccgc caacaacatc tccaagggca tcgtgaagta tgccaactcc     780
ggcagcgtgc gtctgggcgg cctgatctgc aacagccgta acaccgaccg cgaagacgag     840
ctgatcatcg ctctggccaa caagctgggc acccagatga tccacttcgt gccgcgtgac     900
aacgtcgtgc agcgcgccga aatccgccgc atgaccgtga tcgaatacga tccgaaagcc     960
aagcaagccg acgaataccg cgctctggcc cgcaaggtcg tcgacaacaa actgctggtc    1020
```

```
atcccgaacc cgatcaccat ggacgagctc gaagagctgc tgatggaatt cggcatcatg    1080
gaagtcgaag acgaatccat cgtcggcaaa accgccgaag aagtctga                1128
```

<210> SEQ ID NO 78
<211> LENGTH: 377
<212> TYPE: PRT
<213> ORGANISM: Artificial Sequence
<220> FEATURE:
<223> OTHER INFORMATION: Recombinant

<400> SEQUENCE: 78

```
Met Glu Arg Ala Arg Arg Leu Ala Asn Arg Ala Thr Leu Lys Arg Leu
1               5                   10                  15

Leu Ser Glu Ala Lys Gln Asn Arg Lys Thr Glu Ser Thr Ser Thr Thr
            20                  25                  30

Thr Thr Thr Pro Leu Pro Phe Ser Leu Ser Gly Ser Ser Arg Tyr
        35                  40                  45

Val Ser Val Ser Asn Ser Ile Leu Arg Gly Arg Gly Ser Lys Pro
50                  55                  60

Asp Asn Asn Val Ser Arg Arg Val Gly Gly Phe Leu Gly Val Gly Tyr
65                  70                  75                  80

Pro Ser Gln Ser Arg Ser Ile Ser Ala Met Arg Gln Cys Ala Ile Tyr
                85                  90                  95

Gly Lys Gly Gly Ile Gly Lys Ser Thr Thr Thr Gln Asn Leu Val Ala
            100                 105                 110

Ala Leu Ala Glu Met Gly Lys Lys Val Met Ile Val Gly Cys Asp Pro
        115                 120                 125

Lys Ala Asp Ser Thr Arg Leu Ile Leu His Ser Lys Ala Gln Asn Thr
130                 135                 140

Ile Met Glu Met Ala Ala Glu Ala Gly Thr Val Glu Asp Leu Glu Leu
145                 150                 155                 160

Glu Asp Val Leu Lys Ala Gly Tyr Gly Gly Val Lys Cys Val Glu Ser
                165                 170                 175

Gly Gly Pro Glu Pro Gly Val Gly Cys Ala Gly Arg Gly Val Ile Thr
            180                 185                 190

Ala Ile Asn Phe Leu Glu Glu Glu Gly Ala Tyr Glu Asp Asp Leu Asp
        195                 200                 205

Phe Val Phe Tyr Asp Val Leu Gly Asp Val Val Cys Gly Gly Phe Ala
210                 215                 220

Met Pro Ile Arg Glu Asn Lys Ala Gln Glu Ile Tyr Ile Val Cys Ser
225                 230                 235                 240

Gly Glu Met Met Ala Met Tyr Ala Ala Asn Asn Ile Ser Lys Gly Ile
                245                 250                 255

Val Lys Tyr Ala Asn Ser Gly Ser Val Arg Leu Gly Gly Leu Ile Cys
            260                 265                 270

Asn Ser Arg Asn Thr Asp Arg Glu Asp Glu Leu Ile Ile Ala Leu Ala
        275                 280                 285

Asn Lys Leu Gly Thr Gln Met Ile His Phe Val Pro Arg Asp Asn Val
290                 295                 300

Val Gln Arg Ala Glu Ile Arg Arg Met Thr Val Ile Glu Tyr Asp Pro
305                 310                 315                 320

Lys Ala Lys Gln Ala Asp Glu Tyr Arg Ala Leu Ala Arg Lys Val Val
                325                 330                 335

Asp Asn Lys Leu Leu Val Ile Pro Asn Pro Ile Thr Met Asp Glu Leu
            340                 345                 350
```

```
Glu Leu Leu Met Glu Phe Gly Ile Met Glu Val Glu Asp Glu Ser
        355                 360                 365

Ile Val Gly Lys Thr Ala Glu Glu Val
    370                 375

<210> SEQ ID NO 79
<211> LENGTH: 1134
<212> TYPE: DNA
<213> ORGANISM: Artificial Sequence
<220> FEATURE:
<223> OTHER INFORMATION: Recombinant

<400> SEQUENCE: 79
atggaaagag ctagaaggct tgctaataga gcaactctta agagattgct ttctgaggcc      60
aagcaaaata ggaaaactga gtctacatct acaaccacaa ccacgccttt gccattttca     120
ctctctggtt caagttcaag gtatgtttct agtgtttcaa atagtattct gcgtggtaga     180
ggatccaaac ccgataacaa cgtgtccagg cgtgtcggag gcttcttggg agttgggtac     240
ccgtctcaga gccgttcaat ttcagctatg cgtcaatgcg ccatctacgg caaaggtggt     300
atcggtaagt ccaccactac tcagaacctg gtggcagccc tggctgagat gggcaagaag     360
gtcatgatcg ttggttgtga cccgaaagct gactccaccc gcctgatcct gcactccaag     420
gcccagaaca ccatcatgga aatggctgcc gaagccggta ccgtggaaga tctggagctg     480
gaagacgtgc tgaaggctgg ctacggcggc gtcaagtgcg ttgagtccgg tggtccggag     540
ccgggcgttg gctgcgccgg ccgtggtgtt atcaccgcca tcaacttcct ggaagaggaa     600
ggcgcctacg aagacgatct ggacttcgta ttctacgacg tgctgggcga cgtggtgtgt     660
ggcggcttcg ccatgccgat ccgcgagaac aaggcccagg aaatctacat cgtctgctcc     720
ggtgagatga tggccatgta cgccgccaac aacatctcca agggcatcgt gaagtatgcc     780
aactccggca gcgtgcgtct gggcggcctg atctgcaaca gccgtaacac cgaccgcgaa     840
gacgagctga tcatcgctct ggccaacaag ctgggcaccc agatgatcca cttcgtgccg     900
cgtgacaacg tcgtgcagcg cgccgaaatc cgccgcatga ccgtgatcga atacgatccg     960
aaagccaagc aagccgacga ataccgcgct ctggcccgca aggtcgtcga caacaaactg    1020
ctggtcatcc cgaacccgat caccatggac gagctcgaag agctgctgat ggaattcggc    1080
atcatggaag tcgaagacga atccatcgtc ggcaaaaccg ccgaagaagt ctga          1134

<210> SEQ ID NO 80
<211> LENGTH: 341
<212> TYPE: PRT
<213> ORGANISM: Artificial Sequence
<220> FEATURE:
<223> OTHER INFORMATION: Recombinant

<400> SEQUENCE: 80

Met Ala Ala Val Leu Arg Ser Leu Arg Arg Arg Asp Val Ala Ser Ala
1               5                   10                  15

Thr Phe Ser Ala Tyr Arg Ser Leu Thr Gly Ser Thr Lys Pro Ala Tyr
            20                  25                  30

Val Ala Gln Lys Trp Ser Cys Leu Ala Arg Pro Phe Ser Ser Arg Pro
        35                  40                  45

Ala Gly Asn Asp Ala Met Arg Gln Cys Ala Ile Tyr Gly Lys Gly Gly
    50                  55                  60

Ile Gly Lys Ser Thr Thr Thr Gln Asn Leu Val Ala Ala Leu Ala Glu
65                  70                  75                  80
```

Met Gly Lys Lys Val Met Ile Val Gly Cys Asp Pro Lys Ala Asp Ser
                85                  90                  95
Thr Arg Leu Ile Leu His Ser Lys Ala Gln Asn Thr Ile Met Glu Met
            100                 105                 110
Ala Ala Glu Ala Gly Thr Val Glu Asp Leu Glu Leu Glu Asp Val Leu
        115                 120                 125
Lys Ala Gly Tyr Gly Gly Val Lys Cys Val Glu Ser Gly Gly Pro Glu
    130                 135                 140
Pro Gly Val Gly Cys Ala Gly Arg Gly Val Ile Thr Ala Ile Asn Phe
145                 150                 155                 160
Leu Glu Glu Glu Gly Ala Tyr Glu Asp Asp Leu Asp Phe Val Phe Tyr
                165                 170                 175
Asp Val Leu Gly Asp Val Val Cys Gly Gly Phe Ala Met Pro Ile Arg
            180                 185                 190
Glu Asn Lys Ala Gln Glu Ile Tyr Ile Val Cys Ser Gly Glu Met Met
        195                 200                 205
Ala Met Tyr Ala Ala Asn Asn Ile Ser Lys Gly Ile Val Lys Tyr Ala
    210                 215                 220
Asn Ser Gly Ser Val Arg Leu Gly Gly Leu Ile Cys Asn Ser Arg Asn
225                 230                 235                 240
Thr Asp Arg Glu Asp Glu Leu Ile Ile Ala Leu Ala Asn Lys Leu Gly
                245                 250                 255
Thr Gln Met Ile His Phe Val Pro Arg Asp Asn Val Val Gln Arg Ala
            260                 265                 270
Glu Ile Arg Arg Met Thr Val Ile Glu Tyr Asp Pro Lys Ala Lys Gln
        275                 280                 285
Ala Asp Glu Tyr Arg Ala Leu Ala Arg Lys Val Val Asp Asn Lys Leu
    290                 295                 300
Leu Val Ile Pro Asn Pro Ile Thr Met Asp Glu Leu Glu Glu Leu Leu
305                 310                 315                 320
Met Glu Phe Gly Ile Met Glu Val Glu Asp Glu Ser Ile Val Gly Lys
                325                 330                 335
Thr Ala Glu Glu Val
            340

<210> SEQ ID NO 81
<211> LENGTH: 1026
<212> TYPE: DNA
<213> ORGANISM: Artificial Sequence
<220> FEATURE:
<223> OTHER INFORMATION: Recombinant

<400> SEQUENCE: 81
atggctgcag ttcttagatc tttgaggcgt agggatgtgg cttctgctac tttttcagca     60
tatcgatcat taacaggtag taccaagcct gcatacgtcg cccaaaaatg gtcctgtctc    120
gcccggcctt tcagctcgcg cccagcggga aatgacgcta tgcgtcaatg cgccatctac    180
ggcaaaggtg gtatcggtaa gtccaccact actcagaacc tggtggcagc cctggctgag    240
atgggcaaga aggtcatgat cgttggttgt gaccccgaaag ctgactccac cgcctgatc    300 ctgcactcca aggcccagaa caccatcatg gaaatggctg ccgaagccgg taccgtggaa    360
gatctggagc tggaagacgt gctgaaggct ggctacggcg gcgtcaagtg cgttgagtcc    420
ggtggtccgg agccgggcgt tggctgcgcc ggccgtggtg ttatcaccgc catcaacttc    480
ctggaagagg aaggcgccta cgaagacgat ctggacttcg tattctacga cgtgctgggc    540

```
gacgtggtgt gtggcggctt cgccatgccg atccgcgaga acaaggccca ggaaatctac    600
atcgtctgct ccggtgagat gatggccatg tacgccgcca acaacatctc caagggcatc    660
gtgaagtatg ccaactccgg cagcgtgcgt ctgggcggcc tgatctgcaa cagccgtaac    720
accgaccgcg aagacgagct gatcatcgct ctggccaaca agctgggcac ccagatgatc    780
cacttcgtgc cgcgtgacaa cgtcgtgcag cgcgccgaaa tccgccgcat gaccgtgatc    840
gaatacgatc cgaaagccaa gcaagccgac gaataccgcg ctctggcccg caaggtcgtc    900
gacaacaaac tgctggtcat cccgaacccg atcaccatgg acgagctcga agagctgctg    960
atggaattcg gcatcatgga agtcgaagac gaatccatcg tcggcaaaac cgccgaagaa   1020
gtctga                                                              1026
```

<210> SEQ ID NO 82
<211> LENGTH: 343
<212> TYPE: PRT
<213> ORGANISM: Artificial Sequence
<220> FEATURE:
<223> OTHER INFORMATION: Recombinant

<400> SEQUENCE: 82

```
Met Ala Ala Val Leu Arg Ser Leu Arg Arg Arg Asp Val Ala Ser Ala
1               5                   10                  15

Thr Phe Ser Ala Tyr Arg Ser Leu Thr Gly Ser Thr Lys Pro Ala Tyr
            20                  25                  30

Val Ala Gln Lys Trp Ser Cys Leu Ala Arg Pro Phe Ser Ser Arg Pro
        35                  40                  45

Ala Gly Asn Asp Val Ile Ala Met Arg Gln Cys Ala Ile Tyr Gly Lys
    50                  55                  60

Gly Gly Ile Gly Lys Ser Thr Thr Thr Gln Asn Leu Val Ala Ala Leu
65                  70                  75                  80

Ala Glu Met Gly Lys Lys Val Met Ile Val Gly Cys Asp Pro Lys Ala
                85                  90                  95

Asp Ser Thr Arg Leu Ile Leu His Ser Lys Ala Gln Asn Thr Ile Met
            100                 105                 110

Glu Met Ala Ala Glu Ala Gly Thr Val Glu Asp Leu Glu Leu Glu Asp
        115                 120                 125

Val Leu Lys Ala Gly Tyr Gly Gly Val Lys Cys Val Glu Ser Gly Gly
    130                 135                 140

Pro Glu Pro Gly Val Gly Cys Ala Gly Arg Gly Val Ile Thr Ala Ile
145                 150                 155                 160

Asn Phe Leu Glu Glu Glu Gly Ala Tyr Glu Asp Asp Leu Asp Phe Val
                165                 170                 175

Phe Tyr Asp Val Leu Gly Asp Val Val Cys Gly Gly Phe Ala Met Pro
            180                 185                 190

Ile Arg Glu Asn Lys Ala Gln Glu Ile Tyr Ile Val Cys Ser Gly Glu
        195                 200                 205

Met Met Ala Met Tyr Ala Ala Asn Asn Ile Ser Lys Gly Ile Val Lys
    210                 215                 220

Tyr Ala Asn Ser Gly Ser Val Arg Leu Gly Gly Leu Ile Cys Asn Ser
225                 230                 235                 240

Arg Asn Thr Asp Arg Glu Asp Glu Leu Ile Ile Ala Leu Ala Asn Lys
                245                 250                 255

Leu Gly Thr Gln Met Ile His Phe Val Pro Arg Asp Asn Val Val Gln
            260                 265                 270
```

Arg Ala Glu Ile Arg Arg Met Thr Val Ile Glu Tyr Asp Pro Lys Ala
        275                 280                 285

Lys Gln Ala Asp Glu Tyr Arg Ala Leu Ala Arg Lys Val Val Asp Asn
        290                 295                 300

Lys Leu Leu Val Ile Pro Asn Pro Ile Thr Met Asp Glu Leu Glu Glu
305                 310                 315                 320

Leu Leu Met Glu Phe Gly Ile Met Glu Val Glu Asp Glu Ser Ile Val
                325                 330                 335

Gly Lys Thr Ala Glu Glu Val
        340

<210> SEQ ID NO 83
<211> LENGTH: 1032
<212> TYPE: DNA
<213> ORGANISM: Artificial Sequence
<220> FEATURE:
<223> OTHER INFORMATION: Recombinant

<400> SEQUENCE: 83
atggctgcag ttcttagatc tttgaggcgt agggatgtgg cttctgctac tttttcagca      60
tatcgatcat taacaggtag taccaagcct gcatacgtcg cccaaaaatg gtcctgtctc     120
gcccggcctt tcagctcgcg cccagcggga aatgacgtca tcgctatgcg tcaatgcgcc     180
atctacggca aggtggtat cggtaagtcc accactactc agaacctggt ggcagccctg      240
gctgagatgg gcaagaaggt catgatcgtt ggttgtgacc cgaaagctga ctccacccgc     300
ctgatcctgc actccaaggc ccagaacacc atcatggaaa tggctgccga agccggtacc     360
gtggaagatc tggagctgga agacgtgctg aaggctggct acggcggcgt caagtgcgtt     420
gagtccggtg gtccggagcc gggcgttggc tgcgccggcc gtggtgttat caccgccatc     480
aacttcctgg aagaggaagg cgcctacgaa gacgatctgg acttcgtatt ctacgacgtg     540
ctgggcgacg tggtgtgtgg cggcttcgcc atgccgatcc gcgagaacaa ggcccaggaa     600
atctacatcg tctgctccgg tgagatgatg gccatgtacg ccgccaacaa catctccaag     660
ggcatcgtga agtatgccaa ctccggcagc gtgcgtctgg cggcctgat ctgcaacagc      720
cgtaacaccg accgcgaaga cgagctgatc atcgctctgg ccaacaagct gggcacccag     780
atgatccact cgtgccgcg tgacaacgtc gtgcagcgcg ccgaaatccg ccgcatgacc      840
gtgatcgaat cgatccgaa agccaagcaa gccgacgaat accgcgctct ggcccgcaag     900
gtcgtcgaca caaaactgct ggtcatcccg aacccgatca ccatggacga gctcgaagag     960
ctgctgatgg aattcggcat catggaagtc gaagacgaat ccatcgtcgg caaaaccgcc    1020
gaagaagtct ga                                                        1032

<210> SEQ ID NO 84
<211> LENGTH: 354
<212> TYPE: PRT
<213> ORGANISM: Artificial Sequence
<220> FEATURE:
<223> OTHER INFORMATION: Recombinant

<400> SEQUENCE: 84

Met Ile Ala Gly Val Leu Pro Arg Ser Ser Leu Pro Ser Arg Gln Thr
1               5                   10                  15

Leu Ser Ala Ala Leu Ala Ser Phe Asn Ser Cys Ile Ser His Asn Leu
            20                  25                  30

Thr Pro Ala Thr Thr Gly Ala Ser Val Ser Ser Arg Phe Thr Leu Ala

```
                35                  40                  45
Ser Ser Pro Asn Ser Phe Gly Ile Arg Ala Arg Asn Ile His Ile Arg
 50                  55                  60

Ser Ala Met Arg Gln Cys Ala Ile Tyr Gly Lys Gly Gly Ile Gly Lys
 65                  70                  75                  80

Ser Thr Thr Thr Gln Asn Leu Val Ala Leu Ala Glu Met Gly Lys
                 85                  90                  95

Lys Val Met Ile Val Gly Cys Asp Pro Lys Ala Asp Ser Thr Arg Leu
                100                 105                 110

Ile Leu His Ser Lys Ala Gln Asn Thr Ile Met Glu Met Ala Ala Glu
            115                 120                 125

Ala Gly Thr Val Glu Asp Leu Glu Leu Glu Asp Val Leu Lys Ala Gly
        130                 135                 140

Tyr Gly Gly Val Lys Cys Val Glu Ser Gly Gly Pro Glu Pro Gly Val
145                 150                 155                 160

Gly Cys Ala Gly Arg Gly Val Ile Thr Ala Ile Asn Phe Leu Glu Glu
                165                 170                 175

Glu Gly Ala Tyr Glu Asp Asp Leu Asp Phe Val Phe Tyr Asp Val Leu
            180                 185                 190

Gly Asp Val Val Cys Gly Gly Phe Ala Met Pro Ile Arg Glu Asn Lys
        195                 200                 205

Ala Gln Glu Ile Tyr Ile Val Cys Ser Gly Glu Met Met Ala Met Tyr
210                 215                 220

Ala Ala Asn Asn Ile Ser Lys Gly Ile Val Lys Tyr Ala Asn Ser Gly
225                 230                 235                 240

Ser Val Arg Leu Gly Gly Leu Ile Cys Asn Ser Arg Asn Thr Asp Arg
                245                 250                 255

Glu Asp Glu Leu Ile Ile Ala Leu Ala Asn Lys Leu Gly Thr Gln Met
            260                 265                 270

Ile His Phe Val Pro Arg Asp Asn Val Val Gln Arg Ala Glu Ile Arg
        275                 280                 285

Arg Met Thr Val Ile Glu Tyr Asp Pro Lys Ala Lys Gln Ala Asp Glu
290                 295                 300

Tyr Arg Ala Leu Ala Arg Lys Val Val Asp Asn Lys Leu Leu Val Ile
                310                 315                 320

Pro Asn Pro Ile Thr Met Asp Glu Leu Glu Glu Leu Leu Met Glu Phe
            325                 330                 335

Gly Ile Met Glu Val Glu Asp Glu Ser Ile Val Gly Lys Thr Ala Glu
        340                 345                 350

Glu Val

<210> SEQ ID NO 85
<211> LENGTH: 1065
<212> TYPE: DNA
<213> ORGANISM: Artificial Sequence
<220> FEATURE:
<223> OTHER INFORMATION: Recombinant

<400> SEQUENCE: 85
atgattgctg tgttttgcc  tagatcttca ttgccatcta ggcaaacttt atctgctgca    60
ctcgcttctt ttaattcatg tatttcacat aatctgacac cagctacaac cggtgcaagt   120
gtgagttcca ggtttacgct agccagttcc cccaatagct tcggaattcg ggcgcgaaac   180
atacacatcc gttcggctat gcgtcaatgc gccatctacg gcaaaggtgg tatcggtaag   240
```

```
tccaccacta ctcagaacct ggtggcagcc ctggctgaga tgggcaagaa ggtcatgatc    300
gttggttgtg acccgaaagc tgactccacc cgcctgatcc tgcactccaa ggcccagaac    360
accatcatgg aaatggctgc cgaagccggt accgtggaag atctggagct ggaagacgtg    420
ctgaaggctg gctacggcgg cgtcaagtgc gttgagtccg gtggtccgga gccgggcgtt    480
ggctgcgccg gccgtggtgt tatcaccgcc atcaacttcc tggaagagga aggcgcctac    540
gaagacgatc tggacttcgt attctacgac gtgctgggcg acgtggtgtg tggcggcttc    600
gccatgccga tccgcgagaa caaggcccag gaaatctaca tcgtctgctc cggtgagatg    660
atggccatgt acgccgccaa caacatctcc aagggcatcg tgaagtatgc caactccggc    720
agcgtgcgtc tgggcggcct gatctgcaac agccgtaaca ccgaccgcga agacgagctg    780
atcatcgctc tggccaacaa gctgggcacc cagatgatcc acttcgtgcc gcgtgacaac    840
gtcgtgcagc gcgccgaaat ccgccgcatg accgtgatcc aatacgatcc gaaagccaag    900
caagccgacg aataccgcgc tctggcccgc aaggtcgtcg acaacaaact gctggtcatc    960
ccgaacccga tcaccatgga cgagctcgaa gagctgctga tggaattcgg catcatggaa   1020
gtcgaagacg aatccatcgt cggcaaaacc gccgaagaag tctga                    1065
```

<210> SEQ ID NO 86
<211> LENGTH: 355
<212> TYPE: PRT
<213> ORGANISM: Artificial Sequence
<220> FEATURE:
<223> OTHER INFORMATION: Recombinant

<400> SEQUENCE: 86

```
Met Ile Ala Gly Val Leu Pro Arg Ser Ser Leu Pro Ser Arg Gln Thr
1               5                   10                  15

Leu Ser Ala Ala Leu Ala Ser Phe Asn Ser Cys Ile Ser His Asn Leu
            20                  25                  30

Thr Pro Ala Thr Thr Gly Ala Ser Val Ser Ser Arg Phe Thr Leu Ala
        35                  40                  45

Ser Ser Pro Asn Ser Phe Gly Ile Arg Ala Arg Asn Ile His Ile Arg
    50                  55                  60

Ser Glu Ala Met Arg Gln Cys Ala Ile Tyr Gly Lys Gly Gly Ile Gly
65                  70                  75                  80

Lys Ser Thr Thr Thr Gln Asn Leu Val Ala Ala Leu Ala Glu Met Gly
                85                  90                  95

Lys Lys Val Met Ile Val Gly Cys Asp Pro Lys Ala Asp Ser Thr Arg
            100                 105                 110

Leu Ile Leu His Ser Lys Ala Gln Asn Thr Ile Met Glu Met Ala Ala
        115                 120                 125

Glu Ala Gly Thr Val Glu Asp Leu Glu Leu Glu Asp Val Leu Lys Ala
    130                 135                 140

Gly Tyr Gly Gly Val Lys Cys Val Glu Ser Gly Gly Pro Glu Pro Gly
145                 150                 155                 160

Val Gly Cys Ala Gly Arg Gly Val Ile Thr Ala Ile Asn Phe Leu Glu
                165                 170                 175

Glu Glu Gly Ala Tyr Glu Asp Asp Leu Asp Phe Val Phe Tyr Asp Val
            180                 185                 190

Leu Gly Asp Val Val Cys Gly Gly Phe Ala Met Pro Ile Arg Glu Asn
        195                 200                 205

Lys Ala Gln Glu Ile Tyr Ile Val Cys Ser Gly Glu Met Met Ala Met
    210                 215                 220
```

Tyr Ala Ala Asn Asn Ile Ser Lys Gly Ile Val Lys Tyr Ala Asn Ser
225                 230                 235                 240

Gly Ser Val Arg Leu Gly Gly Leu Ile Cys Asn Ser Arg Asn Thr Asp
            245                 250                 255

Arg Glu Asp Glu Leu Ile Ile Ala Leu Ala Asn Lys Leu Gly Thr Gln
        260                 265                 270

Met Ile His Phe Val Pro Arg Asp Asn Val Val Gln Arg Ala Glu Ile
    275                 280                 285

Arg Arg Met Thr Val Ile Glu Tyr Asp Pro Lys Ala Lys Gln Ala Asp
290                 295                 300

Glu Tyr Arg Ala Leu Ala Arg Lys Val Val Asp Asn Lys Leu Leu Val
305                 310                 315                 320

Ile Pro Asn Pro Ile Thr Met Asp Glu Leu Glu Glu Leu Leu Met Glu
                325                 330                 335

Phe Gly Ile Met Glu Val Glu Asp Glu Ser Ile Val Gly Lys Thr Ala
            340                 345                 350

Glu Glu Val
        355

<210> SEQ ID NO 87
<211> LENGTH: 1068
<212> TYPE: DNA
<213> ORGANISM: Artificial Sequence
<220> FEATURE:
<223> OTHER INFORMATION: Recombinant

<400> SEQUENCE: 87
atgattgctg gtgttttgcc tagatcttca ttgccatcta ggcaaacttt atctgctgca      60
ctcgcttctt ttaattcatg tatttcacat aatctgacac cagctacaac cggtgcaagt     120
gtgagttcca ggtttacgct agccagttcc cccaatagct tcggaattcg ggcgcgaaac     180
atacacatcc gttcggaagc tatgcgtcaa tgcgccatct acggcaaagg tggtatcggt     240
aagtccacca ctactcagaa cctggtggca gccctggctg agatgggcaa gaaggtcatg     300
atcgttggtt gtgaccccga agctgactcc acccgcctga tcctgcactc caaggcccag     360
aacaccatca tggaaatggc tgccgaagcc ggtaccgtgg aagatctgga gctggaagac     420
gtgctgaagg ctggctacgg cggcgtcaag tgcgttgagt ccggtggtcc ggagccgggc     480
gttggctgcg ccggccgtgg tgttatcacc gccatcaact tcctggaaga ggaaggcgcc     540
tacgaagacg atctggactt cgtattctac gacgtgctgg cgacgtggt gtgtggcggc      600
ttcgccatgc cgatccgcga gaacaaggcc caggaaatct acatcgtctg ctccggtgag     660
atgatggcca tgtacgccgc caacaacatc tccaagggca tcgtgaagta tgccaactcc     720
ggcagcgtgc gtctgggcgg cctgatctgc aacagccgta acaccgaccg cgaagacgag     780
ctgatcatcg ctctggccaa caagctgggc acccagatga tccacttcgt gccgcgtgac     840
aacgtcgtgc agcgcgccga aatccgccgc atgaccgtga tcgaatacga tccgaaagcc     900
aagcaagccg acgaataccg cgctctggcc cgcaaggtcg tcgacaacaa actgctggtc     960
atcccgaacc cgatcaccat ggacgagctc gaagagctgc tgatggaatt cggcatcatg    1020
gaagtcgaag acgaatccat cgtcggcaaa accgccgaag aagtctga                 1068

<210> SEQ ID NO 88
<211> LENGTH: 357
<212> TYPE: PRT
<213> ORGANISM: Artificial Sequence
<220> FEATURE:
<223> OTHER INFORMATION: Recombinant

<400> SEQUENCE: 88

```
Met Ile Ala Gly Val Leu Pro Arg Ser Ser Leu Pro Ser Arg Gln Thr
1               5                   10                  15

Leu Ser Ala Ala Leu Ala Ser Phe Asn Ser Cys Ile Ser His Asn Leu
            20                  25                  30

Thr Pro Ala Thr Thr Gly Ala Ser Val Ser Ser Arg Phe Thr Leu Ala
        35                  40                  45

Ser Ser Pro Asn Ser Phe Gly Ile Arg Ala Arg Asn Ile His Ile Arg
    50                  55                  60

Ser Glu Pro Ser Ala Met Arg Gln Cys Ala Ile Tyr Gly Lys Gly Gly
65                  70                  75                  80

Ile Gly Lys Ser Thr Thr Thr Gln Asn Leu Val Ala Ala Leu Ala Glu
                85                  90                  95

Met Gly Lys Lys Val Met Ile Val Gly Cys Asp Pro Lys Ala Asp Ser
            100                 105                 110

Thr Arg Leu Ile Leu His Ser Lys Ala Gln Asn Thr Ile Met Glu Met
        115                 120                 125

Ala Ala Glu Ala Gly Thr Val Glu Asp Leu Glu Leu Glu Asp Val Leu
    130                 135                 140

Lys Ala Gly Tyr Gly Gly Val Lys Cys Val Glu Ser Gly Gly Pro Glu
145                 150                 155                 160

Pro Gly Val Gly Cys Ala Gly Arg Gly Val Ile Thr Ala Ile Asn Phe
                165                 170                 175

Leu Glu Glu Glu Gly Ala Tyr Glu Asp Asp Leu Asp Phe Val Phe Tyr
            180                 185                 190

Asp Val Leu Gly Asp Val Val Cys Gly Gly Phe Ala Met Pro Ile Arg
        195                 200                 205

Glu Asn Lys Ala Gln Glu Ile Tyr Ile Val Cys Ser Gly Glu Met Met
    210                 215                 220

Ala Met Tyr Ala Ala Asn Asn Ile Ser Lys Gly Ile Val Lys Tyr Ala
225                 230                 235                 240

Asn Ser Gly Ser Val Arg Leu Gly Gly Leu Ile Cys Asn Ser Arg Asn
                245                 250                 255

Thr Asp Arg Glu Asp Glu Leu Ile Ile Ala Leu Ala Asn Lys Leu Gly
            260                 265                 270

Thr Gln Met Ile His Phe Val Pro Arg Asp Asn Val Val Gln Arg Ala
        275                 280                 285

Glu Ile Arg Arg Met Thr Val Ile Glu Tyr Asp Pro Lys Ala Lys Gln
    290                 295                 300

Ala Asp Glu Tyr Arg Ala Leu Ala Arg Lys Val Asp Asn Lys Leu
305                 310                 315                 320

Leu Val Ile Pro Asn Pro Ile Thr Met Asp Glu Leu Glu Glu Leu Leu
                325                 330                 335

Met Glu Phe Gly Ile Met Glu Val Glu Asp Glu Ser Ile Val Gly Lys
            340                 345                 350

Thr Ala Glu Glu Val
            355
```

<210> SEQ ID NO 89
<211> LENGTH: 1074
<212> TYPE: DNA
<213> ORGANISM: Artificial Sequence
<220> FEATURE:
<223> OTHER INFORMATION: Recombinant

<400> SEQUENCE: 89

```
atgattgctg gtgttttgcc tagatcttca ttgccatcta ggcaaacttt atctgctgca      60
ctcgcttctt ttaattcatg tatttcacat aatctgacac cagctacaac cggtgcaagt     120
gtgagttcca ggtttacgct agccagttcc cccaatagct tcggaattcg ggcgcgaaac     180
atacacatcc gttcggaacc gagcgctatg cgtcaatgcg ccatctacgg caaaggtggt     240
atcggtaagt ccaccactac tcagaacctg gtggcagccc tggctgagat gggcaagaag     300
gtcatgatcg ttggttgtga cccgaaagct gactccaccc gcctgatcct gcactccaag     360
gcccagaaca ccatcatgga atggctgccg aagccggta ccgtggaaga tctggagctg     420
gaagacgtgc tgaaggctgg ctacggcggc gtcaagtgcg ttgagtccgg tggtccggag     480
ccgggcgttg gctgcgccgg ccgtggtgtt atcaccgcca tcaacttcct ggaagaggaa     540
ggcgcctacg aagacgatct ggacttcgta ttctacgacg tgctgggcga cgtggtgtgt     600
ggcggcttcg ccatgccgat ccgcgagaac aaggcccagg aaatctacat cgtctgctcc     660
ggtgagatga tggccatgta cgccgccaac aacatctcca agggcatcgt gaagtatgcc     720
aactccggca gcgtgcgtct gggcggcctg atctgcaaca gccgtaacac cgaccgcgaa     780
gacgagctga tcatcgctct ggccaacaag ctgggcaccc agatgatcca cttcgtgccg     840
cgtgacaacg tcgtgcagcg cgccgaaatc cgccgcatga ccgtgatcga atacgatccg     900
aaagccaagc aagccgacga ataccgcgct ctggcccgca aggtcgtcga caacaaactg     960
ctggtcatcc cgaacccgat caccatggac gagctcgaag agctgctgat ggaattcggc    1020
atcatggaag tcgaagacga atccatcgtc ggcaaaaccg ccgaagaagt ctga          1074
```

<210> SEQ ID NO 90
<211> LENGTH: 335
<212> TYPE: PRT
<213> ORGANISM: Artificial Sequence
<220> FEATURE:
<223> OTHER INFORMATION: Recombinant

<400> SEQUENCE: 90

```
Met Ala Pro Ser Val Met Ala Ser Ser Ala Thr Thr Val Ala Pro Phe
1               5                   10                  15

Gln Gly Leu Lys Ser Thr Ala Gly Met Pro Val Ala Arg Arg Ser Gly
            20                  25                  30

Asn Ser Ser Phe Gly Asn Val Ser Asn Gly Gly Arg Ile Arg Cys Met
        35                  40                  45

Arg Gln Cys Ala Ile Tyr Gly Lys Gly Gly Ile Gly Lys Ser Thr Thr
    50                  55                  60

Thr Gln Asn Leu Val Ala Ala Leu Ala Glu Met Gly Lys Lys Val Met
65                  70                  75                  80

Ile Val Gly Cys Asp Pro Lys Ala Asp Ser Thr Arg Leu Ile Leu His
                85                  90                  95

Ser Lys Ala Gln Asn Thr Ile Met Glu Met Ala Ala Glu Ala Gly Thr
            100                 105                 110

Val Glu Asp Leu Glu Leu Glu Asp Val Leu Lys Ala Gly Tyr Gly Gly
        115                 120                 125

Val Lys Cys Val Glu Ser Gly Gly Pro Glu Pro Gly Val Gly Cys Ala
    130                 135                 140

Gly Arg Gly Val Ile Thr Ala Ile Asn Phe Leu Glu Glu Glu Gly Ala
```

```
145                 150                 155                 160
Tyr Glu Asp Asp Leu Asp Phe Val Phe Tyr Asp Val Leu Gly Asp Val
                165                 170                 175

Val Cys Gly Gly Phe Ala Met Pro Ile Arg Glu Asn Lys Ala Gln Glu
            180                 185                 190

Ile Tyr Ile Val Cys Ser Gly Glu Met Met Ala Met Tyr Ala Ala Asn
        195                 200                 205

Asn Ile Ser Lys Gly Ile Val Lys Tyr Ala Asn Ser Gly Ser Val Arg
    210                 215                 220

Leu Gly Gly Leu Ile Cys Asn Ser Arg Asn Thr Asp Arg Glu Asp Glu
225                 230                 235                 240

Leu Ile Ile Ala Leu Ala Asn Lys Leu Gly Thr Gln Met Ile His Phe
                245                 250                 255

Val Pro Arg Asp Asn Val Val Gln Arg Ala Glu Ile Arg Arg Met Thr
            260                 265                 270

Val Ile Glu Tyr Asp Pro Lys Ala Lys Gln Ala Asp Glu Tyr Arg Ala
        275                 280                 285

Leu Ala Arg Lys Val Val Asp Asn Lys Leu Leu Val Ile Pro Asn Pro
    290                 295                 300

Ile Thr Met Asp Glu Leu Glu Glu Leu Leu Met Glu Phe Gly Ile Met
305                 310                 315                 320

Glu Val Glu Asp Glu Ser Ile Val Gly Lys Thr Ala Glu Glu Val
                325                 330                 335

<210> SEQ ID NO 91
<211> LENGTH: 1008
<212> TYPE: DNA
<213> ORGANISM: Artificial Sequence
<220> FEATURE:
<223> OTHER INFORMATION: Recombinant

<400> SEQUENCE: 91
atggctcctt ctgttatggc ttcttcagca actacagtgg cacctttca aggtcttaag       60 tcaaccgccg gtatgccagt cgcgagaagg agtggaaatt ccagcttcgg aaatgtatcg      120
aacggcggga gaattcgttg tatgcgtcaa tgcgccatct acggcaaagg tggtatcggt      180
aagtccacca ctactcagaa cctggtggca gccctggctg agatgggcaa gaaggtcatg      240
atcgttggtt gtgacccgaa agctgactcc acccgcctga tcctgcactc caaggcccag      300
aacaccatca tggaaatggc tgccgaagcc ggtaccgtgg aagatctgga gctggaagac      360
gtgctgaagg ctggctacgg cggcgtcaag tgcgttgagt ccggtggtcc ggagccgggc      420
gttggctgcg ccggccgtgg tgttatcacc gccatcaact cctggaaga ggaaggcgcc      480 tacgaagacg atctggactt cgtattctac gacgtgctgg gcgacgtggt gtgtggcggc      540
ttcgccatgc cgatccgcga gaacaaggcc caggaaatct acatcgtctg ctccggtgag      600
atgatggcca tgtacgccgc caacaacatc tccaagggca tcgtgaagta tgccaactcc      660
ggcagcgtgc gtctgggcgg cctgatctgc aacagccgta acaccgaccg cgaagacgag      720
ctgatcatcg ctctggccaa caagctgggc acccagatga tccacttcgt gccgcgtgac      780
aacgtcgtgc agcgcgccga atccgccgc atgaccgtga tcgaatacga tccgaaagcc      840
aagcaagccg acgaataccg cgctctggcc cgcaaggtcg tcgacaacaa actgctggtc      900
atcccgaacc cgatcaccat ggacgagctc gaagagctgc tgatggaatt cggcatcatg      960
gaagtcgaag acgaatccat cgtcggcaaa accgccgaag aagtctga                 1008
```

-continued

```
<210> SEQ ID NO 92
<211> LENGTH: 340
<212> TYPE: PRT
<213> ORGANISM: Artificial Sequence
<220> FEATURE:
<223> OTHER INFORMATION: Recombinant

<400> SEQUENCE: 92

Met Ala Pro Ser Val Met Ala Ser Ser Ala Thr Thr Val Ala Pro Phe
1               5                   10                  15

Gln Gly Leu Lys Ser Thr Ala Gly Met Pro Val Ala Arg Arg Ser Gly
            20                  25                  30

Asn Ser Ser Phe Gly Asn Val Ser Asn Gly Gly Arg Ile Arg Cys Met
        35                  40                  45

Ala Ser Glu Arg Leu Ala Asp Gly Asp Ser Arg Tyr Tyr Leu Leu Lys
    50                  55                  60

Val Ala His Glu Gln Phe Gly Cys Ala Pro Gly Glu Leu Ser Glu Glu
65                  70                  75                  80

Gln Leu Gln Gln Ala Asp Arg Ile Ile Gly Arg Gln Arg His Ile Glu
                85                  90                  95

Asp Ala Val Leu Arg Ser Pro Asp Ala Ile Gly Val Ile Pro Pro
            100                 105                 110

Ser Gln Leu Glu Glu Ala Trp Ala His Ile Ala Ser Arg Tyr Glu Ser
        115                 120                 125

Pro Glu Ala Leu Gln Gln Ala Leu Asp Ala Gln Ala Leu Asp Ala Ala
    130                 135                 140

Gly Met Arg Ala Met Leu Ala Arg Glu Leu Arg Val Glu Ala Val Leu
145                 150                 155                 160

Asp Cys Val Cys Ala Gly Leu Pro Glu Ile Ser Asp Thr Asp Val Ser
                165                 170                 175

Leu Tyr Tyr Phe Asn His Ala Glu Gln Phe Lys Val Pro Ala Gln His
            180                 185                 190

Lys Ala Arg His Ile Leu Val Thr Ile Asn Glu Asp Phe Pro Glu Asn
        195                 200                 205

Thr Arg Glu Ala Ala Arg Thr Arg Ile Glu Thr Ile Leu Lys Arg Leu
    210                 215                 220

Arg Gly Lys Pro Glu Arg Phe Ala Glu Gln Ala Met Lys His Ser Glu
225                 230                 235                 240

Cys Pro Thr Ala Met Gln Gly Gly Leu Leu Gly Glu Val Val Pro Gly
                245                 250                 255

Thr Leu Tyr Pro Glu Leu Asp Ala Cys Leu Phe Gln Met Ala Arg Gly
            260                 265                 270

Glu Leu Ser Pro Val Leu Glu Ser Pro Ile Gly Phe His Val Leu Tyr
        275                 280                 285

Cys Glu Ser Val Ser Pro Ala Arg Gln Leu Thr Leu Glu Glu Ile Leu
    290                 295                 300

Pro Arg Leu Arg Asp Arg Leu Gln Leu Arg Gln Lys Ala Tyr Gln
305                 310                 315                 320

Arg Lys Trp Leu Glu Ser Leu Leu Gln Gln Asn Ala Thr Leu Glu Asn
                325                 330                 335

Leu Ala His Gly
            340

<210> SEQ ID NO 93
<211> LENGTH: 1023
```

```
<212> TYPE: DNA
<213> ORGANISM: Artificial Sequence
<220> FEATURE:
<223> OTHER INFORMATION: Recombinant

<400> SEQUENCE: 93
atggctcctt ctgttatggc ttcttcagca actacagtgg cacctttca aggtcttaag      60
tcaaccgccg gtatgccagt cgcgagaagg agtggaaatt ccagcttcgg aaatgtatcg    120
aacggcggga gaattcgttg tatggcatct gagcgtctcg ccgacggcga cagccgctat    180
tacttgctga aggtcgccca cgagcagttc ggctgcgcgc ccggcgagct cagcgaggag    240
cagctccagc aggccgaccg catcatcggc cggcagaggc atatcgagga cgccgtgttg    300
cgcagccccg atgcgatcgg tgtggtgatc ccgccctccc agctcgaaga ggcctgggca    360
cacatcgcca ccgctacga gagtcccgag gcgctacagc aggccctcga cgcgcaggcg    420
ctggatgctg ccggcatgcg cgccatgctg gcccgggagc tcagggtcga ggccgttctc    480
gactgcgtct cgccggcct gccggagatc agcgacaccg atgtgagcct ctactacttc    540
aaccacgccg agcaattcaa ggtgcccgcc agcacaagg cccggcacat cctggtcacc    600
atcaacgagg attttccgga aaacacccgc gaagccgccc ggacgcgcat cgagaccatc    660
ctcaagcggc tgcgcggcaa gccggagcgc ttcgccgagc aggcgatgaa gcactccgaa    720
tgtcccaccg cgatgcaggg cggattgctc ggcgaggtgg tcccgggaac gctttatccc    780
gaactggacg cctgcctgtt ccagatggcg cggggagaac tgagtccggt actggaatcg    840
ccgatcggtt ttcacgtgct gtactgcgaa agcgtgagcc ccgccggca gctcaccctc    900
gaggagatcc tgccgcgtct gcgcgacagg ctgcagctcc ggcagcgcaa ggcgtatcag    960
cgcaaatggc tggaaagcct gctccaacaa aacgctactt tggagaacct cgcccatgga   1020
taa                                                                  1023

<210> SEQ ID NO 94
<211> LENGTH: 340
<212> TYPE: PRT
<213> ORGANISM: Artificial Sequence
<220> FEATURE:
<223> OTHER INFORMATION: Recombinant

<400> SEQUENCE: 94

Met Ala Pro Ser Val Met Ala Ser Ser Ala Thr Thr Val Ala Pro Phe
1               5                   10                  15

Gln Gly Leu Lys Ser Thr Ala Gly Met Pro Val Ala Arg Arg Ser Gly
            20                  25                  30

Asn Ser Ser Phe Gly Asn Val Ser Asn Gly Gly Arg Ile Arg Cys Met
        35                  40                  45

Thr Met Arg Gln Cys Ala Ile Tyr Gly Lys Gly Ile Gly Lys Ser
    50                  55                  60

Thr Thr Thr Gln Asn Leu Val Ala Ala Leu Ala Glu Met Gly Lys Lys
65                  70                  75                  80

Val Met Ile Val Gly Cys Asp Pro Lys Ala Asp Ser Thr Arg Leu Ile
                85                  90                  95

Leu His Ala Lys Ala Gln Asn Thr Ile Met Glu Met Ala Ala Glu Val
            100                 105                 110

Gly Ser Val Glu Asp Leu Glu Leu Glu Asp Val Leu Gln Ile Gly Tyr
        115                 120                 125

Gly Asp Val Arg Cys Ala Glu Ser Gly Gly Pro Glu Pro Gly Val Gly
    130                 135                 140
```

Cys Ala Gly Arg Gly Val Ile Thr Ala Ile Asn Phe Leu Glu Glu
145                 150                 155                 160

Gly Ala Tyr Glu Asp Asp Leu Asp Phe Val Phe Tyr Asp Val Leu Gly
                165                 170                 175

Asp Val Val Cys Gly Gly Phe Ala Met Pro Ile Arg Glu Asn Lys Ala
            180                 185                 190

Gln Glu Ile Tyr Ile Val Cys Ser Gly Glu Met Met Ala Met Tyr Ala
        195                 200                 205

Ala Asn Asn Ile Ser Lys Gly Ile Val Lys Tyr Ala Lys Ser Gly Lys
    210                 215                 220

Val Arg Leu Gly Gly Leu Ile Cys Asn Ser Arg Gln Thr Asp Arg Glu
225                 230                 235                 240

Asp Glu Leu Ile Ile Ala Leu Ala Glu Lys Leu Gly Thr Gln Met Ile
                245                 250                 255

His Phe Val Pro Arg Asp Asn Ile Val Gln Arg Ala Glu Ile Arg Arg
            260                 265                 270

Met Thr Val Ile Glu Tyr Asp Pro Ala Cys Lys Gln Ala Asn Glu Tyr
        275                 280                 285

Arg Thr Leu Ala Gln Lys Ile Val Asn Asn Thr Met Lys Val Val Pro
    290                 295                 300

Thr Pro Cys Thr Met Asp Glu Leu Glu Ser Leu Leu Met Glu Phe Gly
305                 310                 315                 320

Ile Met Glu Glu Glu Asp Thr Ser Ile Ile Gly Lys Thr Ala Ala Glu
                325                 330                 335

Glu Asn Ala Ala
            340

<210> SEQ ID NO 95
<211> LENGTH: 1023
<212> TYPE: DNA
<213> ORGANISM: Artificial Sequence
<220> FEATURE:
<223> OTHER INFORMATION: Recombinant

<400> SEQUENCE: 95
atggctcctt ctgttatggc ttcttcagca actacagtgg cacctttca aggtcttaag      60 tcaaccgccg gtatgccagt cgcgagaagg agtggaaatt ccagcttcgg aaatgtatcg     120
aacggcggga gaattcgttg tatgaccatg cgtcaatgcg ctatttacgg taaaggcggt     180
atcggtaaat ccaccaccac gcagaacctc gtcgccgcgc tggcggagat gggtaagaaa     240
gtgatgatcg tcggctgcga tccgaaggcg gactccaccc gtctgattct gcacgccaaa     300
gcacagaaca ccattatgga gatggccgcg aagtcggct cggtcgagga cctcgaactc      360
gaagacgtgc tgcaaattgg ctacggcgat gtgcgctgcg cggaatccgg cggcccggag     420
ccaggcgtcg gctgcgcggg acgcggcgtg atcacggcga tcaactttct gaagaagaa      480 ggcgcctacg aggacgatct cgatttcgtg ttctatgacg tgctcggcga cgtggtctgc     540
ggcggcttcg ccatgccgat ccgcgaaaac aaagcccagg agatctacat cgtctgctcc     600
ggcgaaatga tggcgatgta cgcggccaac aatatctcca agggatcgt taaatacgcc     660 aaatccggca aggtgcgcct cggcggcctg atctgtaact cacgtcagac cgaccgtgaa     720
gacgaactga ttattgccct ggcggaaaag ctcggtaccc agatgatcca ctttgtgccc     780
cgcgacaaca tcgtgcagcg cgcggagatc cgccgcatga cggttatcga gtacgacccc     840
gcctgtaaac aggccaacga ataccgcacc ctggcgcaga gatcgtcaa caacaccatg     900

```
aaagtggtgc cgacgccctg caccatggat gagctggaat cgctgctgat ggagttcggc    960
atcatggaag aggaagacac cagcatcatt ggcaaaaccg ccgccgaaga aaacgcggcc   1020
tga                                                                 1023
```

<210> SEQ ID NO 96
<211> LENGTH: 340
<212> TYPE: PRT
<213> ORGANISM: Artificial Sequence
<220> FEATURE:
<223> OTHER INFORMATION: Recombinant

<400> SEQUENCE: 96

```
Met Ala Pro Ser Val Met Ala Ser Ser Ala Thr Thr Val Ala Pro Phe
1               5                   10                  15

Gln Gly Leu Lys Ser Thr Ala Gly Met Pro Val Ala Arg Arg Ser Gly
            20                  25                  30

Asn Ser Ser Phe Gly Asn Val Ser Asn Gly Gly Arg Ile Arg Cys Met
        35                  40                  45

Thr Met Arg Gln Cys Ala Ile Tyr Gly Lys Gly Gly Ile Gly Lys Ser
    50                  55                  60

Thr Thr Thr Gln Asn Leu Val Ala Ala Leu Ala Glu Met Gly Lys Lys
65                  70                  75                  80

Val Met Ile Val Gly Cys Asp Pro Lys Ala Asp Ser Thr Arg Leu Ile
                85                  90                  95

Leu His Ala Lys Ala Gln Asn Thr Ile Met Glu Met Ala Ala Glu Val
            100                 105                 110

Gly Ser Val Glu Asp Leu Glu Leu Glu Asp Val Leu Gln Ile Gly Tyr
        115                 120                 125

Gly Asp Val Arg Cys Ala Glu Ser Gly Gly Pro Glu Pro Gly Val Gly
    130                 135                 140

Cys Ala Gly Arg Gly Val Ile Thr Ala Ile Asn Phe Leu Glu Glu Glu
145                 150                 155                 160

Gly Ala Tyr Glu Asp Asp Leu Asp Phe Val Phe Tyr Asp Val Leu Gly
                165                 170                 175

Asp Val Val Cys Gly Gly Phe Ala Met Pro Ile Arg Glu Asn Lys Ala
            180                 185                 190

Gln Glu Ile Tyr Ile Val Cys Ser Gly Glu Met Met Ala Met Tyr Ala
        195                 200                 205

Ala Asn Asn Ile Ser Lys Gly Ile Val Lys Tyr Ala Lys Ser Gly Lys
    210                 215                 220

Val Arg Leu Gly Gly Leu Ile Cys Asn Ser Arg Gln Thr Asp Arg Glu
225                 230                 235                 240

Asp Glu Leu Ile Ile Ala Leu Ala Glu Lys Leu Gly Thr Gln Met Ile
                245                 250                 255

His Phe Val Pro Arg Asp Asn Ile Val Gln Arg Ala Glu Ile Arg Arg
            260                 265                 270

Met Thr Val Ile Glu Tyr Asp Pro Ala Cys Lys Gln Ala Asn Glu Tyr
        275                 280                 285

Arg Thr Leu Ala Gln Lys Ile Val Asn Asn Thr Met Lys Val Val Pro
    290                 295                 300

Thr Pro Cys Thr Met Asp Glu Leu Glu Ser Leu Leu Met Glu Phe Gly
305                 310                 315                 320

Ile Met Glu Glu Glu Asp Thr Ser Ile Ile Gly Lys Thr Ala Ala Glu
                325                 330                 335
```

Glu Asn Ala Ala
            340

<210> SEQ ID NO 97
<211> LENGTH: 1023
<212> TYPE: DNA
<213> ORGANISM: Artificial Sequence
<220> FEATURE:
<223> OTHER INFORMATION: Recombinant

<400> SEQUENCE: 97

```
atggcacctt ctgttatggc ctcttctgct accactgtgg cccctttca aggattgaag     60
tctactgctg gtatgccggt tgctaggagg tccggcaata gttcattcgg aaacgtcagc    120
aatggtggga gaatacgatg catgacaatg agacaatgcg caatttacgg aaaaggtgga    180
attggaaaaa gtactacaac acagaatttg gtggctgccc tggctgaaat ggggaaaaaa    240
gttatgatcg tggggtgcga cccaaaagca gatagcactc gattgattct gcatgcaaaa    300
gcacagaaca ctattatgga gatggccgca gaagttggca gcgtagaaga tttggaactt    360
gaagatgtgt tacaaattgg ttatggggat gtgcgttgtg ctgaatcagg aggccctgag    420
cctggggtgg gttgtgccgg tcgagggggtt attactgcca taattttct gaggaagag    480
ggagcatacg aagacgatct tgactttgtt ttttacgatg tgcttggtga tgtggtttgt    540
gggggtttg caatgccaat cagagagaac aaagctcagg atctacat tgtttgttcc    600
ggagagatga tggcaatgta cgcagctaac aacatcagca aagggattgt taagtatgca    660
aagagcggaa aggttagact aggggggttta atctgtaata gtagacaaac tgatagagaa    720
gatgaattga ttattgccct ggctgaaaag ttaggtactc aaatgattca ttttgttcct    780
cgagataata tagttcaacg agctgaaata cgtagaatga cagtaattga atatgatcct    840
gcttgtaaac aagctaatga ataccgaaca cttgcccaaa agatcgtgaa caacactatg    900
aaggtggttc ctactccttg tactatggat gaattagaat ccttgttgat ggagtttggc    960
ataatggaag aggaagatac ctctatcatc ggtaagactg ctgctgaaga aaatgcagct   1020
taa                                                                 1023
```

<210> SEQ ID NO 98
<211> LENGTH: 313
<212> TYPE: PRT
<213> ORGANISM: Artificial Sequence
<220> FEATURE:
<223> OTHER INFORMATION: Recombinant

<400> SEQUENCE: 98

Met Ala Pro Ser Val Met Ala Ser Ser Ala Thr Thr Val Ala Pro Phe
1               5                   10                  15

Gln Gly Leu Lys Ser Thr Ala Gly Met Pro Val Ala Arg Arg Ser Gly
            20                  25                  30

Asn Ser Ser Phe Gly Asn Val Ser Asn Gly Gly Arg Ile Arg Cys Met
        35                  40                  45

Glu Pro Trp Gln Arg Phe Gly Arg Gln Arg Leu Ala Gln Ser Arg Trp
    50                  55                  60

Asn Cys Glu Pro Ala Ala Ile Ala Ala Val Asp Arg Gln Ala Phe Glu
65                  70                  75                  80

Ala Ala Trp Gln Arg Gln Ala Gln Met Glu Gln Val Ile Val Ala Gln
                85                  90                  95

Ile Ala Pro Glu Ala Ile Pro Ala Ala Leu Gln Glu Gly Leu Ala Thr

```
              100                 105                 110
Ser Leu Gly Ala Trp Leu Asp Glu Gly Gly Phe Thr Pro Ala Glu Arg
        115                 120                 125

Ala Ala Ile Val Leu His His Ala Arg Leu Glu Thr Ala Phe Ala Gly
        130                 135                 140

Ile Ala Ser Gln Ala Pro Arg Pro Asp Pro Ala Thr Val Gln Ala Trp
145                 150                 155                 160

Tyr Leu Arg His Gln Ala Gln Phe Met Arg Pro Glu Gln Arg Leu Thr
                165                 170                 175

Arg His Leu Leu Leu Thr Val Asp Gly Asp Asp Gln Thr Val Tyr Ser
                180                 185                 190

Arg Ile Arg Glu Leu His Gly Gln Ile Glu Ala Ser Arg Glu Ala Phe
                195                 200                 205

Ala Pro Leu Ala Gln Arg His Ser His Cys Pro Ser Ala Leu Asp Gly
        210                 215                 220

Gly Leu Leu Gly Trp Ile Gly Arg Gly Leu Leu Tyr Pro Gln Leu Glu
225                 230                 235                 240

Glu Ala Leu Phe Ala Leu Ala Glu Asn Ala Leu Ser Ala Pro Val Ala
                245                 250                 255

Ser Glu Leu Gly Trp His Leu Val Trp Cys Glu Ala Ile Arg Pro Ala
                260                 265                 270

Ala Pro Met Thr Pro Glu Gln Ala Leu Glu Ser Ala Arg Asp Tyr Leu
                275                 280                 285

Ser Gln Gln Ser Gln Arg Arg His Gln Arg Gln Trp Leu Ala Glu Met
        290                 295                 300

Leu Ala Arg Gln Pro Gly Leu Cys Gly
305                 310

<210> SEQ ID NO 99
<211> LENGTH: 942
<212> TYPE: DNA
<213> ORGANISM: Artificial Sequence
<220> FEATURE:
<223> OTHER INFORMATION: Recombinant

<400> SEQUENCE: 99
atggctcctt ctgttatggc ttcttcagca actacagtgg cacctttca aggtcttaag      60 tcaaccgccg gtatgccagt cgcgagaagg agtggaaatt ccagcttcgg aaatgtatcg     120
aacggcggga gaattcgttg tatggagccc tggcaacgat ttggccggca gcggctggcg     180
cagagccgct ggaactgcga gccggcggcc atcgccgcgg tcgaccggca ggccttcgag     240
gcggcctggc agcgccaggc ccagatggag caggttattg tcgcccagat gcgccggag      300 gcgatcccg ccgcgctgca ggagggcctc gccacttcgc tgggcgcctg gctggatgag      360
ggaggattta cgccagcgga gcgggcggcg atcgtcctgc accacgcccg gctggaaacc     420
gccttcgccg gaattgccag ccaggcgccg cggccggatc cgccacggt gcaggcctgg      480 tatctgcggc atcaggcgca gtttatgcgc ccggaacagc gcctgacccg ccatctgctg     540
ctcaccgtcg atggcgacga ccagacggtt tactcgcgca tacgggagct tcatgggcaa     600
atcgaagcct cccgcgaggc gtttgcgccg ctggcccagc gacactccca ctgcccgagc     660
gcgctggacg gcggactgct gggctggatc ggccgggggc tgctctatcc gcagctggag     720
gaggcgctgt ttgcgctggc ggaaaatgcg ctgagcgcgc cggtggccag cgagctcggc     780
tggcatctgg tctggtgtga ggccattcgc cctgccgcgc cgatgacgcc tgagcaggcg     840
```

```
ctggaaagcg cccgcgatta cctcagtcaa cagagccagc gccgccacca gcgccagtgg    900
ctggccgaga tgctagcgcg ccagccgggg ctgtgcggat aa                       942
```

<210> SEQ ID NO 100
<211> LENGTH: 374
<212> TYPE: PRT
<213> ORGANISM: Artificial Sequence
<220> FEATURE:
<223> OTHER INFORMATION: Recombinant

<400> SEQUENCE: 100

```
Met Ala Pro Ser Val Met Ala Ser Ser Ala Thr Thr Val Ala Pro Phe
1               5                   10                  15

Gln Gly Leu Lys Ser Thr Ala Gly Met Pro Val Ala Arg Arg Ser Gly
            20                  25                  30

Asn Ser Ser Phe Gly Asn Val Ser Asn Gly Gly Arg Ile Arg Cys Met
        35                  40                  45

Gly Arg Asn Ser Gln Gly Phe Leu Thr Thr Ile Arg Ile Ile Val Thr
    50                  55                  60

Ser Ala Thr Asp Gln Pro Ser Asn Phe Ile His Ser Leu Ser Asn Lys
65                  70                  75                  80

Arg Glu Ser Thr Met Arg Gln Ile Ala Phe Tyr Gly Lys Gly Gly Ile
                85                  90                  95

Gly Lys Ser Thr Thr Ser Gln Asn Thr Ile Ala Ala Leu Ala Glu Thr
            100                 105                 110

Asn Arg Ile Met Ile Val Gly Cys Asp Pro Lys Ala Asp Ser Thr Arg
        115                 120                 125

Leu Met Leu His Thr Lys Ala Gln Thr Thr Ile Leu His Leu Ala Ala
    130                 135                 140

Glu Arg Gly Thr Val Glu Asp Ile Glu Leu Glu Glu Val Leu Leu Glu
145                 150                 155                 160

Gly Tyr Gln Gly Val Lys Cys Val Glu Ser Gly Gly Pro Glu Pro Gly
                165                 170                 175

Val Gly Cys Ala Gly Arg Gly Ile Ile Thr Ala Ile Asn Phe Leu Glu
            180                 185                 190

Glu Glu Gly Ala Tyr Glu Asp Leu Asp Phe Val Ser Tyr Asp Val Leu
        195                 200                 205

Gly Asp Val Val Cys Gly Gly Phe Ala Met Pro Ile Arg Glu Gly Lys
    210                 215                 220

Ala Gln Glu Ile Tyr Ile Val Thr Ser Gly Glu Met Met Ala Met Tyr
225                 230                 235                 240

Ala Ala Asn Asn Ile Ala Arg Gly Ile Leu Lys Tyr Ala His Thr Gly
                245                 250                 255

Gly Val Arg Leu Gly Gly Leu Ile Cys Asn Ser Arg Asn Val Asn Cys
            260                 265                 270

Glu Ala Glu Leu Ile Glu Glu Leu Ala Arg Arg Leu Gly Thr Gln Met
        275                 280                 285

Ile His Phe Val Pro Arg Ser Lys Gln Val Gln Ala Glu Leu Arg
    290                 295                 300

Arg Met Thr Val Ile Glu Tyr Ser Pro Asp His Pro Gln Ala Gln Glu
305                 310                 315                 320

Tyr Arg Glu Leu Ser Arg Lys Ile Glu Asn Asn Thr Asn Leu Val Ile
                325                 330                 335

Pro Thr Pro Ile Thr Met Glu Glu Leu Glu Glu Leu Leu Val Asp Phe
            340                 345                 350
```

Gly Ile Leu Gly Gly Glu Asp Glu Tyr Glu Lys Ala Leu Gln Ala Asp
        355                 360                 365

Lys Ala Ala Thr Lys Ala
    370

<210> SEQ ID NO 101
<211> LENGTH: 1125
<212> TYPE: DNA
<213> ORGANISM: Artificial Sequence
<220> FEATURE:
<223> OTHER INFORMATION: Recombinant

<400> SEQUENCE: 101

```
atggctcctt ctgttatggc ttcttcagca actacagtgg cacctttca aggtcttaag      60
tcaaccgccg gtatgccagt cgcgagaagg agtggaaatt ccagcttcgg aaatgtatcg    120
aacggcggga gaattcgttg tatgggacgc aactcccaag gtttcctaac acaatacga    180
atcatcgtta cgtcagcaac ggatcaacct tccaacttta tacactcact gtctaacaag    240
cgagaatcaa ctatgcgtca gattgcattt tacggaaaag gcggtatcgg taagtctacc    300
acttctcaga ataccattgc tgcgttagct gaaaccaacc gcatcatgat tgttggttgt    360
gacccctaaag ctgattctac ccgcttaatg cttcacacca agcacaaac caccattctg    420
cacttagcag cagaacgggg aaccgttgaa gacatcgaac tcgaagaagt attactcgaa    480
ggataccaag gagtcaagtg tgttgagtcc ggtggtcctg agcctggagt tggatgtgcg    540
ggtcgtggta ttatcaccgc cattaacttc ttagaagaag aaggtgctta cgaagaccta    600
gacttcgtat cctacgacgt attaggagac gttgtatgtg gtggtttcgc tatgcctatc    660
cgtgaaggaa aagcacaaga aatctacatc gtaacctccg gggaaatgat ggcgatgtac    720
gctgcaaaca acattgctcg tggtattta aaatacgctc acactggtgg tgttcgttta    780
ggtggtttaa tttgtaacag ccgtaacgtt aactgtgaag ctgagttaat cgaagaatta    840
gctcgtcgtc tcggaaccca aatgattcac ttcgtacccc gttctaagca ggtacaagaa    900
gctgaattac gtcgtatgac tgttatcgaa tattctcctg atcaccctca ggctcaggaa    960
taccgtgagt tatctcgcaa aatcgagaat aacaccaacc tcgttattcc tactcctatc  1020
accatggaag aactcgaaga actcttagtt gacttcggta ttctcggtgg tgaagacgag  1080
tatgagaaag ctcttcaagc tgataaagct gctaccaaag cttag                  1125
```

<210> SEQ ID NO 102
<211> LENGTH: 531
<212> TYPE: PRT
<213> ORGANISM: Artificial Sequence
<220> FEATURE:
<223> OTHER INFORMATION: Recombinant

<400> SEQUENCE: 102

Met Ala Gln Val Ser Arg Ile Cys Asn Gly Val Gln Asn Pro Ser Leu
1               5                  10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met Leu His Gly
65                  70                  75                  80

```
Ala Ser Ser Arg Pro Ala Thr Ala Arg Lys Ser Ser Gly Leu Ser Gly
                85                  90                  95

Thr Val Arg Ile Pro Gly Asp Lys Ser Ile Ser His Arg Ser Phe Met
            100                 105                 110

Phe Gly Gly Leu Ala Ser Gly Glu Thr Arg Ile Thr Gly Leu Leu Glu
        115                 120                 125

Gly Glu Asp Val Ile Asn Thr Gly Lys Ala Met Gln Ala Met Gly Ala
130                 135                 140

Arg Ile Arg Lys Glu Gly Asp Thr Trp Ile Ile Asp Gly Val Gly Asn
145                 150                 155                 160

Gly Gly Leu Leu Ala Pro Glu Ala Pro Leu Asp Phe Gly Asn Ala Ala
                165                 170                 175

Thr Gly Cys Arg Leu Thr Met Gly Leu Val Gly Val Tyr Asp Phe Asp
            180                 185                 190

Ser Thr Phe Ile Gly Asp Ala Ser Leu Thr Lys Arg Pro Met Gly Arg
        195                 200                 205

Val Leu Asn Pro Leu Arg Glu Met Gly Val Gln Val Lys Ser Glu Asp
        210                 215                 220

Gly Asp Arg Leu Pro Val Thr Leu Arg Gly Pro Lys Thr Pro Thr Pro
225                 230                 235                 240

Ile Thr Tyr Arg Val Pro Met Ala Ser Ala Gln Val Lys Ser Ala Val
                245                 250                 255

Leu Leu Ala Gly Leu Asn Thr Pro Gly Ile Thr Thr Val Ile Glu Pro
            260                 265                 270

Ile Met Thr Arg Asp His Thr Glu Lys Met Leu Gln Gly Phe Gly Ala
        275                 280                 285

Asn Leu Thr Val Glu Thr Asp Ala Asp Gly Val Arg Thr Ile Arg Leu
        290                 295                 300

Glu Gly Arg Gly Lys Leu Thr Gly Gln Val Ile Asp Val Pro Gly Asp
305                 310                 315                 320

Pro Ser Ser Thr Ala Phe Pro Leu Val Ala Ala Leu Leu Val Pro Gly
                325                 330                 335

Ser Asp Val Thr Ile Leu Asn Val Leu Met Asn Pro Thr Arg Thr Gly
            340                 345                 350

Leu Ile Leu Thr Leu Gln Glu Met Gly Ala Asp Ile Glu Val Ile Asn
        355                 360                 365

Pro Arg Leu Ala Gly Gly Glu Asp Val Ala Asp Leu Arg Val Arg Ser
        370                 375                 380

Ser Thr Leu Lys Gly Val Thr Val Pro Glu Asp Arg Ala Pro Ser Met
385                 390                 395                 400

Ile Asp Glu Tyr Pro Ile Leu Ala Val Ala Ala Phe Ala Glu Gly
                405                 410                 415

Ala Thr Val Met Asn Gly Leu Glu Glu Leu Arg Val Lys Glu Ser Asp
            420                 425                 430

Arg Leu Ser Ala Val Ala Asn Gly Leu Lys Leu Asn Gly Val Asp Cys
        435                 440                 445

Asp Glu Gly Glu Thr Ser Leu Val Val Arg Gly Arg Pro Asp Gly Lys
450                 455                 460

Gly Leu Gly Asn Ala Ser Gly Ala Ala Val Ala Thr His Leu Asp His
465                 470                 475                 480

Arg Ile Ala Met Ser Phe Leu Val Met Gly Leu Val Ser Glu Asn Pro
                485                 490                 495
```

Val Thr Val Asp Asp Ala Thr Met Ile Ala Thr Ser Phe Pro Glu Phe
                500                 505                 510

Met Asp Leu Met Ala Gly Leu Gly Ala Lys Ile Glu Leu Ser Asp Thr
        515                 520                 525

Lys Ala Ala
    530

<210> SEQ ID NO 103
<211> LENGTH: 1596
<212> TYPE: DNA
<213> ORGANISM: Artificial Sequence
<220> FEATURE:
<223> OTHER INFORMATION: Recombinant

<400> SEQUENCE: 103

```
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcgtgcat gcttcacggt     240
gcaagcagcc gtccagcaac tgctcgtaag tcctctggtc tttctggaac cgtccgtatt     300
ccaggtgaca gtctatctc ccacaggtcc ttcatgtttg aggtctcgc tagcggtgaa     360 actcgtatca ccggtctttt ggaaggtgaa gatgttatca acactggtaa ggctatgcaa     420
gctatgggtg ccagaatccg taaggaaggt gatacttgga tcattgatgg tgttggtaac     480
ggtggactcc ttgctcctga ggctcctctc gatttcggta acgctgcaac tggttgccgt     540
ttgactatgg gtcttgttgg tgtttacgat tcgatagca ctttcattgg tgacgcttct     600
ctcactaagc gtccaatggg tcgtgtgttg aacccacttc gcgaaatggg tgtgcaggtg     660
aagtctgaag acggtgatcg tcttccagtt accttgcgtg gaccaaagac tccaacgcca     720
atcacctaca gggtacctat ggcttccgct caagtgaagt ccgctgttct gcttgctggt     780
ctcaacaccc caggtatcac cactgttatc gagccaatca tgactcgtga ccacactgaa     840
aagatgcttc aaggttttgg tgctaacctt accgttgaga ctgatgctga cggtgtgcgt     900
accatccgtc ttgaaggtcg tggtaagctc accggtcaag tgattgatgt tccaggtgat     960
ccatcctcta ctgctttccc attggttgct gccttgcttg ttccaggttc cgacgtcacc    1020
atccttaacg ttttgatgaa cccaacccgt actggtctca tcttgactct gcaggaaatg    1080
ggtgccgaca tcgaagtgat caacccacgt cttgctggtg agaagacgt ggctgacttg    1140 cgtgttcgtt cttctacttt gaagggtgtt actgttccag aagaccgtgc tccttctatg    1200
atcgacgagt atccaattct cgctgttgca gctgcattcg ctgaaggtgc taccgttatg    1260
aacggtttgg aagaactccg tgttaaggaa agcgaccgtc tttctgctgt cgcaaacggt    1320
ctcaagctca acggtgttga ttgcgatgaa ggtgagactt ctctcgtcgt gcgtggtcgt    1380
cctgacggta agggtctcgg taacgcttct ggagcagctg tcgctaccca cctcgatcac    1440
cgtatcgcta tgagcttcct cgttatgggt ctcgtttctg aaaaccctgt tactgttgat    1500
gatgctacta tgatcgctac tagcttccca gagttcatgg atttgatggc tggtcttgga    1560
gctaagatcg aactctccga cactaaggct gcttga                              1596
```

<210> SEQ ID NO 104
<211> LENGTH: 577
<212> TYPE: PRT
<213> ORGANISM: Arabidopsis thaliana

<400> SEQUENCE: 104

```
Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
            20                  25                  30

Ala Lys Glu Ile Lys Phe Gly Val Glu Ala Arg Ala Leu Met Leu Lys
        35                  40                  45

Gly Val Glu Asp Leu Ala Asp Ala Val Lys Val Thr Met Gly Pro Lys
    50                  55                  60

Gly Arg Asn Val Val Ile Glu Gln Ser Trp Gly Ala Pro Lys Val Thr
65                  70                  75                  80

Lys Asp Gly Val Thr Val Ala Lys Ser Ile Glu Phe Lys Asp Lys Ile
                85                  90                  95

Lys Asn Val Gly Ala Ser Leu Val Lys Gln Val Ala Asn Ala Thr Asn
            100                 105                 110

Asp Val Ala Gly Asp Gly Thr Thr Cys Ala Thr Val Leu Thr Arg Ala
        115                 120                 125

Ile Phe Ala Glu Gly Cys Lys Ser Val Ala Ala Gly Met Asn Ala Met
    130                 135                 140

Asp Leu Arg Arg Gly Ile Ser Met Ala Val Asp Ala Val Val Thr Asn
145                 150                 155                 160

Leu Lys Ser Lys Ala Arg Met Ile Ser Thr Ser Glu Glu Ile Ala Gln
                165                 170                 175

Val Gly Thr Ile Ser Ala Asn Gly Glu Arg Glu Ile Gly Glu Leu Ile
            180                 185                 190

Ala Lys Ala Met Glu Lys Val Gly Lys Glu Gly Val Ile Thr Ile Gln
        195                 200                 205

Asp Gly Lys Thr Leu Phe Asn Glu Leu Glu Val Val Glu Gly Met Lys
    210                 215                 220

Leu Asp Arg Gly Tyr Thr Ser Pro Tyr Phe Ile Thr Asn Gln Lys Thr
225                 230                 235                 240

Gln Lys Cys Glu Leu Asp Asp Pro Leu Ile Leu Ile His Glu Lys Lys
                245                 250                 255

Ile Ser Ser Ile Asn Ser Ile Val Lys Val Leu Glu Leu Ala Leu Lys
            260                 265                 270

Arg Gln Arg Pro Leu Leu Ile Val Ser Glu Asp Val Glu Ser Asp Ala
        275                 280                 285

Leu Ala Thr Leu Ile Leu Asn Lys Leu Arg Ala Gly Ile Lys Val Cys
    290                 295                 300

Ala Ile Lys Ala Pro Gly Phe Gly Glu Asn Arg Lys Ala Asn Leu Gln
305                 310                 315                 320

Asp Leu Ala Ala Leu Thr Gly Gly Glu Val Ile Thr Asp Glu Leu Gly
                325                 330                 335

Met Asn Leu Glu Lys Val Asp Leu Ser Met Leu Gly Thr Cys Lys Lys
            340                 345                 350

Val Thr Val Ser Lys Asp Asp Thr Val Ile Leu Asp Gly Ala Gly Asp
        355                 360                 365

Lys Lys Gly Ile Glu Glu Arg Cys Glu Gln Ile Arg Ser Ala Ile Glu
    370                 375                 380

Leu Ser Thr Ser Asp Tyr Asp Lys Glu Lys Leu Gln Glu Arg Leu Ala
385                 390                 395                 400

Lys Leu Ser Gly Gly Val Ala Val Leu Lys Ile Gly Gly Ala Ser Glu
                405                 410                 415
```

```
Ala Glu Val Gly Glu Lys Lys Asp Arg Val Thr Asp Ala Leu Asn Ala
            420                 425                 430

Thr Lys Ala Ala Val Glu Gly Ile Leu Pro Gly Gly Val Ala
        435                 440                 445

Leu Leu Tyr Ala Ala Arg Glu Leu Glu Lys Leu Pro Thr Ala Asn Phe
    450                 455                 460

Asp Gln Lys Ile Gly Val Gln Ile Ile Gln Asn Ala Leu Lys Thr Pro
465                 470                 475                 480

Val Tyr Thr Ile Ala Ser Asn Ala Gly Val Glu Gly Ala Val Ile Val
                485                 490                 495

Gly Lys Leu Leu Glu Gln Asp Asn Pro Asp Leu Gly Tyr Asp Ala Ala
            500                 505                 510

Lys Gly Glu Tyr Val Asp Met Val Lys Ala Gly Ile Ile Asp Pro Leu
            515                 520                 525

Lys Val Ile Arg Thr Ala Leu Val Asp Ala Ala Ser Val Ser Ser Leu
            530                 535                 540

Leu Thr Thr Thr Glu Ala Val Val Val Asp Leu Pro Lys Asp Glu Ser
545                 550                 555                 560

Glu Ser Gly Ala Ala Gly Ala Gly Met Gly Gly Met Gly Gly Met Asp
                565                 570                 575

Tyr

<210> SEQ ID NO 105
<211> LENGTH: 349
<212> TYPE: PRT
<213> ORGANISM: Typhonium venosum

<400> SEQUENCE: 105

Met Met Ser Ser Arg Leu Val Gly Thr Ala Leu Cys Arg Gln Leu Ser
1               5                   10                  15

His Val Pro Val Pro Gln Tyr Leu Pro Ala Leu Arg Pro Thr Ala Asp
            20                  25                  30

Thr Ala Ser Ser Leu Leu His Gly Cys Ser Ala Ala Pro Ala Gln
        35                  40                  45

Arg Ala Gly Leu Trp Pro Pro Ser Trp Phe Ser Pro Pro Arg His Ala
    50                  55                  60

Ser Thr Leu Ser Ala Pro Ala Gln Asp Gly Gly Lys Glu Lys Ala Ala
65                  70                  75                  80

Gly Thr Ala Gly Lys Val Pro Pro Gly Glu Asp Gly Gly Ala Glu Lys
                85                  90                  95

Glu Ala Val Val Ser Tyr Trp Ala Val Pro Pro Ser Lys Val Ser Lys
            100                 105                 110

Glu Asp Gly Ser Glu Trp Arg Trp Thr Cys Phe Arg Pro Trp Glu Thr
        115                 120                 125

Tyr Gln Ala Asp Leu Ser Ile Asp Leu His Lys His Val Pro Thr
    130                 135                 140

Thr Ile Leu Asp Lys Leu Ala Leu Arg Thr Val Lys Ala Leu Arg Trp
145                 150                 155                 160

Pro Thr Asp Ile Phe Phe Gln Arg Arg Tyr Ala Cys Arg Ala Met Met
                165                 170                 175

Leu Glu Thr Val Ala Ala Val Pro Gly Met Val Gly Gly Val Leu Leu
            180                 185                 190

His Leu Lys Ser Leu Arg Arg Phe Glu His Ser Gly Gly Trp Ile Arg
        195                 200                 205
```

```
Ala Leu Leu Glu Glu Ala Glu Asn Glu Arg Met His Leu Met Thr Phe
        210                 215                 220

Met Glu Val Ala Gln Pro Arg Trp Tyr Glu Arg Ala Leu Val Leu Ala
225                 230                 235                 240

Val Gln Gly Val Phe Asn Ala Tyr Phe Leu Gly Tyr Leu Leu Ser
            245                 250                 255

Pro Lys Phe Ala His Arg Val Val Gly Tyr Leu Glu Glu Ala Ile
        260                 265                 270

His Ser Tyr Thr Glu Phe Leu Lys Asp Ile Asp Ser Gly Ala Ile Gln
        275                 280                 285

Asp Cys Pro Ala Pro Ala Ile Ala Leu Asp Tyr Trp Arg Leu Pro Gln
        290                 295                 300

Gly Ser Thr Leu Arg Asp Val Val Thr Val Arg Ala Asp Glu Ala
305                 310                 315                 320

His His Arg Asp Val Asn His Phe Ala Ser Asp Val His Tyr Gln Asp
                325                 330                 335

Leu Glu Leu Lys Thr Thr Pro Ala Pro Leu Gly Tyr His
        340                 345

<210> SEQ ID NO 106
<211> LENGTH: 147
<212> TYPE: PRT
<213> ORGANISM: Neurospora crassa

<400> SEQUENCE: 106

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Tyr Ser Ser Glu Ile Ala Gln Ala Met Val Glu Val Ser Lys
65                  70                  75                  80

Asn Leu Gly Met Gly Ser Ala Ala Ile Gly Leu Thr Gly Ala Gly Ile
                85                  90                  95

Gly Ile Gly Leu Val Phe Ala Ala Leu Leu Asn Gly Val Ala Arg Asn
            100                 105                 110

Pro Ala Leu Arg Gly Gln Leu Phe Ser Tyr Ala Ile Leu Gly Phe Ala
        115                 120                 125

Phe Val Glu Ala Ile Gly Leu Phe Asp Leu Met Val Ala Leu Met Ala
    130                 135                 140

Lys Phe Thr
145

<210> SEQ ID NO 107
<211> LENGTH: 501
<212> TYPE: PRT
<213> ORGANISM: Pisum sativum

<400> SEQUENCE: 107

Met Ala Met Ala Asn Leu Ala Arg Arg Lys Gly Tyr Ser Leu Leu Ser
1               5                   10                  15

Ser Glu Thr Leu Arg Tyr Ser Phe Ser Leu Arg Ser Arg Ala Phe Ala
            20                  25                  30
```

```
Ser Gly Ser Asp Glu Asn Asp Val Val Ile Ile Gly Gly Pro Gly
        35                  40                  45

Gly Tyr Val Ala Ala Ile Lys Ala Ala Gln Leu Gly Phe Lys Thr Thr
    50                  55                  60

Cys Ile Glu Lys Arg Gly Ala Leu Gly Gly Thr Cys Leu Asn Val Gly
65                  70                  75                  80

Cys Ile Pro Ser Lys Ala Leu Leu His Ser His Met Tyr His Glu
                85                  90                  95

Ala Lys His Ser Phe Ala Asn His Gly Val Lys Val Ser Asn Val Glu
            100                 105                 110

Ile Asp Leu Ala Ala Met Met Gly Gln Lys Asp Lys Ala Val Ser Asn
            115                 120                 125

Leu Thr Arg Gly Ile Glu Gly Leu Phe Lys Lys Asn Lys Val Thr Tyr
        130                 135                 140

Val Lys Gly Tyr Gly Lys Phe Val Ser Pro Ser Glu Ile Ser Val Asp
145                 150                 155                 160

Thr Ile Glu Gly Glu Asn Thr Val Val Lys Gly Lys His Ile Ile Ile
                165                 170                 175

Ala Thr Gly Ser Asp Val Lys Ser Leu Pro Gly Val Thr Ile Asp Glu
            180                 185                 190

Lys Lys Ile Val Ser Ser Thr Gly Ala Leu Ala Leu Ser Glu Ile Pro
        195                 200                 205

Lys Lys Leu Val Val Ile Gly Ala Gly Tyr Ile Gly Leu Glu Met Gly
    210                 215                 220

Ser Val Trp Gly Arg Ile Gly Ser Glu Val Thr Val Val Glu Phe Ala
225                 230                 235                 240

Ser Glu Ile Val Pro Thr Met Asp Ala Glu Ile Arg Lys Gln Phe Gln
                245                 250                 255

Arg Ser Leu Glu Lys Gln Gly Met Lys Phe Lys Leu Lys Thr Lys Val
            260                 265                 270

Val Gly Val Asp Thr Ser Gly Asp Gly Val Lys Leu Thr Val Glu Pro
        275                 280                 285

Ser Ala Gly Gly Glu Gln Thr Ile Ile Glu Ala Asp Val Val Leu Val
    290                 295                 300

Ser Ala Gly Arg Thr Pro Phe Thr Ser Gly Leu Asn Leu Asp Lys Ile
305                 310                 315                 320

Gly Val Glu Thr Asp Lys Leu Gly Arg Ile Leu Val Asn Glu Arg Phe
                325                 330                 335

Ser Thr Asn Val Ser Gly Val Tyr Ala Ile Gly Asp Val Ile Pro Gly
            340                 345                 350

Pro Met Leu Ala His Lys Ala Glu Glu Asp Gly Val Ala Cys Val Glu
        355                 360                 365

Tyr Leu Ala Gly Lys Val Gly His Val Asp Tyr Asp Lys Val Pro Gly
    370                 375                 380

Val Val Tyr Thr Asn Pro Glu Val Ala Ser Val Gly Lys Thr Glu Glu
385                 390                 395                 400

Gln Val Lys Glu Thr Gly Val Glu Tyr Arg Val Gly Lys Phe Pro Phe
                405                 410                 415

Met Ala Asn Ser Arg Ala Lys Ala Ile Asp Asn Ala Glu Gly Leu Val
            420                 425                 430

Lys Ile Ile Ala Glu Lys Glu Thr Asp Lys Ile Leu Gly Val His Ile
        435                 440                 445
```

```
Met Ala Pro Asn Ala Gly Glu Leu Ile His Glu Ala Ala Ile Ala Leu
            450                 455                 460

Gln Tyr Asp Ala Ser Ser Glu Asp Ile Ala Arg Val Cys His Ala His
465                 470                 475                 480

Pro Thr Met Ser Glu Ala Ile Lys Glu Ala Ala Met Ala Thr Tyr Asp
                485                 490                 495

Lys Pro Ile His Ile
            500

<210> SEQ ID NO 108
<211> LENGTH: 1037
<212> TYPE: PRT
<213> ORGANISM: Flaveria pringlei

<400> SEQUENCE: 108

Met Asp Arg Ala Arg Arg Leu Ala Asn Lys Ala Ile Leu Gly Arg Leu
1               5                   10                  15

Val Ser Gln Thr Lys His Asn Pro Ser Ile Ser Pro Ala Leu Cys
                20                  25                  30

Ser Pro Ser Arg Tyr Val Ser Ser Leu Ser Pro Tyr Val Cys Ser Gly
            35                  40                  45

Thr Asn Val Arg Ser Asp Arg Asn Leu Asn Gly Phe Gly Ser Gln Val
    50                  55                  60

Arg Thr Ile Ser Val Glu Ala Leu Lys Pro Ser Asp Thr Phe Pro Arg
65                  70                  75                  80

Arg His Asn Ser Ala Thr Pro Glu Glu Gln Thr Lys Met Ala Glu Phe
                85                  90                  95

Val Gly Phe Pro Asn Leu Asp Ser Leu Ile Asp Ala Thr Val Pro Lys
            100                 105                 110

Ser Ile Arg Leu Asp Ser Met Lys Tyr Ser Lys Phe Asp Glu Gly Leu
        115                 120                 125

Thr Glu Ser Gln Met Ile Ala His Met Gln Asp Leu Ala Ser Lys Asn
    130                 135                 140

Lys Ile Phe Lys Ser Phe Ile Gly Met Gly Tyr Tyr Asn Thr Ser Val
145                 150                 155                 160

Pro Thr Val Ile Leu Arg Asn Ile Met Glu Asn Pro Gly Trp Tyr Thr
                165                 170                 175

Gln Tyr Thr Pro Tyr Gln Ala Glu Ile Ala Gln Gly Arg Leu Glu Ser
            180                 185                 190

Leu Leu Asn Phe Gln Thr Met Val Thr Asp Leu Thr Gly Leu Pro Met
        195                 200                 205

Ser Asn Ala Ser Leu Leu Asp Glu Gly Thr Ala Ala Ala Glu Ala Met
    210                 215                 220

Ala Met Cys Asn Asn Ile Gln Lys Gly Lys Lys Lys Thr Phe Ile Ile
225                 230                 235                 240

Ala Ser Asn Cys His Pro Gln Thr Ile Asp Ile Cys Lys Thr Arg Ala
                245                 250                 255

Asp Gly Phe Asp Leu Lys Val Val Thr Ser Asp Leu Lys Asp Phe Asp
            260                 265                 270

Tyr Ser Ser Gly Asp Val Cys Gly Val Leu Val Gln Tyr Pro Gly Thr
        275                 280                 285

Glu Gly Glu Leu Leu Asp Tyr Ser Glu Phe Ile Lys Asn Ala His Ala
    290                 295                 300

Asn Gly Val Lys Val Val Met Ala Ser Asp Leu Leu Ala Leu Thr Ile
305                 310                 315                 320
```

```
Leu Lys Pro Pro Gly Glu Leu Ala Asp Ile Val Gly Ser Ala
            325                 330                 335

Gln Arg Phe Gly Val Pro Met Gly Tyr Gly Pro His Ala Ala Phe
            340                 345                 350

Leu Ala Thr Ser Gln Glu Tyr Lys Arg Met Met Pro Gly Arg Ile Ile
            355                 360                 365

Gly Val Ser Val Asp Ser Ser Gly Lys Pro Ala Leu Arg Met Ala Met
            370                 375                 380

Gln Thr Arg Glu Gln His Ile Arg Arg Asp Lys Ala Thr Ser Asn Ile
385                 390                 395                 400

Cys Thr Ala Gln Ala Leu Leu Ala Asn Met Ala Ala Met Phe Gly Val
            405                 410                 415

Tyr His Gly Pro Glu Gly Leu Lys Thr Ile Ala Lys Arg Val His Gly
            420                 425                 430

Leu Ala Gly Thr Phe Ala Ala Gly Leu Lys Lys Leu Gly Thr Val Gln
            435                 440                 445

Val Gln Asp Leu Pro Phe Phe Asp Thr Val Lys Val Thr Cys Val Asp
            450                 455                 460

Ser Lys Ala Ile Ala Glu Glu Ala Tyr Lys His Lys Met Asn Leu Arg
465                 470                 475                 480

Ile Val Asp Lys Asn Thr Ile Thr Val Ala Phe Asp Glu Thr Ile Thr
            485                 490                 495

Ile Glu Asp Val Asp Thr Leu Phe Lys Val Phe Ala Leu Gly Lys Pro
            500                 505                 510

Val Thr Phe Thr Ala Ala Ser Ile Ala Pro Glu Val Gln Asp Ala Ile
            515                 520                 525

Pro Ser Gly Leu Val Arg Glu Thr Pro Tyr Leu Thr His Pro Ile Phe
            530                 535                 540

Asn Met Tyr His Thr Glu His Glu Leu Leu Arg Tyr Ile Ser Lys Leu
545                 550                 555                 560

Gln Ser Lys Asp Leu Ser Leu Cys His Ser Met Ile Pro Leu Gly Ser
            565                 570                 575

Cys Thr Met Lys Leu Asn Ala Thr Thr Glu Met Met Pro Val Thr Trp
            580                 585                 590

Pro Ala Phe Ala Asp Ile His Pro Phe Ala Pro Thr Glu Gln Ala Gln
            595                 600                 605

Gly Tyr Gln Glu Met Phe Lys Asn Leu Gly Asp Leu Leu Cys Thr Ile
            610                 615                 620

Thr Gly Phe Asp Ser Phe Ser Leu Gln Pro Asn Ala Gly Ala Ala Gly
625                 630                 635                 640

Glu Tyr Ala Gly Leu Met Val Ile Arg Ala Tyr His Met Ala Arg Gly
            645                 650                 655

Asp His His Arg Asn Val Cys Ile Ile Pro Val Ser Ala His Gly Thr
            660                 665                 670

Asn Pro Ala Ser Ala Ala Met Cys Gly Met Lys Ile Ile Thr Val Gly
            675                 680                 685

Thr Asp Ser Lys Gly Asn Ile Asn Ile Glu Glu Leu Arg Lys Ala Ala
            690                 695                 700

Glu Ala Asn Lys Glu Asn Leu Ser Ala Leu Met Val Thr Tyr Pro Ser
705                 710                 715                 720

Thr His Gly Val Tyr Glu Glu Gly Ile Asp Glu Ile Cys Lys Ile Ile
            725                 730                 735
```

His Asp Asn Gly Gly Gln Val Tyr Met Asp Gly Ala Asn Met Asn Ala
                740                 745                 750

Gln Val Gly Leu Thr Ser Pro Gly Trp Ile Gly Ala Asp Val Cys His
        755                 760                 765

Leu Asn Leu His Lys Thr Phe Cys Ile Pro His Gly Gly Gly Gly Pro
    770                 775                 780

Gly Met Gly Pro Ile Gly Val Lys Lys His Leu Ala Pro Tyr Leu Pro
785                 790                 795                 800

Ser His Pro Val Val Ala Thr Gly Gly Ile Pro Ala Pro Glu Gln Ser
                805                 810                 815

Gln Pro Leu Gly Thr Ile Ala Ala Ala Pro Trp Gly Ser Ala Leu Ile
        820                 825                 830

Leu Pro Ile Ser Tyr Thr Tyr Ile Ala Met Met Gly Ser Gln Gly Ile
    835                 840                 845

Thr Asn Ala Ser Lys Ile Ala Ile Leu Asn Ala Asn Tyr Met Ala Lys
    850                 855                 860

Arg Leu Glu Asn His Tyr Pro Ile Leu Phe Arg Gly Val Asn Gly Thr
865                 870                 875                 880

Val Ala His Glu Phe Ile Val Asp Leu Arg Pro Leu Lys Thr Thr Ala
                885                 890                 895

Gly Ile Glu Pro Glu Asp Val Ala Lys Arg Leu Ile Asp Tyr Gly Phe
        900                 905                 910

His Gly Pro Thr Met Ser Trp Pro Val Pro Gly Thr Leu Met Ile Glu
    915                 920                 925

Pro Thr Glu Ser Glu Ser Lys Ala Glu Leu Asp Arg Phe Cys Asp Ala
    930                 935                 940

Leu Ile Ser Ile Arg Gln Glu Ile Ala Glu Ile Glu Lys Gly Asn Val
945                 950                 955                 960

Asp Leu Asn Asn Asn Val Ile Lys Gly Ala Pro His Pro Gln Leu
                965                 970                 975

Leu Met Ala Asp Lys Trp Thr Lys Pro Tyr Ser Arg Glu Tyr Ala Ala
        980                 985                 990

Tyr Pro Ala Pro Trp Leu Arg Ala Ala Lys Phe Trp Pro Thr Thr Cys
    995                 1000                1005

Arg Val Asp Asn Val Tyr Gly Asp Arg Asn Leu Ile Cys Thr Leu
    1010                1015                1020

Gln Pro Pro Gln Glu Tyr Glu Glu Lys Ala Glu Ala Thr Ala
    1025                1030                1035

<210> SEQ ID NO 109
<211> LENGTH: 1057
<212> TYPE: PRT
<213> ORGANISM: Pisum sativum

<400> SEQUENCE: 109

Met Glu Arg Ala Arg Arg Leu Ala Asn Arg Ala Thr Leu Lys Arg Leu
1               5                   10                  15

Leu Ser Glu Ala Lys Gln Asn Arg Lys Thr Glu Ser Thr Ser Thr Thr
            20                  25                  30

Thr Thr Thr Pro Leu Pro Phe Ser Leu Ser Gly Ser Ser Arg Tyr
        35                  40                  45

Val Ser Ser Val Ser Asn Ser Ile Leu Arg Gly Arg Gly Ser Lys Pro
    50                  55                  60

Asp Asn Asn Val Ser Arg Arg Val Gly Gly Phe Leu Gly Val Gly Tyr
65                  70                  75                  80

```
Pro Ser Gln Ser Arg Ser Ile Ser Val Glu Ala Leu Lys Pro Ser Asp
                85                  90                  95
Thr Phe Pro Arg Arg His Asn Ser Ala Thr Pro Asp Glu Gln Thr Lys
            100                 105                 110
Met Ala Glu Ser Val Gly Phe Asp Thr Leu Asp Ser Leu Val Asp Ala
        115                 120                 125
Thr Val Pro Lys Ser Ile Arg Leu Lys Glu Met Lys Phe Asn Lys Phe
130                 135                 140
Asp Gly Gly Leu Thr Glu Gly Gln Met Ile Glu His Met Lys Asp Leu
145                 150                 155                 160
Ala Ser Lys Asn Lys Val Phe Lys Ser Phe Ile Gly Met Gly Tyr Tyr
                165                 170                 175
Asn Thr His Val Pro Pro Val Ile Leu Arg Asn Ile Met Glu Asn Pro
            180                 185                 190
Ala Trp Tyr Thr Gln Tyr Thr Pro Tyr Gln Ala Glu Ile Ser Gln Gly
        195                 200                 205
Arg Leu Glu Ser Leu Leu Asn Phe Gln Thr Met Ile Thr Asp Leu Thr
210                 215                 220
Gly Leu Pro Met Ser Asn Ala Ser Leu Leu Asp Glu Gly Thr Ala Ala
225                 230                 235                 240
Ala Glu Ala Met Ser Met Cys Asn Asn Ile Gln Lys Gly Lys Lys Lys
                245                 250                 255
Thr Phe Ile Ile Ala Ser Asn Cys His Pro Gln Thr Ile Asp Ile Cys
            260                 265                 270
Gln Thr Arg Ala Asp Gly Phe Glu Leu Lys Val Val Lys Asp Leu
        275                 280                 285
Lys Asp Ile Asp Tyr Lys Ser Gly Asp Val Cys Gly Val Leu Val Gln
290                 295                 300
Tyr Pro Gly Thr Glu Gly Glu Val Leu Asp Tyr Gly Glu Phe Ile Lys
305                 310                 315                 320
Lys Ala His Ala Asn Glu Val Lys Val Val Met Ala Ser Asp Leu Leu
                325                 330                 335
Ala Leu Thr Val Leu Lys Pro Pro Gly Glu Phe Gly Ala Asp Ile Val
            340                 345                 350
Val Gly Ser Ala Gln Arg Phe Gly Val Pro Met Gly Tyr Gly Gly Pro
        355                 360                 365
His Ala Ala Phe Leu Ala Thr Ser Gln Glu Tyr Lys Arg Met Met Pro
370                 375                 380
Gly Arg Ile Ile Gly Val Ser Val Asp Ser Ser Gly Lys Gln Ala Leu
385                 390                 395                 400
Arg Met Ala Met Gln Thr Arg Glu Gln His Ile Arg Arg Asp Lys Ala
                405                 410                 415
Thr Ser Asn Ile Cys Thr Ala Gln Ala Leu Leu Ala Asn Met Ala Ala
            420                 425                 430
Met Tyr Ala Val Tyr His Gly Pro Glu Gly Leu Lys Ala Ile Ala Gln
        435                 440                 445
Arg Val His Gly Leu Ala Gly Val Phe Ala Leu Gly Leu Lys Lys Leu
450                 455                 460
Gly Leu Glu Val Gln Asp Leu Gly Phe Phe Asp Thr Val Lys Val Lys
465                 470                 475                 480
Thr Ser Asn Ala Lys Ala Ile Ala Asp Ala Ile Lys Ser Glu Ile
                485                 490                 495
```

Asn Leu Arg Val Val Asp Gly Asn Thr Ile Thr Ala Ala Phe Asp Glu
            500                 505                 510

Thr Thr Thr Leu Glu Asp Val Asp Lys Leu Phe Lys Val Phe Ala Gly
        515                 520                 525

Gly Lys Pro Val Ser Phe Thr Ala Ala Ser Leu Ala Pro Glu Phe Gln
        530                 535                 540

Asn Ala Ile Pro Ser Gly Leu Val Arg Glu Ser Pro Tyr Leu Thr His
545                 550                 555                 560

Pro Ile Phe Asn Thr Tyr Gln Thr Glu His Glu Leu Leu Arg Tyr Ile
            565                 570                 575

His Arg Leu Gln Ser Lys Asp Leu Ser Leu Cys His Ser Met Ile Pro
        580                 585                 590

Leu Gly Ser Cys Thr Met Lys Leu Asn Ala Thr Thr Glu Met Met Pro
        595                 600                 605

Val Thr Trp Pro Ser Phe Thr Asp Leu His Pro Phe Ala Pro Thr Glu
        610                 615                 620

Gln Ala Gln Gly Tyr Gln Glu Met Phe Asn Asn Leu Gly Asp Leu Leu
625                 630                 635                 640

Cys Thr Ile Thr Gly Phe Asp Ser Phe Ser Leu Gln Pro Asn Ala Gly
            645                 650                 655

Ala Ala Gly Glu Tyr Ala Gly Leu Met Val Ile Arg Ala Tyr His Leu
        660                 665                 670

Ser Arg Gly Asp His His Arg Asn Val Cys Ile Ile Pro Ala Ser Ala
        675                 680                 685

His Gly Thr Asn Pro Ala Ser Ala Ala Met Val Gly Met Lys Ile Val
        690                 695                 700

Thr Ile Gly Thr Asp Ala Lys Gly Asn Ile Asn Ile Glu Glu Leu Lys
705                 710                 715                 720

Lys Ala Ala Glu Lys His Lys Asp Asn Leu Ser Ala Phe Met Val Thr
            725                 730                 735

Tyr Pro Ser Thr His Gly Val Tyr Glu Glu Gly Ile Asp Asp Ile Cys
        740                 745                 750

Lys Ile Ile His Asp Asn Gly Gly Gln Val Tyr Met Asp Gly Ala Asn
        755                 760                 765

Met Asn Ala Gln Val Gly Leu Thr Ser Pro Gly Trp Ile Gly Ala Asp
770                 775                 780

Val Cys His Leu Asn Leu His Lys Thr Phe Cys Ile Pro His Gly Gly
785                 790                 795                 800

Gly Gly Pro Gly Met Gly Pro Ile Gly Val Lys Lys His Leu Ala Pro
            805                 810                 815

Phe Leu Pro Ser His Pro Val Val Pro Thr Gly Gly Ile Pro Ala Pro
        820                 825                 830

Glu Asn Pro Gln Pro Leu Gly Ser Ile Ser Ala Ala Pro Trp Gly Ser
        835                 840                 845

Ala Leu Ile Leu Pro Ile Ser Tyr Thr Tyr Ile Ala Met Met Gly Ser
        850                 855                 860

Gln Gly Leu Thr Asp Ala Ser Lys Ile Ala Ile Leu Asn Ala Asn Tyr
865                 870                 875                 880

Met Ala Lys Arg Leu Glu Ser Tyr Tyr Pro Val Leu Phe Arg Gly Val
            885                 890                 895

Asn Gly Thr Val Ala His Glu Phe Ile Ile Asp Leu Arg Gly Phe Lys
        900                 905                 910

Asn Thr Ala Gly Ile Glu Pro Glu Asp Val Ala Lys Arg Leu Met Asp

```
                915                 920                 925

Tyr Gly Phe His Gly Pro Thr Met Ser Trp Pro Val Ala Gly Thr Leu
        930                 935                 940

Met Ile Glu Pro Thr Glu Ser Glu Ser Lys Ala Glu Leu Asp Arg Phe
945                 950                 955                 960

Cys Asp Ala Leu Ile Ser Ile Arg Lys Glu Ile Ala Glu Val Glu Lys
                965                 970                 975

Gly Asn Ala Asp Val His Asn Asn Val Leu Lys Gly Ala Pro His Pro
            980                 985                 990

Pro Ser Leu Leu Met Ala Asp Ala Trp Thr Lys Pro Tyr Ser Arg Glu
            995                1000                1005

Tyr Ala Ala Phe Pro Ala Ala Trp Leu Arg Gly Ala Lys Phe Trp
        1010                1015                1020

Pro Thr Thr Gly Arg Val Asp Asn Val Tyr Gly Asp Arg Asn Leu
        1025                1030                1035

Val Cys Thr Leu Leu Pro Ala Ser Gln Ala Val Glu Glu Gln Ala
        1040                1045                1050

Ala Ala  Thr Ala
        1055

<210> SEQ ID NO 110
<211> LENGTH: 675
<212> TYPE: PRT
<213> ORGANISM: Phaseolus vulgaris

<400> SEQUENCE: 110

Met Ala Ala Val Leu Arg Ser Leu Arg Arg Arg Asp Val Ala Ser Ala
1               5                   10                  15

Thr Phe Ser Ala Tyr Arg Ser Leu Thr Gly Ser Thr Lys Pro Ala Tyr
            20                  25                  30

Val Ala Gln Lys Trp Ser Cys Leu Ala Arg Pro Phe Ser Ser Arg Pro
        35                  40                  45

Ala Gly Asn Asp Val Ile Gly Ile Asp Leu Gly Thr Thr Asn Ser Cys
    50                  55                  60

Val Ser Val Met Glu Gly Lys Asn Pro Lys Val Ile Glu Asn Ser Glu
65                  70                  75                  80

Gly Ala Arg Thr Thr Pro Ser Val Val Ala Phe Asn Gln Lys Gly Glu
                85                  90                  95

Leu Leu Val Gly Thr Pro Ala Lys Arg Gln Ala Val Thr Asn Pro Thr
            100                 105                 110

Asn Thr Val Phe Gly Thr Lys Arg Leu Ile Gly Arg Arg Phe Asp Asp
        115                 120                 125

Pro Gln Thr Gln Lys Glu Met Lys Met Val Pro Phe Lys Ile Val Lys
    130                 135                 140

Ala Pro Asn Gly Asp Ala Trp Val Glu Ala Asn Gly Gln Gln Tyr Ser
145                 150                 155                 160

Pro Ser Gln Ile Gly Ala Phe Val Leu Thr Lys Met Lys Glu Thr Ala
                165                 170                 175

Glu Ala Tyr Leu Gly Lys Ser Val Ser Lys Ala Val Ile Thr Val Pro
            180                 185                 190

Ala Tyr Phe Asn Asp Ala Gln Arg Gln Ala Thr Lys Asp Ala Gly Arg
        195                 200                 205

Ile Ala Gly Leu Asp Val Gln Arg Ile Ile Asn Glu Pro Thr Ala Ala
    210                 215                 220
```

```
Ala Leu Ser Tyr Gly Met Asn Asn Lys Glu Gly Leu Ile Ala Val Phe
225                 230                 235                 240

Asp Leu Gly Gly Gly Thr Phe Asp Val Ser Ile Leu Glu Ile Ser Asn
            245                 250                 255

Gly Val Phe Glu Val Lys Ala Thr Asn Gly Asp Thr Phe Leu Gly Gly
        260                 265                 270

Glu Asp Phe Asp Asn Ala Leu Leu Asp Phe Leu Val Asn Glu Phe Lys
    275                 280                 285

Arg Thr Glu Ser Ile Asp Leu Ser Lys Asp Arg Leu Ala Leu Gln Arg
290                 295                 300

Leu Arg Glu Ala Ala Glu Lys Ala Lys Ile Glu Leu Ser Ser Thr Ser
305                 310                 315                 320

Gln Thr Glu Ile Asn Leu Pro Phe Ile Thr Ala Asp Ala Ser Gly Ala
            325                 330                 335

Lys His Leu Asn Ile Thr Leu Thr Arg Ser Lys Phe Glu Ala Leu Val
            340                 345                 350

Asn His Leu Ile Glu Arg Thr Lys Ala Pro Cys Lys Ser Cys Leu Lys
        355                 360                 365

Asp Ala Asn Val Ser Ile Lys Asp Val Asp Glu Val Leu Leu Val Gly
370                 375                 380

Gly Met Thr Arg Val Pro Lys Val Gln Glu Val Val Leu Asn Ile Phe
385                 390                 395                 400

Gly Lys Ser Pro Ser Lys Gly Val Asn Pro Asp Glu Ala Val Ala Met
            405                 410                 415

Gly Ala Ala Ile Gln Gly Gly Ile Leu Arg Gly Asp Val Lys Glu Leu
            420                 425                 430

Leu Leu Leu Asp Val Thr Pro Leu Ser Leu Gly Ile Glu Thr Leu Gly
        435                 440                 445

Gly Ile Phe Thr Arg Leu Ile Asn Arg Asn Thr Thr Ile Pro Thr Lys
    450                 455                 460

Lys Ser Gln Val Phe Ser Thr Ala Ala Asp Asn Gln Thr Gln Val Gly
465                 470                 475                 480

Ile Lys Val Leu Gln Gly Glu Arg Glu Met Ala Ser Asp Asn Lys Met
            485                 490                 495

Leu Gly Glu Phe Asp Leu Val Gly Ile Pro Pro Ala Pro Arg Gly Leu
        500                 505                 510

Pro Gln Ile Glu Val Thr Phe Asp Ile Asp Ala Asn Gly Ile Val Thr
    515                 520                 525

Val Ser Ala Lys Asp Lys Ser Thr Gly Lys Glu Gln Gln Ile Thr Ile
530                 535                 540

Arg Ser Ser Gly Gly Leu Ser Glu Asp Glu Ile Glu Lys Met Val Lys
545                 550                 555                 560

Glu Ala Glu Leu His Ala Gln Lys Asp Gln Glu Arg Lys Thr Leu Ile
            565                 570                 575

Asp Ile Arg Asn Ser Ala Asp Thr Thr Ile Tyr Ser Ile Glu Lys Ser
        580                 585                 590

Leu Gly Glu Tyr Arg Glu Lys Ile Pro Ser Glu Thr Ala Lys Glu Ile
    595                 600                 605

Glu Asp Ala Val Ser Asp Leu Arg Lys Ala Met Ser Gly Asp Asn Val
    610                 615                 620

Asp Glu Ile Lys Ser Lys Leu Asp Ala Ala Asn Lys Ala Val Ser Lys
625                 630                 635                 640

Ile Gly Glu His Met Ser Gly Gly Ser Ser Gly Gly Ser Ser Ala Gly
```

```
                        645                 650                 655
Gly Ser Gln Gly Gly Gly Asp Gln Ala Pro Glu Ala Glu Tyr Glu Glu
                660                 665                 670

Val Lys Lys
        675

<210> SEQ ID NO 111
<211> LENGTH: 241
<212> TYPE: PRT
<213> ORGANISM: Arabidopsis thaliana

<400> SEQUENCE: 111

Met Ile Ala Gly Val Leu Pro Arg Ser Ser Leu Pro Ser Arg Gln Thr
1               5                   10                  15

Leu Ser Ala Ala Leu Ala Ser Phe Asn Ser Cys Ile Ser His Asn Leu
                20                  25                  30

Thr Pro Ala Thr Thr Gly Ala Ser Val Ser Ser Arg Phe Thr Leu Ala
                35                  40                  45

Ser Ser Pro Asn Ser Phe Gly Ile Arg Ala Arg Asn Ile His Ile Arg
        50                  55                  60

Ser Glu Pro Ser Met Ile Val Pro Ala Gly Ile Ala Ser Gln Gly Tyr
65                  70                  75                  80

Ala Thr Val Thr Lys Asp Arg Lys Asn Glu Ile Lys Lys Ala Lys Ile
                85                  90                  95

Lys Ile Ser Pro Asp Asn Val Arg Pro Leu Ser Arg Lys Glu Ile Ala
                100                 105                 110

Leu Gln Lys Glu Ala Ala Glu Ser Thr Ser Lys Ile Lys Gly Thr
                115                 120                 125

Lys Ile Cys Ile Ala Ile Arg Ser Phe Val Asn Pro Glu Lys Gln Ala
        130                 135                 140

Trp Cys Leu Pro Pro His Thr Arg Lys Val Ala Met Pro Asp Thr Arg
145                 150                 155                 160

Thr Leu Tyr Thr Val Leu Arg Ser Pro His Val Asp Lys Lys Ser Arg
                165                 170                 175

Glu Gln Phe Glu Met Arg Phe Lys Lys Arg Phe Leu Val Ile Lys Ala
                180                 185                 190

Gln Ser His Glu Leu Ser Lys Lys Leu Phe Trp Leu Lys Arg Tyr Arg
                195                 200                 205

Ile Leu Gly Ala Gln Tyr Glu Leu Gln Phe His Cys Lys Thr Arg Leu
        210                 215                 220

Asp Met Thr Gln Val Leu Gly Asn Ile Asn Gly Ser Thr Thr Asn Ala
225                 230                 235                 240

Tyr

<210> SEQ ID NO 112
<211> LENGTH: 175
<212> TYPE: PRT
<213> ORGANISM: Oryza sativa

<400> SEQUENCE: 112

Met Ala Pro Ser Val Met Ala Ser Ala Thr Thr Val Ala Pro Phe
1               5                   10                  15

Gln Gly Leu Lys Ser Thr Ala Gly Met Pro Val Ala Arg Arg Ser Gly
                20                  25                  30

Asn Ser Ser Phe Gly Asn Val Ser Asn Gly Gly Arg Ile Arg Cys Met
        35                  40                  45
```

```
Gln Val Trp Pro Ile Glu Gly Ile Lys Lys Phe Glu Thr Leu Ser Tyr
        50                  55                  60

Leu Pro Pro Leu Thr Val Glu Asp Leu Leu Lys Gln Ile Glu Tyr Leu
 65                  70                  75                  80

Leu Arg Ser Lys Trp Val Pro Cys Leu Glu Phe Ser Lys Val Gly Phe
                85                  90                  95

Val Tyr Arg Glu Asn His Arg Ser Pro Gly Tyr Tyr Asp Gly Arg Tyr
            100                 105                 110

Trp Thr Met Trp Lys Leu Pro Met Phe Gly Cys Thr Asp Ala Thr Gln
            115                 120                 125

Val Leu Lys Glu Leu Glu Glu Ala Lys Lys Ala Tyr Pro Asp Ala Phe
130                 135                 140

Val Arg Ile Ile Gly Phe Asp Asn Val Arg Gln Val Gln Leu Ile Ser
145                 150                 155                 160

Phe Ile Ala Tyr Lys Pro Pro Gly Cys Glu Glu Ser Gly Gly Asn
                165                 170                 175

<210> SEQ ID NO 113
<211> LENGTH: 114
<212> TYPE: DNA
<213> ORGANISM: Nicotiana tabacum

<400> SEQUENCE: 113
gctcccccgc cgtcgttcaa tgagaatgga taagaggctc gtgggattga cgtgaggggg    60
cagggatggc tatatttctg ggagcgaact ccgggcgaat tgtagaaata attt         114

<210> SEQ ID NO 114
<211> LENGTH: 39
<212> TYPE: DNA
<213> ORGANISM: T7 bacteriophage

<400> SEQUENCE: 114
tgtagaaata attttgttta actttaagaa ggagatata                           39

<210> SEQ ID NO 115
<211> LENGTH: 149
<212> TYPE: DNA
<213> ORGANISM: Artificial Sequence
<220> FEATURE:
<223> OTHER INFORMATION: Recombinant

<400> SEQUENCE: 115
gaaattcaat taaggaaata aattaaggaa atacaaaaag gggggtagtc atttgtatat    60
aactttgtat gactttctct ttctattttt ttgtatttcc tcccttttcct tttctatttg   120 tattttttta tcattgcttc cattgaatt                                     149

<210> SEQ ID NO 116
<211> LENGTH: 185
<212> TYPE: DNA
<213> ORGANISM: Nicotiana tabacum

<400> SEQUENCE: 116
atttttaaat tgattcaatt gtgaaataac acgacatgtg tatctaggga atagtttctt    60
caaagcgaat tctccctaga tacatctatt caatttaatt ctgaatttat tttgaatata   120
tgatatatta atatattaat tgtgctaaag agtttcaatc tatttcact aagtaagtcc    180 aatag                                                              185
```

<210> SEQ ID NO 117
<211> LENGTH: 867
<212> TYPE: DNA
<213> ORGANISM: Azotobacter vinelandii

<400> SEQUENCE: 117

| | | | | | |
|---|---|---|---|---|---|
| atgcgtcaat | gcgccatcta | cggcaaaggt | ggtatcggta | agtccaccac | tactcagaac | 60 |
| ctggtggcag | ccctggctga | gatgggcaag | aaggtcatga | tcgttggttg | tgacccgaaa | 120 |
| gctgactcca | cccgcctgat | cctgcactcc | aaggcccaga | acaccatcat | ggaaatggct | 180 |
| gccgaagccg | gtaccgtgga | agatctggag | ctggaagacg | tgctgaaggc | tggctacggc | 240 |
| ggcgtcaagt | gcgttgagtc | cggtggtccg | gagccgggcg | ttggctgcgc | cggccgtggt | 300 |
| gttatcaccg | ccatcaactt | cctggaagag | aaggcgcct | acgaagacga | tctggacttc | 360 |
| gtattctacg | acgtgctggg | cgacgtggtg | tgtggcggct | cgccatgcc | gatccgcgag | 420 |
| aacaaggccc | aggaaatcta | catcgtctgc | tccggtgaga | tgatggccat | gtacgccgcc | 480 |
| aacaacatct | ccaagggcat | cgtgaagtat | gccaactccg | gcagcgtgcg | tctgggcggc | 540 |
| ctgatctgca | cagccgtaa | caccgaccgc | gaagacgagc | tgatcatcgc | tctggccaac | 600 |
| aagctgggca | cccagatgat | ccacttcgtg | ccgcgtgaca | cgtcgtgca | gcgcgccgaa | 660 |
| atccgccgca | tgaccgtgat | cgaatacgat | ccgaaagcca | gcaagccga | cgaataccgc | 720 |
| gctctggccc | gcaaggtcgt | cgacaacaaa | ctgctggtca | tcccgaaccc | gatcaccatg | 780 |
| gacgagctcg | aagagctgct | gatggaattc | ggcatcatgg | aagtcgaaga | cgaatccatc | 840 |
| gtcggcaaaa | ccgccgaaga | agtctga | | | | 867 |

<210> SEQ ID NO 118
<211> LENGTH: 792
<212> TYPE: DNA
<213> ORGANISM: Nicotiana benthamiana

<400> SEQUENCE: 118

| | | | | | |
|---|---|---|---|---|---|
| atgagggaag | cggtgatcgc | cgaagtatcg | actcaactat | cagaggtagt | tggcgtcatc | 60 |
| gagcgccatc | tcgaaccgac | gttgctggcc | gtacatttgt | acggctccgc | agtggatggc | 120 |
| ggcctgaagc | cacacagtga | tattgatttg | ctggttacgg | tgaccgtaag | gcttgatgaa | 180 |
| acaacgcggc | gagctttgat | caacgacctt | ttggaaactt | cggcttcccc | tggagagagc | 240 |
| gagattctcc | gcgctgtaga | agtcaccatt | gttgtgcacg | acgacatcat | tccgtggcgt | 300 |
| tatccagcta | agcgcgaact | gcaatttgga | gaatggcagc | gcaatgacat | tcttgcaggt | 360 |
| atcttcgagc | cagccacgat | cgacattgat | ctggctatct | tgctgacaaa | agcaagagaa | 420 |
| catagcgttg | ccttggtagg | tccagcggcg | gaggaactct | ttgatccggt | tcttgaacag | 480 |
| gatctatttg | aggcgctaaa | tgaaaccta | acgctatgga | actcgccgcc | cgactgggct | 540 |
| ggcgatgagc | gaaatgtagt | gcttacgttg | tcccgcattt | ggtacagcgc | agtaaccggc | 600 |
| aaaatcgcgc | cgaaggatgt | cgctgccgac | tgggcaatgg | agcgcctgcc | ggcccagtat | 660 |
| cagcccgtca | tacttgaagc | tagacaggct | tatcttggac | aagaagaaga | tcgcttggcc | 720 |
| tcgcgcgcag | atcagttgga | agaatttgtc | cactacgtga | aaggcgagat | caccaaggta | 780 |
| gtcggcaaat | aa | | | | | 792 |

<210> SEQ ID NO 119
<211> LENGTH: 160
<212> TYPE: DNA
<213> ORGANISM: Nicotiana benthamiana

<400> SEQUENCE: 119

| aaatcctgca | gggatctaca | tacaccttgg | ttgacacgag | tatataagtc | atgttatact | 60 |
| gttgaataaa | aagccttcca | ttttctattt | tctattttga | tttgtagaaa | actagtgtgc | 120 |
| ttgggagtcc | ctgatgatta | aataaaccaa | gattttacca | | | 160 |

<210> SEQ ID NO 120
<211> LENGTH: 184
<212> TYPE: DNA
<213> ORGANISM: Nicotiana tabacum

<400> SEQUENCE: 120

| tcctggccta | gtctatagga | ggttttgaaa | agaaaggagc | aataatcatt | ttcttgttct | 60 |
| atcaagaggg | tgctattgct | cctttctttt | tttcttttta | tttatttact | agtattttac | 120 |
| ttacatagac | ttttttgttt | acattataga | aaaagaagga | gaggttattt | tcttgcattt | 180 |
| attc | | | | | | 184 |

<210> SEQ ID NO 121
<211> LENGTH: 2954
<212> TYPE: DNA
<213> ORGANISM: Nicotiana tabacum

<400> SEQUENCE: 121

| ggagctcctg | tgtcaatcac | ttccattcct | ctcgttagac | cctctgtagc | actcatagct | 60 |
| acagccctaa | ctcgattatt | tcctaataat | tgctgtacct | cacaagccac | attaattggt | 120 |
| tgaccaacac | tatctcgacc | ttgaactacc | agagcgttat | aaatattcgg | catcttgccc | 180 |
| ggggaaagg | ctacatctag | taccggaccg | atgattgga | cgacacgccc | cgggtttttt | 240 |
| ttttcaagcg | tggaaacccc | agaaccagaa | gtagtaggat | tgattctcat | aataataaaa | 300 |
| taaataaata | tgtcgaaatg | ttttgcaaa | aattatcgaa | ttcaaaataa | atgtccgcta | 360 |
| gcacgtcgat | cggttaattc | aataaaatgg | gaattagcac | tcgatttcgt | tggcaccatg | 420 |
| caattgaacc | gattcaattg | tttacttatt | cactgagact | gagtgaattt | gcaagcccac | 480 |
| ccaacctatt | ttaattttaa | aatctcaagt | ggatgaatca | gaatcttgag | aaagtctttc | 540 |
| atttgtctat | cattatagac | aatcccatcc | atattatcta | ttctatggaa | ttcgaacctg | 600 |
| aactttattt | tctatttcta | ttacgattca | ttatttgtat | ctaattggct | cctcttctta | 660 |
| tttattttg | atttcaattt | cagcatatcg | atttatgcct | agcctattct | tttctttgtg | 720 |
| tttttctttc | ttttttatac | ctttcataga | ttcatagagg | aattccgtat | attttcacat | 780 |
| ctaggattta | catatacaac | atataccact | gtcaggggg | aagttcttat | tatttaggtt | 840 |
| agtcaggtat | ttccatttca | aaaaaaaaa | aagtaaaaaa | gaaaattgg | gttgcgctat | 900 |
| atatatgaaa | gagtatacaa | taatgatgta | tttggcaaat | caaataccat | ggtctaataa | 960 |
| tcaaacattc | tgattagttg | ataatattag | tattagttgg | aaattttgtg | aaagattcct | 1020 |
| gtgaaaagtt | tcattaacac | ggaattcgtg | tcgagtagac | cttgttgttg | tgagaattct | 1080 |
| taattaatga | gttgtaggga | gggatttatg | tcaccacaaa | cagagactaa | agcaagtgtt | 1140 |
| ggattcaaag | ctggtgttaa | agagtacaaa | ttgacttatt | atactcctga | gtaccaaacc | 1200 |
| aaggatactg | atatattggc | agcattccga | gtaactcctc | aacctggagt | tccacctgaa | 1260 |
| gaagcagggg | ccgcggtagc | tgccgaatct | tctactggta | catggacaac | tgtatggacc | 1320 |
| gatggactta | ccagccttga | tcgttacaaa | gggcgatgct | accgcatcga | gcgtgttgtt | 1380 |

-continued

```
ggagaaaaag atcaatatat tgcttatgta gcttacccct tagacctttt tgaagaaggt   1440
tctgttacca acatgtttac ttccattgta ggtaacgtat ttgggttcaa agccctgcgc   1500
gctctacgtc tggaagatct gcgaatccct cctgcttatg ttaaaacttt ccaaggtccg   1560
cctcatggga tccaagttga aagagataaa ttgaacaagt atggtcgtcc cctgttggga   1620
tgtactatta aacctaaatt ggggttatct gctaaaaact acggtagagc tgtttatgaa   1680
tgtcttcgcg gtggacttga ttttaccaaa gatgatgaga acgtgaactc acaaccattt   1740
atgcgttgga gagatcgttt cttattttgt gccgaagcac tttataaagc acaggctgaa   1800
acaggtgaaa tcaaagggca ttacttgaat gctactgcag gtacatgcga agaaatgatc   1860
aaaagagctg tatttgctag agaattgggc gttccgatcg taatgcatga ctacttaacg   1920
gggggattca ccgcaaatac tagcttggct cattattgcc gagataatgg tctacttctt   1980
cacatccacc gtgcaatgca tgcggttatt gatagacaga gaatcatgg tatccacttc    2040
cgggtattag caaaagcgtt acgtatgtct ggtggagatc atattcactc tggtaccgta   2100
gtaggtaaac ttgaaggtga aagagacata actttgggct ttgttgattt actgcgtgat   2160
gattttgttg aacaagatcg aagtcgcggt atttatttca ctcaagattg gtctctttta   2220
ccaggtgttc tacccgtggc ttcaggaggt attcacgttt ggcatatgcc tgctctgacc   2280
gagatctttg gggatgattc cgtactacag ttcggtggag aactttagg acatccttgg    2340
ggtaatgcgc caggtgccgt agctaatcga gtagctctag aagcatgtgt aaaagctcgt   2400
aatgaaggac gtgatcttgc tcaggaaggt aatgaaatta ttcgcgaggc ttgcaaatgg   2460
agcccggaac tagctgctgc ttgtgaagta tggaaagaga tcgtatttaa ttttgcagca   2520
gtggacgttt tggataagta aaaacagtag acattagcag attaattaag caggaaataa   2580
agaaggataa ggaaaagaa ctcaagtaat tatccttcgt tctcttaatt gaattgcaat    2640
taaactcggc ccaatctttt actaaaagga ttgagccgaa tacaacaaag attctattgc   2700
atatattttg actaagtata tacttaccta gatatacaag attgaaata caaaatctag    2760
aaaactaaat caaatctaa gactcaaatc tttctattgt tgtcttggat ccacaattaa    2820
tcctacggat ccttaggatt ggtatattct tttctatcct gtagtttgta gtttccctga   2880
atcaagccaa gtatcacacc tctttctacc catcctgtat attgtcccct tgttccgtg    2940
ttgaaataga acct                                                     2954
```

<210> SEQ ID NO 122
<211> LENGTH: 1472
<212> TYPE: DNA
<213> ORGANISM: Nicotiana tabacum

<400> SEQUENCE: 122

```
gtgattagat attagtatta gacgagattt tacgaaacaa ttatttttt atttctttat     60
aggagaggac aaatctcttt tttcgatgcg aatttgacac gacataggag aagccgccct   120
ttattaaaaa ttatattatt ttaaataata taaggggggt tccaacatat taatatatag   180
tgaagtgttc ccccagattc agaactttt ttcaatactc acaatcctta ttagttaata   240
atcctagtga ttggatttct atgcttagtc tgataggaaa taagatattc aaataaataa   300
ttttatagcg aatgactatt catctattgt attttcatgc aaataggggg caagaaaact   360
ctatggaaag atggtggttt aattcgatgt tgtttaagaa ggagttcgaa cgcaggtgtg   420
ggctaaaata atcaatgggc agtccttgtc ctattgaaaa taccaatgaa gatccaaatc   480
gaaaagtgaa aaacattcat agttggagga atcgtgacaa ttctagttgc agtaatgttg   540
```

```
attatttatt cggcgttaaa gacattcgga atttcatctc tgatgacact tttttagtta    600
gtgataggaa tggagacagt tattccatct attttgatat tgaaaatcat attttttgaga   660 ttgacaacga tcattctttt ctgagtgaac tagaaagttc tttttatagt tatcgaaact    720
cgaattatcg gaataatgga tttaggggcg aagatcccta ctataattct tacatgtatg    780
atactcaata tagttggaat aatcacatta atagttgcat tgatagttat cttcagtctc    840
aaatctgtat agatacttcc attataagtg gtagtgagaa ttacggtgac agttacattt    900
atagggccgt ttgtggtggt gaaagtcgaa atagtagtga aaacgagggt tccagtagac    960
gaactcgcac gaagggcagt gatttaacta taagagaaag ttctaatgat ctcgaggtaa   1020
ctcaaaaata caggcatttg tgggttcaat gcgaaaattg ttatggatta aattataaga   1080 aattttttgaa atcaaaaatg aatatttgtg aacaatgtgg atatcatttg aaaatgagta  1140
gttcagatag aattgaactt ttgatcgatc cgggtacttg ggatcctatg gatgaagaca   1200
tggtctctct agatcccatt gaatttcatt cggaggagga gccttataaa gatcgtattg   1260
attcttatca agaaagaca ggattaaccg aggctgttca acaggcata ggccaactaa     1320 acggcattcc cgtagcaatt ggggttatgg attttcagtt tatggggggt agtatgggat   1380
ccgtagtcgg agagaaaatc acccgtttga ttgaatacgc tgccaatcaa attttaccc    1440 ttattatagt gtgtgcttct gggggggcgc gc                                 1472

<210> SEQ ID NO 123
<211> LENGTH: 867
<212> TYPE: DNA
<213> ORGANISM: Artificial Sequence
<220> FEATURE:
<223> OTHER INFORMATION: Probe

<400> SEQUENCE: 123
atgcgtcaat gcgccatcta cggcaaaggt ggtatcggta agtccaccac tactcagaac     60
ctggtggcag ccctggctga gatgggcaag aaggtcatga tcgttggttg tgacccgaaa    120
gctgactcca cccgcctgat cctgcactcc aaggcccaga acaccatcat ggaaatggct    180
gccgaagccg gtaccgtgga agatctggag ctggaagacg tgctgaaggc tggctacggc    240
ggcgtcaagt gcgttgagtc cggtggtccg gagccgggcg ttggctgcgc cggccgtggt    300
gttatcaccg ccatcaactt cctggaagag aaggcgcct acgaagacga tctggacttc    360
gtattctacg acgtgctggg cgacgtggtg tgtggcggct cgccatgcc gatccgcgag    420 aacaaggccc aggaaatcta catcgtctgc tccggtgaga tgatggccat gtacgccgcc    480
aacaacatct ccaagggcat cgtgaagtat gccaactccg gcagcgtgcg tctgggcggc    540
ctgatctgca cagccgtaa caccgaccgc gaagacgagc tgatcatcgc tctggccaac    600
aagctgggca cccagatgat ccacttcgtg ccgcgtgaca cgtcgtgca gcgcgccgaa    660 atccgccgca tgaccgtgat cgaatacgat ccgaaagcca agcaagccga cgaataccgc    720
gctctggccc gcaaggtcgt cgacaacaaa ctgctggtca tcccgaaccc gatcaccatg    780
gacgagctcg aagagctgct gatggaattc ggcatcatgg aagtcgaaga cgaatccatc    840
gtcggcaaaa ccgccgaaga agtctga                                       867

<210> SEQ ID NO 124
<211> LENGTH: 882
<212> TYPE: DNA
<213> ORGANISM: Artificial Sequence
<220> FEATURE:
```

<223> OTHER INFORMATION: Probe

<400> SEQUENCE: 124

| | | |
|---|---|---|
| atggcatctg agcgtctcgc cgacggcgac agccgctatt acttgctgaa ggtcgcccac | 60 |
| gagcagttcg gctgcgcgcc cggcgagctc agcgaggagc agctccagca ggccgaccgc | 120 |
| atcatcggcc ggcagaggca tatcgaggac gccgtgttgc gcagccccga tgcgatcggt | 180 |
| gtggtgatcc cgccctccca gctcgaagag gcctgggcac acatcgccag ccgctacgag | 240 |
| agtcccgagg cgctacagca ggccctcgac gcgcaggcgc tggatgctgc cggcatgcgc | 300 |
| gccatgctgg cccgggagct cagggtcgag gccgttctcg actgcgtctg cgccggcctg | 360 |
| ccggagatca gcgacaccga tgtgagcctc tactacttca accacgccga gcaattcaag | 420 |
| gtgcccgccc agcacaaggc ccggcacatc ctggtcacca tcaacgagga ttttccggaa | 480 |
| aacacccgcg aagccgcccg gacgcgcatc gagaccatcc tcaagcggct gcgcggcaag | 540 |
| ccggagcgct tcgccgagca ggcgatgaag cactccgaat gtcccaccgc gatgcagggc | 600 |
| ggattgctcg gcgaggtggt cccgggaacg ctttatcccg aactggacgc ctgcctgttc | 660 |
| cagatggcgc ggggagaact gagtccggta ctggaatcgc cgatcggttt tcacgtgctg | 720 |
| tactgcgaaa gcgtgagccc cgcccggcag ctcacctcg aggagatcct gccgcgtctg | 780 |
| cgcgacaggc tgcagctccg gcagcgcaag gcgtatcagc gcaaatggct ggaaagcctg | 840 |
| ctccaacaaa acgctacttt ggagaacctc gcccatggat aa | 882 |

<210> SEQ ID NO 125
<211> LENGTH: 1383
<212> TYPE: DNA
<213> ORGANISM: Artificial Sequence
<220> FEATURE:
<223> OTHER INFORMATION: Probe

<400> SEQUENCE: 125

| | | |
|---|---|---|
| aaagagtaca aattgactta ttatactcct gagtaccaaa ccaaggatac tgatatattg | 60 |
| gcagcattcc gagtaactcc tcaacctgga gttccacctg aagaagcagg ggccgcggta | 120 |
| gctgccgaat cttctactgg tacatggaca actgtatgga ccgatggact taccagcctt | 180 |
| gatcgttaca agggcgatg ctaccgcatc gagcgtgttg ttggagaaaa agatcaatat | 240 |
| attgcttatg tagcttaccc tttagacctt tttgaagaag gttctgttac caacatgttt | 300 |
| acttccattg taggtaacgt atttgggttc aaagccctgc gcgctctacg tctggaagat | 360 |
| ctgcgaatcc ctcctgctta tgttaaaact ttccaaggtc cgcctcatgg gatccaagtt | 420 |
| gaaagagata aattgaacaa gtatggtcgt cccctgttgg gatgtactat taaacctaaa | 480 |
| ttggggttat ctgctaaaaa ctacggtaga gctgtttatg aatgtcttcg cggtggactt | 540 |
| gattttacca agatgatga aacgtgaac tcacaaccat ttatgcgttg gagagatcgt | 600 |
| ttcttatttt gtgccgaagc actttataaa gcacaggctg aaacaggtga atcaaaggg | 660 |
| cattacttga atgctactgc aggtacatgc gaagaaatga tcaaaagagc tgtatttgct | 720 |
| agagaattgg gcgttccgat cgtaatgcat gactacttaa cgggggatt caccgcaaat | 780 |
| actagcttgg ctcattattg ccgagataat ggtctacttc ttcacatcca ccgtgcaatg | 840 |
| catgcggtta ttgatagaca aagaatcat ggtatccact tccgggtatt agcaaaagcg | 900 |
| ttacgtatgt ctggtggaga tcatattcac tctggtaccg tagtaggtaa acttgaaggt | 960 |
| gaaagagaca taactttggg ctttgttgat ttactgcgtg atgattttgt tgaacaagat | 1020 |
| cgaagtcgcg gtatttattt cactcaagat tgggtctctt taccaggtgt tctacccgtg | 1080 |

```
gcttcaggag gtattcacgt ttggcatatg cctgctctga ccgagatctt tggggatgat    1140
tccgtactac agttcggtgg aggaacttta ggacatcctt ggggtaatgc gccaggtgcc    1200
gtagctaatc gagtagctct agaagcatgt gtaaaagctc gtaatgaagg acgtgatctt    1260
gctcaggaag gtaatgaaat tattcgcgag gcttgcaaat ggagcccgga actagctgct    1320
gcttgtgaag tatggaaaga gatcgtattt aattttgcag cagtggacgt tttggataag    1380
taa                                                                 1383
```

<210> SEQ ID NO 126
<211> LENGTH: 492
<212> TYPE: PRT
<213> ORGANISM: Azotobacter vinelandii

<400> SEQUENCE: 126

```
Met Thr Gly Met Ser Arg Glu Glu Val Glu Ser Leu Ile Gln Glu Val
1               5                   10                  15

Leu Glu Val Tyr Pro Glu Lys Ala Arg Lys Asp Arg Asn Lys His Leu
            20                  25                  30

Ala Val Asn Asp Pro Ala Val Thr Gln Ser Lys Lys Cys Ile Ile Ser
        35                  40                  45

Asn Lys Lys Ser Gln Pro Gly Leu Met Thr Ile Arg Gly Cys Ala Tyr
    50                  55                  60

Ala Gly Ser Lys Gly Val Val Trp Gly Pro Ile Lys Asp Met Ile His
65                  70                  75                  80

Ile Ser His Gly Pro Val Gly Cys Gly Gln Tyr Ser Arg Ala Gly Arg
                85                  90                  95

Arg Asn Tyr Tyr Ile Gly Thr Thr Gly Val Asn Ala Phe Val Thr Met
            100                 105                 110

Asn Phe Thr Ser Asp Phe Gln Glu Lys Asp Ile Val Phe Gly Gly Asp
        115                 120                 125

Lys Lys Leu Ala Lys Leu Ile Asp Glu Val Glu Thr Leu Phe Pro Leu
    130                 135                 140

Asn Lys Gly Ile Ser Val Gln Ser Glu Cys Pro Ile Gly Leu Ile Gly
145                 150                 155                 160

Asp Asp Ile Glu Ser Val Ser Lys Val Lys Gly Ala Glu Leu Ser Lys
                165                 170                 175

Thr Ile Val Pro Val Arg Cys Glu Gly Phe Arg Gly Val Ser Gln Ser
            180                 185                 190

Leu Gly His His Ile Ala Asn Asp Ala Val Arg Asp Trp Val Leu Gly
        195                 200                 205

Lys Arg Asp Glu Asp Thr Thr Phe Ala Ser Thr Pro Tyr Asp Val Ala
    210                 215                 220

Ile Ile Gly Asp Tyr Asn Ile Gly Gly Asp Ala Trp Ser Ser Arg Ile
225                 230                 235                 240

Leu Leu Glu Glu Met Gly Leu Arg Cys Val Ala Gln Trp Ser Gly Asp
                245                 250                 255

Gly Ser Ile Ser Glu Ile Glu Leu Thr Pro Lys Val Lys Leu Asn Leu
            260                 265                 270

Val His Cys Tyr Arg Ser Met Asn Tyr Ile Ser Arg His Met Glu Glu
        275                 280                 285

Lys Tyr Gly Ile Pro Trp Met Glu Tyr Asn Phe Phe Gly Pro Thr Lys
    290                 295                 300

Thr Ile Glu Ser Leu Arg Ala Ile Ala Ala Lys Phe Asp Glu Ser Ile
```

```
             305                 310                 315                 320
Gln Lys Lys Cys Glu Glu Val Ile Ala Lys Tyr Lys Pro Trp Glu
                325                 330                 335

Ala Val Val Ala Lys Tyr Arg Pro Arg Leu Glu Gly Lys Arg Val Met
                340                 345                 350

Leu Tyr Ile Gly Gly Leu Arg Pro Arg His Val Ile Gly Ala Tyr Glu
                355                 360                 365

Asp Leu Gly Met Glu Val Val Gly Thr Gly Tyr Glu Phe Ala His Asn
        370                 375                 380

Asp Tyr Asp Arg Thr Met Lys Glu Met Gly Asp Ser Thr Leu Leu
385                 390                 395                 400

Tyr Asp Asp Val Thr Gly Tyr Glu Phe Glu Glu Phe Val Lys Arg Ile
                405                 410                 415

Lys Pro Asp Leu Ile Gly Ser Gly Ile Lys Glu Lys Phe Ile Phe Gln
                420                 425                 430

Lys Met Gly Ile Pro Phe Arg Gln Met His Ser Trp Asp Tyr Ser Gly
                435                 440                 445

Pro Tyr His Gly Phe Asp Gly Phe Ala Ile Phe Ala Arg Asp Met Asp
        450                 455                 460

Met Thr Leu Asn Asn Pro Cys Trp Lys Lys Leu Gln Ala Pro Trp Glu
465                 470                 475                 480

Ala Ser Glu Gly Ala Glu Lys Val Ala Ala Ser Ala
                485                 490

<210> SEQ ID NO 127
<211> LENGTH: 1479
<212> TYPE: DNA
<213> ORGANISM: Azotobacter vinelandii

<400> SEQUENCE: 127
atgaccggta tgtcgcgcga agaggttgaa tccctcatcc aggaagttct ggaagtttat      60
cccgagaagg ctcgcaagga tcgtaacaag cacctggccg tcaacgaccc ggcggttacc     120
cagtccaaga agtgcatcat ctccaacaag aagtcccagc ccgtctgat gaccatccgc     180 ggctgcgcct acgccggttc caaaggcgtg gtctggggcc ccatcaagga catgatccac     240
atctcccacg tccggtaggc tgcggccag tattcgcgcg ccggccgtcg taactactac     300
atcggtacca ccggtgtgaa cgccttcgtc accatgaact tcacctcgga cttccaggag     360
aaggacatcg tgttcggtgg cgacaagaag ctcgccaaac tgatcgacga agtggaaacc     420
ctgttcccgc tgaacaaggg tatctccgtc cagtccgagt gcccgatcgg cctgatcggc     480
gacgacatcg aatccgtgtc caaggtcaag gcgccgagc tcagcaagac catcgtaccg     540
gtccgttgcg aaggcttccg cggcgtttcc cagtccctgg ccaccacat cgccaacgac     600 gcagtccgcg actgggtcct gggcaagcgt gacgaagaca ccaccttcgc cagcactcct     660
tacgatgtgg ccatcatcgg cgactacaac atcggcggcg acgcctggtc ttcccgcatc     720
ctgctggaag aaatgggcct gcgttgcgta gcccagtggt ccggcgacgg ctccatctcc     780
gaaatcgagc tgaccccgaa ggtcaagctg aacctggttc actgctaccg ctcgatgaac     840
tacatctccc gtcacatgga agagaagtac ggtatcccat ggatggagta caacttcttc     900
ggcccgacca agaccatcga gtcgctgcgt gccatcgccg ccaagttcga cgagagcatc     960
cagaagaagt gcgaagaggt catcgccaag tacaagcccg agtgggaagc ggtggtcgcc    1020
aagtaccgtc cgcgcctgga aggcaagcgc gtcatgctct acatcggtgg cctgcgtccg    1080
```

-continued

```
cgccacgtga tcggcgccta cgaagacctg ggcatggaag tggtgggtac cggctacgag    1140
ttcgcccaca acgacgacta tgaccgcacc atgaaagaaa tgggtgactc caccctgctg    1200
tacgatgacg tgaccggcta cgaattcgaa gaattcgtca agcgcatcaa gcccgacctg    1260
atcggctccg gtatcaagga gaagttcatc ttccagaaga tgggcatccc cttccgtcaa    1320
atgcactcct gggattattc cggcccctac cacggcttcg atggcttcgc catcttcgcc    1380
cgtgacatgg acatgaccct gaacaatccg tgctggaaga aactgcaggc tccctgggaa    1440
gcttccgaag cgccgagaa agtcgccgcc agcgcctga                            1479
```

<210> SEQ ID NO 128
<211> LENGTH: 523
<212> TYPE: PRT
<213> ORGANISM: Azotobacter vinelandii

<400> SEQUENCE: 128

```
Met Ser Gln Gln Val Asp Lys Ile Lys Ala Ser Tyr Pro Leu Phe Leu
1               5                   10                  15

Asp Gln Asp Tyr Lys Asp Met Leu Ala Lys Lys Arg Asp Gly Phe Glu
            20                  25                  30

Glu Lys Tyr Pro Gln Asp Lys Ile Asp Glu Val Phe Gln Trp Thr Thr
        35                  40                  45

Thr Lys Glu Tyr Gln Glu Leu Asn Phe Gln Arg Glu Ala Leu Thr Val
    50                  55                  60

Asn Pro Ala Lys Ala Cys Gln Pro Leu Gly Ala Val Leu Cys Ala Leu
65                  70                  75                  80

Gly Phe Glu Lys Thr Met Pro Tyr Val His Gly Ser Gln Gly Cys Val
                85                  90                  95

Ala Tyr Phe Arg Ser Tyr Phe Asn Arg His Phe Arg Glu Pro Val Ser
            100                 105                 110

Cys Val Ser Asp Ser Met Thr Glu Asp Ala Ala Val Phe Gly Gly Gln
        115                 120                 125

Gln Asn Met Lys Asp Gly Leu Gln Asn Cys Lys Ala Thr Tyr Lys Pro
    130                 135                 140

Asp Met Ile Ala Val Ser Thr Thr Cys Met Ala Glu Val Ile Gly Asp
145                 150                 155                 160

Asp Leu Asn Ala Phe Ile Asn Asn Ser Lys Lys Glu Gly Phe Ile Pro
                165                 170                 175

Asp Glu Phe Pro Val Pro Phe Ala His Thr Pro Ser Phe Val Gly Ser
            180                 185                 190

His Val Thr Gly Trp Asp Asn Met Phe Glu Gly Ile Ala Arg Tyr Phe
        195                 200                 205

Thr Leu Lys Ser Met Asp Asp Lys Val Val Gly Ser Asn Lys Lys Ile
    210                 215                 220

Asn Ile Val Pro Gly Phe Glu Thr Tyr Leu Gly Asn Phe Arg Val Ile
225                 230                 235                 240

Lys Arg Met Leu Ser Glu Met Gly Val Gly Tyr Ser Leu Leu Ser Asp
                245                 250                 255

Pro Glu Glu Val Leu Asp Thr Pro Ala Asp Gly Gln Phe Arg Met Tyr
            260                 265                 270

Ala Gly Gly Thr Thr Gln Glu Glu Met Lys Asp Ala Pro Asn Ala Leu
        275                 280                 285

Asn Thr Val Leu Leu Gln Pro Trp His Leu Glu Lys Thr Lys Lys Phe
    290                 295                 300
```

```
Val Glu Gly Thr Trp Lys His Glu Val Pro Lys Leu Asn Ile Pro Met
305                 310                 315                 320
Gly Leu Asp Trp Thr Asp Glu Phe Leu Met Lys Val Ser Glu Ile Ser
            325                 330                 335
Gly Gln Pro Ile Pro Ala Ser Leu Thr Lys Glu Arg Gly Arg Leu Val
        340                 345                 350
Asp Met Met Thr Asp Ser His Thr Trp Leu His Gly Lys Arg Phe Ala
            355                 360                 365
Leu Trp Gly Asp Pro Asp Phe Val Met Gly Leu Val Lys Phe Leu Leu
    370                 375                 380
Glu Leu Gly Cys Glu Pro Val His Ile Leu Cys His Asn Gly Asn Lys
385                 390                 395                 400
Arg Trp Lys Lys Ala Val Asp Ala Ile Leu Ala Ala Ser Pro Tyr Gly
                405                 410                 415
Lys Asn Ala Thr Val Tyr Ile Gly Lys Asp Leu Trp His Leu Arg Ser
            420                 425                 430
Leu Val Phe Thr Asp Lys Pro Asp Phe Met Ile Gly Asn Ser Tyr Gly
            435                 440                 445
Lys Phe Ile Gln Arg Asp Thr Leu His Lys Gly Lys Glu Phe Glu Val
    450                 455                 460
Pro Leu Ile Arg Ile Gly Phe Pro Ile Phe Asp Arg His His Leu His
465                 470                 475                 480
Arg Ser Thr Thr Leu Gly Tyr Glu Gly Ala Met Gln Ile Leu Thr Thr
                485                 490                 495
Leu Val Asn Ser Ile Leu Glu Arg Leu Asp Glu Thr Arg Gly Met
            500                 505                 510
Gln Ala Thr Asp Tyr Asn His Asp Leu Val Arg
    515                 520

<210> SEQ ID NO 129
<211> LENGTH: 1572
<212> TYPE: DNA
<213> ORGANISM: Azotobacter vinelandii

<400> SEQUENCE: 129
atgagccagc aagtcgataa aatcaaagcc agctaccccgc tgttcctcga tcaggactac    60
aaggacatgc ttgccaagaa gcgcgacggc ttcgaggaaa agtatccgca ggacaagatc   120
gacgaagtat tccagtggac caccaccaag gaataccagg agctgaactt ccagcgcgaa   180
gccctgaccg tcaacccggc caaggcttgc agccgctgg cgccgttct ctgcgccctc     240 ggtttcgaga agaccatgcc ctacgtgcac ggttcccagg gttgcgtcgc ctacttccgc   300
tcctacttca accgtcattt ccgcgagccg gtttcctgcg tttccgactc catgaccgaa   360
gacgcggcag tgttcggcgg ccagcagaac atgaaggacg tctgcagaa ctgtaaggct    420 acctacaagc ccgacatgat cgcagtgtcc accacctgca tggccgaggt catcggtgac   480
gacctcaacg ccttcatcaa caactcgaag aaggaaggtt tcattcctga cgagttcccg   540
gtgccgttcg cccataccc gagcttcgtg ggcagccacg tgaccggctg gacaacatg     600 ttcgaaggca ttgctcgcta cttcaccctg aagtccatgg acgacaaggt ggttggcagc   660
aacaagaaga tcaacatcgt ccccggcttc gagacctacc tgggcaactt ccgcgtgatc   720
aagcgcatgc tttcggaaat gggcgtgggc tacagcctgc tctccgatcc ggaagaagtg   780
ctggacaccc cggctgacgg ccagttccgc atgtacgcgg cggcaccac tcaggaagag   840 atgaaggacg ctccgaacgc cctcaacacc gtcctgctgc agccgtggca cctggagaag   900
```

```
accaagaagt tcgtcgaggg tacctggaag cacgaagtac cgaagctgaa catcccgatg    960
ggcctggact ggaccgacga gttcctgatg aaagtcagcg aaatcagcgg ccagccgatt   1020
ccggcgagcc tgaccaagga gcgtggccgt ctggtcgaca tgatgaccga ctcccacacc   1080
tggctgcacg gcaagcgttt cgccctgtgg ggtgatccgg acttcgtgat gggcctggtc   1140
aagttcctgc tggaactggg ttgcgagccg gtacacattc tctgccacaa cggcaacaag   1200
cgttggaaga aggcggtcga cgccatcctc gccgcttcgc cctacggcaa gaatgctacc   1260
gtctacatcg gcaaggacct gtggcacctg cgttcgctgg tcttcaccga caagccggac   1320
ttcatgatcg gcaacagcta cggtaagttc atccagcgcg acaccctgca aagggcaag    1380 gagttcgagg ttccgctgat ccgtatcggc ttcccgatct tcgaccgtca tcacctgcat   1440
cgctccacca ccctgggtta cgagggcgcc atgcagatcc tgaccaccct ggtgaactcg   1500
atcctggaac gtctggacga ggaaacccgc ggtatgcagg ccaccgacta caaccacgac   1560
ctggtacgct ga                                                       1572

<210> SEQ ID NO 130
<211> LENGTH: 503
<212> TYPE: PRT
<213> ORGANISM: Azotobacter vinelandii

<400> SEQUENCE: 130

Met Glu Leu Ser Val Leu Gly Gln Asn Asn Gly Gly Gln His Ser Ala
1               5                   10                  15

Gly Gly Cys Ser Ser Ser Cys Gly Ser Thr His Asp Gln Leu Ser
            20                  25                  30

His Leu Pro Glu Asn Ile Arg Ala Lys Val Gln Asn His Pro Cys Tyr
        35                  40                  45

Ser Glu Glu Ala His His Tyr Phe Ala Arg Met His Val Ala Val Ala
    50                  55                  60

Pro Ala Cys Asn Ile Gln Cys His Tyr Cys Asn Arg Lys Tyr Asp Cys
65                  70                  75                  80

Ala Asn Glu Ser Arg Pro Gly Val Val Ser Glu Val Leu Thr Pro Glu
                85                  90                  95

Gln Ala Val Lys Lys Val Lys Ala Val Ala Ala Ile Pro Gln Met
            100                 105                 110

Ser Val Leu Gly Ile Ala Gly Pro Gly Asp Pro Leu Ala Asn Pro Lys
        115                 120                 125

Arg Thr Leu Asp Thr Phe Arg Met Leu Ser Glu Gln Ala Pro Asp Ile
    130                 135                 140

Lys Leu Cys Val Ser Thr Asn Gly Leu Ala Leu Pro Glu Cys Val Glu
145                 150                 155                 160

Glu Leu Ala Lys His Asn Ile Asp His Val Thr Ile Thr Ile Asn Cys
                165                 170                 175

Val Asp Pro Glu Ile Gly Ala Lys Ile Tyr Pro Trp Ile Tyr Trp Asn
            180                 185                 190

Asn Lys Arg Ile Arg Gly Val Lys Ala Ala Lys Ile Leu Ile Glu Gln
        195                 200                 205

Gln Gln Lys Gly Leu Glu Met Leu Val Ala Arg Gly Ile Leu Val Lys
    210                 215                 220

Val Asn Ser Val Met Ile Pro Gly Val Asn Asp Glu His Leu Lys Glu
225                 230                 235                 240

Val Ser Lys Ile Val Lys Ala Lys Gly Ala Phe Leu His Asn Val Met
```

```
                245                 250                 255
Pro Leu Ile Ala Glu Pro Glu His Gly Thr Phe Tyr Gly Val Met Gly
            260                 265                 270

Gln Arg Ser Pro Glu Pro Glu Leu Gln Asp Leu Gln Asp Ala Cys
        275                 280                 285

Ala Gly Asp Met Asn Met Met Arg His Cys Arg Gln Cys Arg Ala Asp
    290                 295                 300

Ala Val Gly Met Leu Gly Glu Asp Arg Gly Asp Glu Phe Thr Leu Asp
305                 310                 315                 320

Lys Ile Glu Ser Met Glu Ile Asp Tyr Glu Ala Ala Met Val Lys Arg
                325                 330                 335

Ala Ala Ile His Ala Ala Ile Lys Glu Glu Leu Asp Glu Lys Ala Ala
            340                 345                 350

Lys Lys Glu Arg Leu Ala Gly Leu Ser Val Ala Ser Val Gln Asn Gly
        355                 360                 365

Thr Ser Gly Arg Tyr Arg Pro Val Leu Met Ala Val Ala Thr Ser Gly
    370                 375                 380

Gly Gly Leu Ile Asn Gln His Phe Gly His Ala Thr Glu Phe Leu Val
385                 390                 395                 400

Tyr Glu Ala Ser Pro Ser Gly Val Arg Phe Ile Gly His Arg Arg Val
                405                 410                 415

Asp Gln Tyr Cys Val Gly Asn Asp Thr Cys Gly Glu Lys Glu Ser Ala
            420                 425                 430

Leu Ala Gly Ser Ile Arg Ala Leu Lys Gly Cys Glu Ala Val Leu Cys
        435                 440                 445

Ser Lys Ile Gly Phe Glu Pro Trp Ser Asp Leu Glu Thr Ala Gly Ile
    450                 455                 460

Gln Pro Asn Gly Glu His Ala Met Glu Pro Ile Glu Glu Ala Val Met
465                 470                 475                 480

Ala Val Tyr Arg Glu Met Ile Glu Ser Gly Arg Leu Glu Asn Asp Gly
                485                 490                 495

Ala Leu Leu Gln Ala Lys Ala
            500

<210> SEQ ID NO 131
<211> LENGTH: 1512
<212> TYPE: DNA
<213> ORGANISM: Azotobacter vinelandii

<400> SEQUENCE: 131
atggaactga gcgtacttgg gcaaaacaat gggggacagc acagcgctgg cggctgttcc        60
tcaagtagct gcggcagcac gcacgatcag ctctcccacc tgccggaaaa cattcgtgcg       120
aaggtgcaga accatccgtg ctattcggaa gaggcgcacc actatttcgc gcgcatgcac       180
gtggcggtgg cgcctgcctg caacatccag tgccactact gcaaccgcaa gtacgactgc       240
gccaacgagt cgcgtccggg cgtggtgtcc gaagtgctga cccccgagca ggcggtcaag       300
aaggtcaagg ccgtggccgc cgccatcccg cagatgagcg tgctcggcat cgccggcccc       360
ggcgacccct tggccaaccc gaagcgcacc ctcgacacct tccgcatgct cagcgagcag       420
gccccggaca tcaagctgtg cgtttccacc aacggcctgg ccctgccgga gtgcgtcgag       480
gaactggcca agcacaacat cgaccacgtc accatcacca tcaactgcgt ggacccggag       540
atcggcgcca agatctatcc gtggatctac tggaacaaca gcgcatccg cggcgtcaag       600 gccgccaaga tcctcatcga gcagcagcag aagggtctgg agatgctggt ggcgcgcggc       660
```

```
atcctggtga aggtcaattc ggtgatgatc cccggcgtca acgacgagca cctgaaggaa      720
gtcagcaaga tcgtcaaggc caagggcgcc ttcctgcaca acgtcatgcc gctgatcgcc      780
gagcccgagc acggcacctt ctacggcgtg atgggccagc gcagccccga gccggaagaa      840
ctgcaggacc tgcaggacgc ctgcgccggc gacatgaaca tgatgcgcca ctgccgccag      900
tgccgcgccg acgcggtcgg catgctcggc gaggaccgcg cgacgagtt cacccctggac      960 aagatcgagt cgatggagat cgattacgag gcggcgatgg tcaagcgcgc cgccatccat     1020
gcggcgatca aggaagagct ggacgagaag gcggcgaaga aggaacggct ggctggcctg     1080
tccgttgcat ccgtccagaa cggcacgagc ggtcgctacc gtccggtgct gatggccgtg     1140
gccaccagcg gcggcggcct gatcaaccag cacttcgggc acgccaccga gttcctggtg     1200
tacgaagcct cgccgtccgg ggtgcgcttc atcggccatc gccgggtcga ccagtactgc     1260
gtcggcaacg acacctgcgg cgagaaggaa agtgcactcg ccggcagcat ccgtgccctg     1320
aagggatgcg aggcggtgct ctgctcgaag atcggtttcg aaccctggag cgacctggag     1380
accgccggca tccagcccaa tggcgagcac gccatggagc ccatcgagga agcggtcatg     1440
gcggtctacc gggaaatgat cgagtcgggt cggctggaga atgacggagc cctgctgcag     1500
gccaaggcct ga                                                        1512
```

<210> SEQ ID NO 132
<211> LENGTH: 195
<212> TYPE: PRT
<213> ORGANISM: Azotobacter vinelandii

<400> SEQUENCE: 132

```
Met Gly Ser Ala Ala His Arg Gly Asp Thr Thr Gln Ala Val Arg
1               5                   10                  15

His Asp Arg Ala Asn His Leu Trp Leu Glu Arg Ile Val Arg Ser Gln
            20                  25                  30

Arg Asp Gly Leu Ser Cys Leu Pro Phe His Leu Gly Leu Asp Glu Arg
        35                  40                  45

Ser Tyr Ala Glu Leu Ile Arg Thr His Phe Pro Glu Leu Ala Gly Gln
50                  55                  60

Thr Ser Ala Ser Leu Gly Ser Leu Ala His Glu Cys Ser Glu Leu Arg
65                  70                  75                  80

Glu Asp Leu Leu Glu Met Arg Arg Asp Glu Trp Glu Glu Leu Arg Val
                85                  90                  95

Leu Leu Leu Asp Gly Arg Arg Gly Asp Pro Glu Glu Leu Trp Met
            100                 105                 110

Ala Ser Ile Val Ala Ala Ala Cys Leu Gly Gly Asp His Leu Trp Arg
        115                 120                 125

Asp Leu Gly Leu Glu Ser Arg Glu Thr Leu Arg Val Leu Leu Met His
130                 135                 140

Asn Phe Pro His Leu Ala Glu Arg Asn Val Lys Asn Met Arg Trp Lys
145                 150                 155                 160

Lys Phe Phe Tyr Lys Gln Leu Cys Glu Gln Asp Gly Gly Tyr Val Cys
                165                 170                 175

Arg Ser Pro Ser Cys Glu Gln Cys Pro Ser His His Asp Cys Phe Gly
            180                 185                 190

Ala Glu Ile
        195
```

<210> SEQ ID NO 133
<211> LENGTH: 588
<212> TYPE: DNA
<213> ORGANISM: Azotobacter vinelandii

<400> SEQUENCE: 133

```
atgggcagcg ccgcggccca tcgggggat accacccaag ccgtgcgtca tgacagagcc      60
aaccacctct ggctggagcg catcgtccgc tcccagcgcg acggtctgag ctgcctgccg     120
ttccatctgg gcctcgacga gcggagctat gccgaactga tccgcaccca ttttcccgag    180
ctggccggcc agaccagcgc cagcctgggc tcgctggccc acgaatgcag cgagctgcgc    240
gaagacctac tggaaatgcg ccgcgacgaa tgggaggaac tgcgcgtcct gttgctggac    300
ggccgccgcg gcgacgaccc cgaagagctc tggatggcga catcgtcgc cgccgcctgc    360
ctgggtggcg atcacctgtg cgcgacctg ggactcgaga gccgcgagac gctgagggtc     420
ctgctgatgc acaatttccc ccaccttgcc gagcgcaacg tgaaaaacat cgctggaag    480
aagttttct acaagcaact gtgcgaacag gatggcggct acgtctgccg ctcccccagt    540
tgcgagcagt gcccgtctca tcacgattgt tttggagcag agatatga                588
```

<210> SEQ ID NO 134
<211> LENGTH: 458
<212> TYPE: PRT
<213> ORGANISM: Azotobacter vinelandii

<400> SEQUENCE: 134

```
Met Ala Glu Ile Ile Asn Arg Asn Lys Ala Leu Ala Val Ser Pro Leu
1               5                   10                  15

Lys Ala Ser Gln Thr Met Gly Ala Ala Leu Ala Ile Leu Gly Leu Ala
            20                  25                  30

Arg Ser Met Pro Leu Phe His Gly Ser Gln Gly Cys Thr Ala Phe Ala
        35                  40                  45

Lys Val Phe Phe Val Arg His Phe Arg Glu Pro Val Pro Leu Gln Thr
    50                  55                  60

Thr Ala Met Asp Gln Val Ser Ser Val Met Gly Ala Asp Glu Asn Val
65                  70                  75                  80

Val Glu Ala Leu Lys Thr Ile Cys Glu Arg Gln Asn Pro Ser Val Ile
                85                  90                  95

Gly Leu Leu Thr Thr Gly Leu Ser Glu Thr Gln Gly Cys Asp Leu His
            100                 105                 110

Thr Ala Leu His Glu Phe Arg Thr Gln Tyr Glu Glu Tyr Lys Asp Val
        115                 120                 125

Pro Ile Val Pro Val Asn Thr Pro Asp Phe Ser Gly Cys Phe Glu Ser
    130                 135                 140

Gly Phe Ala Ala Ala Val Lys Ala Ile Val Glu Thr Leu Val Pro Glu
145                 150                 155                 160

Arg Arg Asp Gln Val Gly Lys Arg Pro Arg Gln Val Asn Val Leu Cys
                165                 170                 175

Ser Ala Asn Leu Thr Pro Gly Asp Leu Glu Tyr Ile Ala Glu Ser Ile
            180                 185                 190

Glu Ser Phe Gly Leu Arg Pro Leu Ile Pro Asp Leu Ser Gly Ser
        195                 200                 205

Leu Asp Gly His Leu Asp Glu Asn Arg Phe Asn Ala Leu Thr Thr Gly
    210                 215                 220

Gly Leu Ser Val Ala Glu Leu Ala Thr Ala Gly Gln Ser Val Ala Thr
225                 230                 235                 240
```

```
Leu Val Val Gly Gln Ser Leu Ala Gly Ala Ala Asp Ala Leu Ala Glu
                245                 250                 255

Arg Thr Gly Val Pro Asp Arg Arg Phe Gly Met Leu Tyr Gly Leu Asp
            260                 265                 270

Ala Val Asp Ala Trp Leu Met Ala Leu Ala Glu Ile Ser Gly Asn Pro
        275                 280                 285

Val Pro Asp Arg Tyr Lys Arg Gln Arg Ala Gln Leu Gln Asp Ala Met
    290                 295                 300

Leu Asp Thr His Phe Met Leu Ser Ser Ala Arg Thr Ala Ile Ala Ala
305                 310                 315                 320

Asp Pro Asp Leu Leu Leu Gly Phe Asp Ala Leu Leu Arg Ser Met Gly
                325                 330                 335

Ala His Thr Val Ala Ala Val Val Pro Ala Arg Ala Ala Leu Val
            340                 345                 350

Asp Ser Pro Leu Pro Ser Val Arg Val Gly Asp Leu Glu Asp Leu Glu
        355                 360                 365

His Ala Ala Arg Ala Gly Gln Ala Gln Leu Val Ile Gly Asn Ser His
    370                 375                 380

Ala Leu Ala Ser Ala Arg Arg Leu Gly Val Pro Leu Leu Arg Ala Gly
385                 390                 395                 400

Phe Pro Gln Tyr Asp Leu Leu Gly Gly Phe Gln Arg Cys Trp Ser Gly
                405                 410                 415

Tyr Arg Gly Ser Ser Gln Val Leu Phe Asp Leu Ala Asn Leu Leu Val
            420                 425                 430

Glu His His Gln Gly Ile Gln Pro Tyr His Ser Ile Tyr Ala Gln Lys
    435                 440                 445

Pro Ala Thr Glu Gln Pro Gln Trp Arg His
    450                 455

<210> SEQ ID NO 135
<211> LENGTH: 1377
<212> TYPE: DNA
<213> ORGANISM: Azotobacter vinelandii

<400> SEQUENCE: 135
atggccgaga tcatcaatcg caacaaggcc ctggccgtca gcccgctgaa ggccagtcag      60
accatgggcg ccgcgctggc catcctcggc ctggcgcgca gcatgccgct gtttcacggc     120
tcgcagggtt gcaccgcgtt cgccaaggtg ttcttcgttc gccatttccg cgagccggtc     180
ccgctgcaga ccaccgccat ggaccaggtc agttcggtga tgggcgccga cgagaacgtc     240
gtcgaggcgc tgaagaccat ctgcgaacgg cagaatccct cggtcatcgg cctgctcacc     300
accggcctgt cggaaaccca gggctgcgac ctgcacaccg ccctgcacga gttccgtacc     360
cagtacgagg agtacaagga cgtgccgatc gttccggtga acacgccgga cttcagcggc     420
tgcttcgaga gcggcttcgc cgcggcggtc aaggcgatcg tcgagacgct ggtgcccgaa     480
cggcgcgatc aggtgggcaa gcgtccgcgc caggtcaacg tgctgtgctc ggccaatctc     540
accccgggcg atctggagta catcgccgaa agcatcgaga gcttcggtct gcgcccgttg     600
ctgatccccg acctgtccgg ctcgctcgac ggccacctgg acgagaaccg tttcaatgcc     660
ctgaccaccg gcggactgag cgtggccgaa ctggccaccg ccggacagag cgtcgccact     720
ctggtggtcg gcagagcct ggcgggtgcg ccgacgccc tggccgagcg caccggcgtg     780
cccgaccggc gcttcggcat gctctacggt ctggatgcgg tcgatgcctg gctgatggcg     840
```

```
ctggccgaga tcagcggcaa tccggtgccc gaccgctaca agcgccagcg tgcccaattg    900
caggacgcca tgctcgacac ccacttcatg ctcagttccg cacgcacggc catcgccgcc    960
gatcccgatc tgctgctcgg tttcgatgcc ctgctgcgca gcatgggcgc gcacacggta   1020
gccgccgtgg tgccggcccg ggccgccgcg ctggtcgatt cgcctctgcc ctccgtgcgg   1080
gtcggcgacc tggaggacct cgagcatgcc gcccgcgccg gccaggccca actggtgatc   1140
ggcaacagcc acgccctggc cagcgcccgt cgcctcggtg tgccactgtt gcgtgccggc   1200
ttcccgcagt acgatctgct gggcggtttc caacgctgct ggtccggcta ccgcggcagc   1260
agtcaggtgc tgttcgatct ggccaacctg ctggtcgaac accaccaggg tatccagccc   1320
tatcattcga tctatgcgca aaaaccggca accgaacagc cgcaatggag gcactga      1377
```

<210> SEQ ID NO 136
<211> LENGTH: 384
<212> TYPE: PRT
<213> ORGANISM: Azotobacter vinelandii

<400> SEQUENCE: 136

```
Met Ala Ser Val Ile Ile Asp Asp Thr Thr Leu Arg Asp Gly Glu Gln
1               5                   10                  15

Ser Ala Gly Val Ala Phe Asn Ala Asp Glu Lys Ile Ala Ile Ala Arg
            20                  25                  30

Ala Leu Ala Glu Leu Gly Val Pro Glu Leu Glu Ile Gly Ile Pro Ser
        35                  40                  45

Met Gly Glu Glu Glu Arg Glu Val Met His Ala Ile Ala Gly Leu Gly
    50                  55                  60

Leu Ser Ser Arg Leu Leu Ala Trp Cys Arg Leu Cys Asp Val Asp Leu
65                  70                  75                  80

Ala Ala Ala Arg Ser Thr Gly Val Thr Met Val Asp Leu Ser Leu Pro
                85                  90                  95

Val Ser Asp Leu Met Leu His His Lys Leu Asn Arg Asp Arg Asp Trp
            100                 105                 110

Ala Leu Arg Glu Val Ala Arg Leu Val Gly Glu Ala Arg Met Ala Gly
        115                 120                 125

Leu Glu Val Cys Leu Gly Cys Glu Asp Ala Ser Arg Ala Asp Leu Glu
    130                 135                 140

Phe Val Val Gln Val Gly Glu Val Ala Gln Ala Gly Ala Arg Arg
145                 150                 155                 160

Leu Arg Phe Ala Asp Thr Val Gly Val Met Glu Pro Phe Gly Met Leu
                165                 170                 175

Asp Arg Phe Arg Phe Leu Ser Arg Arg Leu Asp Met Glu Leu Glu Val
            180                 185                 190

His Ala His Asp Asp Phe Gly Leu Ala Thr Ala Asn Thr Leu Ala Ala
        195                 200                 205

Val Met Gly Gly Ala Thr His Ile Asn Thr Thr Val Asn Gly Leu Gly
    210                 215                 220

Glu Arg Ala Gly Asn Ala Ala Leu Glu Glu Cys Val Leu Ala Leu Lys
225                 230                 235                 240

Asn Leu His Gly Ile Asp Thr Gly Ile Asp Thr Arg Gly Ile Pro Ala
                245                 250                 255

Ile Ser Ala Leu Val Glu Arg Ala Ser Gly Arg Gln Val Ala Trp Gln
            260                 265                 270

Lys Ser Val Val Gly Ala Gly Val Phe Thr His Glu Ala Gly Ile His
        275                 280                 285
```

Val Asp Gly Leu Leu Lys His Arg Arg Asn Tyr Glu Gly Leu Asn Pro
    290                 295                 300

Asp Glu Leu Gly Arg Ser His Ser Leu Val Leu Gly Lys His Ser Gly
305                 310                 315                 320

Ala His Met Val Arg Asn Thr Tyr Arg Asp Leu Gly Ile Glu Leu Ala
                325                 330                 335

Asp Trp Gln Ser Gln Ala Leu Leu Gly Arg Ile Arg Ala Phe Ser Thr
                340                 345                 350

Arg Thr Lys Arg Ser Pro Gln Pro Ala Glu Leu Gln Asp Phe Tyr Arg
            355                 360                 365

Gln Leu Cys Glu Gln Gly Asn Pro Glu Leu Ala Ala Gly Gly Met Ala
    370                 375                 380

<210> SEQ ID NO 137
<211> LENGTH: 1155
<212> TYPE: DNA
<213> ORGANISM: Azotobacter vinelandii

<400> SEQUENCE: 137

```
atggctagcg tgatcatcga cgacactacc ctgcgtgacg gtgaacagag tgccggggtc      60
gccttcaatg ccgacgagaa gatcgctatc gcccgcgcgc tcgccgaact gggcgtgccg     120
gagttggaga tcggcattcc cagcatgggc gaggaagagc gcgaggtgat gcacgccatc     180
gccggtctcg gcctgtcgtc tcgcctgctg gcctggtgcc ggctatgcga cgtcgatctc     240
gcggcggcgc gctccaccgg ggtgaccatg gtcgaccttt cgctgccggt ctccgacctg     300
atgctgcacc acaagctcaa tcgcgatcgc gactgggcct tgcgcgaagt ggccaggctg     360
gtcggcgaag cgcgcatggc cgggctcgag gtgtgcctgg gctgcgagga cgcctcgcgg     420
gcggatctgg agttcgtcgt gcaggtgggc gaagtggcgc aggccgccgg cgcccgtcgg     480
ctgcgcttcg ccgacaccgt cggggtcatg gagcccttcg gcatgctcga ccgcttccgt     540
ttcctcagcc ggcgcctgga catggagctg gaagtgcacg cccacgatga tttcgggctg     600
gccacggcca acaccctggc cgcggtgatg ggcggggcga ctcatatcaa caccacggtc     660
aacgggctcg gcgagcgtgc cggcaacgcc gcgctggaag agtgcgtgct ggcgctcaag     720
aacctccacg gtatcgacac cggtatcgat acccgcggca tcccggccat ctccgcgctg     780
gtcgagcggg cctcggggcg ccaggtggcc tggcagaaga gcgtggtcgg cgccggggtg     840
ttcactcacg aggccggtat ccacgtcgac ggactgctca gcatcggcg caactacgag     900
gggctgaatc ccgacgaact cggtcgcagc cacagtctgg tgctgggcaa gcattccggg     960
gcgcacatgg tgcgcaacac gtaccgcgat ctgggtatcg agctggcgga ctggcagagc    1020
caagcgctgc tcgccgcat ccgtgccttc tccaccagga ccaagcgcag cccgcagcct    1080
gccgagctgc aggatttcta tcggcagttg tgcgagcaag caatcccga actggccgca    1140
ggaggaatgg catga                                                    1155
```

<210> SEQ ID NO 138
<211> LENGTH: 475
<212> TYPE: PRT
<213> ORGANISM: Azotobacter vinelandii

<400> SEQUENCE: 138

Met Lys Ala Lys Asp Ile Ala Glu Leu Leu Asp Glu Pro Ala Cys Ser
1               5                   10                  15

His Asn Lys Lys Glu Lys Ser Gly Cys Ala Lys Pro Lys Pro Gly Ala

```
                    20                  25                  30
Thr Asp Gly Gly Cys Ser Phe Asp Gly Ala Gln Ile Ala Leu Leu Pro
                35                  40                  45
Val Ala Asp Val Ala His Ile Val His Gly Pro Ile Ala Cys Ala Gly
            50                  55                  60
Ser Ser Trp Asp Asn Arg Gly Thr Arg Ser Ser Gly Pro Asp Leu Tyr
65                  70                  75                  80
Arg Ile Gly Met Thr Thr Asp Leu Thr Glu Asn Asp Val Ile Met Gly
                    85                  90                  95
Arg Ala Glu Lys Arg Leu Phe His Ala Ile Arg Gln Ala Val Glu Ser
                100                 105                 110
Tyr Ser Pro Pro Ala Val Phe Val Tyr Asn Thr Cys Val Pro Ala Leu
                115                 120                 125
Ile Gly Asp Asp Val Asp Ala Val Cys Lys Ala Ala Glu Arg Phe
                130                 135                 140
Gly Thr Pro Val Ile Pro Val Asp Ser Ala Gly Phe Tyr Gly Thr Lys
145                 150                 155                 160
Asn Leu Gly Asn Arg Ile Ala Gly Glu Ala Met Leu Lys Tyr Val Ile
                165                 170                 175
Gly Thr Arg Glu Pro Asp Pro Leu Pro Val Gly Ser Glu Arg Pro Gly
                180                 185                 190
Ile Arg Val His Asp Val Asn Leu Ile Gly Glu Tyr Asn Ile Ala Gly
                195                 200                 205
Glu Phe Trp His Val Leu Pro Leu Leu Asp Glu Leu Gly Leu Arg Val
                210                 215                 220
Leu Cys Thr Leu Ala Gly Asp Ala Arg Tyr Arg Glu Val Gln Thr Met
225                 230                 235                 240
His Arg Ala Glu Val Asn Met Met Val Cys Ser Lys Ala Met Leu Asn
                245                 250                 255
Val Ala Arg Lys Leu Gln Glu Thr Tyr Gly Thr Pro Trp Phe Glu Gly
                260                 265                 270
Ser Phe Tyr Gly Ile Thr Asp Thr Ser Gln Ala Leu Arg Asp Phe Ala
                275                 280                 285
Arg Leu Leu Asp Asp Pro Asp Leu Thr Ala Arg Thr Glu Ala Leu Ile
                290                 295                 300
Ala Arg Glu Glu Ala Lys Val Arg Ala Ala Leu Glu Pro Trp Arg Ala
305                 310                 315                 320
Arg Leu Glu Gly Lys Arg Val Leu Leu Tyr Thr Gly Gly Val Lys Ser
                325                 330                 335
Trp Ser Val Val Ser Ala Leu Gln Asp Leu Gly Met Lys Val Val Ala
                340                 345                 350
Thr Gly Thr Lys Lys Ser Thr Glu Asp Lys Ala Arg Ile Arg Glu
                355                 360                 365
Leu Met Gly Asp Asp Val Lys Met Leu Asp Glu Gly Asn Ala Arg Val
                370                 375                 380
Leu Leu Lys Thr Val Asp Glu Tyr Gln Ala Asp Ile Leu Ile Ala Gly
385                 390                 395                 400
Gly Arg Asn Met Tyr Thr Ala Leu Lys Gly Arg Val Pro Phe Leu Asp
                405                 410                 415
Ile Asn Gln Glu Arg Glu Phe Gly Tyr Ala Gly Tyr Asp Gly Met Leu
                420                 425                 430
Glu Leu Val Arg Gln Leu Cys Ile Thr Leu Glu Cys Pro Val Trp Glu
                435                 440                 445
```

Ala Val Arg Arg Pro Ala Pro Trp Asp Ile Pro Ala Ser Gln Asp Ala
         450                 455                 460

Ala Pro Ser Ala Pro Ala Arg Ser Ala Asn Ala
465                 470                 475

<210> SEQ ID NO 139
<211> LENGTH: 1428
<212> TYPE: DNA
<213> ORGANISM: Azotobacter vinelandii

<400> SEQUENCE: 139

```
atgaaagcca aggatattgc cgaactgctc gacgagcccg cctgcagtca caacaagaag      60
gaaaagtccg gctgcgccaa gcccaagccg gcgccaccg acggtggctg ctccttcgac     120
ggcgcgcaga tcgccctgct gcccgtcgcc gacgtggcgc atatcgttca cgggccgatc     180
gcttgcgccg gcagttcctg gacaaccgc ggcacccgct ccagcgggcc ggacctgtac     240
cgcatcggca tgaccaccga tctcaccgag aacgacgtga tcatgggcg cgccgagaag     300
cgcctgttcc atgccatccg ccaggcggtg aaagctatt cgccgccggc ggtgttcgtc     360
tacaacacct gcgtgccggc gctgatcgg gacgacgtcg acgcagtgtg caaagccgcc     420
gccgagcgct tcggcacccc ggtcatcccg gtcgactcgg ccggcttcta cggcaccaag     480
aacctcggca accgcatcgc cggtgaggcc atgctcaagt acgtgatcgg cacccgcgag     540
cccgatccgc tgcccgtcgg cagcgagcgt ccgggcatcc gcgtgcacga cgtcaacctg     600
atcggcgagt acaacatcgc cggcgagttc tggcatgtcc tgccgctgct cgacgaactg     660
ggcctgcggg tgctctgcac cctggccggc gatgcgcgct accgcgaggt gcagaccatg     720
caccgcgccg aagtgaacat gatggtctgc tccaaggcca tgctcaatgt cgctcgcaag     780
ctgcaggaaa cctacggcac gccctggttc gagggcagct tctacggcat caccgacacc     840
tcccaggcgc tgcgcgactt cgcccggctg ctcgatgatc ccgacctgac cgcccgcacc     900
gaggcgctga tcgcgcgcga ggaggccaag gtccgcgccg ccctcgaacc ctggcgtgcg     960
cgtctggagg gcaagcgcgt gctgctctac accggcggcg tgaagtcctg gtcggtggtt    1020
tccgccctgc aggacctggg catgaaggtg gtcgccaccg gcaccaagaa gtccaccgag    1080
gaagacaagg cacgcatccg cgaactgatg ggcgacgacg tcaagatgct cgacgagggc    1140
aatgcgcggg tgctgctgaa gaccgtcgac gagtaccagg ccgacatcct catcgccggc    1200
ggacgcaaca tgtacaccgc gctcaagggc cgcgtgccct tcctcgacat caaccaggag    1260
cgcgaattcg gctatgccgg ctacgacggc atgctggaac tggtgcgtca gctctgcatc    1320
accctggaat gcccggtgtg ggaggcggtg cgccgccccg cgccctggga catccccgcc    1380
agccaggacg ccgcgccgag cgcgccggcc cgttcggcga acgcctga              1428
```

<210> SEQ ID NO 140
<211> LENGTH: 933
<212> TYPE: PRT
<213> ORGANISM: Artificial sequence
<220> FEATURE:
<223> OTHER INFORMATION: Recombinant

<400> SEQUENCE: 140

Met Lys Ala Lys Asp Ile Ala Glu Leu Leu Asp Glu Pro Ala Cys Ser
1               5                   10                  15

His Asn Lys Lys Glu Lys Ser Gly Cys Ala Lys Pro Lys Pro Gly Ala
            20                  25                  30

```
Thr Asp Gly Gly Cys Ser Phe Asp Gly Ala Gln Ile Ala Leu Leu Pro
         35                  40                  45

Val Ala Asp Val Ala His Ile Val His Gly Pro Ile Ala Cys Ala Gly
 50                  55                  60

Ser Ser Trp Asp Asn Arg Gly Thr Arg Ser Ser Gly Pro Asp Leu Tyr
 65                  70                  75                  80

Arg Ile Gly Met Thr Thr Asp Leu Thr Glu Asn Asp Val Ile Met Gly
                 85                  90                  95

Arg Ala Glu Lys Arg Leu Phe His Ala Ile Arg Gln Ala Val Glu Ser
                100                 105                 110

Tyr Ser Pro Pro Ala Val Phe Val Tyr Asn Thr Cys Val Pro Ala Leu
            115                 120                 125

Ile Gly Asp Asp Val Asp Ala Val Cys Lys Ala Ala Ala Glu Arg Phe
            130                 135                 140

Gly Thr Pro Val Ile Pro Val Asp Ser Ala Gly Phe Tyr Gly Thr Lys
145                 150                 155                 160

Asn Leu Gly Asn Arg Ile Ala Gly Glu Ala Met Leu Lys Tyr Val Ile
                165                 170                 175

Gly Thr Arg Glu Pro Asp Pro Leu Pro Val Gly Ser Glu Arg Pro Gly
            180                 185                 190

Ile Arg Val His Asp Val Asn Leu Ile Gly Glu Tyr Asn Ile Ala Gly
            195                 200                 205

Glu Phe Trp His Val Leu Pro Leu Leu Asp Glu Leu Gly Leu Arg Val
            210                 215                 220

Leu Cys Thr Leu Ala Gly Asp Ala Arg Tyr Arg Glu Val Gln Thr Met
225                 230                 235                 240

His Arg Ala Glu Val Asn Met Met Val Cys Ser Lys Ala Met Leu Asn
                245                 250                 255

Val Ala Arg Lys Leu Gln Glu Thr Tyr Gly Thr Pro Trp Phe Glu Gly
            260                 265                 270

Ser Phe Tyr Gly Ile Thr Asp Thr Ser Gln Ala Leu Arg Asp Phe Ala
            275                 280                 285

Arg Leu Leu Asp Asp Pro Asp Leu Thr Ala Arg Thr Glu Ala Leu Ile
            290                 295                 300

Ala Arg Glu Glu Ala Lys Val Arg Ala Ala Leu Glu Pro Trp Arg Ala
305                 310                 315                 320

Arg Leu Glu Gly Lys Arg Val Leu Leu Tyr Thr Gly Gly Val Lys Ser
                325                 330                 335

Trp Ser Val Val Ser Ala Leu Gln Asp Leu Gly Met Lys Val Val Ala
            340                 345                 350

Thr Gly Thr Lys Lys Ser Thr Glu Glu Asp Lys Ala Arg Ile Arg Glu
            355                 360                 365

Leu Met Gly Asp Asp Val Lys Met Leu Asp Glu Gly Asn Ala Arg Val
            370                 375                 380

Leu Leu Lys Thr Val Asp Glu Tyr Gln Ala Asp Ile Leu Ile Ala Gly
385                 390                 395                 400

Gly Arg Asn Met Tyr Thr Ala Leu Lys Gly Arg Val Pro Phe Leu Asp
                405                 410                 415

Ile Asn Gln Glu Arg Glu Phe Gly Tyr Ala Gly Tyr Asp Gly Met Leu
            420                 425                 430

Glu Leu Val Arg Gln Leu Cys Ile Thr Leu Glu Cys Pro Val Trp Glu
            435                 440                 445

Ala Val Arg Arg Pro Ala Pro Trp Asp Ile Pro Ala Ser Gln Asp Ala
```

```
            450                 455                 460
Ala Pro Ser Ala Pro Ala Arg Ser Ala Asn Ala Met Ala Glu Ile Ile
465                 470                 475                 480

Asn Arg Asn Lys Ala Leu Ala Val Ser Pro Leu Lys Ala Ser Gln Thr
                485                 490                 495

Met Gly Ala Ala Leu Ala Ile Leu Gly Leu Ala Arg Ser Met Pro Leu
                500                 505                 510

Phe His Gly Ser Gln Gly Cys Thr Ala Phe Ala Lys Val Phe Phe Val
                515                 520                 525

Arg His Phe Arg Glu Pro Val Pro Leu Gln Thr Thr Ala Met Asp Gln
                530                 535                 540

Val Ser Ser Val Met Gly Ala Asp Glu Asn Val Val Glu Ala Leu Lys
545                 550                 555                 560

Thr Ile Cys Glu Arg Gln Asn Pro Ser Val Ile Gly Leu Leu Thr Thr
                565                 570                 575

Gly Leu Ser Glu Thr Gln Gly Cys Asp Leu His Thr Ala Leu His Glu
                580                 585                 590

Phe Arg Thr Gln Tyr Glu Glu Tyr Lys Asp Val Pro Ile Val Pro Val
                595                 600                 605

Asn Thr Pro Asp Phe Ser Gly Cys Phe Glu Ser Gly Phe Ala Ala Ala
                610                 615                 620

Val Lys Ala Ile Val Glu Thr Leu Val Pro Glu Arg Arg Asp Gln Val
625                 630                 635                 640

Gly Lys Arg Pro Arg Gln Val Asn Val Leu Cys Ser Ala Asn Leu Thr
                645                 650                 655

Pro Gly Asp Leu Glu Tyr Ile Ala Glu Ser Ile Glu Ser Phe Gly Leu
                660                 665                 670

Arg Pro Leu Leu Ile Pro Asp Leu Ser Gly Ser Leu Asp Gly His Leu
                675                 680                 685

Asp Glu Asn Arg Phe Asn Ala Leu Thr Thr Gly Gly Leu Ser Val Ala
                690                 695                 700

Glu Leu Ala Thr Ala Gly Gln Ser Val Ala Thr Leu Val Val Gly Gln
705                 710                 715                 720

Ser Leu Ala Gly Ala Ala Asp Ala Leu Ala Glu Arg Thr Gly Val Pro
                725                 730                 735

Asp Arg Arg Phe Gly Met Leu Tyr Gly Leu Asp Ala Val Asp Ala Trp
                740                 745                 750

Leu Met Ala Leu Ala Glu Ile Ser Gly Asn Pro Val Pro Asp Arg Tyr
                755                 760                 765

Lys Arg Gln Arg Ala Gln Leu Gln Asp Ala Met Leu Asp Thr His Phe
                770                 775                 780

Met Leu Ser Ser Ala Arg Thr Ala Ile Ala Ala Asp Pro Asp Leu Leu
785                 790                 795                 800

Leu Gly Phe Asp Ala Leu Leu Arg Ser Met Gly Ala His Thr Val Ala
                805                 810                 815

Ala Val Val Pro Ala Arg Ala Ala Leu Val Asp Ser Pro Leu Pro
                820                 825                 830

Ser Val Arg Val Gly Asp Leu Glu Asp Leu Glu His Ala Ala Arg Ala
                835                 840                 845

Gly Gln Ala Gln Leu Val Ile Gly Asn Ser His Ala Leu Ala Ser Ala
                850                 855                 860

Arg Arg Leu Gly Val Pro Leu Leu Arg Ala Gly Phe Pro Gln Tyr Asp
865                 870                 875                 880
```

Leu Leu Gly Gly Phe Gln Arg Cys Trp Ser Gly Tyr Arg Gly Ser Ser
            885                 890                 895

Gln Val Leu Phe Asp Leu Ala Asn Leu Leu Val Glu His His Gln Gly
        900                 905                 910

Ile Gln Pro Tyr His Ser Ile Tyr Ala Gln Lys Pro Ala Thr Glu Gln
    915                 920                 925

Pro Gln Trp Arg His
    930

<210> SEQ ID NO 141
<211> LENGTH: 2802
<212> TYPE: DNA
<213> ORGANISM: Artificial sequence
<220> FEATURE:
<223> OTHER INFORMATION: Recombinant

<400> SEQUENCE: 141

| | | | | | |
|---|---|---|---|---|---|
| atgaaagcca | aggatattgc | cgaactgctc | gacgagcccg | cctgcagtca | caacaagaag | 60 |
| gaaaagtccg | gctgcgccaa | gcccaagccg | ggcgccaccg | acggtggctg | ctccttcgac | 120 |
| ggcgcgcaga | tcgccctgct | gcccgtcgcc | gacgtggcgc | atatcgttca | cgggccgatc | 180 |
| gcttgcgccg | gcagttcctg | gacaaccgc | ggcacccgct | ccagcgggcc | ggacctgtac | 240 |
| cgcatcggca | tgaccaccga | tctcaccgag | aacgacgtga | tcatggggcg | cgccgagaag | 300 |
| cgcctgttcc | atgccatccg | ccaggcggtg | aaagctatt | cgccgccggc | ggtgttcgtc | 360 |
| tacaacacct | gcgtgccggc | gctgatcggc | gacgacgtcg | acgcagtgtg | caaagccgcc | 420 |
| gccgagcgct | tcggcacccc | ggtcatcccg | gtcgactcgg | ccggcttcta | cggcaccaag | 480 |
| aacctcggca | accgcatcgc | cggtgaggcc | atgctcaagt | acgtgatcgg | cacccgcgag | 540 |
| cccgatccgc | tgcccgtcgg | cagcgagcgt | ccgggcatcc | gcgtgcacga | cgtcaacctg | 600 |
| atcggcgagt | acaacatcgc | cggcgagttc | tggcatgtcc | tgccgctgct | cgacgaactg | 660 |
| ggcctgcggg | tgctctgcac | cctggccggc | gatgcgcgct | accgcgaggt | gcagaccatg | 720 |
| caccgcgccg | aagtgaacat | gatggtctgc | tccaaggcca | tgctcaatgt | cgctcgcaag | 780 |
| ctgcaggaaa | cctacggcac | gccctggttc | gagggcagct | tctacggcat | caccgacacc | 840 |
| tcccaggcgc | tgcgcgactt | cgcccggctg | ctcgatgatc | ccgacctgac | cgcccgcacc | 900 |
| gaggcgctga | tcgcgcgcga | ggaggccaag | gtccgcgccg | ccctcgaacc | ctggcgtgcg | 960 |
| cgtctggagg | gcaagcgcgt | gctgctctac | accggcggcg | tgaagtcctg | gtcggtggtt | 1020 |
| tccgccctgc | aggacctggg | catgaaggtg | gtcgccaccg | gcaccaagaa | gtccaccgag | 1080 |
| gaagacaagg | cacgcatccg | cgaactgatg | ggcgacgacg | tcaagatgct | cgacgagggc | 1140 |
| aatgcgcggg | tgctgctgaa | gaccgtcgac | gagtaccagg | ccgacatcct | catcgccggc | 1200 |
| ggacgcaaca | tgtacaccgc | gctcaagggc | cgcgtgccct | tcctcgacat | caaccaggag | 1260 |
| cgcgaattcg | gctatgccgg | ctacgacggc | atgctgaac | tggtgcgtca | gctctgcatc | 1320 |
| accctggaat | gcccggtgtg | ggaggcggtg | cgccgccccg | cgccctggga | catccccgcc | 1380 |
| agccaggacg | ccgcgccgag | cgcgccggcc | cgttcggcga | acgccatggc | cgagatcatc | 1440 |
| aatcgcaaca | aggccctggc | cgtcagcccg | ctgaaggcca | gtcagaccat | gggcgccgcg | 1500 |
| ctggccatcc | tcggcctggc | gcgcagcatg | ccgctgtttc | acggctcgca | gggttgcacc | 1560 |
| gcgttcgcca | aggtgttctt | cgttcgccat | ttcgcgagc | cggtcccgct | gcagaccacc | 1620 |
| gccatggacc | aggtcagttc | ggtgatgggc | gccgacgaga | acgtcgtcga | ggcgctgaag | 1680 |

-continued

```
accatctgcg aacggcagaa tccctcggtc atcggcctgc tcaccaccgg cctgtcggaa    1740
acccagggct gcgacctgca caccgccctg cacgagttcc gtacccagta cgaggagtac    1800
aaggacgtgc cgatcgttcc ggtgaacacg ccggacttca gcggctgctt cgagagcggc    1860
ttcgccgcgg cggtcaaggc gatcgtcgag acgctggtgc ccgaacggcg cgatcaggtg    1920
ggcaagcgtc cgcgccaggt caacgtgctg tgctcggcca atctcacccc gggcgatctg    1980
gagtacatcg ccgaaagcat cgagagcttc ggtctgcgcc ccttgctgat ccccgacctg    2040
tccggctcgc tcgacggcca cctggacgag aaccgtttca atgccctgac caccggcgga    2100
ctgagcgtgg ccgaactggc caccgccgga cagagcgtcg ccactctggt ggtcgggcag    2160
agcctggcgg gtgcggccga cgccctggcc gagcgcaccg gcgtgcccga ccggcgcttc    2220
ggcatgctct acggtctgga tgcggtcgat gcctggctga tggcgctggc cgagatcagc    2280
ggcaatccgg tgcccgaccg ctacaagcgc cagcgtgccc aattgcagga cgccatgctc    2340
gacacccact tcatgctcag ttccgcacgc acggccatcg ccgccgatcc cgatctgctg    2400
ctcggtttcg atgccctgct gcgcagcatg ggcgcgcaca cggtagccgc cgtggtgccg    2460
gcccgggccg ccgcgctggt cgattcgcct ctgccctccg tgcgggtcgg cgacctggag    2520
gacctcgagc atgccgcccg cgccggccag gcccaactgg tgatcggcaa cagccacgcc    2580
ctggccagcg cccgtcgcct cggtgtgcca ctgttgcgtg ccggcttccc gcagtacgat    2640
ctgctgggcg gtttccaacg ctgctggtcc ggctaccgcg gcagcagtca ggtgctgttc    2700
gatctggcca acctgctggt cgaacaccac cagggtatcc agccctatca ttcgatctat    2760
gcgcaaaaac cggcaaccga acagccgcaa tggaggcact ga                      2802
```

COMPOSITIONS AND METHODS FOR EXPRESSION OF NITROGENASE IN PLANT CELLS

CROSS-REFERENCE TO RELATED APPLICATIONS

This application claims the benefit of U.S. Provisional Application No. 62/141,733 (filed Apr. 1, 2015) and 62/236,340 (filed Oct. 2, 2015), both of which are herein incorporated by reference in their entirety.

INCORPORATION OF SEQUENCE LISTING

The sequence listing that is contained in the file named "MONS376US_ST25.txt", which is 293 KB (measured in MS-Windows) and was created on Mar. 24, 2016, is filed herewith by electronic submission and incorporated herein by reference.

FIELD OF THE INVENTION

The disclosure relates to recombinant DNA molecules for expression of active nitrogenase, including its components dinitrogenase reductase and dinitrogenase, in plant cells. The disclosure further relates to methods of producing a plant cell expressing active dinitrogenase reductase and related compositions.

BACKGROUND OF THE INVENTION

Nitrogen is an essential element in plant development and a limiting factor in plant growth. Plants cannot directly utilize dinitrogen ($N_2$) gas, which makes up about 80% of the atmosphere. Nitrogen fixing bacteria are however able to reduce the strong triple bond of the $N_2$ molecule to produce ammonium, which may be used by plants as a source of nitrogen. The enzyme complex underlying the ATP-dependent reduction of dinitrogen ($N_2$) to ammonia ($NH_3$) in these nitrogen-fixing bacteria is known as nitrogenase. Nitrogenase accounts for roughly half of the bioavailable nitrogen supporting extant life (Boyd & Peters, *Frontiers in Microbiology*, 4:2013, doi: 10.3389).

Nitrogenase consists of two oxygen-sensitive protein components: dinitrogenase and dinitrogenase reductase. Dinitrogenase is also referred to as "MoFe" protein or protein I. Dinitrogenase is an alpha2-beta2-heterotetramer of the products of the nifD and nifK genes. Dinitrogenase reductase is also referred to as "Fe" protein or protein II. Dinitrogenase reductase is a homodimer of the product of the nifH gene.

Aside from the nitrogen fixing prokaryotes, nitrogen fertilizer (for example, ammonia) can be produced by industrial chemical manufacturing using fossil fuels. However, this process is costly, has associated manufacturing risks, and application of fertilizer can contribute to ground water pollution. Although legumes have the capacity to form root nodules of nitrogen fixing bacteria, other crops do not have this ability.

Previous studies to enhance the capacity of crops for nitrogen fixation and/or utilization have included, for instance, attempts to make non-legume crops form root nodules of nitrogen fixing bacteria, to develop crops containing an intracellular organelle of nitrogen fixing bacteria, improving nitrogen use efficiency, and generating crops with nuclear encoded nitrogenase. To date, there has been no report of successful transformation of plants with nitrogenase component enzymes (dinitrogenase or dinitrogenase reductase) that have been shown to be active in a nitrogenase activity assay.

SUMMARY OF THE INVENTION

In one aspect, the present disclosure provides a recombinant DNA construct comprising at least one polynucleotide sequence selected from the group consisting of: (a) a polynucleotide sequence encoding a dinitrogenase reductase or a dinitrogenase polypeptide operably linked to a mitochondrial-targeting peptide, wherein the polynucleotide sequence is operably linked to a promoter sequence functional in plants; (b) a polynucleotide sequence encoding a dinitrogenase reductase or dinitrogenase polypeptide operably linked to a chloroplast-targeting peptide, wherein the polynucleotide sequence is operably linked to a promoter sequence functional in plants; and (c) a polynucleotide sequence encoding a dinitrogenase reductase or dinitrogenase polypeptide operably linked to: a promoter sequence functional in plants, a ribosome binding site region, a 3' untranslated region, and sequences allowing for integration into a plant cell plastid genome, for expression of at least a first subunit of nitrogenase in said plastid; wherein expression of the recombinant DNA construct in a plant cell is capable of resulting in dinitrogenase reductase, dinitrogenase, or nitrogenase activity in the plant cell.

In one embodiment, the invention provides such a recombinant DNA construct, wherein the polynucleotide sequence encoding a dinitrogenase reductase polypeptide comprises a sequence encoding at least one dinitrogenase reductase component selected from the group consisting of NifH, and NifH and NifM. In another embodiment the polynucleotide sequence encoding dinitrogenase polypeptides comprises sequences encoding NifD and NifK. In certain embodiments of the recombinant DNA construct, the dinitrogenase reductase polypeptide comprises a sequence at least 70% identical to at least one sequence selected from the group consisting of: SEQ ID NO:24, SEQ ID NO:32, SEQ ID NO:36, SEQ ID NO:26 and SEQ ID NO:34. In some embodiments of the recombinant DNA construct, the dinitrogenase polypeptide comprises a sequence at least 70% identical to at least one sequence selected from the group consisting of: SEQ ID NOs: 126, and SEQ ID NO:128.

In certain embodiments, the recombinant DNA construct comprises a polynucleotide sequence encoding a mitochondrial-targeting peptide operably linked to a polypeptide with dinitrogenase reductase activity wherein the mitochondrial-targeted dinitrogenase reductase polypeptide comprises a sequence at least 70% identical to a sequence selected from the group consisting of: SEQ ID NO:40, SEQ ID NO:42, SEQ ID NO:44, SEQ ID NO:46, SEQ ID NO:48, SEQ ID NO:50, SEQ ID NO:64, SEQ ID NO:66, SEQ ID NO:72, SEQ ID NO:74, SEQ ID NO:78, and SEQ ID NO:80. In some embodiments, the promoter sequence, ribosome binding site region, 3' untranslated region, and sequences allowing for integration into a plant cell plastid genome for expression of the nitrogenase subunit(s) in the plastid are selected from the group consisting of: SEQ ID NO:113, SEQ ID NO:114, SEQ ID NO:115, SEQ ID NO:116, SEQ ID NO:119, SEQ ID NO:120, SEQ ID NO:121, and SEQ ID NO:122. In other embodiments the recombinant DNA construct further comprises at least a first expression element selected from the group consisting of: an enhancer, an intron, a transcription termination sequence, a ribosomal RNA operon promoter, a 5'-untranslated leader, a translational control region active in plant plastids, and a 3'-untranslated region active in plant plastids.

In still other embodiments the recombinant DNA construct further comprises a polynucleotide sequence encoding one or more additional polypeptides allowing for dinitrogenase or dinitrogenase reductase expression, assembly, stability, or activity, selected from the group consisting of: NifB, NifQ, NifN, NifV, NifE, NifM, NifS, and NifU. In particular embodiments of the recombinant DNA construct the polynucleotide sequence encoding the additional polypeptide is operably linked to a polynucleotide sequence encoding a mitochondrial-targeting peptide or a chloroplast-targeting peptide, and the polynucleotide sequence is further operably linked to a promoter functional in plants. Further, in still other embodiments of the recombinant DNA construct, the polynucleotide sequence encoding the additional polypeptide is operably linked to a promoter and ribosome binding site region, and polynucleotide sequences allowing for integration into a plant cell plastid genome for expression of the nitrogenase subunit(s) in the plastid. In certain embodiments, wherein the polynucleotide sequence encodes the additional polypeptide, the additional polypeptide sequence is selected from the group consisting of: SEQ ID NO:130 (NifB), SEQ ID NO:132 (NifQ), SEQ ID NO:134 (NifN), SEQ ID NO:136 (NifV), SEQ ID NO:138 (NifE), SEQ ID NO:26 (NifM), SEQ ID NO:34 (NifM), SEQ ID NO: 28 (NifS), and SEQ ID NO:30 (NifU).

In another aspect, the invention provides a method of producing a plant that reduces dinitrogen (N2) gas in a plant cell comprising: (a) introducing into the plant cell at least one polynucleotide sequence selected from the group consisting of: (i) a polynucleotide sequence encoding a dinitrogenase reductase or dinitrogenase polypeptide operably linked to a mitochondrial-targeting peptide, wherein the polynucleotide sequence is operably linked to a promoter functional in plants; (ii) a polynucleotide sequence encoding a dinitrogenase reductase or dinitrogenase polypeptide operably linked to a chloroplast-targeting peptide, wherein the polynucleotide sequence is operably linked to a promoter functional in plants; and (iii) a polynucleotide sequence encoding a dinitrogenase reductase or dinitrogenase polypeptide operably linked to a promoter and ribosome binding site region, and sequences allowing for integration into a plant cell plastid genome for expression of at least a first subunit of nitrogenase in said plastid, wherein expression of the recombinant DNA construct in a plant cell results in dinitrogenase reductase, dinitrogenase, or nitrogenase activity in the plant cell, and (b) identifying a plant that reduces dinitrogen (N2) gas by expression of active nitrogenase enzyme in the plant cell.

In certain embodiments of the method, the recombinant DNA construct is transiently introduced into the plant cell. In other embodiments the recombinant DNA construct is stably integrated into the genome of the plant cell, wherein the genome comprises the nuclear genome or a plastid genome.

In some embodiments the dinitrogenase reductase polypeptide comprises a sequence at least 70% identical to at least one sequence selected from the group consisting of: SEQ ID NO:24, SEQ ID NO:32, SEQ ID NO:36, SEQ ID NO:26 and SEQ ID NO:34. In other embodiments the dinitrogenase polypeptide comprises a sequence at least 70% identical to at least one sequence selected from the group consisting of: SEQ ID NOs: 126, and SEQ ID NO:128.

In still other embodiments of the method, the recombinant DNA construct comprises a polynucleotide sequence encoding a mitochondrial-targeting peptide operably linked to a polypeptide with dinitrogenase reductase activity wherein the mitochondrial-targeted dinitrogenase reductase polypeptide comprises a sequence at least 70% identical to a sequence selected from the group consisting of: SEQ ID NO:40, SEQ ID NO:42, SEQ ID NO:44, SEQ ID NO:46, SEQ ID NO:48, SEQ ID NO:50, SEQ ID NO:64, SEQ ID NO:66, SEQ ID NO:72, SEQ ID NO:74, SEQ ID NO:78, and SEQ ID NO:80. In certain embodiments of the method, the promoter, ribosome binding site region, 3' untranslated region, and sequences allowing for integration into a plant cell plastid genome for expression of the nitrogenase subunit(s) in said plastid are selected from the group consisting of: SEQ ID NO:113, SEQ ID NO:114, SEQ ID NO:115, SEQ ID NO:116, SEQ ID NO:119, SEQ ID NO:120, SEQ ID NO:121, and SEQ ID NO:122. In some embodiments of the method the recombinant DNA construct further comprises a sequence encoding one or more additional polypeptides allowing for dinitrogenase or dinitrogenase reductase expression, assembly, stability, or activity selected from the group consisting of: NifB, NifQ, NifN, NifV, NifE, NifM, NifS, and NifU. Further, in certain embodiments of the method, the polynucleotide sequence encoding the additional polypeptide is operably linked to a polynucleotide sequence encoding a mitochondrial-targeting polypeptide or a chloroplast-targeting peptide, and wherein the polynucleotide sequence is further operably linked to a promoter functional in plants.

In particular embodiments of the method, the polynucleotide sequence encoding one or more additional polypeptides is operably linked to a promoter and ribosome binding site region, and polynucleotide sequences allowing for integration into a plant cell plastid genome for expression of the nitrogenase subunit(s) in said plastid. In some embodiments the sequence encoding the additional polypeptide is selected from the group consisting of: SEQ ID NO:130 (NifB), SEQ ID NO:132 (NifQ), SEQ ID NO:134 (NifN), SEQ ID NO:136 (NifV), SEQ ID NO:138 (NifE), SEQ ID NO:26 (NifM), SEQ ID NO:34 (NifM), SEQ ID NO: 28 (NifS), and SEQ ID NO:30 (NifU).

In still another aspect, there is provided a plant that reduces dinitrogen (N2) gas in the plant cell, wherein said plant comprises a recombinant DNA construct comprising at least one polynucleotide sequence selected from the group consisting of: (a) a polynucleotide sequence encoding a dinitrogenase reductase or a dinitrogenase polypeptide operably linked to a mitochondrial-targeting peptide, wherein the polynucleotide sequence is operably linked to a promoter sequence functional in plants; (b) a polynucleotide sequence encoding a dinitrogenase reductase or dinitrogenase polypeptide operably linked to a chloroplast-targeting peptide, wherein the polynucleotide sequence is operably linked to a promoter sequence functional in plants; and (c) a polynucleotide sequence encoding a dinitrogenase reductase or dinitrogenase polypeptide operably linked to: a promoter sequence functional in plants, a ribosome binding site region, a 3' untranslated region, and sequences allowing for integration into a plant cell plastid genome, for expression of at least a first subunit of nitrogenase in said plastid; wherein expression of the recombinant DNA construct in a plant cell is capable of resulting in dinitrogenase reductase, dinitrogenase, or nitrogenase activity in the plant cell.

BRIEF DESCRIPTION OF THE DRAWINGS

FIG. 9. Alignment of NifH sequences from *Cyanothece* sp., *A. vinelandii*, and *K. pneumoniae*.

BRIEF DESCRIPTION OF THE SEQUENCE LISTING

Figure 1:
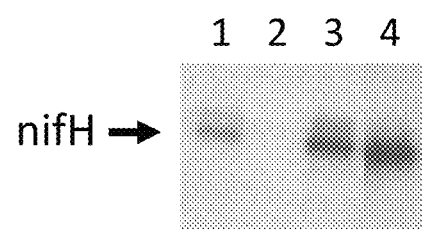
FIG. 1. Western blot analysis of NifH peptide expressed in the chloroplast fraction of tobacco plants infiltrated with the chimeric chloroplast-targeted RbcS-nifH+RbcS-nifM (pMON135488) construct. Total protein fractions were prepared, as indicated. Lane 1 is sample from infiltrated tobacco plants exposed to ambient air and light for 2 hours prior to chloroplast fraction preparation, lane 2 contains no sample, lane 3 is sample from infiltrated tobacco plants exposed to ambient air and dark for 2 hours prior to chloroplast fraction preparation, and lane 4 is sample from infiltrated tobacco plants maintained in a chamber of 10% $O_2$ and low light.

SEQ ID NO:1-6 CPN60-derived mitochondrial targeting peptide sequences
SEQ ID NOs:7-8 AOX-derived mitochondrial targeting peptide sequences
SEQ ID NOs:9-11 ATP synthase protein 9-derived ("ATPSyn") mitochondrial targeting peptide sequences
SEQ ID NOs:12-17 *Glycine* decarboxylase L-derived ("GD") mitochondrial targeting peptide sequences
SEQ ID NOs:18-19 HSP70-derived mitochondrial targeting peptide sequences
SEQ ID NOs:20-22 ribosomal protein S10-derived ("RPS10") mitochondrial targeting peptide sequences
SEQ ID NO:23 chloroplast targeting peptide ("CTP") of RbcS from *Oryza sativa*.
SEQ ID NOs:24-25 polypeptide sequence from *Azotobacter vinelandii* NifH, and associated nifH DNA sequence
SEQ ID NOs:26-27 polypeptide sequence from *Azotobacter vinelandii* NifM, and associated nifM DNA sequence
SEQ ID NOs:28-29 polypeptide sequence from *Azotobacter vinelandii* NifS, and associated nifS DNA sequence
SEQ ID NOs:30-31 polypeptide sequence from *Azotobacter vinelandii* NifU, and associated nifU DNA sequence
SEQ ID NOs:32-33 polypeptide sequence from *Klebsiella pneumoniae* NifH, and associated nifH DNA sequence
SEQ ID NOs:34-35 polypeptide sequence from *Klebsiella pneumoniae* NifM, and associated nifM DNA sequence
SEQ ID NOs:36-37 polypeptide sequence from *Cyanothece* sp. NifH, and associated nifH DNA sequence
SEQ ID NOs:38-39 polypeptide sequence of P21-FLAG peptide and associated DNA sequence
SEQ ID NOs:40-57 polypeptide and associated DNA sequences of CPN60 mitochondrial-targeted nifH, nifM, nifS and nifU chimeric constructs
SEQ ID NOs:58-61 polypeptide and associated DNA sequences of AOX mitochondrial-targeted nifH chimeric constructs
SEQ ID NOs:62-67 polypeptide and associated DNA sequences of ATPSyn mitochondrial-targeted nifH chimeric constructs
SEQ ID NOs:68-79 polypeptide and associated DNA sequences of GD subunit-derived mitochondrial-targeted nifH chimeric constructs
SEQ ID NOs:80-83 polypeptide and associated DNA sequences of HSP70-derived mitochondrial-targeted nifH chimeric constructs
SEQ ID NOs:84-89 polypeptide and associated DNA sequences of Rps10 mitochondrial-targeted nifH chimeric constructs SEQ ID NOs:90-93 polypeptide and associated DNA sequences of chloroplast-targeted *A. vinelandii* nifH and nifM chimeric constructs SEQ ID NOs:94-95 polypeptide and associated DNA sequences of chloroplast-targeted *K. pneumoniae* nifH chimeric constructs SEQ ID NOs:96-97 polypeptide and associated DNA sequences of codon optimized, chloroplast-targeted *K. pneumoniae* nifH chimeric constructs SEQ ID NOs:98-99 polypeptide and associated DNA sequences of chloroplast-targeted *K. pneumoniae* nifM chimeric constructs SEQ ID NO:100-101 polypeptide and associated DNA sequences of chloroplast-targeted *Cyanothece* sp. nifH chimeric constructs SEQ ID NOs:102-103 polypeptide and associated DNA sequences of chloroplast-targeted AroA-CP4 chimeric constructs SEQ ID NOs:104-111 polypeptide sequences of CPN-60, AOX, ATPSyn, GD subunit, HSP70, and RPS10 mitochondrial-targeting peptides SEQ ID NO:112 polypeptide sequence of RbcS from *Oryza sativa*.

SEQ ID NO:113 DNA sequence of Prrn ribosomal RNA operon plastid gene

SEQ ID NO:114 T7 bacteriophage gene 10 leader

SEQ ID NO:115 3' region of the plastid rps16 gene ("T-UNI.TRPS16:1")

SEQ ID NO:116 3' region of the plastid petD gene ("T-Nt.TpetD:1")

SEQ ID NO:117 nifH coding sequence from *A. vinelandii* for expression in chloroplasts ("nifH plastid (CR-Avin.nifH")

SEQ ID NO:118 aadA gene nucleotide sequence ("CR-UNI.AADA:1")

SEQ ID NO:119 nucleotide sequence of ribosome binding site of tobacco plastid gene psbA ("P-Nb.PpsbA:1")

SEQ ID NO:120 nucleotide sequence of expression element derived from the 3' region of the psbA gene ("T-Nt.TpsbA:1")

SEQ ID NOs:121-122 plastid genome sequences for homologous recombination into chloroplast genome SEQ ID NOs:123-125 nucleotide sequences for nifH, nifM, and rbcL probes SEQ ID NOs:126-127 polypeptide sequence from *A. vinelandii* NifD, and associated nifD DNA sequence SEQ ID NOs:128-129 polypeptide sequence from *A. vinelandii* NifK, and associated nifK DNA sequence SEQ ID NOs:130-131 polypeptide sequence from *A. vinelandii* NifB, and associated nifB DNA sequence SEQ ID NO:132-133 polypeptide sequence from *A. vinelandii* NifQ, and associated nifQ DNA sequence SEQ ID NOs:134-135 polypeptide sequence from *A. vinelandii* NifN, and associated nifN DNA sequence SEQ ID NOs:136-137 polypeptide sequence from *A. vinelandii* NifV, and associated nifV DNA sequence SEQ ID NOs:138-139 polypeptide sequence from *A. vinelandii* NifE, and associated nifE DNA sequence SEQ ID NOs:140-141 polypeptide sequence of NifEN fusion protein and associated nifEN DNA sequence

DETAILED DESCRIPTION OF THE INVENTION

The invention overcomes limitations of the prior art by providing nucleic acid constructs for expression of nitrogenase components in plant cells. Also provided are methods for expressing active nitrogenase components in plant cells, and plants and seeds comprising introduced nitrogenase components, that express one or more components of nitrogenase and thus display dinitrogenase reductase and dinitrogenase activities. By "nitrogenase components" is meant the oxygen-sensitive components of the nitrogenase complex, dinitrogenase and dinitrogenase reductase, as well as other nif gene products which allow for expression, stability, and activity of the nitrogenase.

Production of active nitrogenase components in plant cells, absent the protective mechanisms and specialized nodule structure employed by nitrogen-fixing bacteria, is surprising and unexpected, given that nitrogenase and its catalytic components dinitrogenase reductase and dinitrogenase are well known to be highly sensitive to inactivation in the presence of oxygen. For instance, photosynthesizing chloroplasts are known to contain an increased $O_2$ concentration relative to other parts of plant cells (Steiger and Beck, *Pl. Physiol.* 60:903, 1977). For the first time, a bacterial nitrogenase component expressed in a plant cell, targeted for instance to mitochondria or chloroplasts, is shown to possess enzymatic activity in order to allow for fixation of atmospheric nitrogen by plants. Importantly, this may reduce the need to apply an external source of nitrogen to a crop plant as is commonly done in agricultural settings, or to inoculate plants with nitrogen-fixing bacteria.

The following descriptions and definitions are provided to better define the invention and to guide those of ordinary skill in the art in the practice of the invention. Unless otherwise noted, terms are to be understood according to conventional usage by those of ordinary skill in the relevant art.

In specific aspects, the invention provides recombinant DNA molecules and proteins. As used herein, the term "recombinant" refers to a non-naturally occurring DNA, protein, cell, seed, or organism that is the result of genetic engineering and as such would not normally be found in nature. A "recombinant DNA molecule" is a DNA molecule comprising a DNA sequence that does not naturally occur in nature and as such is the result of human intervention, such as a DNA molecule comprised of at least two DNA molecules heterologous to each other. An example of a recombinant DNA molecule is a DNA molecule provided herein encoding a nitrogenase component operably linked to a heterologous regulatory or other element, such as a heterologous promoter for expression in a plant cell. A "recombinant protein" is a protein comprising an amino acid sequence that does not naturally occur and as such is the result of human intervention, such as an engineered protein or a chimeric protein. A recombinant cell, seed, or organism is a cell, seed, or organism comprising transgenic DNA, for example a transgenic cell, seed, plant, or plant part comprising a recombinant DNA molecule and therefore produced as a result of plant transformation.

As used herein, the term "genetic engineering" refers to the creation of a non-natural DNA, protein, or organism that would not normally be found in nature and therefore entails applying human intervention. Genetic engineering can be used to produce an engineered DNA, protein, or organism that was conceived of and created in the laboratory using one or more of the techniques of biotechnology such as molecular biology, protein biochemistry, bacterial transformation, and plant transformation. For example, genetic engineering can be used to create a chimeric gene comprising at least two DNA molecules heterologous to each other using one or more of the techniques of molecular biology, such as gene cloning, DNA ligation, and DNA synthesis. A chimeric gene may consist of two or more heterologous DNA molecules that are operably linked, such as a protein-coding sequence operably linked to a gene expression element such as a transit peptide-coding sequence or a heterologous promoter. Genetic engineering can be used to create an engineered protein whose polypeptide sequence was created using one or more of the techniques of protein engineering, such as protein design using site-directed mutagenesis and directed evolution using random mutagenesis and DNA shuffling. An engineered protein may have one or more deletions, insertions, or substitutions relative to the coding sequence of the wild-type protein and each deletion, insertion, or substitution may consist of one or more amino acids. In another embodiment, an engineered protein may consist of two heterologous peptides that are operably linked, such as an enzyme operably linked to a transit peptide.

The term "plastid" refers to the family of intracellular plant organelles that are specialized to perform various tissue-specific functions, for example, photosynthesis in leaf chloroplasts, starch accumulation in root amyloplasts, fruit and flower coloration in chromoplasts and the like (e.g. Wise, *Advances in Photosynthesis and Respiration* 23:3-26, 2006). All plastid types arise from a progenitor undifferentiated organelle termed the proplastid that replicates and subsequently differentiates into the specialized organelle depending on the tissue type or environmental cues. As used herein, plant plastid refers to a plastid in higher plants (i.e., a dicot or a monocot).

The term "transgene" refers to a DNA molecule artificially incorporated into an organism's genome as a result of human intervention, such as a plant transformation method. As used herein, the term "transgenic" means comprising a transgene, for example a "transgenic plant" refers to a plant comprising a transgene in its genome and a "transgenic trait" refers to a characteristic or phenotype conveyed or conferred by the presence of a transgene incorporated into the plant genome. As a result of such genomic alteration, the transgenic plant is something distinctly different from the related wild-type plant and the transgenic trait is a trait not naturally found in the wild-type plant. Transgenic plants of the invention comprise the recombinant DNA molecules and engineered proteins provided by the invention.

As used herein, the term "heterologous" refers to the relationship between two or more things derived from different sources and thus not normally associated in nature. For example, a protein-coding recombinant DNA molecule is heterologous with respect to an operably linked promoter if such a combination is not normally found in nature. In addition, a particular recombinant DNA molecule may be heterologous with respect to a cell, seed, or organism into which it is inserted when it would not naturally occur in that particular cell, seed, or organism.

As used herein, the term "protein-coding DNA molecule" refers to a DNA molecule comprising a nucleotide sequence that encodes a protein. A "protein-coding sequence" means a DNA sequence that encodes a protein. A "sequence" means a sequential arrangement of nucleotides or amino acids. The boundaries of a protein-coding sequence are usually determined by a translation start codon at the 5'-terminus and a translation stop codon at the 3'-terminus. A protein-coding molecule may comprise a DNA sequence encoding a protein sequence. As used herein, "transgene expression", "expressing a transgene", "protein expression", and "expressing a protein" mean the production of a protein through the process of transcribing a DNA molecule into messenger RNA (mRNA) and translating the mRNA into polypeptide chains, which are ultimately folded into proteins. A protein-coding DNA molecule may be operably linked to a heterologous promoter in a DNA construct for use in expressing the protein in a cell transformed with the recombinant DNA molecule. As used herein, "operably linked" means two DNA molecules linked in manner so that one may affect the function of the other. Operably-linked DNA molecules may be part of a single contiguous molecule and may or may not be adjacent. For example, a promoter is operably linked with a protein-coding DNA molecule in a DNA construct where the two DNA molecules are so arranged that the promoter may affect the expression of the transgene.

As used herein, a "DNA construct" is a recombinant DNA molecule comprising two or more heterologous DNA sequences. DNA constructs are useful for transgene expression and may be comprised in vectors and plasmids. DNA constructs may be used in vectors for the purpose of transformation, that is the introduction of heterologous DNA into a host cell, in order to produce transgenic plants and cells, and as such may also be contained in the plastid DNA or genomic DNA of a transgenic plant, seed, cell, or plant part. As used herein, a "vector" means any recombinant DNA molecule that may be used for the purpose of bacterial or plant transformation. Recombinant DNA molecules as set forth in the sequence listing, can, for example, be inserted into a vector as part of a construct having the recombinant DNA molecule operably linked to a gene expression element that functions in a plant to affect expression of the engineered protein encoded by the recombinant DNA molecule. Methods for constructing DNA constructs and vectors are well known in the art.

The components for a DNA construct, or a vector comprising a DNA construct or plant expression cassette, generally include one or more gene expression elements operably linked to a transcribable DNA sequence, such as the following: a promoter for the expression of an operably linked DNA, an operably linked protein-coding DNA molecule, and a 3' untranslated region (UTR). A promoter drives expression of the recombinant protein molecule. Gene expression elements useful in practicing the present invention also include, but are not limited to, one or more of the following type of elements: 5' UTR, enhancer, leader, cis-acting element, intron, targeting sequence, 3' UTR, and one or more selectable or screenable marker transgenes.

Promoters useful in practicing the present invention include those that function in a cell for expression of an operably linked polynucleotide, such as a bacterial or plant promoter. Plant promoters are varied and well known in the art and include those that are inducible, viral, synthetic, constitutive, temporally regulated, spatially regulated, and/or spatio-temporally regulated. Exemplary promoters for expression of a nucleic acid sequence may include plant promoters such as the CaMV 35S promoter (Odell et al., 1985), or others such as CaMV 19S (Lawton et al., 1987), nos (Ebert et al., 1987), Adh (Walker et al., 1987), and FMV (U.S. Pat. No. 6,018,100) promoters. Tissue specific promoters, such as those for root expression (e.g. U.S. Pat. No. 5,459,252), may also be utilized.

The disclosure provides for localization of the expressed nitrogenase component in plant organelles such as mitochondria and chloroplasts. The DNA constructs of the invention may include a targeting sequence operably linked to the protein-coding DNA molecules provided by the invention, whereby the targeting sequence facilitates localizing the recombinant protein molecule within the cell. Targeting sequences are also known in the art as signal sequences, localization sequences, and transit peptides. An example of a targeting sequence is a chloroplast transit peptide (CTP) or a mitochondrial targeting sequence (MTS). By facilitating protein localization within the cell, the targeting sequence may increase the accumulation of recombinant protein, protect the protein from inactivation or proteolytic degradation, or otherwise facilitate activity of the protein such as by localizing it relative to a substrate pool.

In other embodiments, one or more nitrogenase components may be expressed directly in chloroplasts of the plant cells from DNA incorporated directly into the chloroplast DNA. An exemplary promoter for chloroplast expression is the promoter region of the highly expressed ribosomal RNA operon plastid gene (Prrn, SEQ ID NO:11 (Staub and Maliga, *Plant Cell* 4:39-45, 1992)).

As gene expression in plastid types is primarily controlled at the level of translation, it is preferable to also use translational signals from plastid genes whose protein products are highly abundant (for example, the psbA promoter (PpsbA; Staub and Maliga, *EMBO Journal* 12:601-606 1993) or the rbcL ribosome binding site region (Svab and Maliga, *PNAS* 90:913-917, 1993)) or from bacterial-derived or synthetic ribosome binding site regions of optimal composition to be expressed in plastids (for example, the bacteriophage T7 gene 10 leader region; Staub et. al. *Nature Biotechnol.* 18:333-338, 2000; SEQ ID NO:114)

The term transplastomic refers to transgenic plants that have incorporated transgenic DNA into the plastid genome, but not into the nuclear genome. Insertion of transgenic DNA into the plastid genome is typically the result of homologous recombination of regions of homology between the chloroplast transformation vector and the plastid genome of the plant.

The disclosure further provides nucleotide constructs to express the genes from the plant cell nucleus that may contain one or more of the following elements: a promoter element functional in a plant cell; a 5' untranslated region ("leader", e.g. the Hsp17.9 or DnaK leaders) to enhance expression; an intron element to further enhance expression in certain cell types, such as monocot cells; a multiple-cloning site to provide convenient restriction sites for inserting and manipulating a gene sequence of interest, and other desired elements; including a 3' untranslated region (e.g. RbcS-E9) to provide for efficient termination of the expressed transcript.

The disclosure further provides nucleotide constructs to express the genes from the plant plastid genome. These constructs may contain one or more of the following elements: a promoter region functional in a plant plastid, a ribosome binding site region (for example the T7 bacteriophage gene 10 leader (G10L)), a 5'-untranslated leader sequence, a 3' untranslated region functional in a plant plastid (for example, the 3' region of the plastid rps16 gene (Trps16)), and regions of homology to the plastid genome to ensure incorporation of the transgenes into the plastid genome via homologous recombination (for example, between the plastid rbcL and accD genes).

An expression element from the gene encoding the P21 protein of beet yellows virus (Reed, Virology 306:203, 2003) may be included within the nucleotide sequence of a provided construct. Codons of the P21 gene may be optimized for expression in the target plant species e.g. *N. benthamiana* and a FLAG® peptide tag (Sigma-Aldrich, St. Louis, Mo.) may further be incorporated at the carboxy-terminus of the P21 peptide sequence to assist in future analysis.

Recombinant DNA molecules of the present invention may be synthesized and modified by methods known in the art, either completely or in part, especially where it is desirable to provide sequences useful for DNA manipulation (such as restriction enzyme recognition sites or recombination-based cloning sites), plant-preferred sequences (such as plant-codon usage or Kozak consensus sequences), or sequences useful for DNA construct design (such as spacer or linker sequences). The present invention includes recombinant DNA molecules and engineered proteins having at least 70% sequence identity, at least 80% sequence identity, at least 85% sequence identity, at least 90% sequence identity, at least 95% sequence identity, at least 96% sequence identity, at least 97% sequence identity, at least 98% sequence identity, and at least 99% sequence identity to any of the recombinant DNA molecule or polypeptide sequences provided herein. Such identity may be calculated over the full length of the protein or nucleotide sequence, or over a portion of the length of the sequences of interest, such as 1%, 5%, 10%, 25%, or 50% of the sequence length. Alternatively, identity may be calculated over a portion ("window") of a sequence of interest based on nucleotide length such as 50 nucleotide base-pairs or amino acid residues, 100, 200, 500, 1000, 5000 etc., including intervening lengths In certain embodiments, the DNA sequence encoding a polypeptide of an enzymatically active nitrogenase subunit NifH, NifD, or NifK protein, or other Nif protein described herein, shares at least about 80%, 85%, 90%, 95%, 98%, or 99% percent sequence identity over its full length, to a disclosed Nif polypeptide-encoding sequence such as any one or more of the recombinant DNA molecule or polypeptide sequences provided herein.

Thus the disclosure provides, in certain embodiments, DNA constructs encoding dinitrogenase-reductase ("Fe protein"; a homodimer encoded for instance by nifH from a bacterium such as *Azotobacter vinelandii* (Seefeldt et al., *J. Biol. Chem.* 267:6680, 1992), *Klebsiella pneumoniae* (Holland et al., *J. Biol. Chem.* 262:8814-8820, 1987), or *Cyanothece* sp.; Colon-Lopez, et al., *Biochim. Biophys Acta* 1473:363-375, 1999). Also provided are constructs encoding dinitrogenase ("MoFe protein"; an alpha$_2$-beta$_2$ heterotetramer encoded for instance by nifD and nifK from such bacteria). In some embodiments the nucleotide sequence encoding NifH may be selected from the group consisting of SEQ ID NO:25, SEQ ID NO:33, and SEQ ID NO:37, which respectively encode the polypeptides of SEQ ID NO:24, SEQ ID NO:32, and SEQ ID NO:36. Likewise, the nucleotide sequence encoding NifD may comprise SEQ ID NO:127 which encodes the polypeptide of SEQ ID NO:126, and the nucleotide sequence encoding NifK may comprise SEQ ID NO:129 which encodes the polypeptide of SEQ ID NO:128.

As used herein, the term "percent sequence identity" or "% sequence identity" refers to the percentage of identical nucleotides or amino acids in a linear polynucleotide or polypeptide sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG®

Wisconsin Package® (Accelrys Inc., San Diego, Calif.), MEGAlign (DNAStar, Inc., 1228 S. Park St., Madison, Wis. 53715), and MUSCLE (version 3.6) (Edgar, *Nucleic Acids Research* 32(5):1792-7, 2004) with default parameters. An "identity fraction" for aligned segments of a test sequence and a reference sequence is the number of identical components which are shared by the two aligned sequences divided by the total number of components in the reference sequence segment, that is, the entire reference sequence or a smaller defined part of the reference sequence. Percent sequence identity is represented as the identity fraction multiplied by 100. The comparison of one or more sequences may be to a full-length sequence or a portion thereof, or to a longer sequence.

Engineered proteins may be produced by changing (that is, modifying) a wild-type protein to produce a new protein with a particular cellular localization pattern, such as targeted to the chloroplast or mitochondria, or a novel combination of useful protein characteristics, such as altered Vmax, Km, substrate specificity, substrate selectivity, and protein stability. Modifications may be made at specific amino acid positions in a protein and may be a substitution of the amino acid found at that position in nature (that is, in the wild-type protein) with a different amino acid. Engineered proteins provided by the invention thus provide a new protein with one or more altered protein characteristics relative to a similar protein found in nature. In one embodiment of the invention, an engineered protein has altered protein characteristics such as improved or decreased activity against one or more herbicides or improved protein stability as compared to a similar wild-type protein, or any combination of such characteristics. In one embodiment, the invention provides an engineered protein, and the recombinant DNA molecule encoding it, comprising a nitrogenase component operably linked to a transit peptide for localization to mitochondria or chloroplasts.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including for instance angiosperms (monocotyledonous and dicotyledonous plants), gymnosperms, and ferns.

Expression of one or more nitrogenase components is contemplated in transgenic monocotyledonous or dicotyledonous crop plants including, for instance, maize (corn; *Zea mays*), soybean (*Glycine max*), cotton (*Gossypium hirsutum; Gossypium* sp.), peanut (*Arachis hypogaea*), barley (*Hordeum vulgare*); oats (*Avena sativa*); orchard grass (*Dactylis glomerata*); rice (*Oryza sativa*, including indica and japonica varieties); sorghum (*Sorghum bicolor*); sugar cane (*Saccharum* sp.); tall fescue (*Festuca arundinacea*); turfgrass species (e.g. species: *Agrostis stolonifera, Poa pratensis, Stenotaphrum secundatum*); wheat (*Triticum aestivum*); alfalfa (*Medicago sativa*); members of the genus *Brassica*, including broccoli, cabbage, carrot, cauliflower, Chinese cabbage; cucumber, dry bean and other leguminous plants, eggplant, tobacco (*Nicotiana* sp.), fennel, garden beans, gourd, leek, lettuce, melon, okra, onion, pea, pepper, pumpkin, radish, spinach, squash, sweet corn, tomato, potato, watermelon, *Miscanthus*, ornamental plants, and other fruit, vegetable, tuber, oilseed, and root crops, wherein oilseed crops may include soybean, canola, oil seed rape, oil palm, sunflower, olive, corn, cottonseed, peanut, flaxseed, safflower, and coconut, among others.

Seeds of plants such as those listed above, comprising one or more DNA constructs as disclosed herein, are also contemplated as part of the invention, as well as other plant parts including, for instance, leaves, stems, roots, flowers, pollen, ovaries, embryos, and fruit of such plants. Plant products such as oil, feed, and food derived from such plants are further contemplated. Host cells, such as *Escherichia coli*, and *Agrobacterium* sp. or other Rhizobiaceae, comprising the disclosed constructs are also contemplated as part of the invention.

The transgenic plants, progeny, seeds, plant cells, and plant parts of the invention may also contain or display one or more other transgenic traits in addition to, for instance, nitrogenase activity. Additional transgenic traits may be introduced by crossing a plant containing a transgene comprising the recombinant DNA molecules provided by the invention with another plant containing an additional transgenic trait(s). As used herein, "crossing" means breeding two individual plants to produce a progeny plant. Two transgenic plants may thus be crossed to produce progeny that contain the transgenic traits. As used herein "progeny" means the offspring of any generation of a parent plant, and transgenic progeny comprise a DNA construct provided by the invention and inherited from at least one parent plant. Alternatively, additional transgenic trait(s) may be introduced by co-transforming a DNA construct for that additional transgenic trait(s) with a DNA construct comprising the recombinant DNA molecules provided by the invention (for example, with all the DNA constructs present as part of the same vector used for plant transformation) or by inserting the additional trait(s) into a transgenic plant comprising a DNA construct provided by the invention or vice versa (for example, by using any of the methods of plant transformation on a transgenic plant or plant cell).

Such additional transgenic traits include, but are not limited to, increased insect resistance, increased water use efficiency, increased yield performance, increased drought resistance, increased seed quality, improved nutritional quality, hybrid or inbred seed production, male sterility, grain nutritional or energy value and herbicide tolerance, in which the trait is measured with respect to a wild-type plant. Such additional transgenic traits are known to one of skill in the art; for example, a list of such traits is provided the United States Department of Agriculture's (USDA) Animal and Plant Health Inspection Service (APHIS).

Transgenic plants and progeny that contain a transgenic trait provided by the invention may be used with any breeding methods that are commonly known in the art. In plant lines comprising two or more transgenic traits, the transgenic traits may be independently segregating, linked, or a combination of both in plant lines comprising three or more transgenic traits. Back-crossing to a parental plant and out-crossing with a non-transgenic plant are also contemplated, as is vegetative propagation. Descriptions of breeding methods that are commonly used for different traits and crops are well known to those of skill in the art. To confirm the presence of the transgene(s) in a particular plant or seed, a variety of assays may be performed. Such assays include, for example, molecular biology assays, such as Southern and northern blotting, PCR, and DNA sequencing; biochemical assays, such as detecting the presence of a protein product, for example, by immunological means (ELISAs and Western blots) or by enzymatic function; plant part assays, such as leaf or root assays; and also, by analyzing the phenotype of the whole plant.

Sequences for expression of nitrogenase components may be codon optimized for expression in plants, including monocotyledonous and dicotyledonous plants. The genes for the dinitrogenase reductase component and the dinitrogenase components may be located on the same construct, or on separate constructs, and may be co-transformed, transformed separately, or may be introduced together into a plant cell via a step of plant breeding. Marker-assisted selection may be utilized to confirm the presence of one or more nitrogenase components via a plant breeding approach.

In certain embodiments the nitrogenase component(s) is expressed in the nucleus and targeted to mitochondria or chloroplasts. Targeting of Nif proteins to mitochondria or chloroplasts via nuclear-expressed transgenes may be complicated by the need to identify appropriate organelle targeting sequences and optimization of the nuclear-expressed transgenes. To circumvent some of these complexities, nifH and nifM transgenes may be expressed directly from the chloroplast genome. Cheng et al. (*Biochem. Biophys. Res. Comm.* 329:966-975, 2005) replaced the chlL coding region with a coding region of nifH from *Klebsiella pneumonia* in chloroplast of the alga *Chlamydomonas reinhardtii*. They showed that the NifH protein could be detected by western blot and this partially substituted for the function of the chlL gene, a protein function unrelated to nitrogen fixation. However this was in algae, not a higher plant, and no dinitrogenase activity was demonstrated. Thus there are no published reports of expression of nitrogenase enzymes directly from an organelle genome in a higher plant, and it was unknown if nitrogenase proteins could be expressed in chloroplasts or mitochondria in an active form with no adverse effects on plant growth.

A polypeptide coding for a nitrogenase component as provided herein may thus be chimeric, comprising a sequence encoding a targeting peptide operably linked to the sequence for the nitrogenase component, which directs a component of nitrogenase, e.g. dinitrogenase reductase and/or dinitrogenase, to the mitochondria or chloroplasts in the plant cells. As used herein, the term "chimeric" refers to the product of the fusion of portions of two or more different polynucleotide molecules, or to a gene expression element produced through the manipulation of known elements or other polynucleotide molecules.

Chimeric DNA molecules comprising a DNA encoding a CTP can be prepared by molecular biological methods known to those skilled in the art (e.g. Sambrook et al., *Molecular cloning: a laboratory manual*. Cold Spring Harbor Laboratory Press, Cold Spring Harbor N.Y., 1989). A nucleic acid sequence encoding a CTP sequence may be isolated or synthesized. Thus, in certain embodiments the invention provides nucleic acid constructs, and methods for their use, that encode a chloroplast transit peptide ("CTP") operably linked to a sequence encoding a nitrogenase component peptide. The CTP of any gene that is encoded in the nucleus and the product of which is targeted to chloroplasts can be tested for efficacy in directing a nitrogenase component, or other Nif gene product, to plastids, and utilized accordingly. Examples of such encoded CTP sequences include, for instance, the *Pisum sativum* RbcS small subunit CTP (Coruzzi et al., *EMBO J.*, 3:1671-1679, 1984), the *Oryza sativa* RbcS small subunit CTP of SEQ ID NO:23 ("RbcS [Os]" Jang et al., *Mol. Breed.* 5:253, 1999), and the CTP sequence comprised within SEQ ID NO:103 ("At. ShkG-CTP2").

A sequence specifying mitochondrial localization of nitrogenase component(s) may also be utilized. A mitochondrial targeting peptide sequence of any gene that is encoded in the nucleus and the product of which is targeted to mitochondria can be tested for efficacy in directing the nitrogenase component to mitochondria, and utilized accordingly. Thus, for instance, a nucleotide sequence encoding the N-terminal mitochondrial targeting peptide of the CPN-60 chaperonin protein of *Arabidopsis thaliana*, or a modified version thereof, may be utilized (SEQ ID NOs: 1-6). Non-limiting examples of mitochondrial targeting peptides which may be utilized by creating targeting peptide-NifH chimeric constructs (e.g see Table 4) include for instance, the targeting peptides designated CPN-60 (Logan and Leaver, *J. Exp. Bot.* 51:346, 2000) (SEQ ID NO:1), CPN-60+2 (SEQ ID NO:2), CPN-60+4 (SEQ ID NO:3), CPN-60+14 (SEQ ID NO:4), CPN-60+29 (SEQ ID NO:5) and CPN-60+45 (SEQ ID NO:6), which were derived from the CPN-60 chaperonin protein of *Arabidopsis thaliana* (SEQ ID NO:104). The exemplary targeting peptides designated AOX1[Tv] (SEQ ID NO:7) and AOX1[Tv]+2 (SEQ ID NO:8) were derived from the ubiquinol oxidase 1 protein of *Typhonium venosum* (SEQ ID NO:105). The exemplary targeting peptides designated ATPsyn[Nc] (SEQ ID NO:9), ATPsyn[Nc]+2 (SEQ ID NO:10) and ATPsyn[Nc]+4 (SEQ ID NO:11) were derived from the ATP synthase protein 9 of *Neurospora crassa* (SEQ ID NO:106). The exemplary targeting peptide designated GD(L)[Ps] (SEQ ID NO:12) was derived from the *Glycine* decarboxylase L protein of *Pisum sativum* (SEQ ID NO:107). The exemplary targeting peptides designated GD(P)[Fp] (SEQ ID NO:13), GD(P)[Fp]+2 (SEQ ID NO:14) and GD(P)[Fp]+8 (SEQ ID NO:15) were derived from the *Glycine* decarboxylase P subunit protein of *Flaveria pringlei* (SEQ ID NO:108). The exemplary targeting peptides designated GD(P)[Ps] (SEQ ID NO:16) and GD(P)[Ps]+2 (SEQ ID NO:17) were derived from the *Glycine* decarboxylase P subunit protein of *Pisum sativum* (SEQ ID NO:109). Targeting peptides designated HSP70[Pv]+1 (SEQ ID NO:18) and HSP70[Pv]+3 (SEQ ID NO:19) were derived from the HSP70 heat shock protein of *Phaseolus vulgaris* (SEQ ID NO:110). Targeting peptides designated RPS10[At] (SEQ ID NO:20), RPS10[At]+1 (SEQ ID NO:21) and RPS10[At]+3 (SEQ ID NO:22) were derived from the ribosomal protein S10 of *Arabidopsis thaliana* (SEQ ID NO:111).

Alternatively, if the nitrogenase component is to be expressed from a chloroplast derived transgenic construct, a protocol for chloroplast transformation of plant cells may be utilized in conjunction with a recombinant DNA construct comprising a nucleotide sequence encoding a nitrogenase component operably linked to expression elements and for expression and localization of the gene or gene product in a plant cell chloroplast. Chloroplast transformation is known in the art (e.g. Russell, *Plant Physiol.* 98:1050-1056, 1992) and Maliga et al U.S. Pat. No. 5,877,402).

Other nif gene products encoding subunits, components or cofactors necessary for assembly of active nitrogenase are also included (see Table 10) (e.g. Howard et al., *J. Biol. Chem.* 261:772-778, 1986). Thus, the invention also provides nucleotide constructs encoding, for instance, nifM, nifS, nifU, nifB, nifQ, nifN, nifV, and/or nifE. The disclosure further provides for the ability to produce active dinitrogenase reductase without providing nifS and nifU genes. Before this disclosure it was not known whether these genes were required for expression of active dinitrogenase reductase in plants. The additional Nif proteins would also be targeted to the mitochondria or chloroplasts of a plant cell where the structural proteins (Nif, H, D and K) for nitrogenase are targeted, and may be also be expressed from DNA in the nucleus or in the chloroplast. In certain embodiments the polypeptides of, respectively, SEQ ID NO: 26, SEQ ID NO:28, SEQ ID NO:30, SEQ ID NO:34, and/or SEQ ID NO:36 are contemplated, and the nucleotide sequences encoding them may comprise, for instance, SEQ ID NO:27, SEQ ID NO:29, SEQ ID NO: 31, SEQ ID NO:35, or SEQ ID NO:37. In particular embodiments a nifM sequence is expressed. In other embodiments, a sequence encoding nifB, nifQ, nifN, nifV, nifE, nifU, or nifEN (nifE operably linked to nifN) is contemplated. In particular embodiments such sequences may encode SEQ ID NO:130 (nifB), SEQ ID NO:132 (nifQ), SEQ ID NO:134 (nifN), SEQ ID NO:136 (nifV), SEQ ID NO:126 (nifE), SEQ ID NO:30 (nifU) or SEQ ID NO:140 (nifEN).

Stable or transient expression of constructs encoding one or more nitrogenase components is contemplated. The disclosure contemplates preparation of a plant expression vector that can be bombarded, electroporated, chemically transfected or transported by some other means across the plant cell wall and membrane and into a plant cell, for expression therein. In one embodiment, the vector can replicate in a bacterial host such that the vector can be produced and purified in sufficient quantities for transient expression. In another embodiment, the vector can encode a marker gene to allow for selection or screening for the presence of the vector in a host cell including a bacterial cell and a plant cell, or the vector can also comprise an expression cassette to provide for the expression of the nitrogenase gene in a plant. The selection or marker gene may be expressed in a plant cell nucleus or chloroplast. In some embodiments the expression cassette contains a promoter region, a 5' untranslated region, an optional intron to aid expression, and optionally a multiple cloning site to allow facile introduction of sequences of interest, and a 3' UTR.

Methods for expression of one or more nitrogenase components in plant cells are also contemplated. Such methods may comprise introducing a recombinant DNA construct as described above into a plant cell nucleus or chloroplast, and growing the plant cell in an environment resulting in expression of the one or more nitrogenase components. Manipulation of light intensity, day length, temperature, levels of available nutrients, and atmospheric oxygen content may facilitate nitrogenase activity.

The method may further comprise assaying for the presence of an introduced nif gene in the genome of a plant cell, and/or the presence of a Nif protein in the cell. Thus, well known methods such as Southern blotting and western blotting may be used (Sambrook et al., 1989). The method may further comprise assaying for nitrogenase activity, including dinitrogenase-reductase and/or dinitrogenase activity (e.g. Stewart et al., PNAS 58:2071, 1967). The presence of an introduced nif gene may be transient, or the gene may be stably integrated into a nuclear or chloroplastic cell genome. Activity of nitrogenase or its components may thus be expressed in a transient or stable manner, and may occur in the plant cell nucleus, cytoplasm, mitochondria, or chloroplasts.

Measurement of nitrogenase activity, dinitrogenase activity, and/or dinitrogenase reductase activity may be performed for instance by an acetylene reduction assay (Stewart, PNAS 58:2071, 1967), or other assay known in the art such as by measuring ammonia production, or $N_2$ isotope incorporation, or by production of hydrogen gas ($H_2$). Measurement may further comprise use of whole plants or plant cells, as well as partially isolated organelles and other cell fractions (e.g. Millar et al., Methods Cell Biol. 80:65-90, 2007). The oxygen content of the atmosphere in which the plants or plant cells are grown may also be manipulated to facilitate measurement of nitrogenase activity.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLES

Example 1: Constructs and Assay Methods

The nitrogen fixation associated genes (here after designated nif) nifH, nifM, nifS, and nifU were amplified by PCR from bacterial species *Azotobacter vinelandii* (A.v.), or synthesized based on the bacterial sequences from *Klebsiella pneumonia* (K.p.) and *Cyanothece* spp ATCC51142 (C. spp) and cloned into cassettes containing elements that are used for expression of genes in plant cells. One or more cassettes were subsequently cloned into vector constructs for plant transformation. The corresponding protein and nucleotide SEQ ID NOs for the bacterial codons encoding the Nif peptides NifH, NifM, NifS, and NifU are presented in Table 1.

TABLE 1

SEQ ID NOs of bacterial source for nitrogen fixation associated genes nifH, nifM, nifS, and nifU from *A. vinelandii* (A.v.), nifH and nifM from *Klebsiella pneumonia* (K.p.), and nifH from *Cyanothece* spp ATCC51142 (C. spp).

| Nif subunit (bacterial source) | amino acid SEQ ID NO: | DNA SEQ ID NO: |
|---|---|---|
| nifH (A.v.) | 24 | 25 |
| nifM (A.v.) | 26 | 27 |
| nifS (A.v.) | 28 | 29 |
| nifU (A.v.) | 30 | 31 |
| nifH (K.p.) | 32 | 33 |
| nifM (K.p.) | 34 | 35 |
| nifH (C. spp) | 36 | 37 |

Expression elements used in the different cassettes included one of two promoters, either (a) the promoter of the 35S RNA of Figwort Mosaic Virus (FMV; e.g. U.S. Pat. No. 6,018,100), or (b) the promoter for 35S RNA from Cauliflower Mosaic Virus (CaMV) containing a duplication of the −90 to −350 region (e35S-CaMV; Kay et al., Science 236: 1299-1302, 1987); one of two 5' untranslated leader sequences either (a) the 5' untranslated region of heat shock protein 17.9 (HSP17.9) gene from *Glycine max* (soybean), or (b) the 5' untranslated region of the heat shock protein 70 gene from *Petunia x hybrida* (DnaK); and one of two 3' untranslated termination signals, either (a) the 3' untranslated region of the fiber protein E6 gene (which directs polyadenylation of mRNA) from *Gossypium barbadense* (sea-island cotton) (Gb-E6), or (b) the 3' untranslated region from the ribulose 1,5-bisphosphate carboxylase small subunit E9 (RbcS-E9) gene (which directs polyadenylation of mRNA) of *Pisum sativum* (pea).

To direct dinitrogenase reductase and the associated nif gene products to the mitochondria within the plant cell, various expression cassettes were designed with differing targeting peptide nif gene product chimeras. For example, the N-terminal amino acid mitochondrial-targeting peptide from the CPN-60 chaperonin gene of *Arabidopsis thaliana* (Logan and Leaver, 2000; as shown in SEQ ID NO:104) was used in certain studies. A sequence encoding the first 31 amino acids of this CPN-60 chaperonin protein was cloned into expression cassettes for each of the nif genes shown in Table 2, and these chimeric constructs were designated CPN-60-nifH, CPN-60-nifM, CPN-60-nifS and CPN-60-nifU (Table 2). For both CPN-60-nifH and CPN-60-nifM, two cassette configurations were constructed: one with the promoter e35S-CaMV, the leader Hsp17.9, and the terminator Gb-E6; and one with the promoter FMV, the leader DnaK, and the terminator RbcS-E9. In addition to the vectors expressing a single cassette encoding a targeting peptide nif gene chimera, a vector was also designed containing two cassettes with each cassette encoding a separate targeting peptide plus nif gene chimera, each with distinct expression elements (Table 2).

The gene for the P21 protein of beet yellows virus (Reed, 2003) was also PCR amplified and cloned into a vector for expression in plant cells. Codons of the P21 gene were optimized for expression in *N. benthamiana* and a FLAG® peptide tag (e.g. SEQ ID NOs:38-39) was incorporated into the carboxy-terminus of the P21 peptide sequence.

TABLE 2

SEQ ID NOs for CPN-60-nif chimeric constructs used for mitochondrial-targeting of products of nif genes.

| pMON | Nif subunit | CPN-60 + Nif chimera amino acid SEQ ID NO: | CPN-60 + Nif chimera nucleotide (DNA) SEQ ID NO: |
|---|---|---|---|
| pMON97938* | nifH (A.v.) | 40 | 41 |
| pMON135480** | nifH (A.v.) | 40 | 41 |
| pMON97940* | nifM (A.v.) | 42 | 43 |
| pMON135481** | nifM (A.v.) | 42 | 43 |
| pMON97942* | nifS (A.v.) | 44 | 45 |
| pMON97944* | nifU (A.v.) | 46 | 47 |
| pMON135484*** | nifH* (A.v.) and nifM** (A.v.) | 40 and 42 | 41 and 43 |
| pMON135478* | P21-FLAG | 38 | 39 |

*For these cassettes the promoter was e35S-CaMV, the leader Hsp17.9, and the terminator was Gb-E6
**For these cassettes the promoter was FMV, the leader was DnaK, and the terminator was RbcS-E9
***Dual cassette construct For plant expression, the chimeric targeting peptide nif constructs were transformed into *Agrobacterium tumefaciens* strain ABI (B63). Individual strains (corresponding to the individual constructs containing the sequence encoding the targeting peptide Nif protein chimeras) were grown in Luria-Bertani (LB) medium containing 25 µg/ml chloramphenicol, 100 µg/ml spectinomycin, 50 µg/ml kanamycin, 0.1 mM acetosyringone to an $OD_{600}$ of approximately 0.5 to 0.6. Unless otherwise stated throughout, reagents were obtained from Sigma-Aldrich, St. Louis, Mo., USA. For co-infiltration experiments, cultures of individual *Agrobacterium* strains were mixed together, centrifuged and the pellet was resuspended in cell culture medium (usually 10 ml) to give a final concentration of $OD_{600}$ of 0.6, with the P21-FLAG containing *Agrobacterium* strain contributing OD600 of 0.2, and the remaining individual strains added together totaling OD600 of 0.4 in the suspension. The cloned P21-FLAG containing *Agrobacterium* strain was typically co-infiltrated with the mixture of targeting peptide nif gene chimera containing *Agrobacterium* strains in order to boost expression of the targeting peptide Nif protein chimeras in transiently transformed cells Unless otherwise noted, *Nicotiana benthamiana* (tobacco) plants were used throughout the examples described herein. In general, for instance for transient expression, plant growth conditions consisted of growing the tobacco plants from seed under the following growth conditions: 22° C. day and 18° C. night temperature; 70% humidity; 14 hour light (500 µE $s^{-1}$ $m^{-2}$) and 10 hours dark photoperiod. About 25 days after planting, the plants were used for infiltration. When indicated, after infiltration the plants were incubated in low light (10 µE $s^{-1}$ $m^{-2}$).

For infiltration, 1 ml of the prepared *Agrobacterium* mixture was applied to the underside of two leaves of each tobacco plant using of a blunt-end syringe. After infiltration, plants were maintained in a glove box for two or three days at a controlled atmosphere of $O_2$, $N_2$, and $CO_2$ levels and low light (10 µE $s^{-1}$ $m^{-2}$) to allow the infiltrated leaves to transiently express the targeting peptide nif gene chimeras. Generally, the plants were grown at one of three oxygen concentrations 10% $O_2$, or 15% $O_2$, or 21% $O_2$ (ambient air); the concentration of $CO_2$ was set at 0.3%; and the balance of the atmosphere in the glove box was made up of $N_2$. For comparison air is approximately 21% $O_2$, 80% $N_2$ and 0.04% $CO_2$.

Mitochondria and chloroplasts were partially purified from infiltrated leaves following procedures essentially described by Millar (*Methods Cell Biol.* 80:65-90, 2007). To maintain anaerobic conditions during purification of mitochondria and chloroplasts from leaf tissue, samples and buffers were maintained inside sealed centrifuge tubes, at 4° C. throughout the preparation, and all samples were handled inside a glove box maintained under anaerobic conditions.

The mitochondria and chloroplasts were enriched as follows:

Step 1: Leaves were gently ground for approximately 3 minutes in a mortar and pestle on ice with 6 volumes D-MOPS buffer (0.4 M mannitol, 25 mM MOPS-KOH pH7.5, 10 mM tricine, 0.1% BSA, 1% polyvinylpyrrolidone (PVP-40), 0.5% protease inhibitor cocktail (cat. no. P8340 Sigma-Aldrich, St. Louis, Mo., USA). The solution was filtered through three layers of Miracloth (EMD Millipore, San Diego, Calif., USA), transferred to air-tight centrifuge tubes and centrifuged at 100×g for 10 minutes.

Step 2: The supernatant from step 1, which was enriched for mitochondria and chloroplasts, was transferred to a fresh tube and processed as described in step 3 below. The 100×g pellets, which are enriched for un-lysed cells and larger tissue fragments, was discarded.

Step 3: The supernatant saved from step 2 was centrifuged at 1000×g for 5 minutes. The resulting pellet was enriched for chloroplasts and depleted for mitochondria and was suspended in ⅛ leaf weight D-MOPS buffer, dripped into liquid nitrogen and the frozen beads (approximately 50 µl volume), were stored at −80° C.

Step 4: The supernatant from step 3 was transferred to a fresh tube and centrifuged at 12,000×g for 15 minutes.

Step 5: The supernatant from step 4 was discarded and the 12,000×g pellet, which was enriched for mitochondria, was suspended with ⅛ leaf weight of D-MOPS buffer. The suspension was dripped (approximately 50 µl per drop) into liquid nitrogen and the frozen beads were stored at −80° C.

The 1000×g pellets (step 3) were enriched for chloroplasts, and the 12,000×g pellets (step 5) were enriched for mitochondria as verified by protein immunoblot using antibodies specific for the chloroplast RbcL protein (rubisco large subunit protein), the mitochondrial AOX protein (Alternative Oxidase protein) and the cytoplasmic PEPCase protein (PEP carboxylase). RbcL was enriched in the 1000×g pellet, AOX was enriched in the 12,000×g pellet and PEPCase was enriched in the supernatant. Antibodies to RbcL, AOX, and PEPCase were obtained from Agrisera Company (Sweden). For detection of Nif subunits, specific antibodies against NifH (1:10,000 dilution), NifM (1:1,000 dilution), NifD (1:7,500 dilution) or NifK (1:7,500 dilution) proteins (or their peptides antigens) were used in the analysis. Protein immunoblot results showed that the mitochondrial-targeted CPN-60-nifH, CPN-60-nifM, CPN-60-nifS and CPN-60-nifU chimeric proteins were enriched in the mitochondrial fraction and were depleted in the cell cytoplasm, thus indicating that the CPN-60 mitochondrial-targeting peptide nif chimeras were being targeted to mitochondria. Similarly, the chloroplast-targeted rbcS-nifH and rbcS-nifM chimeric proteins were enriched in the chloroplast.

An acetylene reduction assay was used to detect activity of the dinitrogenase reductase expressed in the tobacco plants infiltrated with *Agrobacterium* strain(s) containing chimeric constructs encoding one or more of the targeting peptide nif protein chimeras. This assay is based on the fact that nitrogenase, in addition to reducing $N_2$ to $NH_3$, is capable of reducing acetylene ($C_2H_2$) to ethylene ($C_2H_4$) and this acetylene reduction assay is a standard procedure for the detection and measurement of active nitrogenase (Stewart, *Proc. Natl. Acad. Sci. USA* 58:2071, 1967). Both active dinitrogenase reductase (Fe protein) and active dinitrogenase (MoFe protein) must be together in the same mixture for acetylene reduction to occur. As standards for the acetylene reduction assay, active dinitrogenase and active dinitrogenase reductase were purified from *A. vinelandii* by standard procedures (Seefeldt et al., *J. Biol. Chem.* 267:6680, 1992). To test for dinitrogenase reductase activity produced in plant cells, extracts from cells containing constructs expected to produce dinitrogenase reductase were combined with active MoFe or dinitrogenase from a bacterial source, for example, *A. vinelandii*, to recapitulate active nitrogenase provided active dinitrogenase reductase was produced in the plant.

A typical assay was done in 10 ml serum vials containing approximately 880 µl nitrogenase buffer (0.4 M mannitol, 25 mM MOPS-KOH pH7.5, 10 mM tricine, 0.1% BSA, 1% PVP-40, 0.5% P8340 protease inhibitor cocktail, 0.07% Tween®20, 6 mM MgCl2, 3 mM ATP, 28 mM creatine phosphate, 0.1 mg/ml creatine phosphokinase, 5 mM Na dithionite), 120 µl partially purified mitochondria or partially purified chloroplasts, and dinitrogenase from *A. vinelandii*. Sufficient partially purified dinitrogenase was added to ensure it was in excess so that the final level of nitrogen fixation activity was dependent on the level of dinitrogenase reductase activity produced in the plant. Vials were sealed with rubber stoppers, sparged with argon, and then 1 ml of acetylene was injected. Vials were gently shaken at 30° C. for approximately 4 hours. After incubation, up to 3 separate 1 ml samples of the vial headspace was injected into a gas chromatograph. Ethylene peaks were detected by $H_2$-flame ionization. An aliquot of the activity assay was spun down for 5 min at 16,000×g, and the supernatant was marked as Soluble Activity Assay Fraction and frozen at −20° C.

Typical results from several experiments are shown Table 3. During the infiltration step for each of the samples shown, the *Agrobacterium* strain containing the P21-FLAG construct was included to augment the expression of the CPN-60-nif chimeras. In the assay acetylene can be reduced to ethylene only by the presence of active nitrogenase, specifically active dinitrogenase reductase plus active dinitrogenase. As seen in Table 3, sample 1 was the negative control with no contribution of dinitrogenase reductase showing the background level of ethylene peak of 1.5 from the assay. This small amount of ethylene detected in the acetylene reduction assay is due to the fact that the method used to prepare acetylene unavoidably contains a small amount of ethylene in the acetylene preparation. Sample 2 served as a positive control for the assay with dinitrogenase reductase purified from *A. vinelandii* added to the assay mix showing a substantial ethylene peak area of 97.4. Typically, the amount of *A. vinelandii* dinitrogenase reductase added was sufficient to produce significant ethylene peak in the range of typically 30-100+). Sample 3 shows that the ethylene peak area was at background level of 1.7 when the mitochondrial fraction was from non-infiltrated plants.

Assay samples 4 and 5 each contained mitochondrial fraction from plant leaves that had been co-infiltrated with *Agrobacterium* strains containing constructs encoding chimeric constructs CPN-60-nifH (pMON97938), CPN-60-nifM (pMON97940), CPN-60-nifS (pMON97942), and CPN-60nifU (pMON97944) and the plants grown in an environment of 10% $O_2$. Immediately prior to the assay, the mitochondrial fraction of sample 5 was exposed to air. The results show that co-expression of the four mitochondrial-targeted dinitrogenase reductase chimeric peptides, CPN-60-nifH, CPN-60-nifM, CPN-60-nifS, and CPN-60nifU, resulted in an ethylene peak area of 6.1 (sample 4), but that the mitochondria were sensitive to dinitrogenase reductase inactivation when exposed to air (sample 5) showing only background level of ethylene peak area of 1.5. This can be explained by the fact that dinitrogenase reductase activity is inhibited by exposure to $O_2$.

Surprisingly, plants with leaves infiltrated with *Agrobacterium* strains containing only constructs encoding mitochondrial-targeting chimeras CPN-60-nifH and CPN-60-nifM, and then grown in an atmosphere of 10% $O_2$ (sample 6) or 15% $O_2$ (sample 7) resulted in approximately 3-fold to 5-fold larger ethylene peak area compared to plants co-infiltrated with mitochondrial-targeting chimeric construct CPN-60-nifH (pMON97938) alone (sample 9), or the chimeric constructs encoding the four nif proteins used in samples 4 and 5 (see Table 3). These results demonstrated that the nifS and nifU proteins were not necessary to obtain active dinitrogenase reductase in the mitochondrial fractions. The levels of ethylene production by mitochondria from plants infiltrated with mitochondrial-targeting chimeric constructs encoding CPN-60-nifH and CPN-60-nifM decreased as the plants are maintained at higher levels of $O_2$ (see Table 3 samples 6, 7, and 8). It is significant that even when infiltrated plants are maintained in air (21% $O_2$) mitochondria from these plants still show the ability to reduce acetylene to ethylene in the assay demonstrating the presence of active dinitrogenase reductase.

Mitochondria from plants infiltrated only with CPN-60-nifH chimeric construct (pMON97944) show little, if any, ability to reduce acetylene to ethylene in the assay (Table 3, sample 9). This result is likely due to the known role of NifM protein to enhance the NifH protein to form active dinitrogenase reductase; there being no plant equivalent to NifM protein that can substitute for NifM activity. Prior reports in the literature indicate that, depending on which form of NifH is used, NifM may not always be necessary to obtain active dinitrogenase reductase (Gavini et al., *J. Bacteriol.* 188:6020-6025, 2006; Wang et al., *PLOS Genetics* 9:1-11, 2013).

Example 2: Plant-Produced Mitochondrial-Targeted Dinitrogenase Reductase

To optimize mitochondrial expression of the NifH protein, several different mitochondrial-targeting peptides were tested by creating targeting peptide-NifH chimeric constructs (Table 4). The targeting peptides designated CPN-60 (SEQ ID NO:1), CPN-60+2 (SEQ ID NO:2), CPN-60+4 (SEQ ID NO:3), CPN-60+14 (SEQ ID NO:4), CPN-60+29 (SEQ ID NO:5) and CPN-60+45 (SEQ ID NO:6) were derived from the CPN-60 chaperonin protein of *Arabidopsis thaliana* (SEQ ID NO:104). The targeting peptides designated AOX1[Tv] (SEQ ID NO:7) and AOX1[Tv]+2 (SEQ ID NO:8) were derived from the ubiquinol oxidase 1 protein of *Typhonium venosum* (SEQ ID NO:105). The targeting peptides designated ATPsyn[Nc] (SEQ ID NO:9), ATPsyn[Nc]+2 (SEQ ID NO:10) and ATPsyn[Nc]+4 (SEQ ID NO:11) were derived from the ATP synthase protein 9 of *Neurospora crassa* (SEQ ID NO:106). The targeting peptide designated GD(L)[Ps] (SEQ ID NO:12) was derived from the *Glycine* decarboxylase L protein of *Pisum sativum* (SEQ ID NO:107). The targeting peptides designated GD(P)[Fp] (SEQ ID NO:13), GD(P)[Fp]+2 (SEQ ID NO:14) and GD(P)[Fp]+8 (SEQ ID NO:15) were derived from the *Glycine* decarboxylase P subunit protein of *Flaveria pringlei* (SEQ ID NO:108). The targeting peptides designated GD(P)[Ps] (SEQ ID NO:16) and GD(P)[Ps]+2 (SEQ ID NO:17) were derived from the *Glycine* decarboxylase P subunit protein of *Pisum sativum* (SEQ ID NO:109). The targeting peptides designated HSP70[Pv]+1 (SEQ ID NO:18) and HSP70[Pv]+3 (SEQ ID NO:19) were derived from the HSP70 heat shock protein of *Phaseolus vulgaris* (SEQ ID NO:110). The targeting peptides designated RPS10[At] (SEQ ID NO:20), RPS10[At]+1 (SEQ ID NO:21) and RPS10[At]+3 (SEQ ID NO:22) were derived from the ribosomal protein S10 of *Arabidopsis thaliana* (SEQ ID NO:111).

TABLE 3

Assay of partially purified mitochondria for dinitrogenase reductase activity in a nitrogenase activity acetylene reduction assay. All samples infiltrated with CPN-60 mitochondrial-targeting peptide nif chimeric constructs were also co-infiltrated with the P21-FLAG construct.

| Sample | Assay Addition | nif chimeras infiltrated | pMONs | plant growth | ethylene peak area |
|---|---|---|---|---|---|
| 1 | None | none | none | not applicable | 1.5 |
| 2 | Dinitrogenase reductase (*A. vinelandii*) | none | none | not applicable | 97.4 |
| 3 | Mitochondria | none | none | 10% O2 | 1.7 |
| 4 | Mitochondria | CPN-60-nifH<br>CPN-60-nifM<br>CPN-60-nifS<br>CPN-60-nifU | pMON97938<br>pMON97940<br>pMON97942<br>pMON97944 | 10% O2 | 6.1 |
| 5 | Mitochondria (air) | CPN-60-nifH<br>CPN-60-nifM<br>CPN-60-nifS<br>CPN-60-nifU | pMON97938<br>pMON97940<br>pMON97942<br>pMON97944 | 10% O2 | 1.5 |
| 6 | Mitochondria | CPN-60-nifH<br>CPN-60-nifM | pMON135484 | 10% O2 | 32.9 |
| 7 | Mitochondria | CPN-60-nifH<br>CPN-60-nifM | pMON97938<br>pMON135481 | 15% O2 | 21.8 |
| 8 | Mitochondria | CPN-60-nifH<br>CPN-60-nifM | pMON135484 | air | 6.0 |
| 9 | Mitochondria | CPN-60-nifH | pMON97938 | 10% O2 | 2.6 |

Mitochondria prepared from plants infiltrated with *Agrobacterium* strains containing chimeric mitochondrial-targeting peptide constructs encoding CPN-60-nifH and CPN-60-nifM but without co-infiltration with the gene for P21 had approximately one-sixth the acetylene reducing ability as mitochondria prepared from plants co-infiltrated with *Agrobacterium* strains containing chimeric mitochondrial-targeting peptide constructs encoding CPN-60-nifH, CPN-60-nifM, and the gene for P21. Western blot analysis showed that mitochondrial fractions from plants co-infiltrated with *Agrobacterium* strains containing the P21 protein and with the *Agrobacterium* strains containing chimeric mitochondrial-targeting peptide constructs encoding CPN-60-nifH and CPN-60-nifM increases the expression of the respective NifH and NifM proteins approximately five-fold. This apparent increase in Nif subunit expression correlates with the higher level of acetylene reduction with mitochondria prepared from plants co-infiltrated with *Agrobacterium* strains containing chimeric mitochondrial-targeting peptide constructs encoding CPN-60-nifH, CPN-60-nifM and the gene for P21.

TABLE 4

SEQ ID NOs for mitochondrial-targeting peptide-nifH chimeras.

| pMON | Mitochondrial Targeting peptide nifH chimera | Targeting peptide amino acid SEQ ID NO: | Targeting peptide nifH chimera amino acid SEQ ID NO: | Targeting peptide nifH chimera nucleotide SEQ ID NO: |
|---|---|---|---|---|
| pMON97938* | CPN-60-nifH | 1 | 40 | 41 |
| pMON135480** | CPN-60-nifH | 1 | 40 | 41 |
| pMON288988 | CPN-60 + 2-nifH | 2 | 48 | 49 |
| pMON288846 | CPN-60 + 4-nifH | 3 | 50 | 51 |
| pMON275231 | CPN-60 + 14-nifH | 4 | 52 | 53 |
| pMON275095 | CPN-60 + 29-nifH | 5 | 54 | 55 |
| pMON274960 | CPN-60 + 45-nifH | 6 | 56 | 57 |
| pMON278732 | AOX1[Tv]-nifH | 7 | 58 | 59 |
| pMON283805 | AOX1[Tv] + 3-nifH | 8 | 60 | 61 |
| pMON286535 | ATPsyn[Nc]-nifH | 9 | 62 | 63 |
| pMON283826 | ATPsyn[Nc] + 2-nifH | 10 | 64 | 65 |
| pMON281523 | ATPsyn[Nc] + 4-nifH | 11 | 66 | 67 |
| pMON135460 | GD(L)[Ps]-nifH | 12 | 68 | 69 |
| pMON263573 | GD(P)[Fp]-nifH | 13 | 70 | 71 |
| pMON286537 | GD(P)[Fp] + 2-nifH | 14 | 72 | 73 |
| pMON278112 | GD(P)[Fp] + 8-nifH | 15 | 74 | 75 |
| pMON269573 | GD(P)[Ps]-nifH | 16 | 76 | 77 |
| pMON286885 | GD(P)[Ps] + 2-nifH | 17 | 78 | 79 |
| pMON277873 | HSP70[Pv] + 1-nifH | 18 | 80 | 81 |
| pMON286925 | HSP70[Pv] + 3-nifH | 19 | 82 | 83 |
| pMON286905 | RPS10[At]-nifH | 20 | 84 | 85 |
| pMON283765 | RPS10[At] + 1-nifH | 21 | 86 | 87 |
| pMON278847 | RPS10[At] + 3-nifH | 22 | 88 | 89 |

*For these cassettes the promoter was e35S-CaMV, the leaderHsp17.9, and the terminator was Gb-E6
**For this cassette the promoter was FMV, the leader was DnaK, and the terminator was RbcS-E9

The various *Agrobacterium* strains containing chimeric constructs encoding mitochondrial-targeting peptide nif peptides (Table 4) were co-infiltrated with *Agrobacterium* strains containing a chimeric construct encoding the mitochondrial-targeting peptide CPN-60-nifM (pMON135481) and the P21-FLAG construct (pMON135478) into tobacco leaves and the plants were grown in an atmosphere of 10% $O_2$, prior to preparation of mitochondrial fractions. Mitochondria from plants that had been infiltrated were tested in the acetylene reduction assay, essentially as described above, and the results are presented in Table 5. These results show that infiltration of tobacco with the CPN-60-nifH (pMON135480), CPN-60+2-nifH (pMON288988), and CPN-60+4-nifH (pMON288846) chimeric constructs resulted in high level of ethylene production in the acetylene reduction assay.

In contrast, adding additional amino acids from the CPN-60 chaperonin protein of *Arabidopsis thaliana* to generate the CPN-60+14-nifH (pMON275231), CPN-60+29-nifH (pMON275095), and CPN-60+45-nifH (pMON274960) chimeric constructs resulted in no detectable ethylene production. For the ATPsyn[Nc]-nifH (pMON286535), ATPsyn[Nc]+2-nifH (pMON283826), and ATPsyn[Nc]+4-nifH (pMON281523) chimeric constructs, only the latter two variants with 2 or 4 additional amino acids gave detectable, but low level of ethylene production. Similarly, for the GD(P)[Fp]-nifH (pMON263573), GD(P)[Fp]+2-nifH (pMON286537), and GD(P)[Fp]+8-nifH (pMON278112) chimeric constructs, expression of the first chimera resulted in no detectable ethylene production, but the +2 and +8 amino acid variants resulted in moderate to high levels of ethylene production. In another result, the GD(P)[Ps]-nifH (pMON269573) and GD(P)[Ps]+2-nifH (pMON286885) resulted in either no detection of ethylene production or a low level of ethylene production, respectively. Finally, similar to the results with the various CPN-60-nifH chimeric constructs, increasing by 2 amino acids from HSP70[Pv]+1-nifH (pMON277873) to HSP70[Pv]+3-nifH (pMON286925) resulted in loss of ethylene production, though the first variant gave rise to only a low level of detectable ethylene production. None of the following mitochondrial-targeting peptide nifH chimeric constructs resulted in expression giving rise to detectable ethylene production: AOX1[Tv]-nifH (pMON278732), AOX1[Tv]+3-nifH (pMON283805), GD(L)[Ps]-nifH (pMON135460), RPS10[At]-nifH (pMON286905), RPS10[At]+1-nifH (pMON283765), or RPS10[At]+3-nifH (pMON278847). These results demonstrate apparent unpredictability in identifying what specific targeting peptide sequence will function when expressing NifH and NifM peptides in plant cells to form an active dinitrogenase reductase.

TABLE 5

Dinitrogenase reductase activity when various mitochondrial-targeting peptides nifH chimeric constructs are co-infiltrated with the mitochondrial-targeted nifM chimeric construct (pMON135481) and the P21-FLAG construct (pMON135478).

| pMON | Targeting Peptide | Fe-protein activity |
|---|---|---|
| pMON97938 | CPN60-nifH | +++ |
| pMON288988 | CPN60 + 2-nifH | +++ |
| pMON288846 | CPN60 + 4-nifH | +++ |
| pMON275231 | CPN60 + 14-nifH | − |
| pMON275095 | CPN60 + 29-nifH | − |
| pMON274960 | CPN60 + 45-nifH | − |
| pMON278732 | AOX1[Tv]-nifH | − |
| pMON283805 | AOX1[Tv] + 3-nifH | − |
| pMON286535 | ATPsyn[Nc]-nifH | − |
| pMON283826 | ATPsyn[Nc] + 2-nifH | + |
| pMON281523 | ATPsyn[Nc] + 4-nifH | + |
| pMON135460 | GD(L)[Ps]-nifH | − |
| pMON263573 | GD(P)[Fp]-nifH | − |
| pMON286537 | GD(P)[Fp] + 2-nifH | ++ |
| pMON278112 | GD(P)[Fp] + 8-nifH | +++ |
| pMON269573 | GD(P)[Ps]-nifH | − |
| pMON286885 | GD(P)[Ps] + 2-nifH | + |
| pMON277873 | HSP70[Pv] + 1-nifH | + |

TABLE 5-continued

Dinitrogenase reductase activity when various mitochondrial-
targeting peptides nifH chimeric constructs are co-infiltrated
with the mitochondrial-targeted nifM chimeric construct (pMON135481)
and the P21-FLAG construct (pMON135478).

| pMON | Targeting Peptide | Fe-protein activity |
|---|---|---|
| pMON286925 | HSP70[Pv] + 3-nifH | – |
| pMON286905 | RPS10[At]-nifH | – |
| pMON283765 | RPS10[At] + 1-nifH | – |
| pMON278847 | RPS10[At] + 3-nifH | – |

– indicates that no ethylene above background levels was detected;
+ indicates that low ethylene of 5-10 was detected;
++ indicates that moderate levels of ethylene of 11-20 was detected; and
+++ indicates that high levels of ethylene of 21-50 was detected.

Example 3: Constructs and Assay for Chloroplast-Targeted Nif Proteins

To test whether active dinitrogenase reductase could be formed in plant chloroplasts, chimeric constructs were constructed using a targeting peptide (here designated RbcS and represented as SEQ ID NO:23) from the ribulose bisphosphate carboxylase small chain c protein of *Oryza sativa* (SEQ ID NO:112) (Jang, 1999). This RbcS targeting peptide sequence was added to each of the chloroplast-targeted nif gene chimeric constructs as indicated in Table 6. In addition to the vectors expressing a single cassette encoding a chloroplast-targeting peptide nif peptide chimera, vectors were designed containing two cassettes with each cassette encoding a separate targeting peptide nif peptide chimera with each cassette having separate expression elements (Table 6). For constructs with two cassettes, expression elements (i.e., promoter, introns, terminator) were not duplicated.

TABLE 6

SEQ ID NOs for chimeric constructs encoding targeting peptide
nif protein used in chloroplast targeting experiments. Single
cassette and double cassette constructs are indicated. In the
case of the double cassette constructs, the 5' cassette
is listed first and the 3' cassette is listed second.

| pMON | Targeting Peptide Nif protein chimeras | chimera amino acid SEQ ID NO: | chimera nucleotide SEQ ID NO: |
|---|---|---|---|
| pMON135488* | RbcS-nifH (*A. vinelandii*) | 90 | 91 |
| pMON135495** | RbcS-nifM (*A. vinelandii*) | 92 | 93 |
| pMON268837** | RbcS-nifM (*K. pneumoniae*) | 98 | 99 |
| pMON283725* | RbcS-nifH (*Cyanothece* spp) | 100 | 101 |
| | Double Cassette Vectors | 1st + 2nd cassette | 1st + 2nd cassette |
| pMON156650 | RbcS-nifH* (*A. vinelandii*) RbcS-nifM** (*A. vinelandii*) | 90 + 92 | 91 + 93 |
| pMON269035 | RbcS-nifH* (*K. pneumoniae*) RbcS-nifM** (*K. pneumoniae*) | 94 + 98 | 95 + 99 |

TABLE 6-continued

SEQ ID NOs for chimeric constructs encoding targeting peptide
nif protein used in chloroplast targeting experiments. Single
cassette and double cassette constructs are indicated. In the
case of the double cassette constructs, the 5' cassette
is listed first and the 3' cassette is listed second.

| pMON | Targeting Peptide Nif protein chimeras | chimera amino acid SEQ ID NO: | chimera nucleotide SEQ ID NO: |
|---|---|---|---|
| pMON283745 | RbcS-nifH*,^ (*K. pneumoniae*) RbcS-nifM** (*K. pneumoniae*) | 96 + 98 | 97 + 99 |

*For these cassettes the promoter was e35S-CaMV, the leader Hsp17.9, and the terminator was Gb-E6
**For this cassette the promoter was FMV, the leader was DnaK, and the terminator was RbcS-E9
^Codon-optimized for expression in *N. benthamiana*

Example 4: Plant-Produced Chloroplast-Targeted Dinitrogenase Reductase

The acetylene reduction activity assay of plant-produced chloroplast-targeted nif proteins showed that ethylene production was higher in samples prepared from plants infiltrated with constructs encoding the RbcS-nifH and RbcS-nifM chimeras compared to negative control samples. For this set of assays, tobacco plant leaves were either (1) not infiltrated, or infiltrated with *Agrobacterium* that contained (2) a negative control construct expressing CP4-EPSPS (5-enolpyruvulshikimate-3-phosphate synthase (EPSPS) enzyme), or (3) a RbcS-nifM chimera (pMON135495), or (4) a RbcS-nifH chimera (pMON135488), or (5) constructs containing the cassettes RbcS-nifH (pMON135488) and RbcS-nifM (pMON135495). Following infiltration, the plants were incubated at 10% oxygen for 2 days, enriched chloroplast fractions were prepared and evaluated using the standard acetylene reduction assay. For each sample, an average of 3 injections is presented along with the standard deviation (STDEV). Due to technical reasons, only the first injection of sample 3 was used in the calculations, therefore no standard deviation was calculated. The data presented in Table 7 show that the amount of ethylene present in sample 5 was higher than the background amount of ethylene detected in negative control samples 1 and 2. The ethylene peak of sample 5 (with both RbcS-nifH and RbcS-nifM chimeras) was about 3-times higher than the ethylene peak of either of sample 3 or sample 4, infiltrated with RbcS-nifM chimera or RbcS-nifH chimera, respectively. These data indicated that the tobacco plants infiltrated with both chloroplast-targeted RbcS-nifH and RbcS-nifM chimeras were able to produce an active chloroplast-targeted dinitrogenase reductase.

TABLE 7

Acetylene Reduction Assay results comparing chloroplast
targeted nif protein chimeras RbcS-nifH, RbcS-nifM,
and RbcS-nifH + RbcS-nifM. Standard deviation (STDEV)
are from n = 3 of gas chromatograph injections.

| Sample | *Agrobacterium* construct | pMON | Average Ethylene Peak | STDEV |
|---|---|---|---|---|
| 1 | no agro | n/a | 1.77 | 0.15 |
| 2 | CP4-EPSPS | n/a | 1.83 | 0.55 |
| 3 | nifM | pMON135495 | 2.60 | * |
| 4 | nifH | pMON135488 | 2.10 | 0.46 |
| 5 | nifH and nifM | pMON135488 pMON135495 | 6.23 | 0.50 |

* STDEV not determined as only one injection was made for this sample
n/a indicates not applicable.

Example 5: Specificity of Chloroplast- and Mitochondrial-Targeting Peptides

As described above for the mitochondrial-targeting peptide nif chimeras, *Agrobacterium* harboring the chloroplast-targeted nif chimeric constructs RbcS-nifH (pMON135488) and RbcS-nifM (pMON135495) and the P21-FLAG construct (pMON135478) where co-infiltrated into *N. benthamiana*. As a control, *Agrobacterium* harboring the dual cassette construct (pMON135484) with both mitochondrial-targeting CPN-60-nifH and CPN-60-nifM chimeras, and the P21-FLAG construct (pMON135478) were co-infiltrated into leaves of separate plants. After infiltration, the plants were maintained for two days under laboratory lighting conditions in a controlled atmosphere chamber having 10% $O_2$. Chloroplast and mitochondrial fractions were partially purified using the method described above and the respective fractions were assayed for the presence of active dinitrogenase reductase by the acetylene reduction assay. Due to the fact that the chloroplast fraction was enriched by low speed centrifugation, some contamination with mitochondria occurred. In contrast, during the enrichment of the mitochondrial fraction, a high speed centrifugation step resulted in a relatively low level of contamination of the mitochondria with chloroplasts. This cross-contamination was confirmed by western blot analysis of the respective chloroplast or mitochondrial fractions and use of chloroplast-specific (rubisco large subunit protein), mitochondrial-specific (Alternative Oxidase protein), or cytoplasmic-specific markers (PEP carboxylase), as described above.

The results from experiments comparing chloroplast- and mitochondrial-targeted nif protein chimeras for activity in an acetylene reduction assay are presented in Table 8. Treatment 1 shows that partially purified chloroplasts from plants infiltrated with chloroplast-targeted RbcS-nifH (pMON135488) and RbcS-nifM (pMON135495) constructs produced an ethylene peak area of 6.9, which was above the background level of ethylene peak area of approximately 2.0, indicating that these chloroplasts have dinitrogenase reductase activity. Treatment 2 shows that partially purified chloroplasts from plants infiltrated with the dual cassette construct (pMON135484) encoding the two mitochondrial-targeted CPN-60-nifH and CPN-60-nifM chimeras have an ethylene peak area of 4.1, also above background. Treatment 3 shows that the mitochondrial fraction from plants infiltrated with the dual cassette construct (pMON135484) encoding the two mitochondrial targeted CPN-60-nifH and CPN-60-nifM chimeras showed high dinitrogenase reductase activity with an ethylene peak area of 22.9. Treatment 4 shows that the mitochondrial fraction from plants infiltrated with two chimeric chloroplast-targeted constructs: RbcS-nifH (pMON135488) and RbcS-nifM (pMON135495), do not have dinitrogenase reductase activity. The detection of active dinitrogenase reductase activity in the partially purified chloroplast fraction prepared from plants infiltrated with the dual cassette construct (pMON135484) encoding the two mitochondrial-targeted CPN-60-nifH and CPN-60-nifM chimeras can be explained by the observation from protein immunoblot data that the partially purified chloroplasts contain a low level of mitochondria that likely contributed to the observed ethylene peak area. In summary, the results indicate that chloroplasts from plants infiltrated with chimeric chloroplast-targeted RbcS-nifH (pMON135488) and RbcS-nifM (pMON135495) constructs have dinitrogenase reductase activity when measured in an acetylene reduction assay for active nitrogenase.

TABLE 8

Acetylene Reduction Assay results comparing chloroplast- and mitochondrial-targeted dinitrogenase reductase in mitochondrial and chloroplast fractions from plants infiltrated with the indicated chimeras.

| Treatment | Organelle | targeting peptide nif chimeras | pMONs | ethylene peak area |
|---|---|---|---|---|
| 1 | Chloroplasts | RbcS-nifH and RbcS-nifM | pMON135488 pMON135495 | 6.9 |
| 2 | Chloroplasts | CPN-60-nifH and CPN-60-nifM | pMON135484 | 4.1 |
| 3 | Mitochondria | CPN-60-nifH and CPN-60-nifM | pMON135484 | 22.9 |
| 4 | Mitochondria | RbcS-nifH and RbcS-nifM | pMON135488 pMON135495 | 2.0 |

Example 6: Inhibition of Plant-Produced Dinitrogenase Reductase Activity by Light and Ambient Oxygen Plants produce oxygen when they are exposed to light. Nitrogenase, and the dinitrogenase reductase in particular, is extremely sensitive to oxygen inactivation. To evaluate the extent of light and oxygen induced inactivation of the plant-produced chloroplast-targeted dinitrogenase reductase, plants were infiltrated with *Agrobacterium* containing the chloroplast-targeted nif protein chimeric constructs RbcS-nifH (pMON135488) and Rbcs-nifM (pMON135495) as described. Following the infiltration, the plants were exposed to varying levels of oxygen and/or light intensities (which change the intracellular level of oxygen) to determine if these conditions would significantly impact the amount of nifH subunit produced.

Western blot analysis was performed with anti-NifH antibodies to detect NifH subunit in the total protein fraction of samples prepared from the chloroplast fractions. As shown in FIG. 1, the lane 1 sample is from plants exposed to ambient air and low light, lane 2 contains no sample, the lane 3 sample is from plants exposed to ambient air and dark, and the lane 4 sample is from plants maintained in a chamber of 10% $O_2$ and low light. These western blot results show that chloroplast fractions incubated in ambient air for 2 hours in the dark (FIG. 1, lane 3) contained more nifH subunit (higher intensity of band on western) than the amount of nifH subunit from chloroplast fractions incubated at ambient air and in the light (FIG. 1, lane 1). The highest level of nifH subunit was detected in the chloroplasts maintained at the lower oxygen concentration (10% $O_2$) and lower light intensity (FIG. 1, lane 4). These data demonstrate that following infiltration with *Agrobacterium* containing chloroplast-targeted nifH protein and chloroplast-targeted nifM protein chimeras, exposure of the plants to light and increased amounts of oxygen negatively impacted the amount of plant-produced chloroplast-targeted NifH subunit expression.

Example 7: Comparison of Plant-Produced Dinitrogenase Reductase Activity Using Nif Proteins from Three Bacterial Species Three bacterial species, *A. vinelandii, Klebsiella pneumoniae*, and *Cyanothece* ATCC 51142 were used as sources of genes encoding various nitrogenase proteins. Specifically, the genes encoding nifH (SEQ ID NO:25) and nifM (SEQ ID NO:27) were cloned from *A. vinelandii*. Genes encoding the following Nif proteins were synthesized based on the bacterial sequences of *K. pneumonia* nifH (SEQ ID NO:33), nifM (SEQ ID NO:35); and nifH (SEQ ID N0:37) from *Cyanothece* ATCC 51142 (the genome of which does not have a nifM homologue). For each of these, constructs comprising chloroplast-targeted Nif protein gene chimeras were generated using sequence encoding the RbcS targeting peptide (SEQ ID NO:23). Additionally, a codon-optimized chloroplast-targeted RbcS-nifH chimera (SEQ ID NO:97) using the nifH gene from *K. pneumonia* was evaluated. See Table 6 for corresponding SEQ ID NOs of the targeting peptide nif protein chimeras.

Following *Agrobacterium* infiltration of leaves, the plants were grown in a chamber with 10% $O_2$ for two days, and then chloroplast fractions were prepared. The constructs infiltrated were: (1) RbcS-nifM from *K. pneumonia* (pMON268837), (2) dual cassette construct with RbcS-nifH and RbcS-nifM from *K. pneumonia* (pMON269305) (3) dual cassette construct with RbcS-nifH (codon optimized for expression in tobacco) and RbcS-nifM from *K. pneumonia* (pMON283745), (4) RbcS-nifH from *Cyanothece* (pMON283725), and (5) dual cassette construct with RbcS-nifH and RbcS-nifM from *A. vinelandii* (pMON156650).

The results from an acetylene reduction assay with the value of the ethylene production from the first injection of the reaction are shown in Table 9. Sample 1 served as negative control for the assay. The data show that the codon optimization of *K. pneumonia* nifH (sample 3) did not show significant improvement compared to the non-codon-optimized version (sample 2). The data also show that chloroplast-targeted plant-produced NifH and NifM from *K. pneumonia* or *A. vinelandii* were both active, although activity of the *K. pneumonia* NifH was slightly higher (Table 9, sample 2, sample 3, and sample 5). The chloroplast-targeted plant-produced NifH from *Cyanothece* showed lower activity (Table 9, sample 4). These data show that plant-produced chloroplast-targeted NifH (the nif protein component of dinitrogenase reductase) from three bacterial species produced active dinitrogenase reductase in plant cells.

TABLE 9

Comparison of nitrogenase activity from chloroplast-targeted plant-produced nif proteins derived from three bacterial sources. Data showing results from a single gas chromatograph injection.

| sample number | Bacterial source of sequence | RbcS-nif chimera | pMON | Ethylene peak of Injection no. 1 |
|---|---|---|---|---|
| 1 | *K. pneumonia* | nifM | pMON268837 | 4.02 |
| 2 | *K. pneumonia* | nifH and nifM | pMON269305 | 17.1 |
| 3 | *K. pneumonia* | nifH^^ and nifM | pMON283745 | 12.57 |
| 4 | *Cyanothece* | nifH | pMON283725 | 5.53 |
| 5 | *A. vinelandii* | nifH and nifM | pMON156650 | 12.17 |

^^Codon-optimized for expression in *N. benthamiana*

Example 8: Evaluation of Mitochondrial-Targeted nifH and nifM Proteins Expressed in Stably Transformed Plants In addition to the detection of active dinitrogenase reductase in the mitochondria of mitochondrial-targeted nifH and nifM chimeras transiently transformed in *N. benthamiana* leaves, as described above, active dinitrogenase reductase was also produced with stable transformation of *N. benthamiana* with nuclear encoded chimeric constructs encoding chimeric mitochondrial-targeted NifH and NifM proteins.

The construct pMON135484 contained the chimeric CPN-60+nifH and CPN-60+nifM cassettes as described in Example 1 and Table 2 was used for stable transformation of *N. benthamiana*. The two expression cassettes for the CPN-60-nifH and CPN-60-nifM chimeras were present on the same T-DNA within the vector construct. To establish stably transformed *N. benthamiana*, a mixture of an *Agrobacterium* strain made with the construct pMON135484 and a second strain that harbored a construct with an nptII selectable marker were used to transform *N. benthamiana* leaf sections using standard plant transformation methods. Kanamycin-resistant shoots that developed on callus were excised and transferred to kanamycin containing rooting media. Kanamycin plants (R0) that had developed roots were transferred to soil.

Multiple R0 events were identified by PCR designed to detect both nifH and nifM sequences in leaf tissue. Copy number assays were used to select a line from the R0 event K6NB-003 that was homozygous, single copy for each of the chimeric CPN-60-nifH and CPN-60-nifM cassettes. These two cassettes were linked, heritable, and produced active dinitrogenase reductase over several generations.

Figure 2:
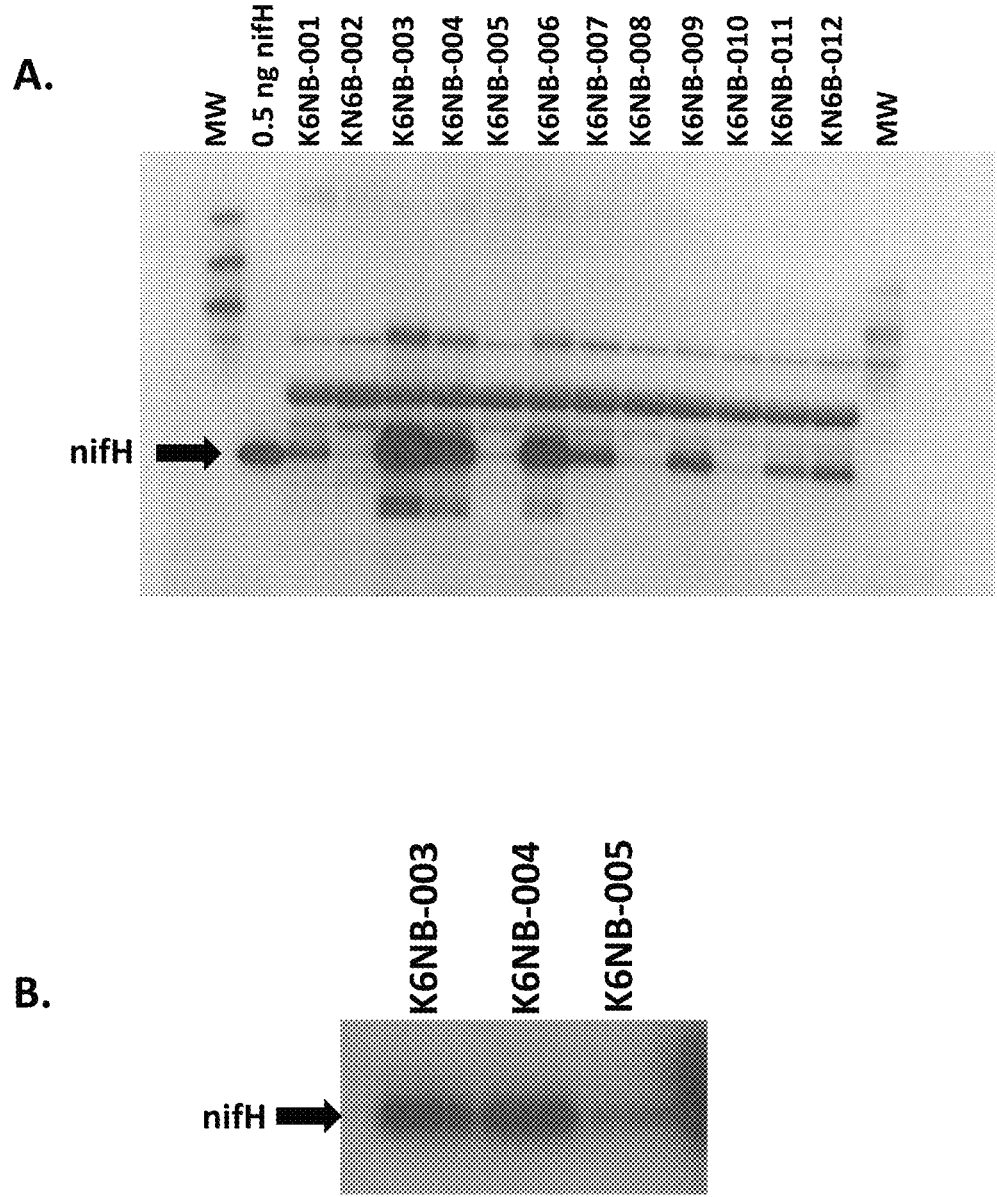
FIG. 2. Western blot analysis of NifH expression in leaf (panel A) and root (panel B) tissue of *N. benthamiana* plants stably transformed with CPN-60 mitochondrial-targeting peptide nifH and nifM chimeric construct (pMON135484). The lanes include molecular weight markers (MW), 0.5 ng nifH (without the CPN-60 mitochondrial-targeting peptide) purified from bacteria, and individual events labeled K6NB-001 through K6NB-012.

Leaf and root tissue was collected from individual events and frozen in liquid nitrogen, ground to a powder using a mortar and pestle, and about 20-50 mg of the frozen leaf powder was extracted in 10 volumes of 2× Laemmli buffer containing 5% 2-mercaptoethanol. Samples were heated at 94° C. for 4 minutes and 20 µl of the extract was loaded onto a Biorad mini-PROTEAN® TGX™ 4-20% SDS PAGE gel (BioRad, Hercules, Calif.). Purified NifH protein (0.5 ng) was loaded as a positive control for western blotting using anti-nifH antibody. Western blotting was carried out using a 1:5000 dilution of anti-NifH antibody according to standard methods. The results of the western blotting of both leaf (FIG. 2A) and root tissue (FIG. 2B) from R0 plants demonstrated the presence of nifH gene product in 12 separate events (K6NB-001 through K6NB-012). The molecular weight (MW) of the expressed NifH polypeptide in the events was consistent with the MW expected if the CPN-60 mitochondrial-targeting peptide had been removed during import into that organelle, as shown by comparison to NifH protein that had been purified from bacteria and lacked the mitochondrial-targeting sequence. These results show for the first time the accumulation of NifH in both the leaf and root tissue of plants stably transformed with chimeric expression constructs encoding mitochondrial-targeted NifH and NifM protein chimeras.

Figure 3:
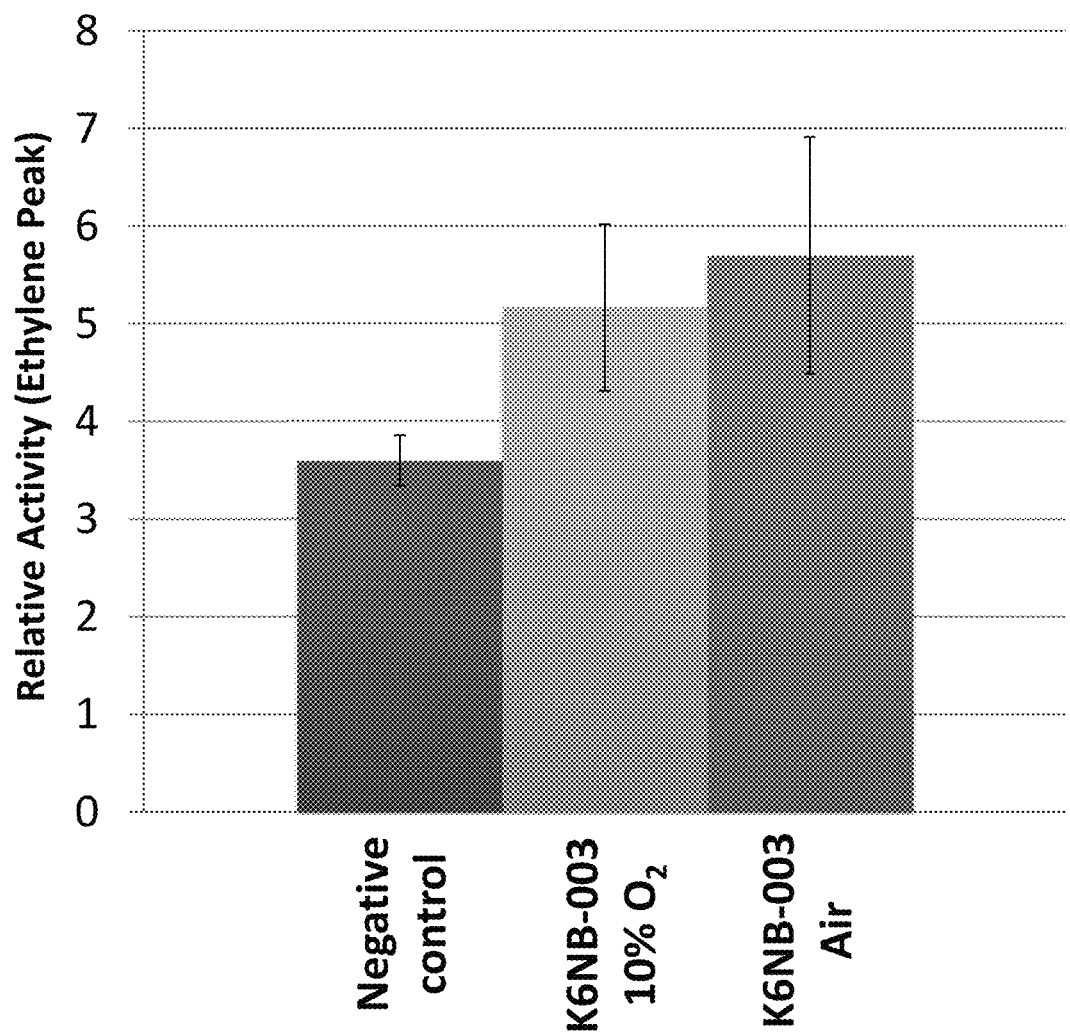
FIG. 3. Results from an acetylene reduction assay of nitrogenase activity of mitochondrial fractions prepared from the stable transformed event K6NB-003-006-36 (labeled K6NB-003) or a non-transformed control (negative control). The event K6NB-003 was grown in low light conditions at 10% 02 or at ambient air prior to preparation of the mitochondrial fraction. The error bars represent the average of three separate experiments.

The stably transformed *N. benthamiana* plants were shown to contain active dinitrogenase reductase as assessed in the standard acetylene reduction assay (e.g. see FIG. 3). For this assessment, R3 seed from line K6NB-003-006-36 (derived from the R0 event K6NB-003) was planted in a growth chamber under the conditions described in Example 1. After about four weeks, plants were either transferred to low light conditions in ambient air or in a glove box containing 10% $O_2$, as described in Example 1. Non-transformed *N. benthamiana* plants were transferred to the same conditions to serve as negative experimental controls. Mitochondrial enriched fractions were isolated from leaf tissue in the absence of oxygen as described in Example 1. The presence of active dinitrogenase reductase in the mitochondrial enriched fractions from the transgenic event K6NB-003-006-36 was shown by mixing it with purified dinitrogenase (MoFe protein) and then demonstrating that the reconstituted nitrogenase could produce ethylene using acetylene as a substrate, using the methods described in Example 1. Results of these acetylene reduction assays are presented in FIG. 3, and shows that active dinitrogenase reductase was detected in mitochondria isolated from leaves of the transgenic event grown at both growth conditions of low light in ambient air and in a glove box containing 10% $O_2$ compared to the activity detected in mitochondria prepared from a non-transformed control plant. The error bars are calculated on the average of at least three independent experiments. These results demonstrate for the first time that plants stably transformed with expression constructs encoding mitochondrial-targeted nifH and nifM chimeras express active dinitrogenase reductase.

Example 9: Expression of Dinitrogenase Reductase Via Integration into the Plant Chloroplast Genome Nif proteins were expressed from the chloroplast genome. Because chloroplast transformation is routine in the model plant tobacco, this transformation system was used to express nif genes directly from the chloroplast genome. The nifH and nifM transgenes were engineered into a chloroplast transformation vector (pMON261406) designed to integrate the transgenes via homologous recombination into the tobacco chloroplast genome.

Constructs were designed for constitutive production of NifH and NifM proteins in chloroplasts using a chimeric two-gene operon expression cassette. Constitutive protein accumulation requires both a promoter and a translational control region (also known as a ribosome binding site region in the 5'-untranslated leader region) active in plant plastids. Transcription of the two-gene transgenic operon expression cassette was therefore driven by a transgenic promoter derived from the strong and constitutively expressed plastid ribosomal RNA operon promoter (Prrn, SEQ ID NO:113; Staub and Maliga, *EMBO J.* 12:601-606, 1993). Transcription of both transgenes in the operon is facilitated due to readthrough transcription and the lack of transcription termination at the first transgene in the operon. Constitutive translation of both transgenes in the operon is facilitated by the constitutively translated ribosome binding site region derived from the T7 bacteriophage gene 10 leader (G10L: SEQ ID NO:114; Staub et al., *Nature Biotechnol* 18:333-338 2000) was included in the 5' leader sequence upstream of each nif coding region in the two-gene operon. Constitutive transcription and translation of the nif genes was used to optimize the protein accumulation throughout the light and dark cycles of plant growth independent of oxygen levels in the chloroplast. In a future embodiment, nif transgenes may be expressed in tissues with limited levels of oxygen such as in non-green tissues of roots or only during the dark cycle of the plant, thus helping to ensure stability of the Nif complex.

Plastid transgenes also require a 3'-untranslated region to facilitate mRNA stability in the plastid. Transgene transcripts were stabilized by inclusion of the 3'-untranslated region of the plastid rps16 gene (Trps16; SEQ ID NO:115; U.S. Pat. No. 5,877,402, Staub and Maliga, *Plant J.* 6:547-553 1994) downstream of the nifH gene and the 3'-untranslated region of the plastid petD gene (TpetD; SEQ ID NO:116) downstream of the nifM gene. The nifH coding sequence was derived from *Azotobacter vinelandii* and is represented by SEQ ID NO: 117. The nifM coding sequence was derived from *Azotobacter vinelandii* and is represented by SEQ ID NO:27.

To enable selection of tobacco chloroplast transformants, an expression cassette expressing a spectinomycin antibiotic resistance gene (aadA) was included in the transformation vector. The aadA gene (SEQ ID NO:118) expression cassette was driven by the promoter and the 5'-untranslated leader of the tobacco plastid psbA gene (PpsbA: SEQ ID NO: 119) and transcript stability was controlled by the 3'-untranslated region of the psbA gene (TpsbA: SEQ ID NO: 120).

To ensure targeting by homologous recombination of the transgenes into the plastid genome via homologous recombination (Maliga et al. U.S. Pat. No. 5,877,402), DNA sequences identical to those in the plastid genome (SEQ ID NO: 121 and SEQ ID NO: 122) were also included in the chloroplast transformation vector, pMON261406. Homologous flanking regions were derived from the endogenous plastid rbcL gene region at the left flanking homologous region and the endogenous accD region as the right flank of the homologous targeting region. The transgenic nif operon and aadA transgene were cloned into the intergenic region between these two endogenous plastid genes (rbcL and accD) such that insertion into the chloroplast genome via homologous recombination would not disrupt any essential functions.

Chloroplast Transformation

To introduce the chimeric vector carrying the nifH and nifM expression cassettes into tobacco (*Nicotiana tabacum* var. *Petit Havana*,) the protocol for chloroplast transformation as described by Russell (*Pl. Physiol.* 98:1050-1056, 1992) and Maliga et al U.S. Pat. No. 5,877,402 was followed.

DNA Analysis

Figure 4:
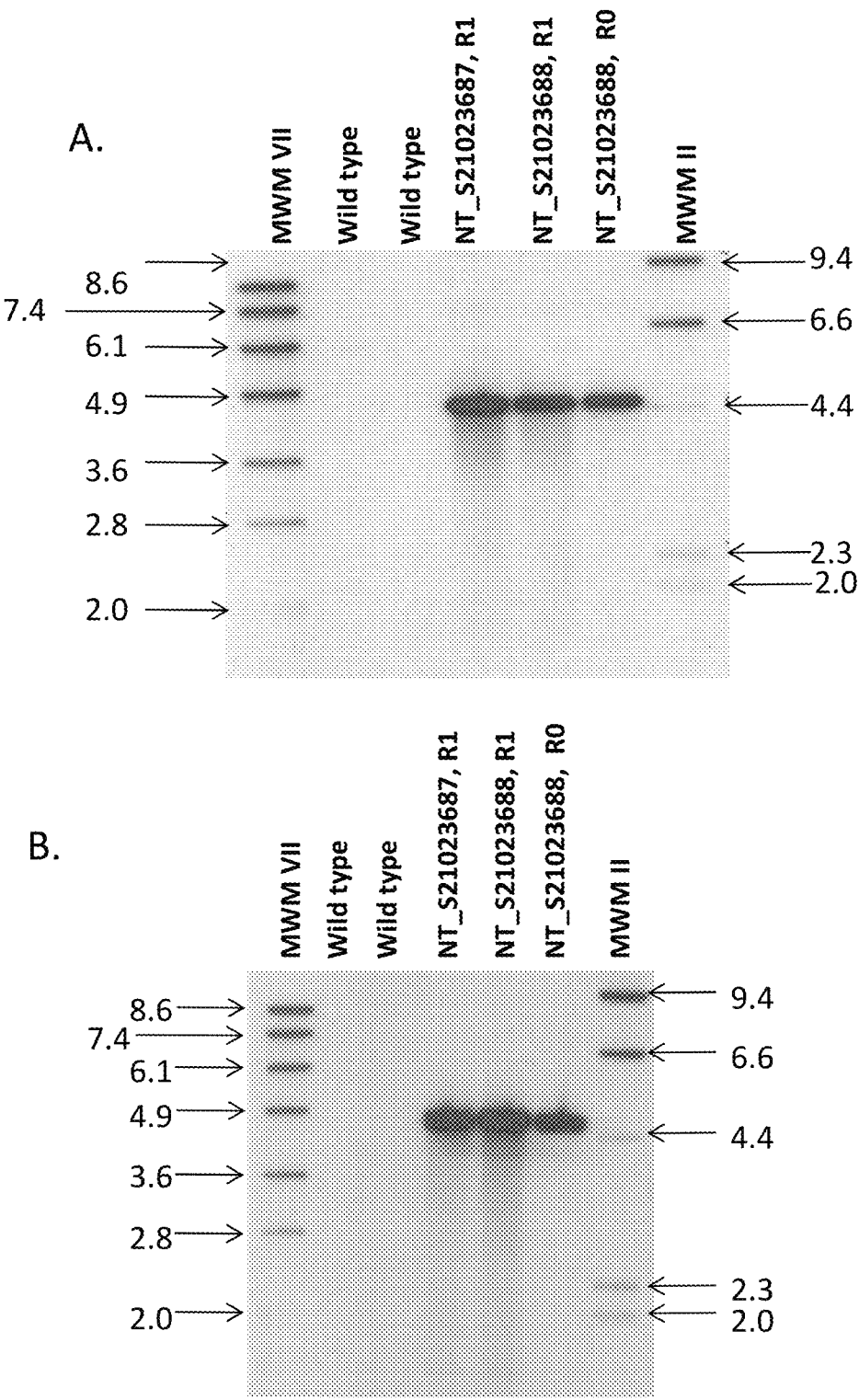
FIG. 4. Southern blots with DNA samples of wild type plants, event NT_S21023687 (R1 event), and event NT_S21023688 (R0 and R1 event), confirming targeted integration of transgenes into the chloroplast genome. (Panel A). Southern blot probed with nifH sequence. (Panel B). Southern blot probed with nifM sequence. MWMVII and MWMII indicate molecular weight markers and sizes (kb) of MWM bands are indicated.

Two events (NT_S21023687 and NT_S21023688) were produced after the plastid transformation with pMON261406. These events were tested for the presence of the desired DNA inserts by Southern blot analysis. FIGS. 4A and 4B show Southern blots of DNA extracted from these events digested with restriction endonuclease EcoO109 I and hybridized with probes (SEQ ID NO:123 and SEQ ID NO:124) for nifH and nifM genes, respectively. The expected band for the intact insertion at 4.5 kb was present when the nifH gene was used as the Southern blot probe. The expected bands for the intact insertion of 4.5 kb and 4.3 kb were shown to be present when the nifM gene was used as the Southern blot probe. Bands of expected sizes were detected for samples from transgenic events, and the results indicated that the events NT_S21023687 and NT_S21023688 contain transgenic nifH and nifM genes. Both R0 and R1 plants contained the bands of the expected size indicating that the transgenes are heritable and stably incorporated into the genome.

Figure 5:
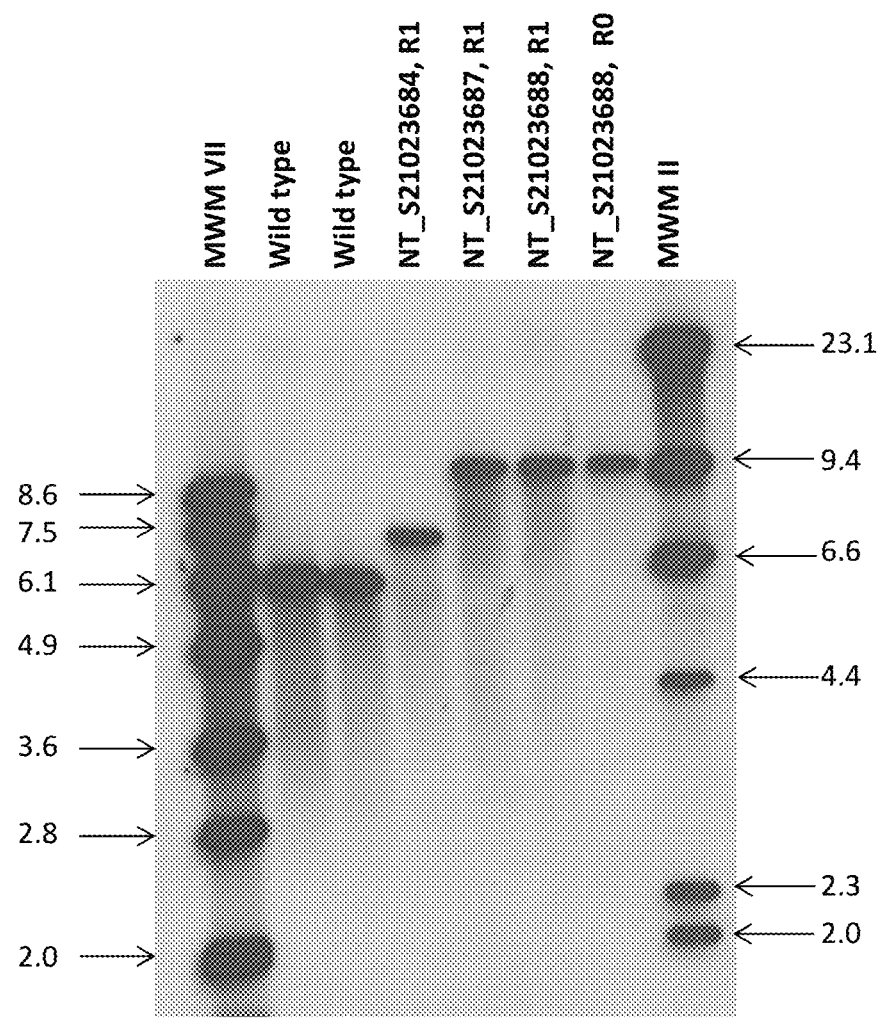
FIG. 5. Southern blot with DNA samples of wild type plants, control event NT_S21023684 (R1 event), event NT_S21023687 (R1 event), and event NT_S21023688 (R0 and R1 event), confirming targeted integration of transgenes into the plastid genome. Probe was rbcL gene sequence. MWMVII and MWMII indicate molecular weight markers and sizes (kb) of MWM bands are indicated.

FIG. 5 shows a Southern blot of the DNA digested with endonuclease PvuII and probed with a probe for the rbcL gene (SEQ ID NO:125) that is located close to the expected insertion site of the transgenes. Wild type DNA showed bands corresponding to the expected uninterrupted region downstream of plastid rbcL gene. The event NT_S21023684, which derived from the plastid transformation using vector pMON253685 and contained the aadA gene but did not contain any nif genes, showed a proportionally larger DNA fragment (~7.5 kb). The other lanes corresponding to DNA digests from the R0 and R1 plants of the events NT_S21023687 and NT_S21023688 showed the expected size of the PvuII fragment at 9.9 kb. These results indicated that the transgenic events (NT_S21023687 and NT_S21023688) contained the insertion of nifH, nifM and aadA in the expected site of chloroplast DNA and that the events were homoplasmic (i.e. all chloroplast genome copies contained the inserted transgenes).

Protein Analysis

Figure 6:
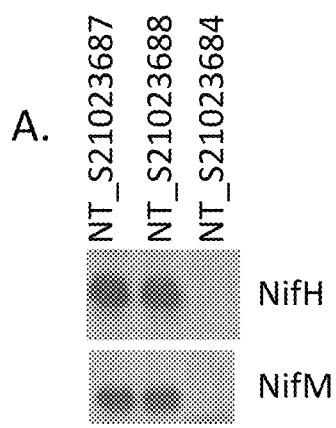
FIG. 6. Immunoblot analyses. (Panel A). Immunoblot analysis confirming expression of NifH and NifM subunits in transplastomic event NT_S21023687 and NT_S2103688, but not in the control event NT_S21023684. (Panel B). Immunoblot analysis showing higher expression level of nifH protein in total protein extract prepared from transplastomic events exceeded the level of the nifH protein in total protein extract prepared from nuclear stably transformed plants event K6 NB-003. Lane 1 contained a protein extract from the event NT_S21023684 which did not contain any nif genes and served as a negative control. Lanes 2 and 3 contained extracts from transplastomic event NT_S21023687 and NT_S21023688. Lane 4 contained a protein extract from the nuclear transformed event K6NB-003.
Figure 6:
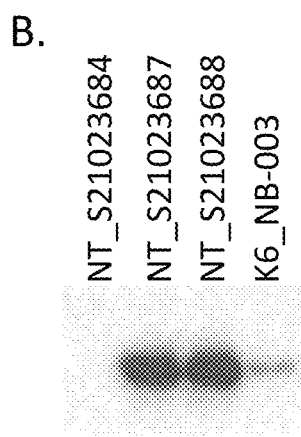

To demonstrate the production of the NifH and NifM proteins, leaf tissue from R0 events NT_S21023687, NT_S21023688 and NT_S21023684 was ground in liquid nitrogen and total protein fractions were extracted using Laemmli buffer (BioRad, Hercules, Calif.). Total cellular proteins were analyzed by western blot to detect proteins that were immunoreactive to antibodies raised against either the NifH or NifM proteins. FIG. 6A shows the resulting immunoblot, where lanes 1 and 2 (events NT_S21023687 and NT_S21023688) contained proteins that produced immunoreactive bands of the expected size for the NifH and NifM proteins. The event NT_S21023684 (lane 3) that resulted from transformation of the vector lacking nif genes did not demonstrate these immunoreactive bands. These results demonstrated that NifH and NifM proteins were produced from transgenic genes integrated into the plastid genome.

FIG. 6B shows results of western blot analysis showing that the level of NifH protein in total protein extract prepared from transplastomic events exceeded the level of the NifH protein in total protein extract prepared from nuclear stably transformed plants (event K6 NB-003 as described in Example 8). Proteins extracted from transgenic R1 events were separated by SDS-PAGE and analyzed via western blotting using antibodies raised against nifH. Lane 1 contained a protein extract from the event NT_S21023684 which did not contain any nif genes and served as a negative control. This event did not yield any specific bands on the western blot. Lanes 2 and 3 contained extracts from transplastomic event NT_S21023687 and NT_S21023688, respectively. Lane 4 contained a protein extract from a nuclear transformed event K6_NB-003. These results demonstrate that the use of the chloroplast genome encoded NifH protein provides distinct benefits over nuclear encoded NifH by allowing much higher levels of Nif proteins to be produced. Antibodies raised against NifM protein were able to detect the nuclear-encoded plant-produced NifM only in mitochondria-enriched fractions, and they were not used in the evaluation of the relative nifM expression in total protein fractions.

Demonstration of Dinitrogenase Reductase Activity

Figure 7:
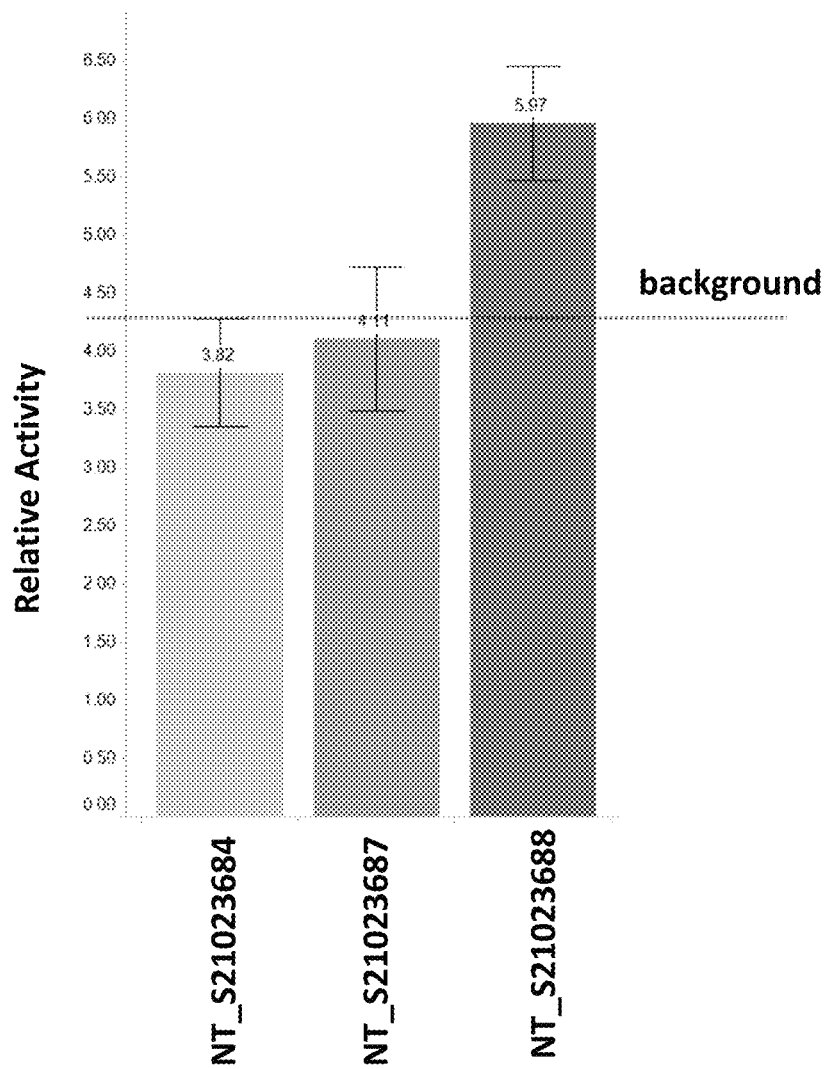
FIG. 7. Dinitrogenase reductase activity in extracts of R1 leaf tissue from transplastomic nif plants. The experiment was conducted 3 times; a representative data set is shown.

Protein extracts from transgenic plants were produced to demonstrate that they contained enzymatically active dinitrogenase reductase. Leaf tissue from plants incubated at 10% $O_2$ were excised, and enriched chloroplast fractions were generated and assayed for dinitrogenase reductase activity using methods as described in Example 1. The experiment was conducted 3 times; a representative data set is shown in FIG. 7. The event NT_S21023687 demonstrated dinitrogenase reductase activity level that was just slightly above the background. The event NT_S21023688 clearly demonstrated dinitrogenase reductase activity by producing ethylene levels beyond the background level present in plants lacking nif genes (event NT_S21023684). Specifically, chloroplast enriched fractions from R1 leaf of the control event, NT_S21023684, had an ethylene peak relative activity of 3.82. Chloroplast enriched fractions from R1 leaf of event NT_S21023687 had an ethylene peak relative activity of 4.11, slightly above that of the control event NT_S2103684. The chloroplast enriched fractions from R1 leaf extracts of event NT_S21023687 had an ethylene peak relative activity of 5.97 (see FIG. 7). These results clearly demonstrate that expression of nifH and nifM in transplastomic plants resulted in detectable dinitrogenase reductase activity by producing ethylene levels beyond the background level present in plants lacking nif genes.

Example 10: Expression of Nitrogenase Subunits Via Integration into the Plant Chloroplast Genome Nif proteins encoding the minimal subunits needed to form an active nitrogenase were expressed from the chloroplast genome. Three chloroplast transformation vectors, each containing three nitrogenase subunit transgenes, were designed to integrate the transgenes via homologous recombination into the tobacco chloroplast genome. The first vector had expression cassettes for nifH, nifD and nifK, a first promoter, homology arms for integration into a first chloroplast genome location, and a gene to confer spectinomycin selection. A second vector had expression cassettes for nifEN (a fusion of the complete ORF of nifE and the complete ORF of nifN, SEQ ID NO:141), nifB, and nifM, a second promoter (promoter 2), homology arms for integration into a second chloroplast genome location, and a gene to confer spectinomycin selection. A third vector also had expression cassettes for nifEN, nifB, and nifM, a different promoter (promoter 2), homology arms for integration into a third chloroplast genome location, and a gene to confer kanamycin selection. In one embodiment, co-transformation with the first and second chloroplast transformation vectors was performed, selection was done with spectinomycin, and stable plants were generated. In a second embodiment, co-transformation with the first and third chloroplast transformation vectors was performed, selection was done with both spectinomycin and kanamycin, and stable plants were generated. In another embodiment, an additional chloroplast transformation vector was designed which targeted insertion of the second set of genes (nifENBM) immediately after the first insertion of nifHDK, resulting in targeting two vectors to the same chloroplast genome location.

In another embodiment, all of the expression cassettes for the different nitrogenase subunit genes are on a single chloroplast transformation vector. In another embodiment, the expression cassettes for the different nitrogenase subunit genes are on three, or four or more separate chloroplast transformation vectors. After stable plants are generated, Southern analysis is used to confirm the integration of the transformation vector into the chloroplast genome by homologous recombination; protein analysis is used to confirm that the NIF subunits are present, and nitrogenase activity assays are done on combined plant extracts which in total contained all essential Nif protein as detailed in Example 9, except that no bacteria-produced active dinitrogenase (MoFe protein) is added to the reaction as all needed polypeptides and ligands are produced by transgenic plants. Expression of additional proteins (such as NifS, NifU, NifQ, NifV and others (as described in the Summary of the Invention)) may be required for optimal activity.

Example 11: Bioinformatic Analysis

Figure 8:
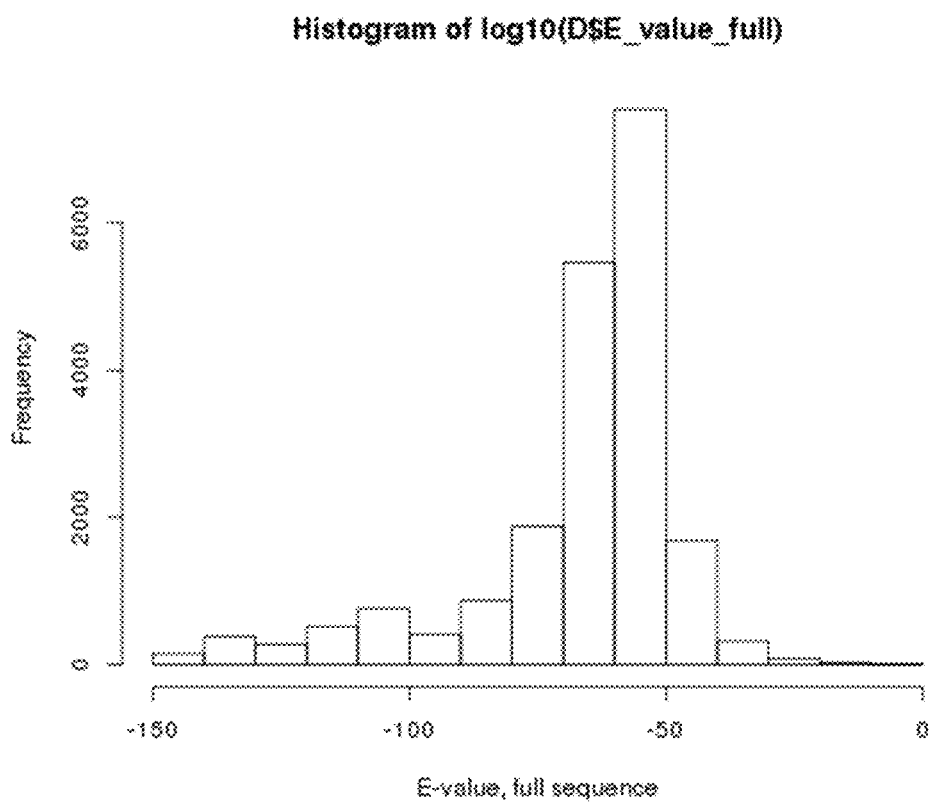
FIG. 8. Histogram of the E-values from this hmm analysis of protein sequences with nifH domains.
Figure 9:
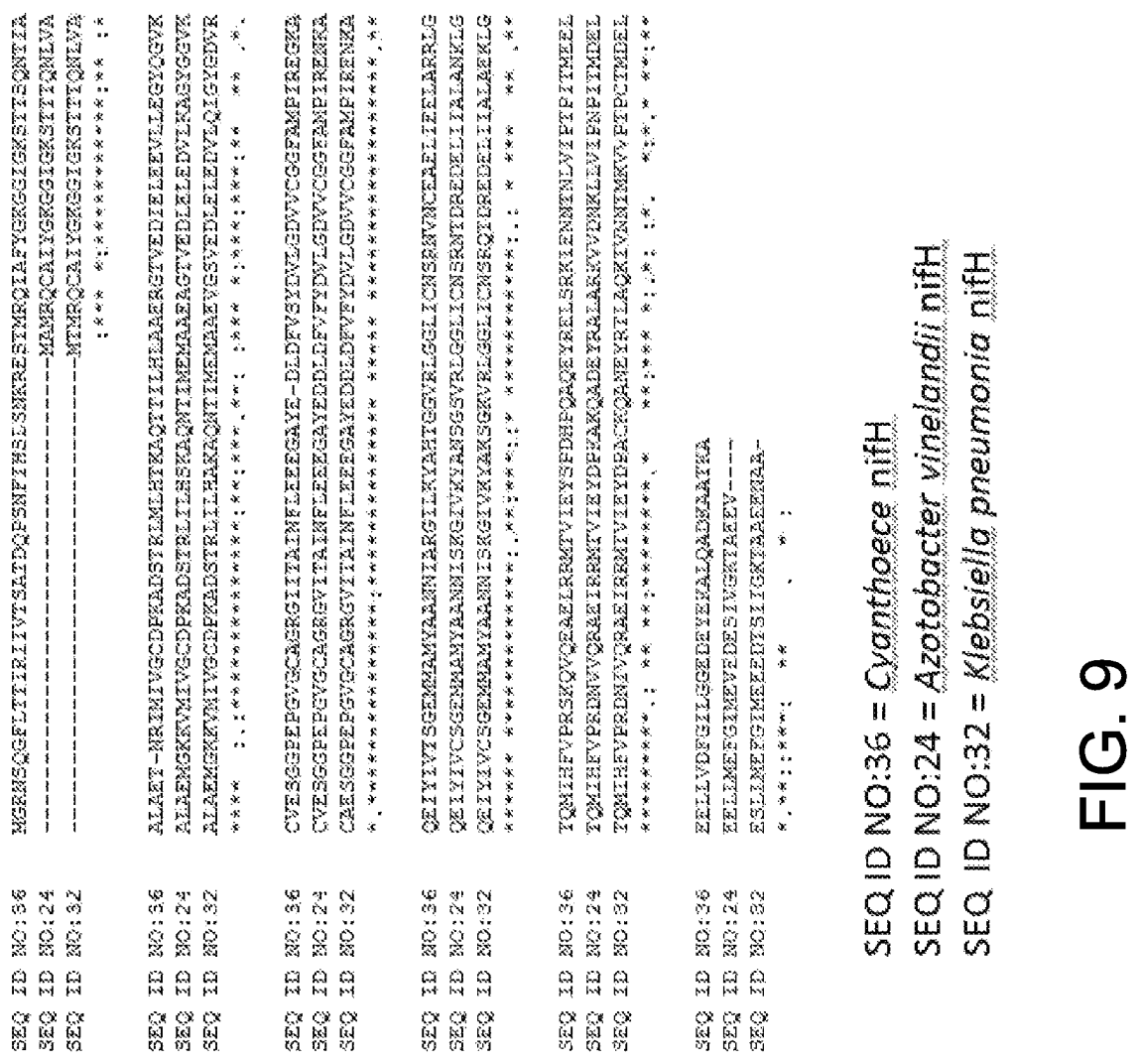

To identify additional proteins with potential to function as a NifH subunit in planta, NifH hidden Markoff model (hmm) and 20327 associated pfam sequences were obtained from the EMBL-EBI PFAM database <<pfam.xfam.org/family/PF00142>> (Finn et al., *NAR Database Issue* 42:D222-D230, 2014). The program hmmscan (Finn et al., *NAR Web Server Issue* 39:W29-W37, 2011) was used to produced a table of E-values for each of the sequences compared to the hmm. For the three nifH sequences described in the above examples the E-values were: *A. vinelandii*—nifH—2.3e-145; *K. pneumoniae*—nifH—1.4e-143; and *Cyanothece*—nifH—1.9e-137. A histogram of the E-values from this analysis is presented in FIG. 7. Three different specified E-value thresholds were set to determine how many NifH proteins would be included in the three E-value thresholds. From this analysis, at an E-value of 1e-137 there would be 296 sequences; at an E-value of 1e-125 there would be 572 sequences, and at an E-value of 1e-100 there would be 2060 sequences. Within each of these groupings analysis was done to determine how many phyla were represented. With the threshold set as phyla observed greater than 10 times, at E-value of less than 1e-137 there were three phyla represented: Proteobacteria, Cyanobacteria, and Firmicutes. At E-value of less than 1e-125 there were five phyla represented: Proteobacteria, Cyanobacteria, Firmicutes, Euryarchaeota, and Chlorobi. At E-value of less than 1e-100 there were eight phyla represented: Proteobacteria, Cyanobacteria, Firmicutes, Euryarchaeota, Chlorobi, Actinobacteria, Viridiplantae, and environmental samples. A sample histogram of E-values is found at FIG. 8. An exemplary alignment of NifH sequences from *Cyanothece* sp., *A. vinelandii*, and *K. pneumoniae* is found at FIG. 9, demonstrating the location of regions of sequence identity or similarity when two Nif proteins are aligned.

Based on this analysis, NifH proteins are selected from one or more of the phyla with an E-value of 1e-137, or with an E-value of 1e-125, or with an E-value of 1e-100. The DNA sequences of the selected NifH proteins are cloned from the corresponding bacterial species and expressed in planta as detailed in the previous examples. Bacterial genes with codon usage significantly different form the target plant species, or bacterial genes containing codons that are rarely used in the target plant species may require modification to encourage optimum gene expression, as is well know in the art. To direct localization to mitochondria or chloroplasts, a targeting peptide is operably linked to the bacterial NifH protein. Non-limiting examples of mitochondrial targeting peptides are presented in Example 2, Table 4. Chloroplast targeting is done as described in Example 3, with for example the RbcS targeting peptide. These constructs are expressed transiently by *Agrobacterium* infiltration of the leaf of a plant, as detailed in Example 1. Alternatively, the constructs are used to generate stable transformation of a plant (as detailed in Example 8) for nuclear expression of the mitochondrial targeted or chloroplast targeted nifH from the bacterial strain of the additional bacterial phyla.

The genes encoding NifH from the additional bacterial phyla are cloned into vectors appropriate for chloroplast genome targeting (see Example 9). For example, the chloroplast targeting vector contains a cassette with a promoter, a nifH gene and a 3' untranslated termination sequence, and the cassette is flanked by sequence of the chloroplast genome to allow for integration into the chloroplast genome and expression in the chloroplasts without import. An alternative chloroplast targeting vector would have two cassettes in tandem, one encoding NifH and one encoding NifM (for example, see Example 9), with these cassettes flanked by the sequence of the chloroplast genome. The encoded NifM may be from the same bacterial strain as the NifH, or the NifM sequence may be from a different bacterial strain, however compatible with the NifH such that the dinitrogenase reductase is active. For plants with nifH and/or nifM cassettes integrated into the chloroplast genome, the plants are assayed for dinitrogen reductase activity by adding purified dinitrogenase to the in vitro assay, as detailed in Example 9. To detect optimal activity of the dinitrogenase reductase, a dinitrogenase from the same bacterial strain as the NifH is used in the assay. Alternatively, a dinitrogenase from a bacterial strain different from the NifH source is used in the to detect activity in the assay.

Example 12: Expression of Dinitrogenase Subunits in Planta

To produce active nitrogenase in a plant cell, as well as producing active dinitrogenase reductase, it is also desirable to express dinitrogenase in planta. Expression of dinitrogenase subunits in plant cells is accomplished using methods as described in prior examples for mitochondrial targeting or chloroplast targeting of nuclear encoded transgene constructs. Alternatively, expression of dinitrogenase is done by transgene expression from a plant chloroplast or plastid genome, as described for dinitrogenase reductase in example 9. Active NifH protein, as well as being a key part of dinitrogenase reductase, is also known to typically be needed for correct assembly of the dinitrogenase subunit.

Figure 10:
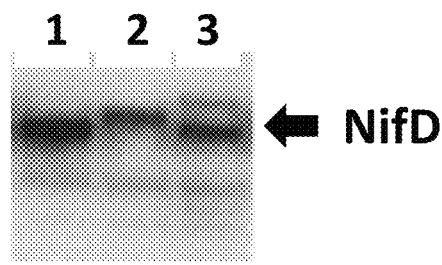
FIG. 10. Western blot analysis of NifD expression in leaf tissue of *N. benthamiana* plants transiently transformed with NifD subunits. Lane 1 is NifD (SEQ ID NO:126) without a targeting peptide. Lane 2 is NifD operably linked to the CPN60 mitochondrial targeting peptide represented by SEQ ID NO: 1. Lane 3 is NifD operably linked to the ATP synthase protein 9-derived+2 amino acids represented by SEQ ID NO:10.

For transient expression of the NifD subunit of dinitrogenase in mitochondria, DNA constructs were generated encoding the NifD subunit without a targeting peptide, and the NifD subunit operably linked to sequences encoding one of four mitochondrial targeting peptides: (1) CPN60 (SEQ ID NO:1); (2) ATPsyn[Nc]+2aa (SEQ ID NO:10); (3) GD(P)[Fp]+8 (SEQ ID NO:15); and (4) RPS10[At]+1 (SEQ ID NO:21). These constructs were expressed transiently by *Agrobacterium* infiltration of the leaf of a plant, as detailed in Example 1. Plant extracts enriched for mitochondria were prepared and protein expression was assessed using standard western blot analysis with antibodies specific to the NifD protein. A representative western blot image is shown in FIG. 10 where lane 1 is NifD (SEQ ID NO:126) without a targeting peptide; lane 2 is NifD operably linked to the CPN60 mitochondrial targeting peptide; and lane 3 is NifD operably linked to the ATPsyn[Nc]+2aa targeting peptide. The CPN60 targeting peptide is not removed from the NifD subunit when targeted to the mitochondria as evidenced by the higher molecular weight of the band in lane 2 compared to the band in lane 1. In contrast, approximately 80% of the NifD subunit had the ATPsyn[Nc]+2aa targeting peptide removed when targeted to the mitochondria, as evidenced by the two bands in lane 3 corresponding to the unprocessed NifD (upper band with a weaker signal) and the processed NifD (lower band with stronger signal).

For transient expression of dinitrogenase in mitochondria, DNA constructs are generated encoding NifD and NifK subunits, each operably linked to a sequence encoding a mitochondrial targeting peptide. Non-limiting examples of mitochondrial targeting peptides are presented in Example 2, Table 4. Constructs encoding each dinitrogenase subunits, NifD and NifK are co-expressed transiently by *Agrobacterium* infiltration of the leaf of a plant, as detailed in Example 1. The NifD and NifK subunits may be on separate constructs, or they may be expressed from a single construct.

Figure 11:
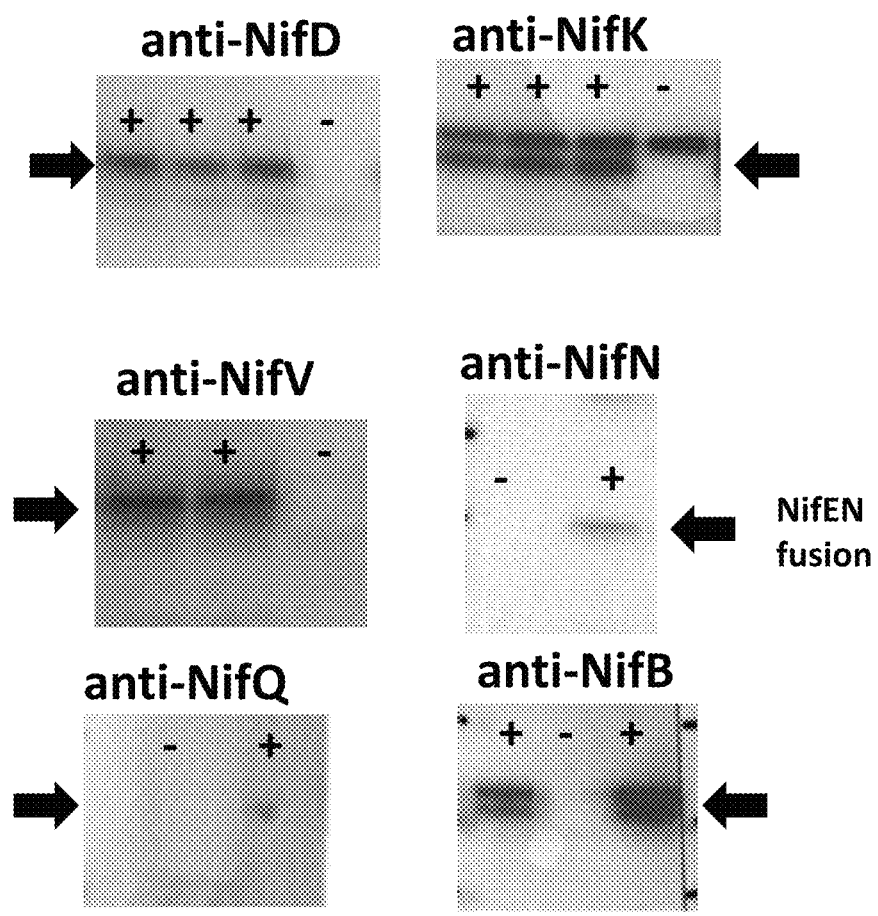
FIG. 11. Western blot analysis demonstrating in planta expression of NifD, NifK, NifV, NifE-N, NifQ, and NifB.
Figure 12:
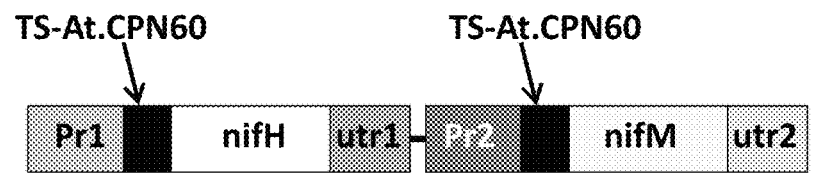
FIG. 12. Stable transformation constructs. (Panel A). Illustration of three constructs used to generate stable transformed events with nitrogenase subunits. (Panel B). PCR analysis showing four events (lanes 1-4) containing each of the constructs used to transform. The three PCR bands in each of the lanes labeled 1-4 correspond to the expected PCR product for each individual construct: NifH+M; NifD+ K+V; NifQ+B+EN (fusion of NifE and NifN). Lane labeled M is molecular weight markers.
Figure 12:
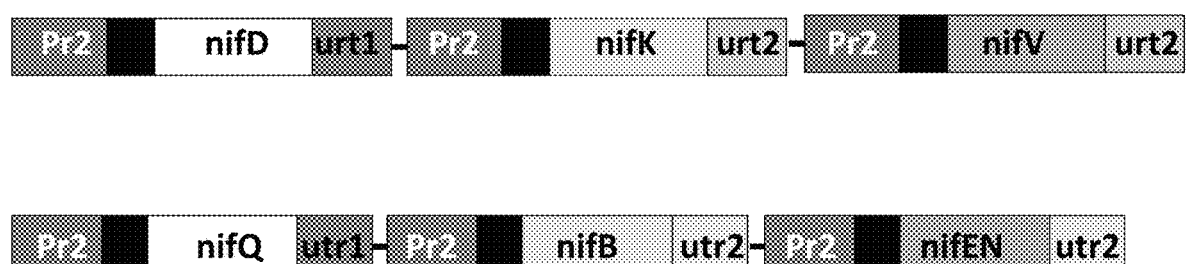
Figure 12:
Figure 12:
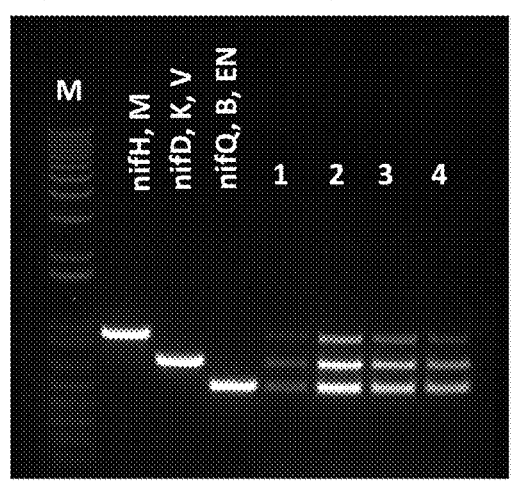

The NifV, NifEN (a fusion of NifE and NifN, SEQ ID NO:140), NifB, and NifQ (Table 10) nitrogenase subunits were cloned into expression vectors, each operably linked to the mitochondrial targeting peptide CPN60 (SEQ ID NO:1). These constructs were individually expressed transiently by *Agrobacterium* infiltration of the leaf of a plant, as detailed in Example 1. Plant extracts enriched for mitochondria were prepared and protein expression was assessed using standard western blot analysis with antibodies specific to the NifV, NifN, NifB, and NifQ proteins. Each of these subunits were detected by western blot. See FIG. 11. Other nif gene components (see Table 10) necessary or useful for expression, assembly, and/or activity of and or to maximize activity of dinitrogenase, are also cloned into one or more expression vectors for mitochondrial targeting, as described here. These constructs are expressed transiently by *Agrobacterium* infiltration of the leaf of a plant, as detailed in Example 1. Plant extracts are prepared and protein expression is assessed using standard western blot analysis with antibodies specific to the NifK and NifD proteins. Acetylene reduction nitrogenase activity assays are conducted essentially as described in Example 1, except for these the plant extract contains the dinitrogenase and dinitrogenase reductase purified from another source is added to the in vitro assay sample.

For transient expression of dinitrogenase in chloroplast, DNA constructs are generated encoding NifD and NifK subunits operably linked to a sequence encoding a chloroplast targeting peptide, for example the RbcS chloroplast targeting peptide. Other nif gene components (see Table 10) necessary or useful for expression, assembly, and/or activity of dinitrogenase, are also cloned into expression vectors for mitochondrial targeting, as described. These constructs are expressed transiently by *Agrobacterium* infiltration of the leaf of a plant, as detailed in Example 1. Plant extracts are prepared and protein expression is assessed using standard western blot analysis with antibodies specific to the NifK and NifD proteins. Acetylene reduction nitrogenase activity assays are conducted essentially as described in example 1, except that for these assays the plant extract contains the dinitrogenase and dinitrogenase reductase purified from another source is added to the in vitro assay sample.

Alternatively, transformation constructs are used to generate stable transformation of a plant (as detailed in Example 8) for nuclear expression of the mitochondrial targeted dinitrogenase subunits. Specifically, a DNA construct is generated encoding NifD and NifK subunits operably linked to a sequence encoding a mitochondrial targeting peptide. Non-limiting examples of mitochondrial targeting peptides are presented in Example 2, Table 4. Alternatively, transformation constructs are used to generate stable transformation of a plant for nuclear expression of the chloroplast targeted dinitrogenase subunits. Specifically, a DNA construct is generated encoding NifD and NifK subunits operably linked to a sequence encoding a chloroplast targeting peptide such as RbcS. Other nif gene components (see Table 10) necessary or useful for expression, assembly, and/or activity of dinitrogenase, are also cloned into transformation vectors (the same vector with nifD and nifK, or separate vectors for stable expression of nif genes operably linked to targeting peptides for either mitochondrial or chloroplast targeting, as described in this example. Stably transformed plants are generated essentially as described in example 8. Targeting and copy number is confirmed by Southern blot analysis. Plant extracts are prepared and protein expression is assessed using standard western blot analysis with antibodies specific to the NifK and NifD proteins. Acetylene reduction nitrogenase activity assays are conducted essentially as described in example 1, except that for these the plant extract contains the dinitrogenase and dinitrogenase reductase purified from another source is added to the in vitro assay sample.

For stable expression of dinitrogenase in chloroplasts, the nifD and nifK genes are cloned into expression constructs of a chloroplast transformation vector as described in example 9. Other nif gene products encoding components or cofactors (see Table 10) necessary or useful for expression and/or activity of dinitrogenase may also be included in separate cassettes within the chloroplast transformation vector construct. Following transformation and selection, targeting is confirmed by Southern blot analysis as detailed in Example 9. Plant extracts are prepared and protein expression is assessed using standard western blot analysis with antibodies specific to the NifK and NifD proteins. Acetylene reduction nitrogenase activity assays are conducted essentially as described in example 1, except that for these assays the plant extract contains the dinitrogenase and dinitrogenase reductase purified from another source is added to the in vitro assay sample.

TABLE 10

| SEQ ID NOs of nitrogen fixation associated genes from *A. vinelandii* (A.v.). | | |
|---|---|---|
| Nif subunit | PRT SEQ ID NO: | DNA SEQ ID NO: |
| nifH | 24 | 25 |
| nifM | 26 | 27 |
| nifS | 28 | 29 |
| nifU | 30 | 31 |
| nifD | 126 | 127 |
| nifK | 128 | 129 |
| nifB | 130 | 131 |
| nifQ | 132 | 133 |
| nifN | 134 | 135 |
| nifV | 136 | 137 |
| nifE | 138 | 139 |
| nifEN | 140 | 141 |

Example 13: Expression of Nitrogenase in Planta

To produce active nitrogenase in a plant cell, it is desirable to express dinitrogenase and dinitrogenase reductase in planta. Expression of nitrogenase nif subunits in plant cells is accomplished using methods as described in prior examples for mitochondrial targeting or chloroplast targeting of nuclear encoded transgene constructs. Alternatively, expression of nitrogenase nif subunits is done by transgene expression from a plant chloroplast genome, as described for dinitrogenase reductase in example 9.

For transient expression of nitrogenase in mitochondria, DNA constructs are generated encoding NifH, NifM, nifD and NifK subunits operably linked to a sequence encoding a mitochondrial targeting peptide. Non-limiting examples of mitochondrial targeting peptides are presented in Example 2, Table 4. Other nif gene components (see Table 10) necessary or useful for expression, assembly, and/or activity of nitrogenase are also cloned into expression vectors for mitochondrial targeting, as described here. These constructs are expressed transiently by *Agrobacterium* infiltration of the leaf of a plant, as detailed in Example 1. Plant extracts are prepared and protein expression is assessed using standard western blot analysis with antibodies specific to the NifH, NifM, NifK or NifD proteins. Acetylene reduction nitrogenase activity assays are conducted essentially as described in example 1, except that the plant extract contains the complete nitrogenase Nif subunit complex.

For transient expression of nitrogenase in chloroplast, DNA constructs are generated encoding NifH, NifM, NifD and NifK subunits operably linked to a sequence encoding a chloroplast targeting peptide, for example the RbcS chloroplast targeting peptide. Other nif gene components (see Table 10) necessary or useful for expression, assembly, and/or activity of nitrogenase are also cloned into expression vectors for mitochondrial targeting, as described here. These constructs are expressed transiently by *Agrobacterium* infiltration of the leaf of a plant, as detailed in Example 1. Plant extracts are prepared and protein expression is assessed using standard western blot analysis with antibodies specific to the NifH, NifM, NifK or NifD proteins. Acetylene reduction nitrogenase activity assays are conducted essentially as described in example 1, except that the plant extract contains the complete nitrogenase Nif subunit complex.

Alternatively, one or more expression vector constructs containing expression cassettes for mitochondrial targeted dinitrogenase subunits, dinitrogenase reductase subunits, and other gene products required for assembly of active nitrogenase in bacteria may be used for stable transformation of plant cells. For instance, three multigene transformation constructs were cloned and used to generate stable transformation of N. benthamiana using the methods detailed in Example 8. The three transformation constructs were: (1) the construct pMON135484 containing the chimeric CPN-60+nifH and CPN-60+nifM cassettes as described in Example 8; (2) a construct containing CPN-60+nifD and CPN-60+nifK and CPN-60+nifV cassettes; and (3) a construct containing CPN-60+nifQ and CPN-60+nifB and CPN-60+nifEN (fusion of NifE and NifN) cassettes. See FIG. 11.

Following transformation and selection, stable events were screened by PCR to identify events with one copy of each of the three transformation constructs. PCR analysis was used to show that at least four events (lanes 1-4) contained each of the constructs used in the transformation. The three PCR bands in each of the lanes labeled 1-4 correspond to the expected PCR product for each individual constructs: NifH+M; NifD+K+V; NifQ+B+EN. Leaf samples from events confirmed to contain each of the three constructs were collected to prepare RNA and protein for analysis. RNA was extracted following standard laboratory practices and subjected to a QuantiGene® 2.0 Plex assay (Affymetrix Inc., Santa Clara. Calif.) to detect mRNA transcribed from the individual Nif gene expression cassettes. Table 11 illustrates that for at least one event, mRNA was detected for all Nif subunits included in the three transformation vectors. Protein extracts were prepared from mitochondrial enriched fraction of leaf samples following standard laboratory practices. Based on western blot analysis, NifH protein was detected (as denoted by "yes" in cells of Table 11) in at least one stable event containing all three transformation vectors. In Table 11, n/a indicates not yet analyzed. Acetylene reduction nitrogenase activity assays are conducted essentially as described in Example 1, except that the plant extract contains the complete nitrogenase nif subunit complex.

TABLE 11

Analysis of stable transformed events.

| Gene | RNA | Protein (western) |
|---|---|---|
| nifH | yes | yes |
| nifM | yes | n/a |

TABLE 11-continued

Analysis of stable transformed events.

| Gene | RNA | Protein (western) |
|---|---|---|
| nifD | yes | n/a |
| nifK | yes | n/a |
| nifB | yes | n/a |
| nifEN | yes | n/a |
| nifQ | yes | n/a |
| nifV | yes | n/a |

Alternatively, transformation constructs are used to generate stable transformation of a plant for nuclear expression of the chloroplast targeted nitrogenase subunits. Specifically, DNA constructs are generated encoding NifH, NifM, NifD and NifK subunits operably linked to a sequence encoding a chloroplast targeting peptide such as RbcS. Other nif gene components (see Table 10) necessary or useful for expression, assembly, and/or activity of nitrogenase, are also cloned into the same transformation vector with NifH, NifM, NifD and NifK subunits, or separate vectors for stable expression of other Nif subunits operably linked to targeting peptides for either mitochondrial or chloroplast targeting, as described in this example. Stably transformed plants are generated essentially as described in Example 8. Targeting and copy number is confirmed by Southern blot analysis. Plant extracts are prepared and protein expression is assessed using standard western blot analysis with antibodies specific to the NifH, NifM, NifK or NifD proteins. Acetylene reduction nitrogenase activity assays are conducted essentially as described in example 1, except that the plant extract contains the complete nitrogenase nif subunit complex.

For stable expression of nitrogenase in chloroplast, the nifH, nifM, nifD and nifK genes are cloned into expression constructs of a chloroplast transformation vector as described in example 9. Other nif gene components (see Table 10) necessary or useful for expression, assembly, and/or activity of nitrogenase may also be included in separate cassettes within the chloroplast transformation vector construct. Following transformation and selection, targeting is confirmed by Southern blot analysis as detailed in Example 9. Plant extracts are prepared and protein expression is assessed using standard western blot analysis with antibodies specific to the NifH, NifM, NifK or NifD proteins. Acetylene reduction nitrogenase activity assays are conducted essentially as described in Example 1, except that the plant extract contains the complete nitrogenase Nif subunit complex.

The invention claimed is:

1. A recombinant DNA construct comprising at least one polynucleotide sequence encoding an NifH dinitrogenase reductase polypeptide and an NifM polypeptide, each operably linked to a mitochondrial-targeting peptide, wherein the polynucleotide sequence is operably linked to a promoter sequence functional in plants;
wherein expression of the recombinant DNA construct in a plant cell is capable of resulting in at least about a 4-fold increase in dinitrogenase reductase activity in the plant cell as compared to a plant cell that does not comprise the recombinant DNA.

2. The recombinant DNA construct of claim 1, wherein the dinitrogenase reductase polypeptide comprises a sequence at least 80% identical to SEQ ID NO:24.

3. The recombinant DNA construct of claim 1 comprising a polynucleotide sequence encoding a mitochondrial-targeted dinitrogenase reductase polypeptide comprising a sequence at least 80% identical to a sequence selected from the group consisting of: SEQ ID NO:40, SEQ ID NO:42, SEQ ID NO:44, SEQ ID NO:46, SEQ ID NO:48, SEQ ID NO:50, SEQ ID NO:64, SEQ ID NO:66, SEQ ID NO:72, SEQ ID NO:74, SEQ ID NO:78, and SEQ ID NO:80.

4. The recombinant DNA construct of claim 1, further comprising at least a first expression element selected from the group consisting of: an enhancer, an intron, a transcription termination sequence, a ribosomal RNA operon promoter, and a 5'-untranslated leader.

5. The recombinant DNA construct of claim 1 comprising a polynucleotide sequence encoding SEQ ID NO:26 (NifM) or SEQ ID NO:34 (NifM).

6. A method of producing a plant that reduces dinitrogen (N2) gas in a plant cell comprising:

a. introducing into the plant cell a recombinant DNA construct comprising at least one polynucleotide sequence encoding an NifH dinitrogenase reductase polypeptide and an NifM polypeptide, each operably linked to a mitochondrial-targeting peptide, wherein the polynucleotide sequence is operably linked to a promoter functional in plants;
wherein expression of the recombinant DNA construct is capable of resulting in at least about a 4-fold increase in dinitrogenase reductase activity in the plant cell as compared to a plant cell that does not comprise the recombinant DNA; and
b. identifying a plant that reduces dinitrogen (N2) gas by expression of active nitrogenase enzyme in the plant cell.

7. The method of claim 6, wherein the recombinant DNA construct is transiently introduced into the plant cell.

8. The method of claim 6, wherein the recombinant DNA construct is stably integrated into the genome of the plant cell, wherein the genome comprises the nuclear genome or a plastid genome.

9. The method of claim 6, wherein the NifH dinitrogenase reductase polypeptide comprises a sequence at least 80% identical to at least one sequence selected from the group consisting of: SEQ ID NO:24, SEQ ID NO:32, and SEQ ID NO:36, or the NifM polypeptide comprises a sequence at least 80% identical to at least one sequence selected from the group consisting of: SEQ ID NO:26 and SEQ ID NO:34.

10. The method of claim 6, wherein the recombinant DNA construct comprises a polynucleotide sequence encoding a mitochondrial-targeted dinitrogenase reductase polypeptide comprising a sequence at least 80% identical to a sequence selected from the group consisting of: SEQ ID NO:40, SEQ ID NO:42, SEQ ID NO:44, SEQ ID NO:46, SEQ ID NO:48, SEQ ID NO:50, SEQ ID NO:64, SEQ ID NO:66, SEQ ID NO:72, SEQ ID NO:74, SEQ ID NO:78, and SEQ ID NO:80.

11. The method of claim 6, wherein the recombinant DNA construct further comprises a sequence encoding one or more additional polypeptides associated with dinitrogenase or dinitrogenase reductase expression, assembly, stability, or activity selected from the group consisting of: NifB, NifQ, NifN, NifV, NifE, NifS, and NifU.

12. The method of claim 11, wherein the polynucleotide sequence encoding the additional polypeptide is operably linked to a polynucleotide sequence encoding a mitochondrial-targeting polypeptide, and wherein the polynucleotide sequence is further operably linked to a promoter functional in plants.

13. The method of claim 11, wherein the sequence encoding the additional polypeptide is selected from the group consisting of: SEQ ID NO:130 (NifB), SEQ ID NO:132 (NifQ), SEQ ID NO:134 (NifN), SEQ ID NO:136 (NifV), SEQ ID NO:138 (NifE), SEQ ID NO: 28 (NifS), and SEQ ID NO:30 (NifU).

14. A plant that reduces dinitrogen (N2) gas in the plant cell, wherein said plant comprises a recombinant DNA construct comprising at least one polynucleotide sequence encoding an NifH dinitrogenase reductase polypeptide and an NifM polypeptide, each operably linked to a mitochondrial-targeting peptide, wherein the polynucleotide sequence is operably linked to a promoter sequence functional in plants;
wherein expression of the recombinant DNA construct in a plant cell is capable of resulting in at least about a 4-fold increase in dinitrogenase reductase activity in the plant cell as compared to a plant cell that does not comprise the recombinant DNA.

15. The recombinant DNA construct of claim 1, wherein the dinitrogenase reductase polypeptide comprises a sequence selected from the group consisting of: SEQ ID NO:24, SEQ ID NO:32, and SEQ ID NO:36.

16. The recombinant DNA construct of claim 1, further comprising a polynucleotide sequence encoding NifQ.

17. The recombinant DNA construct of claim 16 comprising a polynucleotide sequence encoding SEQ ID NO:132 (NifQ).

18. The recombinant DNA construct of claim 1, further comprising a polynucleotide sequence encoding NifN.

19. The recombinant DNA construct of claim 18 comprising a polynucleotide sequence encoding SEQ ID NO:134 (NifN).

20. The recombinant DNA construct of claim 1, further comprising a polynucleotide sequence encoding NifV.

21. The recombinant DNA construct of claim 20 comprising a polynucleotide sequence encoding SEQ ID NO:136 (NifV).

22. The recombinant DNA construct of claim 1, further comprising a polynucleotide sequence encoding NifE.

23. The recombinant DNA construct of claim 22 comprising a polynucleotide sequence encoding SEQ ID NO:138 (NifE).

24. The recombinant DNA construct of claim 5, comprising a polynucleotide sequence encoding SEQ ID NO:26 (NifM).

25. The recombinant DNA construct of claim 5 comprising a polynucleotide sequence encoding SEQ ID NO:34 (NifM).

26. The recombinant DNA construct of claim 1, further comprising a polynucleotide sequence encoding NifS.

27. The recombinant DNA construct of claim 26 comprising a polynucleotide sequence encoding SEQ ID NO: 28 (NifS).

28. The recombinant DNA construct of claim 1, further comprising a polynucleotide sequence encoding NifU.

29. The recombinant DNA construct of claim 28 comprising a polynucleotide sequence SEQ ID NO:30 (NifU).

30. The recombinant DNA construct of claim 1, wherein the sequence of either of the mitochondrial-targeting peptides is selected from the group consisting of: SEQ ID NOs:1-22.

* * * * *